US011180563B2

(12) United States Patent
Wesche et al.

(10) Patent No.: US 11,180,563 B2
(45) Date of Patent: Nov. 23, 2021

(54) FLT3 BINDING PROTEINS AND METHODS OF USE

(71) Applicant: Harpoon Therapeutics, Inc., South San Francisco, CA (US)

(72) Inventors: Holger Wesche, San Francisco, CA (US); Richard J. Austin, San Francisco, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 17/180,435

(22) Filed: Feb. 19, 2021

(65) Prior Publication Data

US 2021/0261671 A1 Aug. 26, 2021

Related U.S. Application Data

(60) Provisional application No. 62/980,051, filed on Feb. 21, 2020.

(51) Int. Cl.
*A61K 39/00* (2006.01)
*C07K 16/28* (2006.01)
*C07K 16/18* (2006.01)
*A61P 35/02* (2006.01)

(52) U.S. Cl.
CPC .......... *C07K 16/2863* (2013.01); *A61P 35/02* (2018.01); *C07K 16/18* (2013.01); *C07K 16/2809* (2013.01); *A61K 2039/505* (2013.01); *C07K 2317/31* (2013.01); *C07K 2317/565* (2013.01); *C07K 2317/569* (2013.01); *C07K 2317/622* (2013.01); *C07K 2317/732* (2013.01); *C07K 2317/92* (2013.01)

(58) Field of Classification Search
CPC .............................................. A61K 2039/505
See application file for complete search history.

(56) References Cited

U.S. PATENT DOCUMENTS

| 4,816,567 | A | 3/1989 | Cabilly et al. |
|---|---|---|---|
| 5,061,620 | A | 10/1991 | Tsukamoto et al. |
| 5,199,942 | A | 4/1993 | Gillis |
| 5,225,539 | A | 7/1993 | Winter |
| 5,350,674 | A | 9/1994 | Boenisch et al. |
| 5,399,346 | A | 3/1995 | Anderson et al. |
| 5,530,101 | A | 6/1996 | Queen et al. |
| 5,565,332 | A | 10/1996 | Hoogenboom et al. |
| 5,580,859 | A | 12/1996 | Felgner et al. |
| 5,585,089 | A | 12/1996 | Queen et al. |
| 5,585,362 | A | 12/1996 | Wilson et al. |
| 5,589,466 | A | 12/1996 | Felgner et al. |
| 5,759,808 | A | 6/1998 | Casterman et al. |
| 5,766,886 | A | 6/1998 | Studnicka et al. |
| 5,773,292 | A | 6/1998 | Bander |
| 5,800,988 | A | 9/1998 | Casterman et al. |
| 5,840,526 | A | 11/1998 | Casterman et al. |
| 5,858,358 | A | 1/1999 | June et al. |
| 5,859,205 | A | 1/1999 | Adair et al. |
| 5,874,541 | A | 2/1999 | Casterman et al. |
| 5,883,223 | A | 3/1999 | Gray |
| 6,005,079 | A | 12/1999 | Casterman et al. |
| 6,015,695 | A | 1/2000 | Casterman et al. |
| 6,107,090 | A | 8/2000 | Bander |
| 6,120,766 | A | 9/2000 | Hale et al. |
| 6,136,311 | A | 10/2000 | Bander |
| 6,326,193 | B1 | 12/2001 | Liu et al. |
| 6,331,415 | B1 | 12/2001 | Cabilly et al. |
| 6,352,694 | B1 | 3/2002 | June et al. |
| 6,407,213 | B1 | 6/2002 | Carter et al. |
| 6,534,055 | B1 | 3/2003 | June et al. |
| 6,548,640 | B1 | 4/2003 | Winter |
| 6,670,453 | B2 | 12/2003 | Frenken et al. |
| 6,692,964 | B1 | 2/2004 | June et al. |
| 6,759,518 | B1 | 7/2004 | Kontermann et al. |
| 6,767,711 | B2 | 7/2004 | Bander |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,163,680 | B2 | 1/2007 | Bander |
| 7,172,869 | B2 | 2/2007 | June et al. |

(Continued)

FOREIGN PATENT DOCUMENTS

| CN | 1563092 A | 1/2005 |
|---|---|---|
| CN | 101646689 A | 2/2010 |

(Continued)

OTHER PUBLICATIONS

Agata et al. Expression of the PD-1 antigen on the surface of stimulated mouse T and B lymphocytes. Int. Immunol 8:765-75 (1996).

(Continued)

*Primary Examiner* — Stephen L Rawlings
(74) *Attorney, Agent, or Firm* — Wilson Sonsini Goodrich & Rosati

(57) ABSTRACT

Provided herein are FLT3 binding proteins, pharmaceutical compositions comprising such proteins or fragments thereof, as well as nucleic acids, recombinant expression vectors and host cells for making such FLT3 binding proteins. Also disclosed are methods of using the disclosed FLT3 binding proteins in the prevention, and/or treatment of diseases, conditions and disorders.

27 Claims, 39 Drawing Sheets
Specification includes a Sequence Listing.

(56) References Cited

U.S. PATENT DOCUMENTS

| | | |
|---|---|---|
| 7,175,843 B2 | 2/2007 | June et al. |
| 7,232,566 B2 | 6/2007 | June et al. |
| 7,262,276 B2 | 8/2007 | Huang et al. |
| 7,666,414 B2 | 2/2010 | Bander |
| 7,807,162 B2 | 10/2010 | Silence |
| 7,850,971 B2 | 12/2010 | Maddon et al. |
| 8,114,965 B2 | 2/2012 | Maddon et al. |
| 8,188,223 B2 | 5/2012 | Beirnaert et al. |
| 8,236,308 B2 | 8/2012 | Kischel et al. |
| 8,470,330 B2 | 6/2013 | Schuelke et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,784,821 B1 | 7/2014 | Kufer et al. |
| 8,846,042 B2 | 9/2014 | Zhou |
| 8,907,071 B2 | 12/2014 | Sullivan et al. |
| 8,937,164 B2 | 1/2015 | Descamps et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,340,621 B2 | 5/2016 | Kufer et al. |
| 9,708,412 B2 | 7/2017 | Baeuerle et al. |
| 9,920,115 B2 | 3/2018 | Dubridge et al. |
| 10,066,016 B2 | 9/2018 | Dubridge et al. |
| 10,100,106 B2 | 10/2018 | Dubridge et al. |
| 10,428,120 B2 | 10/2019 | Kontermann et al. |
| 10,543,271 B2 | 1/2020 | Wesche et al. |
| 10,544,221 B2 | 1/2020 | Dubridge et al. |
| 10,730,954 B2 | 8/2020 | Wesche et al. |
| 10,815,311 B2 | 10/2020 | Wesche et al. |
| 10,844,134 B2 | 11/2020 | Baeuerle et al. |
| 10,849,973 B2 | 12/2020 | Dubridge et al. |
| 10,927,180 B2 | 2/2021 | Wesche et al. |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0259026 A1 | 10/2009 | Tomlinson et al. |
| 2010/0122358 A1 | 5/2010 | Brueggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0231024 A1 | 9/2012 | Elsaesser-Beile et al. |
| 2012/0328619 A1 | 12/2012 | Fey et al. |
| 2013/0017200 A1 | 1/2013 | Scheer et al. |
| 2013/0136744 A1 | 5/2013 | Bouche et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0023664 A1 | 1/2014 | Lowman et al. |
| 2014/0045195 A1 | 2/2014 | Daugherty et al. |
| 2014/0073767 A1 | 3/2014 | Lee et al. |
| 2014/0088295 A1 | 3/2014 | Smith et al. |
| 2014/0205601 A1 | 7/2014 | Beirnaert et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0215063 A1 | 7/2016 | Bernett et al. |
| 2016/0251440 A1 | 9/2016 | Roobrouck et al. |
| 2016/0257721 A1 | 9/2016 | Lieber et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037149 A1 | 2/2017 | Raum et al. |
| 2017/0152316 A1 | 6/2017 | Cobbold et al. |
| 2017/0204164 A1 | 7/2017 | Himmler et al. |
| 2017/0275373 A1 | 9/2017 | Kufer et al. |
| 2017/0298149 A1 | 10/2017 | Baeuerle et al. |
| 2017/0334997 A1 | 11/2017 | Dubridge et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0134789 A1 | 5/2018 | Baeuerle et al. |
| 2018/0148508 A1 | 5/2018 | Wang et al. |
| 2018/0346601 A1 | 12/2018 | Dettling et al. |
| 2019/0031749 A1 | 1/2019 | Dubridge et al. |
| 2019/0092862 A1 | 3/2019 | Cui et al. |
| 2019/0112381 A1 | 4/2019 | Wesche et al. |
| 2019/0225702 A1 | 7/2019 | Baeuerle et al. |
| 2020/0115461 A1 | 4/2020 | Evnin et al. |
| 2020/0148771 A1 | 5/2020 | Paeuerle et al. |
| 2020/0231672 A1 | 7/2020 | Dubridge et al. |
| 2020/0270362 A1 | 8/2020 | Wesche et al. |
| 2020/0289646 A1 | 9/2020 | Wesche et al. |
| 2021/0047439 A1 | 2/2021 | Wesche et al. |

FOREIGN PATENT DOCUMENTS

| | | |
|---|---|---|
| CN | 105968201 A | 9/2016 |
| CN | 105968204 A | 9/2016 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| FR | 901228 A | 7/1945 |
| JP | 2005501517 A | 1/2005 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0190190 A2 | 11/2001 |
| WO | WO-0196584 A2 | 12/2001 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004041867 A2 | 5/2004 |
| WO | WO-2004042404 A1 | 5/2004 |

(56) References Cited

FOREIGN PATENT DOCUMENTS

| | | |
|---|---|---|
| WO | WO-2004049794 A2 | 6/2004 |
| WO | WO-2006020258 A2 | 2/2006 |
| WO | WO-2006122787 A1 | 11/2006 |
| WO | WO-2007024715 A2 | 3/2007 |
| WO | WO-2007042261 A2 | 4/2007 |
| WO | WO-2007062466 A1 | 6/2007 |
| WO | WO-2007115230 A2 | 10/2007 |
| WO | WO-2008028977 A2 | 3/2008 |
| WO | WO-2009025846 A2 | 2/2009 |
| WO | WO-2009030285 A1 | 3/2009 |
| WO | WO-2009147248 A2 | 12/2009 |
| WO | WO-2010003118 A1 | 1/2010 |
| WO | WO-2010037836 A2 | 4/2010 |
| WO | WO-2010037837 A2 | 4/2010 |
| WO | WO-2011039368 A2 | 4/2011 |
| WO | WO-2011051327 A2 | 5/2011 |
| WO | WO-2011117423 A1 | 9/2011 |
| WO | WO-2012131053 A1 | 10/2012 |
| WO | WO-2012138475 A1 | 10/2012 |
| WO | WO-2012158818 A2 | 11/2012 |
| WO | WO-2012175400 A1 | 12/2012 |
| WO | WO-2013036130 A1 | 3/2013 |
| WO | WO-2013104804 A2 | 7/2013 |
| WO | WO-2013110531 A1 | 8/2013 |
| WO | WO-2013128027 A1 | 9/2013 |
| WO | WO-2013128194 A1 | 9/2013 |
| WO | WO-2014033304 A2 | 3/2014 |
| WO | WO-2014052064 A1 | 4/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2015103072 A1 | 7/2015 |
| WO | WO-2015150447 A1 | 10/2015 |
| WO | WO-2015184207 A1 | 12/2015 |
| WO | WO-2016009029 A1 | 1/2016 |
| WO | WO-2016046778 A2 | 3/2016 |
| WO | WO-2016055551 A1 | 4/2016 |
| WO | WO-2016105450 A2 | 6/2016 |
| WO | WO-2016130819 A2 | 8/2016 |
| WO | WO-2016171999 A2 | 10/2016 |
| WO | WO-2016179003 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017021356 A1 | 2/2017 |
| WO | WO-2017025698 A1 | 2/2017 |
| WO | WO-2017027392 A1 | 2/2017 |
| WO | WO-2017041749 A1 | 3/2017 |
| WO | WO-2017079528 A1 | 5/2017 |
| WO | WO-2017136549 A1 | 8/2017 |
| WO | WO-2017156178 A1 | 9/2017 |
| WO | WO-2018017863 A1 | 1/2018 |
| WO | WO-2018067993 A1 | 4/2018 |
| WO | WO-2018071777 A1 | 4/2018 |
| WO | WO-2018098354 A1 | 5/2018 |
| WO | WO-2018098356 A1 | 5/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018204717 A1 | 11/2018 |
| WO | WO-2018209298 A1 | 11/2018 |
| WO | WO-2018209304 A1 | 11/2018 |
| WO | WO-2018232020 A1 | 12/2018 |
| WO | WO-2019075359 A1 | 4/2019 |
| WO | WO-2019075378 A1 | 4/2019 |
| WO | WO-2019222278 A1 | 11/2019 |
| WO | WO-2019222282 A1 | 11/2019 |
| WO | WO-2019222283 A1 | 11/2019 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020232303 A1 | 11/2020 |

OTHER PUBLICATIONS

Al-Lazikani et al. Standard conformations for the canonical structures of immunoglobulins. J. Mol Biology 273(4):927-948 (1997).

Almagro et al. Humanization of antibodies. Front Biosci 13:1619-1633 (2008).

Altschul et al. Basic local alignment search tool. J Mol Biol 215(3):403-410 (1990).

Altschul, et al. Gapped BLAST and PSI-BLAST: a new generation of protein database search programs. Nucleic Acids Res 25:3389-3402 (1997).

Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).

Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).

Baca et al. Antibody humanization using monovalent phage display. J Biol Chem 272(16):10678-10684 (1997).

Baeuerle et al. Bispecific T-cell engaging antibodies for cancer therapy. Cancer Res 69:4941-4944 (2009).

Barrett et al. Treatment of advanced leukemia in mice with mRNA engineered T cells. Hum Gene Ther 22:1575-1586 (2011).

Batzer et al. Enhanced evolutionary PCR using oligonucleotides with inosine at the 3'-terminus. Nucleic Acids Res. 19(18):5081 (1991).

Baum et al. Antitumor activities of PSMAxCD3 diabodies by redirected T-cell lysis of prostate cancer cells. Immunotherapy 5(1):27-38 (2013).

Bedouelle et al. Diversity and junction residues as hotspots of binding energy in an antibody neutralizing the dengue virus. FEBS J 273(1):34-46 (2006).

Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).

Bird et al. Single-chain antigen-binding proteins. Science 242(4877):423-426 (1988).

Blank et al. Interaction of PD-L1 on tumor cells with PD-1 on tumor-specific T cells as a mechanism of immune evasion: implications for tumor immunotherapy. Cancer Immunol Immunother 54:307-314 (2005).

Bortoletto et al. Optimizing anti-CD3 affinity for effective T cell targeting against tumor cells. Eur J Immunol 32:3102-3107 (2002).

Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).

Brauchle et al. Characterization of a Novel FLT3 BiTE Molecule for the Treatment of Acute Myeloid Leukemia. Mol Cancer Ther 19:1875-88 (2020).

Brown et al. Tolerance of single, but not multiple, amino acid replacements in antibody VH CDR 2: a means of minimizing B cell wastage from somatic hypermutation? J Immunol 156(9):3285-3291 (1996).

Caldas et al. Design and synthesis of germline-based hemi-humanized single-chain Fv against the CD18 surface antigen. Protein Eng 13(5):353-360 (2000).

Caldas et al. Humanization of the anti-CD18 antibody 6.7: an unexpected effect of a framework residue in binding to antigen. Mol Immunol. 39(15):941-952 (2003).

Carter et al. Humanization of an anti-p185HER2 antibody for human cancer therapy. PNAS USA 89(10):4285-4289 (1992).

Carter et al. PD-1: PD-L inhibitory pathway affects both CD4(+) and CD8(+) T cells and is overcome by IL-2. Eur J Immunol 32:634-643 (2002).

Casset et al. A peptide mimetic of an anti-CD4 monoclonal antibody by rational design. Biochemical and Biophysical Research Communication 307:198-205 (2003).

(56) References Cited

OTHER PUBLICATIONS

Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prey 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transi Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholineto an anti-DNA autoantibody is due to a single base change in its heavy chain variable region. PNAS USA 84(9):2926-30 (1987).
Glaser et al. Novel antibody hinge regions for efficient production of CH2 domain-deleted antibodies. J. Biol. Chem. 280:41494-503 (2005).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).

(56) References Cited

OTHER PUBLICATIONS

Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prev 15:1751 (2006).
Holliger, et al. "Diabodies": small bivalent and bispecific antibody fragments. Proc Natl Acad Sci USA. Jul. 15, 1993; 90(14): 6444-6448. doi: 10.1073/pnas.90.14.6444.
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).
Huck et al. Sequence of a human immunoglobulin gamma 3 heavy chain constant region gene: comparison with the other human C gamma genes. Nucl. Acids Res. 14:1779-89 (1986).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Škrlec et al. Non-immunoglobulin scaffolds: a focus on their targets. Trends in Biotechnol 33:408-418 (2015).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 xCD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).

Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
Maccallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologies by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).

(56) References Cited

OTHER PUBLICATIONS

Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017/056530 International Search Report and Written Opinion dated Jan. 23, 2018.
PCT/US2017/063121 International Search Report and Written Opinion dated Mar. 26, 2018.
PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055682 International Search Report and Written Opinion dated Mar. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052270 International Search Report and Written Opinion dated Mar. 5, 2020.
PCT/US2019/053017 International Search Report and Written Opinion dated Jan. 31, 2020.
PCT/US/2020/032985 International Search Report and Written Opinion dated Oct. 15, 2020.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1 alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen-binding loops of camel single-domain antibodies. J. Mol. Biol. 352(3):597-607 (2005).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).

(56) References Cited

OTHER PUBLICATIONS

Stepinski et al. Synthesis and properties of mRNAs containing the novel 'anti-reverse' cap analogs 7-methyl(3'0-methyl)GppppG and 7-methyl(e'-deoxy)GppppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stirewalt et al. The role of FLT3 in haematopoietic malignancies. Nat Rev Cancer 3:650-665 (2003).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. Influence of the hinge region on complement activation, C1q binding, and segmental flexibility in chimeric human immunoglobulins. PNAS USA 87:162-166 (1990).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.
U.S. Appl. No. 15/704,620 Office Action dated Oct. 26, 2017.
U.S. Appl. No. 15/821,498 Office Action dated Apr. 21, 2020.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10):e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin for Monitoring and Treating Mesothelioma. Sci Rep 5:9928 (2015).
Zhu et al. COMBODY: one-domain antibody multimer with improved avidity. Immunology and Cell Biology 88(6):667-675 (2010).
PCT/US2021/018853 International Search Report and Written Opinion dated Jul. 8, 2021.

(56) References Cited

OTHER PUBLICATIONS

UniProtKB Accession No. AOA3M1V7M7_9EURY, Ig-like_bact domain-containing protein, Feb. 13, 2019 [online] [Retrieved on Jun. 8, 2021], Retrieved from the internet< url:<ahref="https://www.uniprotorg/uniprot/AOA3M1V7M7.bct">https://www.uniprotorg/uniprot/AOA3M1V7M7.bct</url:<a>.

FLT3 BINDING PROTEINS AND METHODS OF USE

CROSS-REFERENCE

This application claims the benefit of U.S. Provisional Application No. 62/980,051 filed on Feb. 21, 2020, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Feb. 19, 2021, is named 47517-744_201 SL.txt and is 532,727 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

FMS-like tyrosine kinase 3 (FLT3) is a type I transmembrane protein that plays an essential role in normal hematopoiesis and is physiologically expressed on normal hematopoietic stem cells (HSCs), as well as lymphoid, myeloid and granulocyte/macrophage progenitor cells in humans, and are believed to play an important role in early hematopoiesis. In mature hematopoietic cells, FLT3 expression has been reported in subsets of dendritic cells and natural killer cells. Due to its important role in regulating survival, proliferation, and differentiation of hematopoietic cells (B and T cells), aberrant FLT3 activity is involved in the development and progression of cancers of the hematopoietic system. For example, internal tandem duplications of FLT3 are the most common mutations associated with acute myelogenous leukemia (AML). FLT3 is also present on malignant blasts in AML, providing a target for antibody and cellular immunotherapyl. As such, there is a need for therapies, e.g., antibodies, that can specifically target and destroy cells that overexpress FLT3. Further, there is a need for a greater choice of treatment options which allows physicians to select the therapeutic with the best side effect profile for an individual patient. The present disclosure provides novel polypeptides and protein therapeutics useful in methods of treatment, particularly for treatment of conditions associated with abnormal expression of FLT3.

SUMMARY

One embodiment provides an FLT3 binding domain comprising at least three complementarity determining regions (a CDR1, a CDR2, and a CDR3), wherein
the CDR1 comprises a sequence selected from the group consisting of SEQ ID Nos. 77-108, or a sequence comprising one or more amino acid substitutions in a sequence selected from the group consisting of SEQ ID Nos. 77-108;
the CDR2 comprises a sequence selected from the group consisting of SEQ ID Nos. 109-154, and 393-394, or a sequence comprising one or more amino acid substitutions in a sequence selected from the group consisting of SEQ ID Nos. 109-154, and 393-394;
the CDR3 comprises a sequence selected from the group consisting of SEQ ID Nos. 155-195, or a sequence comprising one or more amino acid substitutions in a sequence selected from the group consisting of SEQ ID Nos. 155-195.

In some embodiments, the FLT3 binding domain of claim 1, comprising at least one of the following set of sequences (the CDR1, the CDR2, and the CDR3):
SEQ ID Nos. 77, 109, and 155;
SEQ ID Nos. 78, 109, and 155;
SEQ ID Nos. 79, 110, and 156;
SEQ ID Nos. 80, 111, and 155;
SEQ ID Nos. 81, 112, and 155;
SEQ ID Nos. 77, 113, and 157;
SEQ ID Nos. 82, 110, and 156;
SEQ ID Nos. 77, 114, and 158;
SEQ ID Nos. 80, 111, and 155;
SEQ ID Nos. 83, 115, and 155;
SEQ ID Nos. 84, 111, and 155;
SEQ ID Nos. 79, 116, and 156;
SEQ ID Nos. 85, 111, and 155;
SEQ ID Nos. 86, 110, and 156;
SEQ ID Nos. 87, 110, and 156;
SEQ ID Nos. 88, 117, and 159;
SEQ ID Nos. 88, 118, and 160;
SEQ ID Nos. 88, 119, and 161;
SEQ ID Nos. 88, 120, and 162;
SEQ ID Nos. 88, 121, and 163;
SEQ ID Nos. 88, 122, and 164;
SEQ ID Nos. 88, 121, and 165;
SEQ ID Nos. 88, 121, and 166;
SEQ ID Nos. 88, 122, and 167;
SEQ ID Nos. 88, 122, and 168;
SEQ ID Nos. 88, 121, and 169;
SEQ ID Nos. 88, 118, and 165;
SEQ ID Nos. 88, 123, and 170;
SEQ ID Nos. 88, 124, and 171;
SEQ ID Nos. 88, 117, and 172;
SEQ ID Nos. 89, 125, and 173;
SEQ ID Nos. 90, 126, and 174;
SEQ ID Nos. 90, 127, and 175;
SEQ ID Nos. 90, 125, and 176;
SEQ ID Nos. 90, 128, and 175;
SEQ ID Nos. 90, 128, and 177;
SEQ ID Nos. 91, 129, and 178;
SEQ ID Nos. 91, 130, and 178;
SEQ ID Nos. 92, 131, and 178;
SEQ ID Nos. 93, 132, and 178;
SEQ ID Nos. 94, 133, and 179;
SEQ ID Nos. 91, 134, and 178;
SEQ ID Nos. 95, 135, and 180;
SEQ ID Nos. 96, 136, and 181;
SEQ ID Nos. 97, 137, and 182;
SEQ ID Nos. 97, 138, and 183;
SEQ ID Nos. 98, 139, and 184;
SEQ ID Nos. 99, 139, and 185;
SEQ ID Nos. 100, 140, and 186;
SEQ ID Nos. 101, 141, and 187;
SEQ ID Nos. 102, 142, and 188;
SEQ ID Nos. 103, 143, and 189;
SEQ ID Nos. 104, 144, and 190;
SEQ ID Nos. 105, 145, and 191;
SEQ ID Nos. 106, 146, and 192;
SEQ ID Nos. 107, 147, and 193;
SEQ ID Nos. 108, 148, and 194;

SEQ ID Nos. 91, 149, and 195;
SEQ ID Nos. 91, 150, and 195;
SEQ ID Nos. 100, 151, and 186;
SEQ ID Nos. 92, 152, and 195;
SEQ ID Nos. 93, 153, and 195;
SEQ ID Nos. 91, 154, and 195;
SEQ ID Nos. 89, 393, and 173; and
SEQ ID Nos. 89, 394, and 173.

In some embodiments, the FLT3 binding domain comprises at least one of the following set of sequences (the CDR1, the CDR2, and the CDR3):
SEQ ID Nos. 89, 393, and 173;
SEQ ID Nos. 89, 394, and 173;
SEQ ID Nos. 100, 151, and 186; and
SEQ ID Nos. 91, 149, and 195.

In some embodiments, wherein the binding domain further comprises a framework region 1, a framework region 2, a framework region 3, and a framework region 4, wherein the framework region 1 comprises a sequence selected from the group consisting of SEQ ID Nos. 273-301, the framework region 2 comprises a sequence selected from the group consisting of SEQ ID Nos. 302-322, 395, and 406-407, the framework region 3 comprises a sequence selected from the group consisting of SEQ ID Nos. 323-365, and 396, and the framework region 4 comprises a sequence selected from the group consisting of SEQ ID Nos. 366-371. In some embodiments, the FLT3 binding domain comprises sequence that is at least about 60% identical to a sequence selected from the group consisting of SEQ ID Nos. 1-76, and 389-390. In some embodiments, the FLT3 binding domain comprises a sequence that is at least about 70% identical to a sequence selected from the group consisting of SEQ ID Nos. 71-76, and 389-390.

In some embodiments, the FLT3 binding domain comprises the FLT3 binding domain is an antibody or an antigen binding fragment thereof. In some embodiments, the antibody or an antigen binding fragment thereof comprises at least one of: a monoclonal antibody (mAb), a bispecific antibody, a trispecific antibody, a monovalent antibody, a multivalent antibody, an hcIgG, an Fv, an Fd, an Fab, an F(ab')2, an F(ab'), an Fab2, an Fab3, an scFab, an scFv, an scFvFc, an scFv-zipper, a di-scFv, a tandem scFv, an sdFv, an sdAb, a VH domain, a VL domain, a VHH domain, a half-antibody, a diabody, a single chain diabody, a tandem diabody, a tandem di-scFv, or a tandem tri-scFv. In some embodiments, the FLT3 binding domain is the sdAb. In some embodiments, the FLT3 binding domain is part of an antibody or an antigen binding fragment thereof. In some embodiments, the antibody or an antigen binding fragment thereof comprises at least one of: a monoclonal antibody (mAb), a bispecific antibody, a multispecific antibody, a monovalent antibody, a multivalent antibody, an hcIgG, an Fv, an Fd, an Fab, an F(ab')2, an F(ab'), an Fab2, an Fab3, an scFab, an scFv, an scFvFc, an scFv-zipper, a di-scFv, a tandem scFv, a half-antibody, a diabody, a single chain diabody, a tandem diabody, a tandem di-scFv, or a tandem tri-scFv. In some embodiments, the FLT3 binding domain is part of the antibody or an antigen binding fragment thereof and wherein the antibody or an antigen binding fragment thereof comprises the bispecific antibody.

In some embodiments, the FLT3 binding domain comprises the bispecific antibody comprises (i) the FLT3 binding domain (anti-FLT3) and (ii) a CD3 binding domain. In some embodiments, the FLT3 binding domain comprises the CD3 comprises a human CD3. In some embodiments, the anti-FLT3 domain is an sdAb. In some embodiments, the anti-CD3 domain is an scFv. In some embodiments, the FLT3 binding domain is part of the antibody or an antigen binding fragment thereof and wherein the antibody or an antigen binding fragment thereof comprises the multispecific antibody. In some embodiments, the multispecific antibody comprises (i) the FLT3 binding domain (anti-FLT3); (ii) a CD3 binding domain (anti-CD3); and (iii) an albumin binding domain (anti-ALB). In some embodiments, the CD3 comprises a human CD3. In some embodiments, the albumin comprises a serum albumin. In some embodiments, the serum albumin is a human serum albumin.

In some embodiments, the FLT3 binding domain (anti-FLT3), the CD3 binding domain (anti-CD3), and the albumin binding domain (anti-ALB) are in an at least one of the following formats, from N-terminus to C-terminus:
anti-ALB: anti-FLT3: anti-CD3;
anti-CD3: anti-FLT3: anti-ALB;
anti-FLT3: anti-CD3: anti-ALB;
anti-ALB: anti-CD3: anti-FLT3;
anti-FLT3: anti-ALB: anti-CD3; and
anti-CD3: anti-ALB: anti-FLT3.

In some embodiments, the anti-FLT3 domain is an sdAb. In some embodiments, the anti-CD3 domain is an scFv. In some embodiments, the anti-ALB domain is an sdAb. In some embodiments, the anti-CD3 domain comprises an amino acid sequence that is at least about 90% identical to the sequence set forth in SEQ ID No. 373. In some embodiments, the anti-ALB domain comprises an amino acid sequence that is at least about 90% identical to the sequence set forth in SEQ ID No. 372. In some embodiments, the FLT3 binding domain binds to human FLT3 and cynomolgus FLT3.

One embodiment provides an FLT3 binding domain that has an half-maximal effective concentration ($EC_{50}$) of at least about 0.5 pM to about 6000 pM in a T-cell dependent cellular cytotoxicity assay, wherein the assay measures the $EC_{50}$ of the FLT3 binding domain in T cells mediated killing of FLT-3 expressing cells. In some embodiments, the FLT-3 expressing cells are leukemia cells. In some embodiments, the leukemia cells are from a cell line, wherein the cell line is MV-4-11, EOL1, THP1, MOLM3, or HL60. In some embodiments, the FLT3 binding domain comprises least three complementarity determining regions (a CDR1, a CDR2, and a CDR3), wherein
the CDR1 comprises a sequence selected from the group consisting of SEQ ID Nos. 89, 91, 92, 93, and 100, or a sequence comprising one or more amino acid substitutions in a sequence selected from the group consisting of SEQ ID Nos. 89, 91, 92, 93, and 100;
the CDR2 comprises a sequence selected from the group consisting of SEQ ID Nos. 149, 150, 151, 152, 153, 154, 393, and 394, or a sequence comprising one or more amino acid substitutions in a sequence selected from the group consisting of SEQ ID Nos. 149, 150, 151, 152, 153, 154, 393, and 394;
the CDR3 comprises a sequence selected from the group consisting of SEQ ID Nos. 173, 186, and 195, or a sequence comprising one or more amino acid substitutions in a sequence selected from the group consisting of SEQ ID Nos. 173, 186, and 195.

In some embodiments, the FLT3 binding domain comprises at least one of the following set of sequences (the CDR1, the CDR2, and the CDR3):
SEQ ID Nos. 91, 149, and 195;
SEQ ID Nos. 91, 150, and 195;
SEQ ID Nos. 100, 151, and 186;
SEQ ID Nos. 92, 152, and 195;
SEQ ID Nos. 93, 153, and 195;

SEQ ID Nos. 91, 154, and 195;
SEQ ID Nos. 89, 393, and 173; and
SEQ ID Nos. 89, 394, and 173.

In some embodiments, the FLT3 binding domain comprises a sequence that is at least about 70% identical to a sequence selected from the group consisting of SEQ ID Nos. 71-76, and 389-390.

In some embodiments, the FLT3 binding domain is part of a multispecific antibody. In some embodiments, the multispecific antibody comprises (i) the FLT3 binding domain (anti-FLT3); (ii) a CD3 binding domain (anti-CD3); and (iii) an albumin binding domain (anti-ALB). In some embodiments, the CD3 comprises a human CD3. In some embodiments, the albumin comprises a serum albumin.

In some embodiments, the serum albumin is a human serum albumin. In some embodiments, the FLT3 binding domain (anti-FLT3), the CD3 binding domain (anti-CD3), and the albumin binding domain (anti-ALB) are in an at least one of the following formats, from N-terminus to C-terminus:
  anti-ALB: anti-FLT3: anti-CD3;
  anti-CD3: anti-FLT3: anti-ALB;
  anti-FLT3: anti-CD3: anti-ALB;
  anti-ALB: anti-CD3: anti-FLT3;
  anti-FLT3: anti-ALB: anti-CD3; and
  anti-CD3: anti-ALB: anti-FLT3.

In some embodiments, the anti-FLT3 domain is an sdAb. In some embodiments, anti-CD3 domain is an scFv. In some embodiments, the anti-ALB domain is an sdAb. In some embodiments, the anti-CD3 domain comprises an amino acid sequence that is at least about 90% identical to the sequence set forth in SEQ ID No. 373. In some embodiments, the anti-ALB domain comprises an amino acid sequence that is at least about 90% identical to the sequence set forth in SEQ ID No. 372. In some embodiments, the FLT3 binding domain binds to a human FLT3, a cynomolgus FLT3, or both.

One embodiment provides an FLT3 binding domain that binds to a human FLT3 and to a cynomolgus FLT3 with identical affinities or affinities that differ by up to about 58-fold. One embodiment provides an FLT3 targeting trispecific protein comprising
  (A) a first domain that binds a human CD3;
  (B) a second domain that binds a human serum albumin protein; and
  (C) a third domain that binds a human FLT3 or a cynomolgus FLT3,
wherein the domains are linked according to any one of the following orientations, from N-terminus to C-terminus: H$_2$N-(A)-(C)-(B)-COOH, H$_2$N-(B)-(A)-(C)-COOH, H$_2$N-(C)-(B)-(A)-COOH, H$_2$N-(C)-(A)-(B)-COOH, H$_2$N-(A)-(B)-(C)-COOH, or H$_2$N-(B)-(C)-(A)-COOH, or via linkers L1 and L2, from N-terminus to C-terminus: H$_2$N-(A)-L1-(C)-L2-(B)-COOH, H$_2$N-(B)-L1-(A)-L2-(C)-COOH, H$_2$N-(C)-L1-(B)-L2-(A)-COOH, H$_2$N-(C)-L1-(A)-L2-(B)-COOH, H$_2$N-(A)-L1-(B)-L2-(C)-COOH, or H$_2$N-(B)-L1-(C)-L2-(A)-COOH.

In some embodiments, the first domain is an scFv that comprises a heavy chain comprising HC CDR1, HC CDR2, HC CDR3, and a light chain comprising LC CDR1, LC CDR2, or LC CDR3, wherein the HC CDR1 comprises the amino acid sequence of SEQ ID NO: 397 or an amino acid sequence comprising one or more substitutions in the sequence of SEQ ID NO: 397; the HC CDR2 comprises the amino acid sequence of SEQ ID NO: 398 or an amino acid sequence comprising one or more substitutions in the sequence of SEQ ID NO: 398; the HC CDR3 comprises the amino acid sequence of SEQ ID NO: 399 or an amino acid sequence comprising one or more substitutions in the sequence of SEQ ID NO: 399; the LC CDR1 comprises the amino acid sequence of SEQ ID NO: 400 or an amino acid sequence comprising one or more substitutions in the sequence of SEQ ID NO: 400; the LC CDR2 comprises the amino acid sequence of SEQ ID NO: 401 or an amino acid sequence comprising one or more substitutions in the sequence of SEQ ID NO: 401; and the LC CDR3 comprises the amino acid sequence of SEQ ID NO: 402 or an amino acid sequence comprising one or more substitutions in the sequence of SEQ ID NO: 402. In some embodiments, the first domain is an scFv that comprises an amino acid sequence that is at least about 90% identical to the sequence set forth in SEQ ID No. 373. In some embodiments, the second domain is an sdAb that comprises a CDR1, a CDR2, and a CDR3, wherein the CDR1 comprises the amino acid sequence of SEQ ID NO: 403 or an amino acid sequence comprising one or more substitutions in the sequence of SEQ ID NO: 403; the CDR2 comprises the amino acid sequence of SEQ ID NO: 404 or an amino acid sequence comprising one or more substitutions in the sequence of SEQ ID NO: 404; and the CDR3 comprises the amino acid sequence of SEQ ID NO: 405 or an amino acid sequence comprising one or more substitutions in the sequence of SEQ ID NO: 405.

In some embodiments, the second domain is an sdAb that comprises an amino acid sequence that is at least about 90% identical to the sequence set forth in SEQ ID No. 372. In some embodiments, the third domain is an sdAb comprising at least three complementarity determining regions (a CDR1, a CDR2, and a CDR3), wherein
  the CDR1 comprises a sequence selected from the group consisting of SEQ ID Nos. 77-108, or a sequence comprising one or more amino acid substitutions in a sequence selected from the group consisting of SEQ ID Nos. 77-108;
  the CDR2 comprises a sequence selected from the group consisting of SEQ ID Nos. 109-154, and 393-394, or a sequence comprising one or more amino acid substitutions in a sequence selected from the group consisting of SEQ ID Nos. 109-154, and 393-394;
  the CDR3 comprises a sequence selected from the group consisting of SEQ ID Nos. 155-195, or a sequence comprising one or more amino acid substitutions in a sequence selected from the group consisting of SEQ ID Nos. 155-195.

In some embodiments, the third domain comprises at least one of the following set of sequences (the CDR1, the CDR2, and the CDR3):
  SEQ ID Nos. 77, 109, and 155;
  SEQ ID Nos. 78, 109, and 155;
  SEQ ID Nos. 79, 110, and 156;
  SEQ ID Nos. 80, 111, and 155;
  SEQ ID Nos. 81, 112, and 155;
  SEQ ID Nos. 77, 113, and 157;
  SEQ ID Nos. 82, 110, and 156;
  SEQ ID Nos. 77, 114, and 158;
  SEQ ID Nos. 80, 111, and 155;
  SEQ ID Nos. 83, 115, and 155;
  SEQ ID Nos. 84, 111, and 155;
  SEQ ID Nos. 79, 116, and 156;
  SEQ ID Nos. 85, 111, and 155;
  SEQ ID Nos. 86, 110, and 156;
  SEQ ID Nos. 87, 110, and 156;
  SEQ ID Nos. 88, 117, and 159;
  SEQ ID Nos. 88, 118, and 160;
  SEQ ID Nos. 88, 119, and 161;

SEQ ID Nos. 88, 120, and 162;
SEQ ID Nos. 88, 121, and 163;
SEQ ID Nos. 88, 122, and 164;
SEQ ID Nos. 88, 121, and 165;
SEQ ID Nos. 88, 121, and 166;
SEQ ID Nos. 88, 122, and 167;
SEQ ID Nos. 88, 122, and 168;
SEQ ID Nos. 88, 121, and 169;
SEQ ID Nos. 88, 118, and 165;
SEQ ID Nos. 88, 123, and 170;
SEQ ID Nos. 88, 124, and 171;
SEQ ID Nos. 88, 117, and 172;
SEQ ID Nos. 89, 125, and 173;
SEQ ID Nos. 90, 126, and 174;
SEQ ID Nos. 90, 127, and 175;
SEQ ID Nos. 90, 125, and 176;
SEQ ID Nos. 90, 128, and 175;
SEQ ID Nos. 90, 128, and 177;
SEQ ID Nos. 91, 129, and 178;
SEQ ID Nos. 91, 130, and 178;
SEQ ID Nos. 92, 131, and 178;
SEQ ID Nos. 93, 132, and 178;
SEQ ID Nos. 94, 133, and 179;
SEQ ID Nos. 91, 134, and 178;
SEQ ID Nos. 95, 135, and 180;
SEQ ID Nos. 96, 136, and 181;
SEQ ID Nos. 97, 137, and 182;
SEQ ID Nos. 97, 138, and 183;
SEQ ID Nos. 98, 139, and 184;
SEQ ID Nos. 99, 139, and 185;
SEQ ID Nos. 100, 140, and 186;
SEQ ID Nos. 101, 141, and 187;
SEQ ID Nos. 102, 142, and 188;
SEQ ID Nos. 103, 143, and 189;
SEQ ID Nos. 104, 144, and 190;
SEQ ID Nos. 105, 145, and 191;
SEQ ID Nos. 106, 146, and 192;
SEQ ID Nos. 107, 147, and 193;
SEQ ID Nos. 108, 148, and 194;
SEQ ID Nos. 91, 149, and 195;
SEQ ID Nos. 91, 150, and 195;
SEQ ID Nos. 100, 151, and 186;
SEQ ID Nos. 92, 152, and 195;
SEQ ID Nos. 93, 153, and 195;
SEQ ID Nos. 91, 154, and 195;
SEQ ID Nos. 89, 393, and 173; and
SEQ ID Nos. 89, 394, and 173.

In some embodiments, the FLT3 targeting trispecific protein comprises a sequence selected from the group consisting of SEQ ID Nos. 196-272, and 391-392, or a sequence that is at least about 80% identical to a sequence selected from the group consisting of SEQ ID NOs: 196-272, and 391-392.

One embodiment provides an FLT3 targeting conditionally active binding protein comprising a binding moiety which comprises a non-CDR loop, a cleavable linker, an FLT3 binding domain, and a CD3 binding domain, wherein the non-CDR loop is capable of binding to the FLT3 binding domain, and wherein the binding moiety is capable of masking the binding of the FLT3 binding domain to its target. In some embodiments, the CD3 binding domain is an scFv that comprises a heavy chain comprising HC CDR1, HC CDR2, HC CDR3, and a light chain comprising LC CDR1, LC CDR2, or LC CDR3, wherein the HC CDR1 comprises the amino acid sequence of SEQ ID NO: 397 or an amino acid sequence comprising one or more substitutions in the sequence of SEQ ID NO: 397; the HC CDR2 comprises the amino acid sequence of SEQ ID NO: 398 or an amino acid sequence comprising one or more substitutions in the sequence of SEQ ID NO: 398; the HC CDR3 comprises the amino acid sequence of SEQ ID NO: 399 or an amino acid sequence comprising one or more substitutions in the sequence of SEQ ID NO: 399; the LC CDR1 comprises the amino acid sequence of SEQ ID NO: 400 or an amino acid sequence comprising one or more substitutions in the sequence of SEQ ID NO: 400; the LC CDR2 comprises the amino acid sequence of SEQ ID NO: 401 or an amino acid sequence comprising one or more substitutions in the sequence of SEQ ID NO: 401; and the LC CDR3 comprises the amino acid sequence of SEQ ID NO: 402 or an amino acid sequence comprising one or more substitutions in the sequence of SEQ ID NO: 402.

In some embodiments, the CD3 binding domain is an scFv that comprises an amino acid sequence that is at least about 90% identical to the sequence set forth in SEQ ID No. 373. In some embodiments, the FLT3 binding domain is an sdAb comprising at least three complementarity determining regions (a CDR1, a CDR2, and a CDR3), wherein
  the CDR1 comprises a sequence selected from the group consisting of SEQ ID Nos. 77-108, or a sequence comprising one or more amino acid substitutions in a sequence selected from the group consisting of SEQ ID Nos. 77-108;
  the CDR2 comprises a sequence selected from the group consisting of SEQ ID Nos. 109-154, and 393-394, or a sequence comprising one or more amino acid substitutions in a sequence selected from the group consisting of SEQ ID Nos. 109-154, and 393-394;
  the CDR3 comprises a sequence selected from the group consisting of SEQ ID Nos. 155-195, or a sequence comprising one or more amino acid substitutions in a sequence selected from the group consisting of SEQ ID Nos. 155-195.

In some embodiments, the FLT3 binding domain comprises at least one of the following set of sequences (the CDR1, the CDR2, and the CDR3):
SEQ ID Nos. 77, 109, and 155;
SEQ ID Nos. 78, 109, and 155;
SEQ ID Nos. 79, 110, and 156;
SEQ ID Nos. 80, 111, and 155;
SEQ ID Nos. 81, 112, and 155;
SEQ ID Nos. 77, 113, and 157;
SEQ ID Nos. 82, 110, and 156;
SEQ ID Nos. 77, 114, and 158;
SEQ ID Nos. 80, 111, and 155;
SEQ ID Nos. 83, 115, and 155;
SEQ ID Nos. 84, 111, and 155;
SEQ ID Nos. 79, 116, and 156;
SEQ ID Nos. 85, 111, and 155;
SEQ ID Nos. 86, 110, and 156;
SEQ ID Nos. 87, 110, and 156;
SEQ ID Nos. 88, 117, and 159;
SEQ ID Nos. 88, 118, and 160;
SEQ ID Nos. 88, 119, and 161;
SEQ ID Nos. 88, 120, and 162;
SEQ ID Nos. 88, 121, and 163;
SEQ ID Nos. 88, 122, and 164;
SEQ ID Nos. 88, 121, and 165;
SEQ ID Nos. 88, 121, and 166;
SEQ ID Nos. 88, 122, and 167;
SEQ ID Nos. 88, 122, and 168;
SEQ ID Nos. 88, 121, and 169;
SEQ ID Nos. 88, 118, and 165;
SEQ ID Nos. 88, 123, and 170;

SEQ ID Nos. 88, 124, and 171;
SEQ ID Nos. 88, 117, and 172;
SEQ ID Nos. 89, 125, and 173;
SEQ ID Nos. 90, 126, and 174;
SEQ ID Nos. 90, 127, and 175;
SEQ ID Nos. 90, 125, and 176;
SEQ ID Nos. 90, 128, and 175;
SEQ ID Nos. 90, 128, and 177;
SEQ ID Nos. 91, 129, and 178;
SEQ ID Nos. 91, 130, and 178;
SEQ ID Nos. 92, 131, and 178;
SEQ ID Nos. 93, 132, and 178;
SEQ ID Nos. 94, 133, and 179;
SEQ ID Nos. 91, 134, and 178;
SEQ ID Nos. 95, 135, and 180;
SEQ ID Nos. 96, 136, and 181;
SEQ ID Nos. 97, 137, and 182;
SEQ ID Nos. 97, 138, and 183;
SEQ ID Nos. 98, 139, and 184;
SEQ ID Nos. 99, 139, and 185;
SEQ ID Nos. 100, 140, and 186;
SEQ ID Nos. 101, 141, and 187;
SEQ ID Nos. 102, 142, and 188;
SEQ ID Nos. 103, 143, and 189;
SEQ ID Nos. 104, 144, and 190;
SEQ ID Nos. 105, 145, and 191;
SEQ ID Nos. 106, 146, and 192;
SEQ ID Nos. 107, 147, and 193;
SEQ ID Nos. 108, 148, and 194;
SEQ ID Nos. 91, 149, and 195;
SEQ ID Nos. 91, 150, and 195;
SEQ ID Nos. 100, 151, and 186;
SEQ ID Nos. 92, 152, and 195;
SEQ ID Nos. 93, 153, and 195;
SEQ ID Nos. 91, 154, and 195;
SEQ ID Nos. 89, 393, and 173; and
SEQ ID Nos. 89, 394, and 173.

One embodiment provides a pharmaceutical composition comprising an FLT3 binding domain according to this disclosure, and a pharmaceutically acceptable carrier. One embodiment provides a pharmaceutical composition comprising an FLT3 targeting trispecific protein according to this disclosure, and a pharmaceutically acceptable carrier. One embodiment provides a pharmaceutical composition comprising an FLT3 targeting conditionally active binding protein according to this disclosure, and a pharmaceutically acceptable carrier. One embodiment provides a process for the production of an FLT3 binding domain according to any this disclosure, said process comprising culturing a host transformed or transfected with a vector comprising a nucleic acid sequence encoding the FLT3 binding domain according to this disclosure under conditions allowing the expression of the FLT3 binding domain and recovering and purifying the produced protein from the culture. One embodiment provides a process for the production of an FLT3 targeting trispecific protein according to this disclosure, said process comprising culturing a host transformed or transfected with a vector comprising a nucleic acid sequence encoding the FLT3 targeting trispecific protein according to this disclosure under conditions allowing the expression of the FLT3 targeting trispecific protein and recovering and purifying the produced protein from the culture.

One embodiment provides a process for the production of an FLT3 targeting conditionally active binding protein according to this disclosure, said process comprising culturing a host transformed or transfected with a vector comprising a nucleic acid sequence encoding the FLT3 targeting conditionally active binding protein according to this disclosure under conditions allowing the expression of the FLT3 targeting conditionally active binding protein and recovering and purifying the produced protein from the culture. One embodiment provides a method for the treatment or amelioration of a proliferative disease, or a tumorous disease, comprising the administration of an FLT3 binding domain according to this disclosure, or a pharmaceutical composition according to this disclosure, to a subject in need thereof. One embodiment provides a method for the treatment or amelioration of a proliferative disease, or a tumorous disease, comprising the administration of an FLT3 targeting trispecific protein according to this disclosure, or a pharmaceutical composition according to this disclosure, to a subject in need thereof. One embodiment provides a method for the treatment or amelioration of a proliferative disease, or a tumorous disease, comprising the administration of an FLT3 targeting conditionally active binding protein according to this disclosure, or a pharmaceutical composition according to claim this disclosure, to a subject in need thereof.

In some embodiments, the subject is human. In some embodiments, the method further comprises administration of an agent in combination with an FLT3 binding domain according to this disclosure, an FLT3 targeting trispecific protein according to this disclosure, an FLT3 targeting conditionally active binding protein according to this disclosure, or a pharmaceutical composition according to this disclosure. In some embodiments, the tumorous disease comprises a hematologic malignancy. In some embodiments, the hematologic malignancy comprises an acute myeloid leukemia (AML), myelodysplastic syndrome, or chronic myelomonocytic leukemia. In some embodiments, the tumorous disease is selected from the group consisting of: acute leukemia (ALL), acute myelogenous leukemia (AML), myeloid leukemia, chronic lymphocytic leukemia (CLL), and chronic myelogenous leukemia (CML), chronic myelomonocytic leukemia, undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, marginal zone lymphoma, nodal marginal zone B cell lymphoma, splenic marginal zone lymphoma, follicular lymphoma, diffuse histiocytic lymphoma (DHL), mucosa-associated lymphatic tissue lymphoma, small cell lymphocytic lymphoma, immunoblastic large cell lymphoma, precursor B-lymphoblastic lymphoma, cutaneous T-cell lymphoma (CTLC) (also called mycosis fungoides or Sezary syndrome), intravascular large B-cell lymphoma, lymphomatoid granulomatosis, T cell/histiocyte-rich large B-cell lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphomalymphoplasmactyic lymphoma, and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations thereof.

One embodiment provides an FLT3 binding domain comprising at least three complementarity determining regions (a CDR1, a CDR2, and a CDR3), wherein
the CDR1 comprises a sequence selected from the group consisting of SEQ ID Nos. 89, 91, and 100, or a sequence comprising one or more amino acid substitutions in a sequence selected from the group consisting of SEQ ID Nos. 89, 91, and 100;
the CDR2 comprises a sequence selected from the group consisting of SEQ ID Nos. 149, 151, 393, and 394, or a sequence comprising one or more amino acid substitutions in a sequence selected from the group consisting of SEQ ID Nos. 149, 151, 393, and 394;
the CDR3 comprises a sequence selected from the group consisting of SEQ ID Nos. 173, 186, and 195, or a sequence comprising one or more amino acid substitutions in a sequence selected from the group consisting of SEQ ID Nos. 173, 186, and 195.
In some embodiments, the FLT3 binding domain comprises at least one of the following set of sequences (the CDR1, the CDR2, and the CDR3):
SEQ ID Nos. 89, 393, and 173;
SEQ ID Nos. 89, 394, and 173;
SEQ ID Nos. 100, 151, and 186; and
SEQ ID Nos. 91, 149, and 195.
In some embodiments, the FLT3 binding domain comprises an amino acid sequence that is at least 80% identical to a sequence selected from the group consisting of SEQ ID Nos. 71, 73, 389, and 390. In some embodiments, the FLT3 binding domain comprises an amino acid sequence selected from the group consisting of SEQ ID Nos. 71, 73, 389, and 390. In some embodiments, the FLT3 binding domain is a single domain antibody (sdAb). In some embodiments, the FLT3 binding domain is part of an antibody or an antigen binding fragment thereof. In some embodiments, the FLT3 binding domain comprises is part of the antibody or an antigen binding fragment thereof and wherein the antibody or an antigen binding fragment thereof comprises a bispecific antibody. In some embodiments, the bispecific antibody comprises (i) the FLT3 binding domain (anti-FLT3) and (ii) a CD3 binding domain (anti-CD3). In some embodiments, the anti-CD3 domain is a single chain variable fragment (scFv). In some embodiments, the CD3 comprises a human CD3.

In some embodiments, the FLT3 binding domain is part of the antibody or an antigen binding fragment thereof and wherein the antibody or an antigen binding fragment thereof comprises a multispecific antibody. In some embodiments, the multispecific antibody comprises (i) the FLT3 binding domain (anti-FLT3); (ii) a CD3 binding domain (anti-CD3); and (iii) an albumin binding domain (anti-ALB). In some embodiments, the anti-CD3 domain is an scFv. In some embodiments, the anti-CD3 domain comprises an amino acid sequence that is at least 90% identical to the sequence of SEQ ID No. 373. In some embodiments, the CD3 comprises a human CD3. In some embodiments, the anti-ALB domain is an sdAb. In some embodiments, the anti-ALB domain comprises an amino acid sequence that is at least 90% identical to the sequence of SEQ ID No. 372.

In some embodiments, the albumin comprises a human serum albumin. In some embodiments, the FLT3 binding domain (anti-FLT3), the CD3 binding domain (anti-CD3), and the albumin binding domain (anti-ALB) are in an at least one of the following formats, from N-terminus to C-terminus:
anti-ALB: anti-FLT3: anti-CD3;
anti-CD3: anti-FLT3: anti-ALB;
anti-FLT3: anti-CD3: anti-ALB;
anti-ALB: anti-CD3: anti-FLT3;
anti-FLT3: anti-ALB: anti-CD3; and
anti-CD3: anti-ALB: anti-FLT3.
In some embodiments, the FLT3 binding domain is part of the multispecific antibody, wherein the multispecific antibody comprises a sequence that is at least 80% identical to a sequence selected from the group consisting of SEQ ID Nos. 267, 269, 391, and 392. In some embodiments, the FLT3 binding domain binds to human FLT3.

One embodiment provides an FLT3 targeting trispecific protein comprising
(A) a first domain that binds a human CD3;
(B) a second domain that binds a human serum albumin protein; and
(C) a third domain that binds a human FLT3,
wherein the CDR1 comprises a sequence selected from the group consisting of SEQ ID Nos. 89, 91, and 100, or a sequence comprising one or more amino acid substitutions in a sequence selected from the group consisting of SEQ ID Nos. 89, 91, and 100; the CDR2 comprises a sequence selected from the group consisting of SEQ ID Nos. 149, 151, 393, and 394, or a sequence comprising one or more amino acid substitutions in a sequence selected from the group consisting of SEQ ID Nos. 149, 151, 393, and 394; and the CDR3 comprises a sequence selected from the group consisting of SEQ ID Nos. 173, 186, and 195, or a sequence comprising one or more amino acid substitutions in a sequence selected from the group consisting of SEQ ID Nos. 173, 186, and 195.

In some embodiments, the first domain is an scFv that comprises a heavy chain comprising HC CDR1, HC CDR2, HC CDR3, and a light chain comprising LC CDR1, LC CDR2, or LC CDR3, wherein the HC CDR1 comprises the amino acid sequence of SEQ ID NO: 397 or an amino acid sequence comprising one or more substitutions in the sequence of SEQ ID NO: 397; the HC CDR2 comprises the amino acid sequence of SEQ ID NO: 398 or an amino acid sequence comprising one or more substitutions in the sequence of SEQ ID NO: 398; the HC CDR3 comprises the amino acid sequence of SEQ ID NO: 399 or an amino acid sequence comprising one or more substitutions in the sequence of SEQ ID NO: 399; the LC CDR1 comprises the amino acid sequence of SEQ ID NO: 400 or an amino acid sequence comprising one or more substitutions in the sequence of SEQ ID NO: 400; the LC CDR2 comprises the amino acid sequence of SEQ ID NO: 401 or an amino acid sequence comprising one or more substitutions in the sequence of SEQ ID NO: 401; and the LC CDR3 comprises the amino acid sequence of SEQ ID NO: 402 or an amino acid sequence comprising one or more substitutions in the sequence of SEQ ID NO: 402. In some embodiments, the first domain is an scFv that comprises an amino acid sequence that is at least 90% identical to the sequence set forth in SEQ ID No. 373. In some embodiments, the FLT3 targeting trispecific protein of claim 22, wherein the second domain is an sdAb that comprises a CDR1, a CDR2, and a CDR3, wherein the CDR1 comprises the amino acid sequence of SEQ ID NO: 403 or an amino acid sequence comprising one or more substitutions in the sequence of SEQ ID NO: 403; the CDR2 comprises the amino acid sequence of SEQ ID NO: 404 or an amino acid sequence comprising one or more substitutions in the sequence of SEQ ID NO: 404; and the CDR3 comprises the amino acid sequence of SEQ ID NO: 405 or an amino acid sequence comprising one or more substitutions in the sequence of SEQ ID NO: 405. In some embodiments, the FLT3 targeting trispecific protein of claim 25, wherein the second domain is an sdAb that comprises an amino acid sequence that is at least 90% identical to the sequence set forth in SEQ ID No. 372.

One embodiment provides a method of treating a hematologic malignancy, the method comprising administering to a subject in need thereof a FLT3 targeting trispecific protein comprising
(A) a first domain that binds a human CD3;
(B) a second domain that binds a human serum albumin protein; and
(C) a third domain that binds a human FLT3,
wherein the CDR1 comprises a sequence selected from the group consisting of SEQ ID Nos. 89, 91, and 100, or a sequence comprising one or more amino acid substitutions in a sequence selected from the group consisting of SEQ ID Nos. 89, 91, and 100; the CDR2 comprises a sequence selected from the group consisting of SEQ ID Nos. 149, 151, 393, and 394, or a sequence comprising one or more amino acid substitutions in a sequence selected from the group consisting of SEQ ID Nos. 149, 151, 393, and 394; the CDR3 comprises a sequence selected from the group consisting of SEQ ID Nos. 173, 186, and 195, or a sequence comprising one or more amino acid substitutions in a sequence selected from the group consisting of SEQ ID Nos. 173, 186, and 195. In some embodiments, the third domain comprises an amino acid sequence that is at least 80% identical to a sequence selected from the group consisting of SEQ ID Nos. 71, 73, 389, and 390. In some embodiments, the trispecific protein comprises an amino acid sequence that is at least 80% identical to a sequence selected from the group consisting of SEQ ID Nos. 267, 269, 391, and 392. In some embodiments, the hematologic malignancy comprises an acute myeloid leukemia (AML), a myelodysplastic syndrome, or a chronic myelomonocytic leukemia.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Certain Definitions

Figure 1:
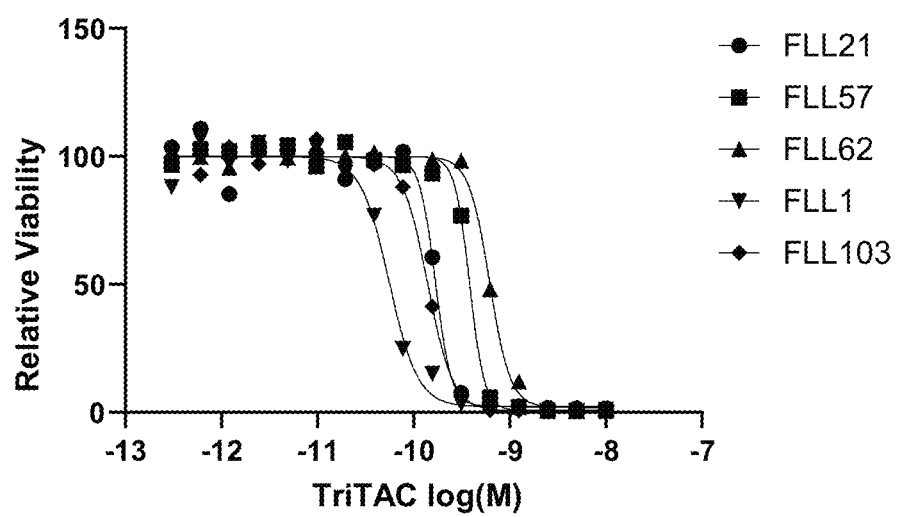
FIG. 1 illustrates the results of a TDCC Assay with MV-4-11 Cells and Anti-CD3/Anti-FLT3 Multispecific Proteins Containing Llama Anti-FLT3 Sequences FLL21, FLL57, FLL62, FLL1, and FLL103, ran in the presence of 15 mg/ml bovine serum albumin (BSA). The y-axis shows the normalized percentage of viability of the cancer cells.
Figure 2:
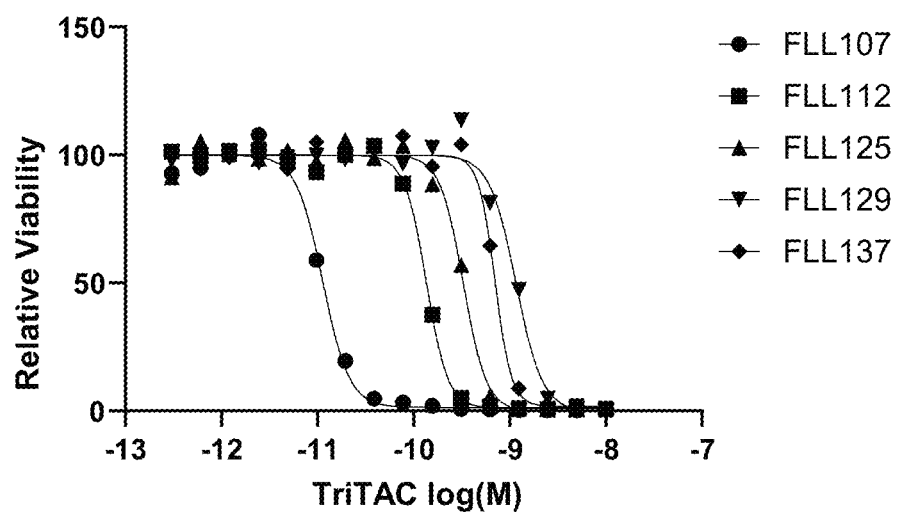
FIG. 2 illustrates the results of a TDCC Assay with MV-4-11 Cells and Anti-CD3/Anti-FLT3 Multispecific Proteins Containing Llama Anti-FLT3 Sequences FLL107, FLL112, FLL125, FLL129, and FLL137, ran in the presence of 15 mg/ml BSA. The y-axis shows the normalized percentage of viability of the cancer cells.
Figure 3:
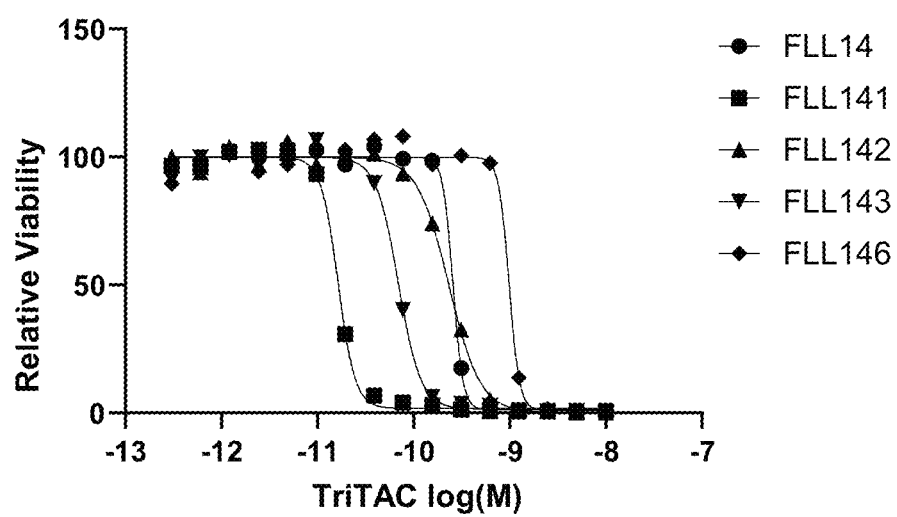
FIG. 3 illustrates the results of a TDCC Assay with MV-4-11 Cells and Anti-CD3/Anti-FLT3 Multispecific Proteins Containing Llama Anti-FLT3 Sequences FLL14, FLL141, FLL142, FLL143, and FLL146, ran in the presence of 15 mg/ml BSA. The y-axis shows the normalized percentage of viability of the cancer cells.
Figure 4:
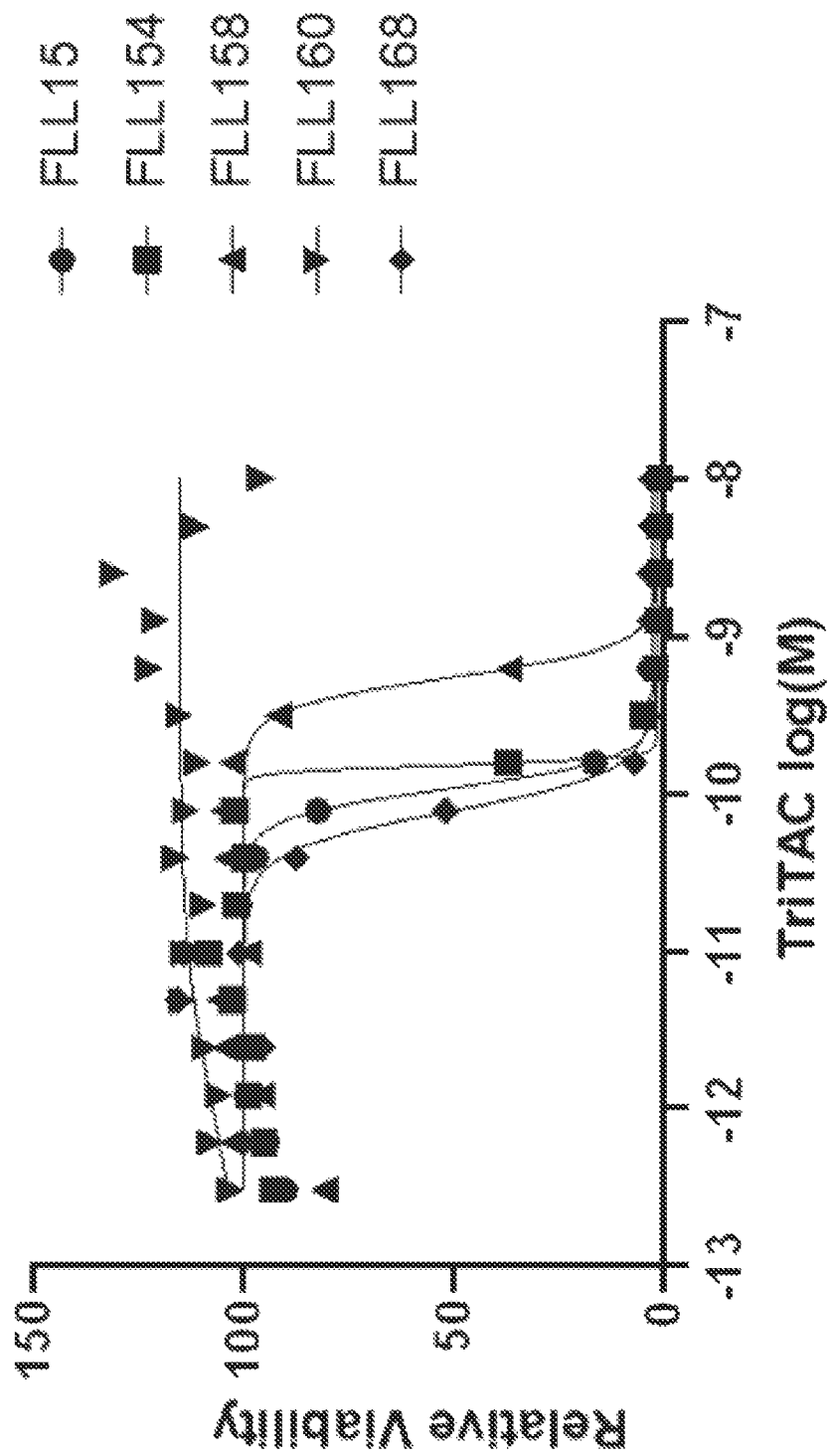
FIG. 4 illustrates the results of a TDCC Assay with MV-4-11 Cells and Anti-CD3/Anti-FLT3 Multispecific Proteins Containing Llama Anti-FLT3 Sequences FLL15, FLL154, FLL158, FLL160, and FLL168, ran in the presence of 15 mg/ml BSA. The y-axis shows the normalized percentage of viability of the cancer cells.
Figure 5:
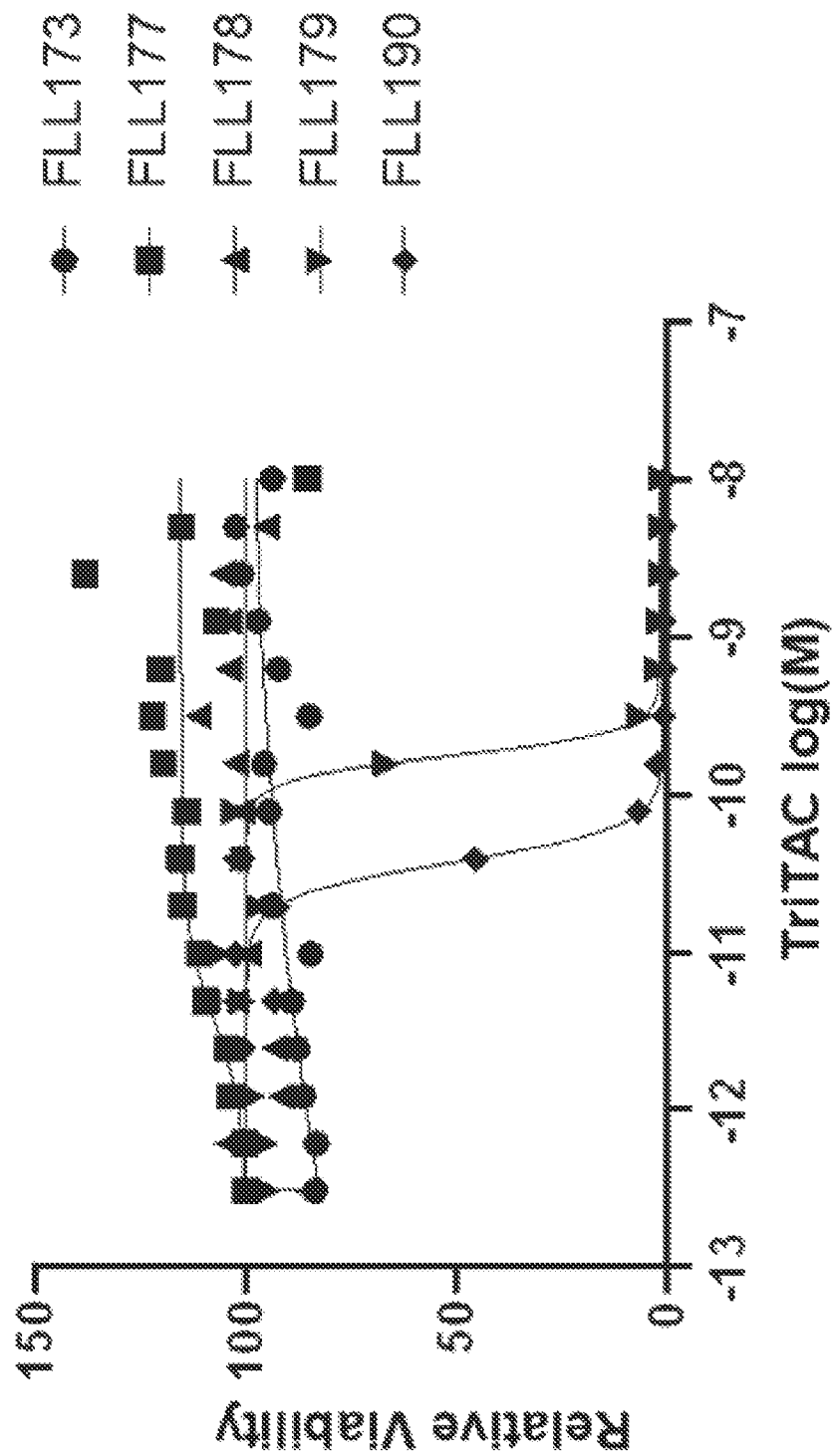
FIG. 5 illustrates the results of a TDCC Assay with MV-4-11 Cells and Anti-CD3/Anti-FLT3 Multispecific Proteins Containing Llama Anti-FLT3 Sequences FLL173, FLL177, FLL178, FLL179, and FLL190, ran in the presence of 15 mg/ml BSA. The y-axis shows the normalized percentage of viability of the cancer cells.
Figure 6:
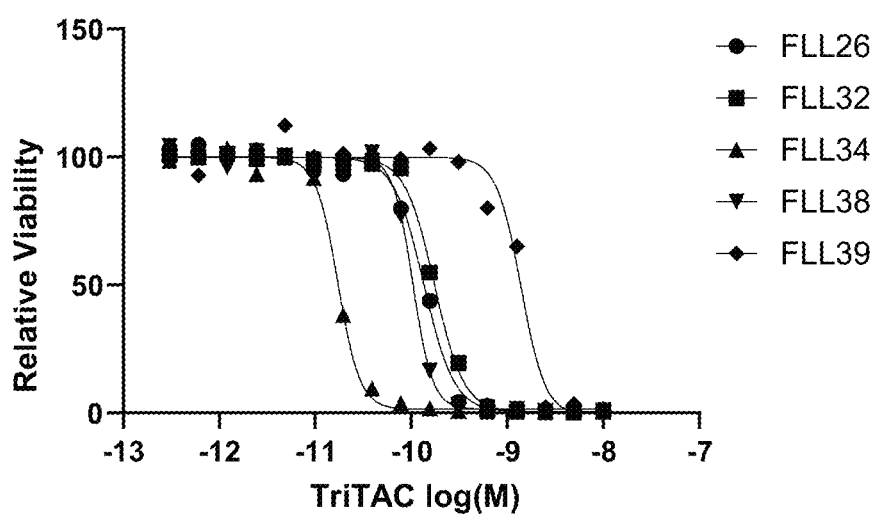
FIG. 6 illustrates the results of a TDCC Assay with MV-4-11 Cells and Anti-CD3/Anti-FLT3 Multispecific Proteins Containing Llama Anti-FLT3 Sequences FLL26, FLL32, FLL34, FLL38, and FLL39, ran in the presence of 15 mg/ml BSA. The y-axis shows the normalized percentage of viability of the cancer cells.
Figure 7:
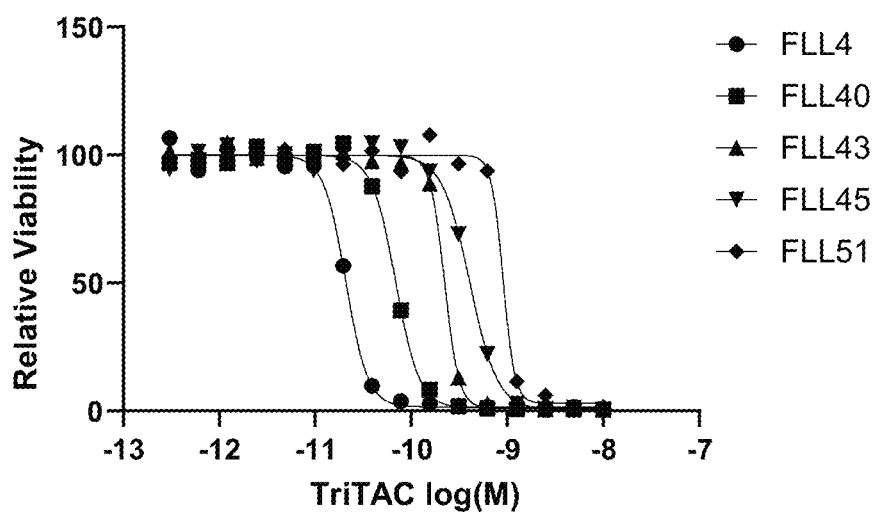
FIG. 7 illustrates the results of a TDCC Assay with MV-4-11 Cells and Anti-CD3/Anti-FLT3 Multispecific Proteins Containing Llama Anti-FLT3 Sequences FLL4, FLL40, FLL43, FLL45, and FLL51, ran in the presence of 15 mg/ml BSA. The y-axis shows the normalized percentage of viability of the cancer cells.
Figure 8:
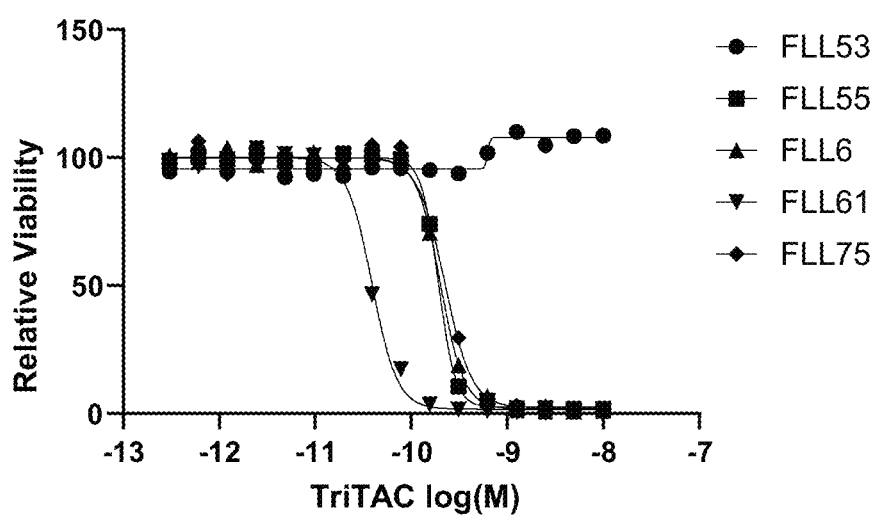
FIG. 8 illustrates the results of a TDCC Assay with MV-4-11 Cells and Anti-CD3/Anti-FLT3 Multispecific Proteins Containing Llama Anti-FLT3 Sequences FLL53, FLL55, FLL6, FLL61, and FLL75, ran in the presence of 15 mg/ml BSA. The y-axis shows the normalized percentage of viability of the cancer cells.
Figure 9:
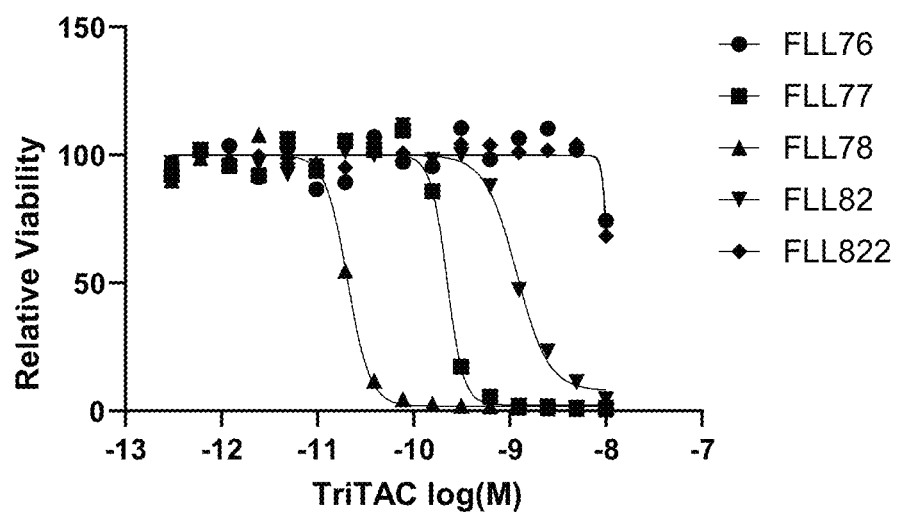
FIG. 9 illustrates the results of a TDCC Assay with MV-4-11 Cells and Anti-CD3/Anti-FLT3 Multispecific Proteins Containing Llama Anti-FLT3 Sequences FLL76, FLL77, FLL78, FLL82, and FLL822, ran in the presence of 15 mg/ml BSA. The y-axis shows the normalized percentage of viability of the cancer cells.
Figure 10:
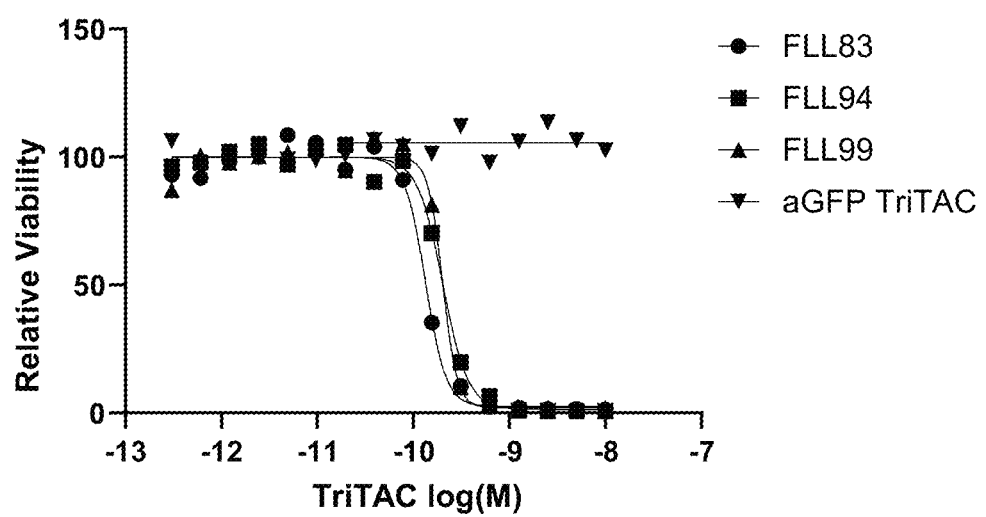
FIG. 10 illustrates the results of a TDCC Assay with MV-4-11 Cells and Anti-CD3/Anti-FLT3 Multispecific Proteins Containing Llama Anti-FLT3 Sequences FLL83, FLL94, and FLL99 and with a negative control molecule targeting GFP, ran in the presence of 15 mg/ml BSA. The y-axis shows the normalized percentage of viability of the cancer cells.
Figure 11:
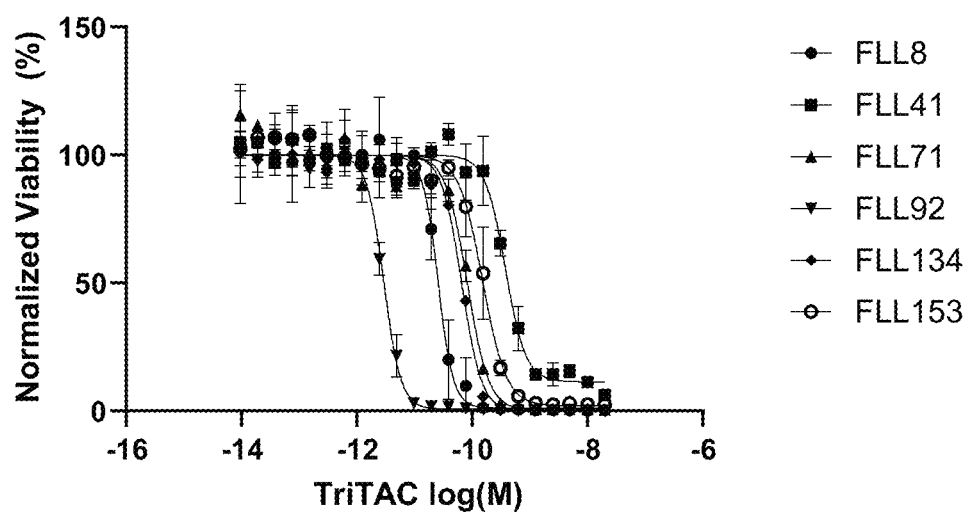
FIG. 11 illustrates the results of a TDCC Assay with MV-4-11 Cells and Anti-CD3/Anti-FLT3 Multispecific Proteins Containing Llama Anti-FLT3 Sequences FLL8, FLL41, FLL71, FLL92, FLL134, and FLL153, ran in the presence of 15 mg/ml BSA. The y-axis shows the normalized percentage of viability of the cancer cells.
Figure 12:
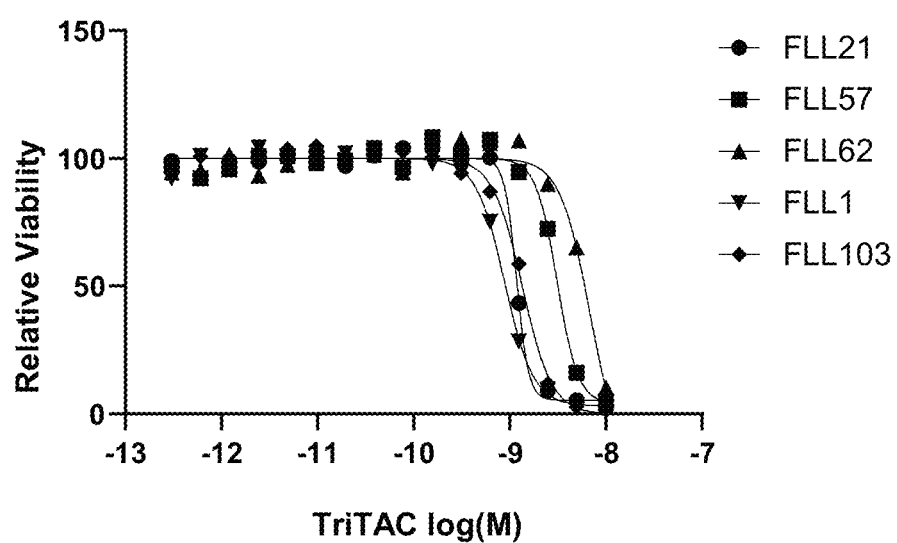
FIG. 12 illustrates the results of a TDCC Assay with MV-4-11 Cells and Anti-CD3/Anti-FLT3 Multispecific Proteins Containing Llama Anti-FLT3 Sequences FLL21, FLL57, FLL62, FLL1, and FLL103, rain in the presence of 15 mg/ml HSA. The y-axis shows the normalized percentage of viability of the cancer cells.
Figure 13:
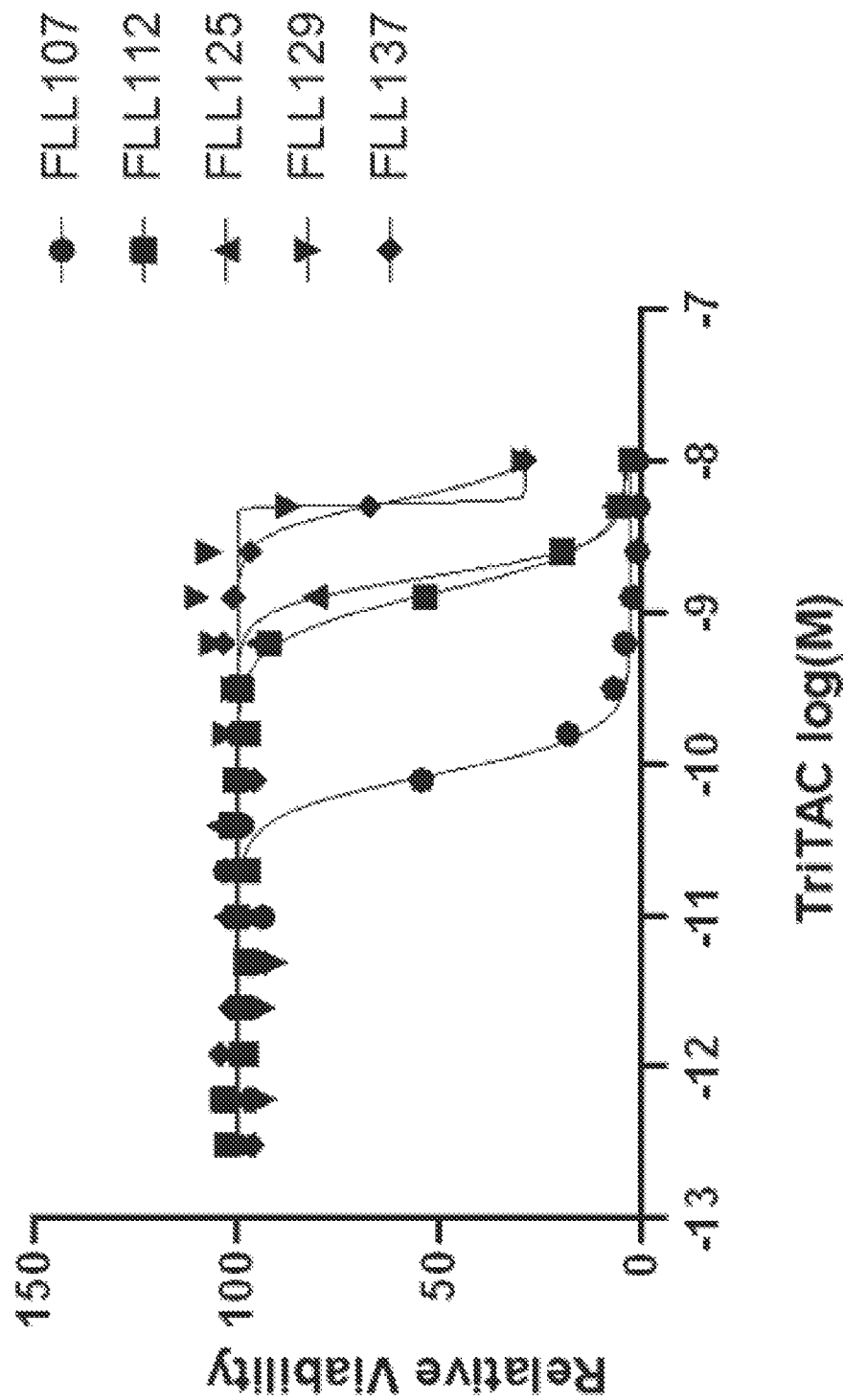
FIG. 13 illustrates the results of a TDCC Assay with MV-4-11 Cells and Anti-CD3/Anti-FLT3 Multispecific Proteins Containing Llama Anti-FLT3 Sequences FLL107, FLL112, FLL125, FLL129, and FLL137, ran in the presence of 15 mg/ml HSA. The y-axis shows the normalized percentage of viability of the cancer cells.
Figure 14:
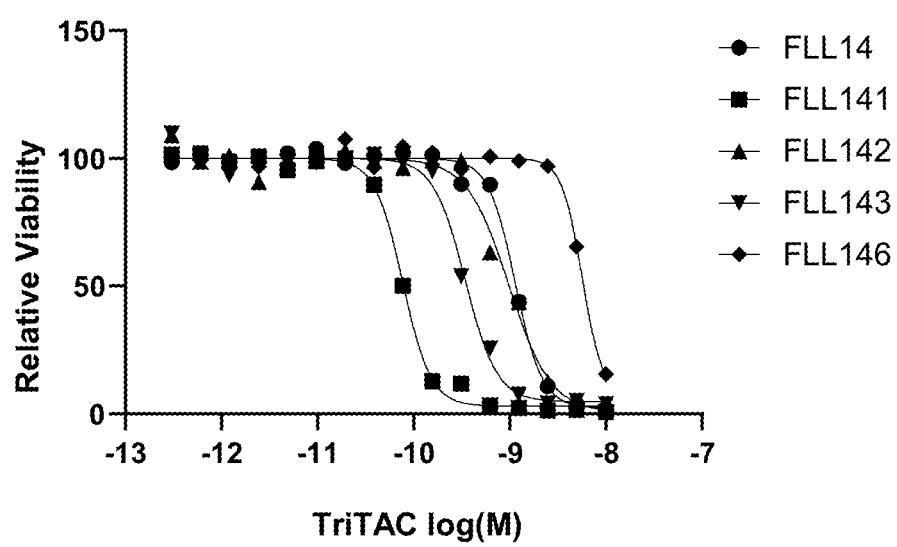
FIG. 14 illustrates the results of a TDCC Assay with MV-4-11 Cells and Anti-CD3/Anti-FLT3 Multispecific Proteins Containing Llama Anti-FLT3 Sequences FLL14, FLL141, FLL142, FLL143, and FLL146, ran in the presence of 15 mg/ml HSA. The y-axis shows the normalized percentage of viability of the cancer cells.
Figure 15:
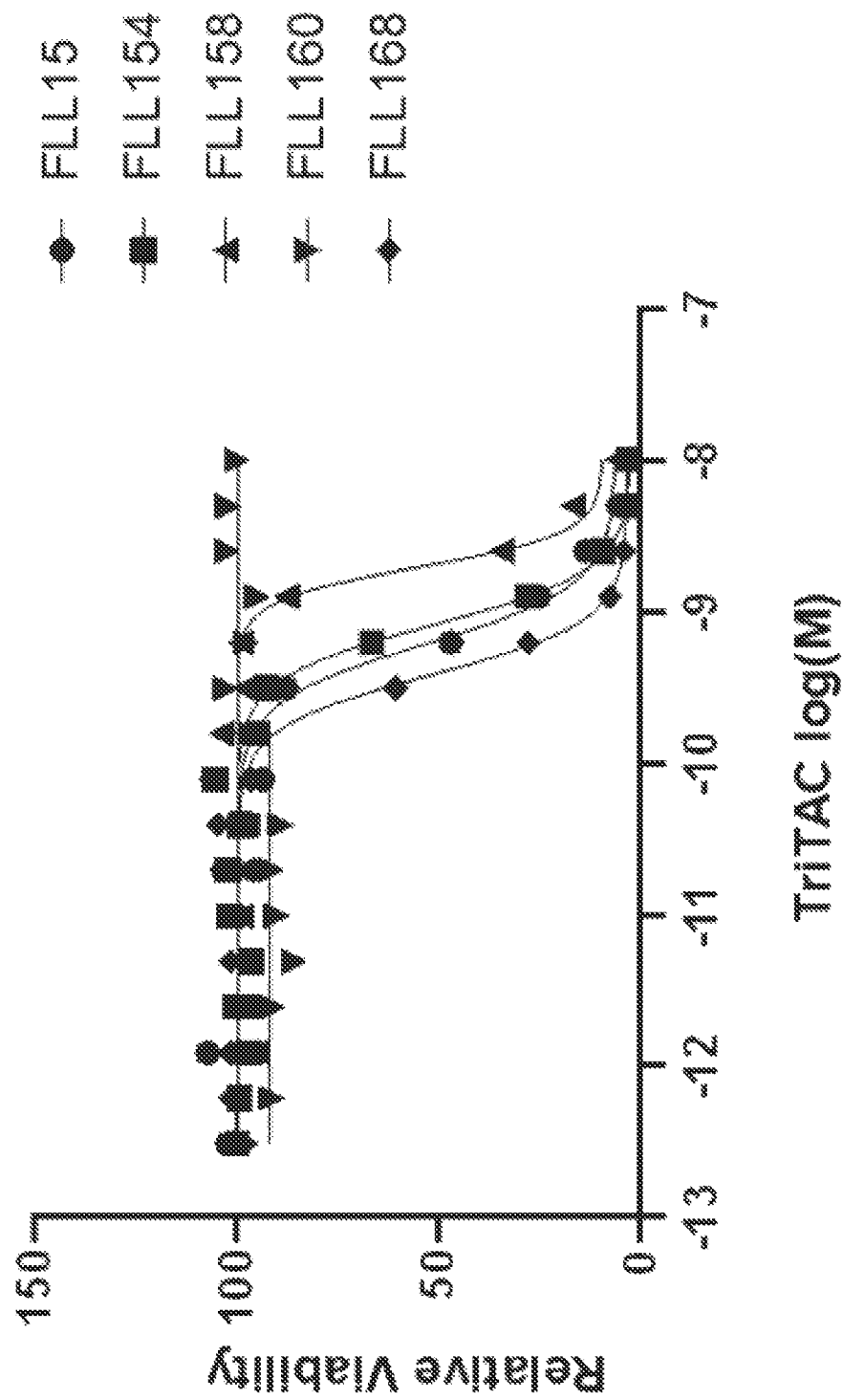
FIG. 15 illustrates the results of a TDCC Assay with MV-4-11 Cells and Anti-CD3/Anti-FLT3 Multispecific Proteins Containing Llama Anti-FLT3 Sequences FLL15, FLL154, FLL158, FLL160, FLL168, ran in the presence of 15 mg/ml HSA. The y-axis shows the normalized percentage of viability of the cancer cells.
Figure 16:
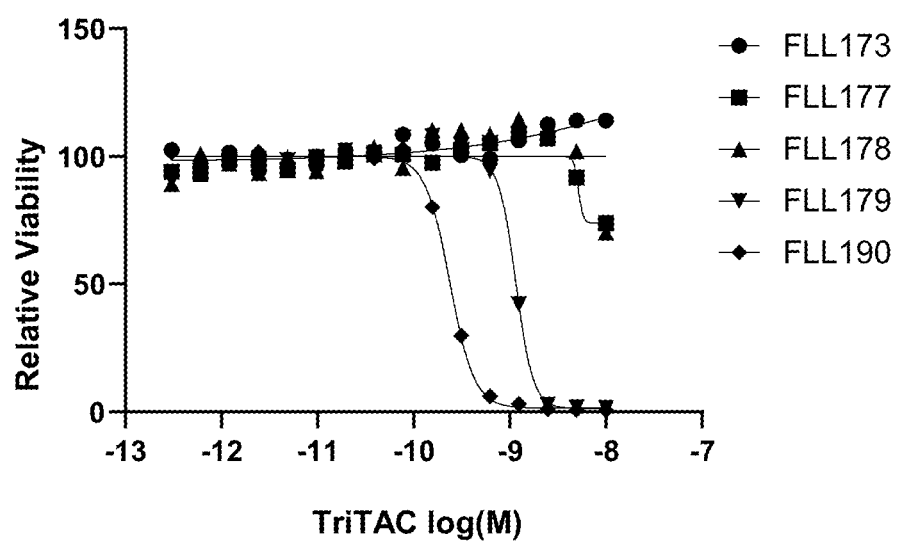
FIG. 16 illustrates the results of a TDCC Assay with MV-4-11 Cells and Anti-CD3/Anti-FLT3 Multispecific Proteins Containing Llama Anti-FLT3 Sequences FLL173, FLL177, FLL178, FLL179, and FLL190, ran in the presence of 15 mg/ml HSA. The y-axis shows the normalized percentage of viability of the cancer cells.
Figure 17:
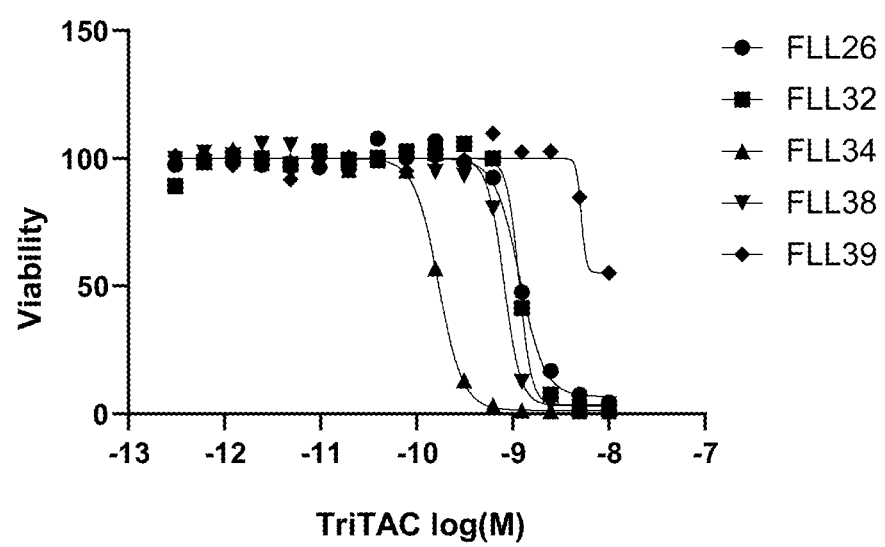
FIG. 17 illustrates the results of a TDCC Assay with MV-4-11 Cells and Anti-CD3/Anti-FLT3 Multispecific Proteins Containing Llama Anti-FLT3 Sequences FLL26, FLL32, FLL34, FLL38, and FLL39, ran the presence of 15 mg/ml HSA. The y-axis shows the normalized percentage of viability of the cancer cells.
Figure 18:
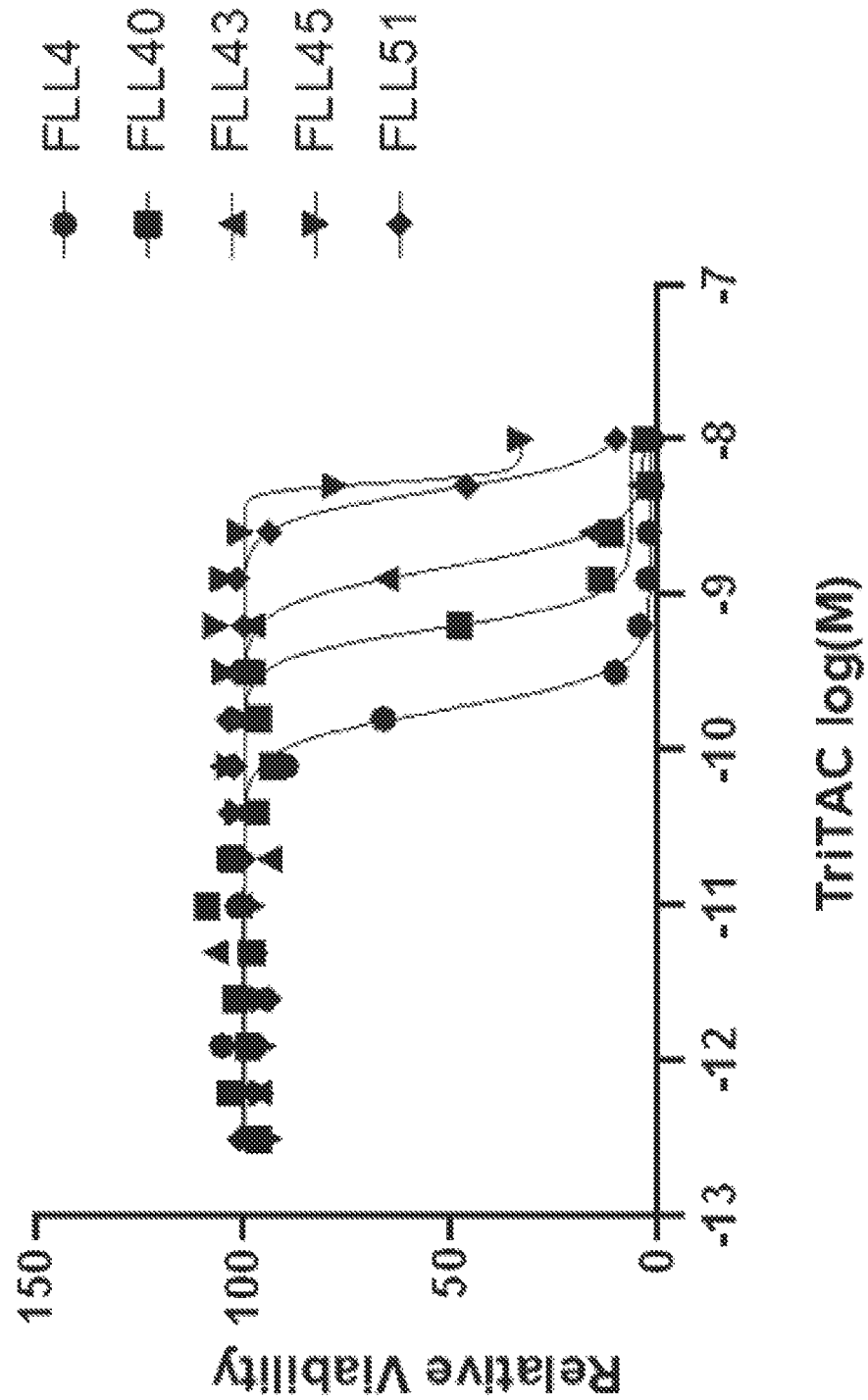
FIG. 18 illustrates the results of a TDCC Assay with MV-4-11 Cells and Anti-CD3/Anti-FLT3 Multispecific Proteins Containing Llama Anti-FLT3 Sequences FLL4, FLL40, FLL43, FLL45, and FLL51, ran in the presence of 15 mg/ml HSA. The y-axis shows the normalized percentage of viability of the cancer cells.
Figure 19:
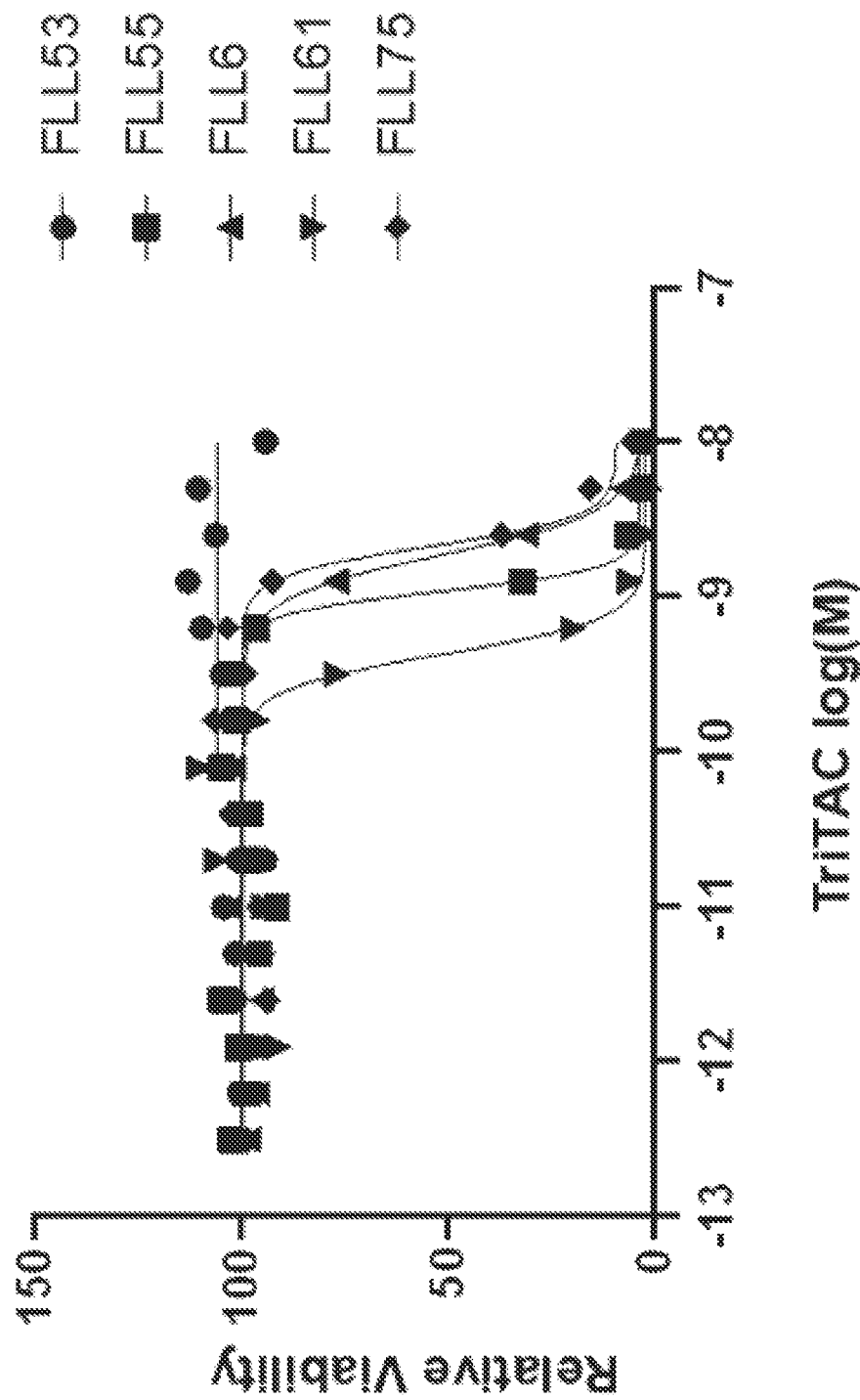
FIG. 19 illustrates the results of a TDCC Assay with MV-4-11 Cells and Anti-CD3/Anti-FLT3 Multispecific Proteins Containing Llama Anti-FLT3 Sequences FLL53, FLL55, FLL6, FLL61, and FLL75, ran in the presence of 15 mg/ml HSA. The y-axis shows the normalized percentage of viability of the cancer cells.
Figure 20:
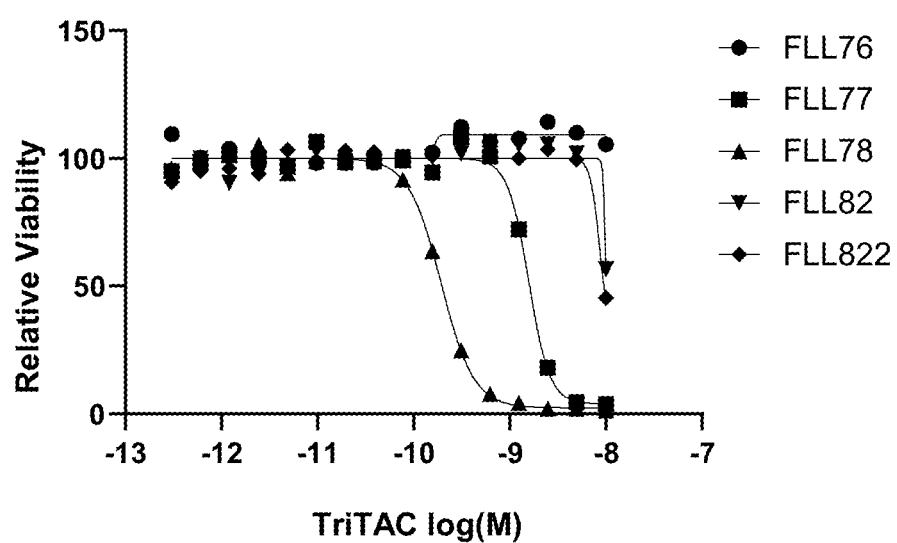
FIG. 20 illustrates the results of a TDCC Assay with MV-4-11 Cells and Anti-CD3/Anti-FLT3 Multispecific Proteins Containing Llama Anti-FLT3 Sequences FLL76, FLL77, FLL78, FLL82, and FLL822, ran in the presence of 15 mg/ml HSA. The y-axis shows the normalized percentage of viability of the cancer cells.
Figure 21:
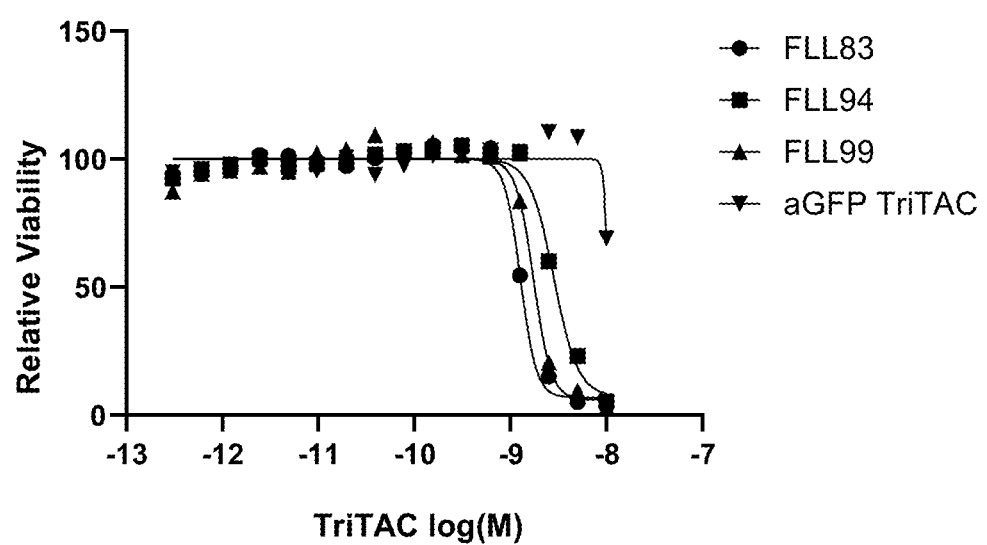
FIG. 21 illustrates the results of a TDCC Assay with MV-4-11 Cells and Anti-CD3/Anti-FLT3 Multispecific Proteins Containing Llama Anti-FLT3 Sequences FLL83, FLL94, and FLL99 and with a negative control molecule targeting GFP, ran in the presence of 15 mg/ml HSA. The y-axis shows the normalized percentage of viability of the cancer cells.
Figure 22:
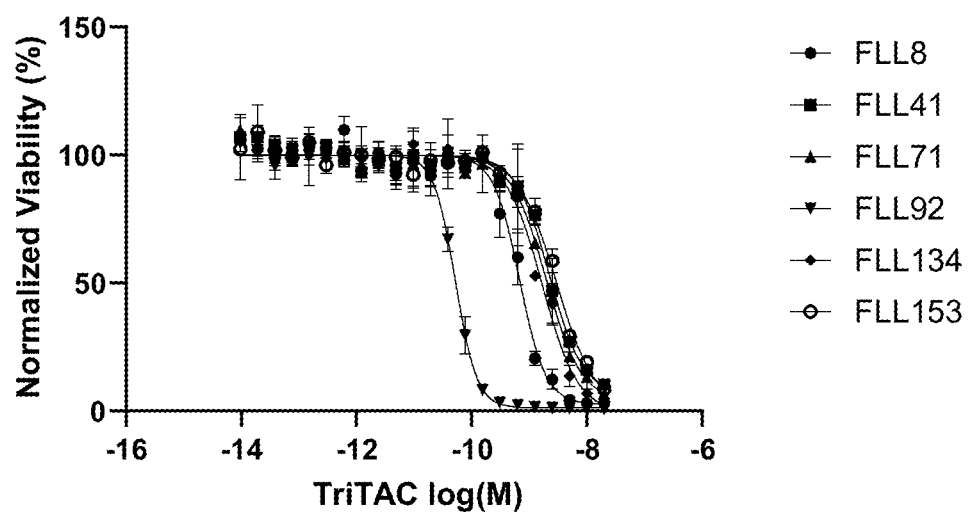
FIG. 22 illustrates the results of a TDCC Assay with MV-4-11 Cells and Anti-CD3/Anti-FLT3 Multispecific Proteins Containing Llama Anti-FLT3 Sequences FLL8, FLL41, FLL71, FLL92, FLL134, and FLL153, ran in the presence of 15 mg/ml HSA. The y-axis shows the normalized percentage of viability of the cancer cells.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

An "antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence and gene loci. Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. There are two types of native disulfide bridges or bonds in immunoglobulin molecules: interchain and intra-chain disulfide bonds. The location and number of interchain disulfide bonds vary according to the immunoglobulin class and species. Interchain disulfide bonds are located on the surface of the immunoglobulin, are accessible to solvent and are usually relatively easily reduced. In the human IgG1 isotype there are four interchain disulfide bonds, one from each heavy chain to the light chain and two between the heavy chains. The interchain disulfide bonds are not required for chain association. As is well known the cysteine rich IgG1 hinge region of the heavy chain has generally been held to consist of three parts: an upper hinge, a core hinge, and a lower hinge. Those skilled in the art will appreciate that that the IgG1 hinge region contain the cysteines in the heavy chain that comprise the interchain disulfide bonds (two heavy/heavy, two heavy/light), which provide structural flexibility that facilitates Fab movements. The interchain disulfide bond between the light and heavy chain of IgG1 are formed between C214 of the kappa or lambda light chain and C220 in the upper hinge region of the heavy chain. The interchain disulfide bonds between the heavy chains are at positions C226 and C229 (all numbered per the EU index according to Kabat, et al., infra.)

As used herein the term "antibody" includes polyclonal antibodies, multiclonal antibodies, monoclonal antibodies, chimeric antibodies, deimmunized, humanized and primatized antibodies, CDR grafted antibodies, human antibodies, recombinantly produced antibodies, intrabodies, multispecific antibodies, bispecific antibodies, monovalent antibodies (e.g., a monovalent IgG), multivalent antibodies, anti-idiotypic antibodies, synthetic antibodies, including muteins and variants thereof, immunospecific antibody fragments such as: hcIgG, a V-NAR, Fv, Fd, Fab, F(ab')2, F(ab'), Fab2, Fab3 fragments, single-chain fragments (e.g., di-scFv, scFv, scFvFc, scFv-zipper, scFab), disulfide-linked Fvs (sdFv), a Fd fragment consisting of the VH and CH1 domains, linear antibodies, single domain antibodies such as nanobodies or single variable domain antibodies comprising merely one variable domain such as sdAb (VH, VL, or VHH domains), "r IgG" ("half antibody"), diabodies, single chain diabodies, tandem diabodies (Tandab's), tandem di-scFv, tandem tri-scFv, "minibodies" are in some instances exemplified by a structure which is as follows: (VH-VL-CH3)2, (scFv-CH3)2, ((scFv)2-CH3+CH3), ((scFv)2-CH3) or (scFv-CH3-scFv)2, multibodies such as triabodies or tetrabodies, and derivatives thereof including Fc fusions and other modifications, and any other immunoreactive molecule so long as it comprises a domain having a binding site for preferential association or binding with an FLT3 protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter alpha, delta, epsilon, gamma, and mu, respectively. Light chains of the antibodies from any vertebrate species can be assigned to one of two clearly distinct types, called kappa (kappa) and lambda (lambda), based on the amino acid sequences of their constant domains.

In some embodiments, the FLT3 binding proteins comprise a heavy chain only antibody, such as a VH or a VHH domain. In some cases, the FLT3 binding proteins comprise a heavy chain only antibody that is an engineered human VH domain. In some examples, the engineered human VH domain is produced by panning of phage display libraries. In some embodiments, the FLT3 binding proteins comprise a VHH. The term "VHH," as used herein, refers to single chain antibody binding domain devoid of light chain. In some cases, a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. A VHH, in some cases, is a natural VHH, such as a Camelid-derived VHH, or a recombinant protein comprising a heavy chain variable domain. In some embodiments, the VHH is derived from a species selected from the group consisting of camels, llamas, vicunas, guanacos, and cartilaginous fish (such as, but not limited to, sharks). In another embodiment, the VHH is derived from an alpaca (such as, but not limited to, a Huacaya Alpaca or a Suri alpaca).

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. The assignment of amino acids to each domain, framework region and CDR is, in some embodiments, in accordance with one of the numbering schemes provided by Kabat et al. (1991) Sequences of Proteins of Immunological Interest (5th Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) Handbook of Therapeutic Antibodies, 3rd Ed., Wily-VCH Verlag GmbH and Co or AbM (Oxford Molecular/MSI Pharmacopeia) unless otherwise noted. In some embodiments of this disclosure, the FLT3 binding proteins comprise heavy chain only antibodies, such as VH or VHH domains, and comprise three CDRs. Such heavy chain only antibodies, in some embodiments, bind FLT3 as a monomer with no dependency on dimerisation with a VL (light chain variable) region for optimal binding affinity.

"Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of $H_2$ and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

The term "epitope," as used herein, refers to an antigenic determinant that interacts with a specific antigen binding site in the variable region of an antibody molecule known as a paratope. A single antigen may have more than one epitope.

Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Alignment for purposes of determining percent amino acid sequence identity can for example be achieved using publicly available sequence comparison computer program ALIGN-2. The source code for the ALIGN-2 sequence comparison computer program is available with user documentation in the U.S. Copyright Office, Washington D.C., 20559, where it is registered under U.S. Copyright Registration No. TXU510087. The ALIGN-2 program can be compiled for use on a UNIX operating system, such as a digital UNIX V4.0D. All sequence comparison parameters are set by the ALIGN-2 program and do not vary.

As used herein, "elimination half-time" is used in its ordinary sense, as is described in Goodman and Gillman's The Pharmaceutical Basis of Therapeutics 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, tin, the time required for 50% completion of the process. The units of these two constants are time—1 and time, respectively. A first-order rate constant and the half-time of the reaction are simply related ($k \times t_{1/2}=0.693$) and may be interchanged accordingly. Since first-order elimination kinetics dictates that a constant fraction of drug is lost per unit time, a plot of the log of drug concentration versus time is linear at all times following the initial distribution phase (i.e., after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (MA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human or cynomolgus FLT3, is immobilized on the OCTET® streptavidin capillary sensor tip surface which streptavidin tips are then activated according to manufacturer's instructions using about 20-50 µg/ml human or cynomolgus FLT3 protein. A solution of PBS/Casein is also introduced as a blocking agent. For association kinetic measurements, FLT3 binding protein variants are introduced at a concentration ranging from about 10 ng/mL to about 100 µg/mL, about 50 ng/mL to about 5 µg/mL, or about 2 ng/mL to about 20 µg/mL. In some embodiments, the FLT3 binding single domain proteins are used at a concentration ranging from about 2 ng/mL to about 20 µg/mL. Complete dissociation is observed in case of the negative control, assay buffer without the binding proteins. The kinetic parameters of the binding reactions are then determined using an appropriate tool, e.g., ForteBio software.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

An "FLT3 targeting TriTAC," or an "FLT3 targeting trispecific protein," as used herein refers to a trispecific binding protein that comprises a binding moiety that is specific for a bulk serum protein, a first target antigen binding domain, and a second target antigen binding domain, wherein at least one of the first target antigen binding domain and the second target antigen binding domain comprises an FLT3 binding protein as described herein, and at least one of the first target antigen binding domain and the second target antigen binding domain comprises a domain that binds a CD3.

A "ProTriTAC," or an "FLT3 targeting protrispecific protein," as used herein refers to a trispecific binding protein that is conditionally activated, and comprises (i) a cleavable linker; (ii) a dual binding moiety that is specific for a bulk serum protein and also comprises a masking moiety which prohibits the binding of a first target antigen binding domain or a second target antigen binding domain to its target, wherein at least one of the first target antigen binding domain and the second target antigen binding domain comprises an FLT3 binding domain as described herein. The ProTriTAC proteins of this disclosure are, in some cases, activated from a masked state to an active state by cleavage of the cleavable linker, for example, in a protease rich environment, such as in a tumor microenvironment.

FLT3 Binding Proteins

FLT3, also known as fetal liver kinase 2 (FLK-2), stem cell tyrosine kinase 1 (STK-1) and CD135, is a member of the class III receptor tyrosine kinases. Normally, FLT3 is expressed on immature myeloid-lymphocytic precursor cells and dendritic cell precursors, but rarely on mature adult cells. FLT3 is overexpressed in approximately 90% of acute myeloid leukemia (AML), a majority of acute lymphocytic leukemia (ALL) and the blast-crisis phase of chronic myeloid leukemia (BC-CML). Stimulation by FLT3 ligand (FL) enhances the proliferation and survival of leukemia cells. Inhibition of FLT3 signaling leads to apoptosis in dendritic cells and inhibition of immune responses. The MAPK, PI3K and Stat5 pathways have been identified to be involved in the downstream signaling of activated FLT3 (See e.g., Stirewalt D L and J P, Radich, J P. Nat Rev Cancer 3:650-665 (2003)).

Described herein are proteins that comprise an FLT3 binding domain, pharmaceutical compositions thereof, as well as nucleic acids, recombinant expression vectors and host cells for making such proteins thereof. Also provided are methods of using the disclosed proteins comprising an FLT3 binding domain of this disclosure, in the prevention, and/or treatment of diseases, conditions and disorders. In some embodiments, an FLT3 binding domain of this disclosure inhibits FL-induced phosphorylation of wild-type FLT3 and downstream kinases of MPK, PI3K, and STAT5 pathways in a disease such as leukemia. In some embodiments, an FLT3 binding domain of this disclosure has an improved ability to activate downstream immune effector functions such as antibody dependent cellular cytotoxicity (ADCC).

In some embodiments, the FLT3 binding domain binds to a human FLT3 protein comprising a sequence as set forth in SEQ ID No. 388 (UniProt ID: P36888). In some embodiments, the FLT3 binding domain binds to a protein comprising a truncated sequence compared to SEQ ID No. 388 (UniProt ID: P36888).

In some embodiments, the FLT3 binding domains disclosed herein recognize full-length FLT3 (e.g., an FLT3 protein comprising the sequence of SEQ ID No. 388 (UniProt ID: P36888). In certain instances, the FLT3 binding domains disclosed herein recognize an epitope within FLT3, such as, in some cases the FLT3 binding proteins interact with one or more amino acids found within a domain of human FLT3. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within a domain of FLT3 (e.g., an FLT3 protein comprising the sequence of SEQ ID No. 388 (UniProt ID: P36888). Alternatively, the epitope may consist of a plurality of non-contiguous amino acids (or amino acid sequences) located within a domain of FLT3 (e.g., an FLT3 protein comprising the sequence of SEQ ID No. 388 (UniProt ID: P36888).

In some embodiments, the FLT3 binding proteins of this disclosure binds to the full length of an FLT3 protein or to a fragment thereof, such as epitope containing fragments within the full length FLT3 protein, as described above. In some cases, the epitope containing fragment comprises antigenic or immunogenic fragments and derivatives thereof of the FLT3 protein. Epitope containing fragments, including antigenic or immunogenic fragments, are, in some embodiments, 12 amino acids or more, e.g., 20 amino acids or more, 50 or 100 amino acids or more. The FLT3 fragments, in some embodiments, comprises 95% or more of the length of the full protein, 90% or more, 75% or 50% or 25% or 10% or more of the length of the full protein. In some embodiments, the epitope-containing fragments of FLT3 including antigenic or immunogenic fragments are capable of eliciting a relevant immune response in a patient. Derivatives of FLT3 include, in some embodiments, variants on the sequence in which one or more (e.g., 1-20 such as 15 amino acids, or up to 20% such as up to 10% or 5% or 1% by number of amino acids based on the total length of the protein) deletions, insertions or substitutions have been made to the FLT3 sequence (e.g., an FLT3 protein comprising the sequence of SEQ ID No. 388 (UniProt ID: P36888).

In some embodiments, substitutions comprise conservative substitutions. Derivatives and variants of, in some examples, have essentially the same biological function as the protein from which they are derived. For instance, derivatives and variants of FLT3 are, in some cases, comparably antigenic or immunogenic to the protein from which they are derived, have either the ligand-binding activity, or the active receptor-complex forming ability, or preferably both, of the protein from which they are derived, and have the same tissue distribution as FLT3.

In some embodiments, the FLT3 binding protein specifically binds FLT3 with equivalent or better affinity as that of a reference FLT3 binding protein, and the FLT3 binding protein in such embodiments comprises an affinity matured FLT3 binding molecule, and is derived from the FLT3 binding parental molecule, comprising one or more amino acid mutations (e.g., a stabilizing mutation, a destabilizing mutation) with respect to the FLT3 binding parental molecule. In some embodiments, the affinity matured FLT3 binding molecule has superior stability with respect to selected destabilizing agents, as that of a reference FLT3 binding parental molecule. In some embodiments, the affinity matured FLT3 binding molecule is identified in a process comprising panning of one or more pre-candidate FLT3 binding molecules derived from one or more FLT3 binding parental molecule, expressed in a phage display library, against an FLT3 protein, such as a human FLT3 protein. The pre-candidate FLT3 binding molecule comprises, in some embodiments, amino acid substitutions in the variable regions, CDRs, or framework residues, relative to a parental molecule.

As used herein, "Phage display," refers to a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently selected for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. See e.g., Wells and Lowman, Curr. Opin. Struct. Biol, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations. See e.g., Lowman and Wells, Methods: A companion to Methods in Enzymology, 3:205-0216 (1991).

In some embodiments, the panning comprises using varying binding times and concentrations to identify FLT3 binding molecules with increased or decreased on-rates, from pre-candidate FLT3 binding molecules. In some embodiments, the panning comprises using varying wash times to identify FLT3 binding molecules with increased or decreased off-rates, from pre-candidate FLT3 molecules. In some embodiments, the panning comprises using both varying binding times and varying wash times. In some embodiments, one or more stabilizing mutations are combined to increase the stability of the affinity matured FLT3 binding molecule, for example, by shuffling to create a second-stage combinatorial library from such mutants and conducting a second round of panning followed by a binding selection.

In some embodiments, the affinity matured FLT3 binding molecule comprises an equivalent or better affinity to a FLT3 protein (such as human FLT3 protein) as that of a FLT3 binding parental molecule, but that has reduced cross reactivity, or in some embodiments, increased cross reactivity, with selected substances, such as ligands, proteins, antigens, or the like, other than the FLT3 epitope for which the FLT3 binding parental molecule is specific, or is designed to be specific for. In regard to the latter, an affinity matured FLT3 binding molecule, in some embodiments, is more successfully tested in animal models if the affinity matured FLT3 binding molecule is reacted with both human FLT3 and the corresponding target of the animal model, e.g. mouse FLT3 or cynomolgus FLT3.

In some embodiments, the FLT3 binding protein comprises an antigen-specific binding domain polypeptide that specifically bind to targets, such as targets on diseased cells, or targets on other cells that support the diseased state, such as targets on stromal cells that support tumor growth or targets on immune cells that support disease-mediated immunosuppression. In some examples, the antigen-specific binding domain includes antibodies, single chain antibodies, Fabs, Fv, T-cell receptor binding domains, ligand binding domains, receptor binding domains, domain antibodies, single domain antibodies, minibodies, nanobodies, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins).

In some embodiments, the FLT3 binding domain is an anti-FLT3 antibody or an antigen binding fragment thereof, or a variant of the anti-FLT3 or an antigen binding fragment thereof. As used herein, the term "variant" refers to variants and derivatives of an antibody or an antigen binding fragment thereof, as described herein. In certain embodiments, amino acid sequence variants of the anti-FLT3 antibodies or antigen binding fragments thereof described herein are contemplated. For example, in certain embodiments amino acid sequence variants of anti-FLT3 antibodies or antigen binding fragments thereof described herein are contemplated to improve the binding affinity and/or other biological properties of the same. Exemplary method for preparing amino acid variants include, but are not limited to, introducing appropriate modifications into the nucleotide sequence encoding the antibody or antigen binding fragments thereof, or by peptide synthesis. Such modifications include, for example, deletions from, and/or insertions into and/or substitutions of residues within the amino acid sequences of the antibody or antigen binding fragments thereof.

Any combination of deletion, insertion, and substitution can be made to arrive at the final construct, provided that the final construct possesses the desired characteristics, e.g., antigen-binding. In certain embodiments, variants having one or more amino acid substitutions are provided. Sites of interest for substitution mutagenesis include the CDRs and framework regions. Examples of such substitutions are described below. Amino acid substitutions may be introduced into an antibody or antigen binding fragments thereof of interest and the products screened for a desired activity, e.g., retained/improved antigen binding, decreased immunogenicity, altered Antibody dependent cellular cytotoxicity (ADCC), or improved T-cell mediated cytotoxicity (TDCC). Both conservative and non-conservative amino acid substitutions are contemplated for preparing the variants.

In another example of a substitution to create a variant anti-FLT3 antibody or antigen binding fragments thereof, one or more hypervariable region residues of a parent antibody or antigen binding fragments thereof are substituted. In general, variants are then selected based on improvements in desired properties compared to a parent antibody, for example, increased affinity, reduced affinity, reduced immunogenicity, increased pH dependence of binding.

In some embodiments, the FLT3 binding domain is a single domain antibody (sdAb), such as a heavy chain variable domain (VH), a variable domain (VHH) of a llama derived sdAb, a peptide, a ligand or a small molecule entity specific for FLT3. In some embodiments, the FLT3 binding domain described herein is any domain that binds to FLT3 including but not limited to domains from a monoclonal antibody, a polyclonal antibody, a recombinant antibody, a human antibody, a humanized antibody. In certain embodiments, the FLT3 binding domain is a single-domain antibody. In other embodiments, the FLT3 binding domain is a peptide. In further embodiments, the FLT3 binding domain is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelization" of a "domain antibody" or "Dab," or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against FLT3. As further described herein, such VHH sequences can generally be generated or obtained by suitably immunizing a species of Llama with FLT3, (i.e., so as to raise an immune response and/or heavy chain antibodies directed against FLT3), by obtaining a suitable biological sample from said Llama (such as a blood sample, serum sample or sample of B-cells), and by generating VHH sequences directed against FLT3, starting from said sample, using any suitable technique.

In another embodiment, such naturally occurring VHH domains against FLT3, are obtained from naïve libraries of Camelid VHH sequences, for example by screening such a library using FLT3, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507.

In a further embodiment, yet another technique for obtaining VHH sequences directed against FLT3, involves suitably immunizing a transgenic mammal that is capable of expressing heavy chain antibodies (i.e., so as to raise an immune response and/or heavy chain antibodies directed against FLT3), obtaining a suitable biological sample from said transgenic mammal (such as a blood sample, serum sample or sample of B-cells), and then generating VHH sequences directed against FLT3, starting from said sample, using any suitable technique known in the field. For example, for this purpose, the heavy chain antibody-expressing rats or mice and the further methods and techniques described in WO 02/085945 and in WO 04/049794 can be used.

In some embodiments, an anti-FLT3 single domain antibody of this disclosure comprises a single domain antibody with an amino acid sequence that corresponds to the amino acid sequence of a non-human antibody and/or a naturally occurring VHH domain, e.g., a llama anti-FLT3 antibody, but that has been "humanized," i.e., by replacing one or more amino acid residues in the amino acid sequence of said non-human anti-FLT3 and/or the naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-FLT3 single domain antibodies of the disclosure are obtained in any suitable manner known per se (i.e., as indicated under points (1)-(8) above) and thus are not strictly limited to polypeptides that have been obtained using a polypeptide that comprises a non-human anti-FLT3 antibody and/or the naturally occurring VHH sequence as a starting material. In some additional embodiments, a single domain anti-FLT3 antibody, as described herein, comprises a single domain antibody with an amino acid sequence that corresponds to the amino acid sequence of a naturally occurring VH domain, but that has been "camelized" i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues. See e.g., WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-FLT3 single domain antibodies of the disclosure, in certain embodiments, are obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide a desired anti-FLT3 single domain antibody of the disclosure. Alternatively, in other embodiments, based on the amino acid sequence of a naturally occurring VHH domain or VH domain, respectively, the amino acid sequence of the desired humanized or camelized anti-FLT3 single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-FLT3 single domain antibody of the disclosure, respectively, is designed and then synthesized de novo using known techniques for nucleic acid synthesis, after which the nucleic acid thus obtained is expressed in using known expression techniques, so as to provide the desired anti-FLT3 single domain antibody of the disclosure.

Other suitable methods and techniques for obtaining the anti-FLT3 single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-FLT3 single domain antibody of the disclosure or a nucleotide sequence or nucleic acid encoding the same.

In some embodiments, the FLT3 binding domain is an anti-FLT3 specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the FLT3 binding domain comprises any domain that binds to FLT3 including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the FLT3 binding domain is a single domain antibody. In some embodiments, the anti-FLT3 single domain antibody comprises heavy chain variable complementarity determining regions (CDR), CDR1, CDR2, and CDR3.

In some embodiments, the FLT3 binding domain is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the FLT3 binding protein of the present disclosure comprise, for example, 75, 76, 77, 78, 79, 80, 81, 82, 83, 84, 85, 86, 87, 88, 89, 90, 91, 92, 93, or 94 amino acid residues, and the complementarity determining regions comprise, for example, 24, 25, 26, 27, 28, 29, 30, 31, 32, 33, 34, 35, or 36 amino acid residues.

In some embodiments, the binding proteins described herein comprise a polypeptide having a sequence selected from SEQ ID Nos. 1-76, and 389-390, subsequences thereof, and variants thereof. In some embodiments, the FLT3 binding protein comprises at least 60%-95% or more homology to a sequence selected from SEQ ID Nos. 1-76, and 389-390, subsequences thereof, and variants thereof. In some embodiments, the FLT3 binding protein comprises at least 60%, 61%, 62%, 63%, 63%, 65%, 66%, 67%, 68%, 69%, 70%, 75%, 80%, 85%, 90%, 95%, 96%, 97%, 98%, 99%, or more homology to a sequence selected from SEQ ID Nos. 1-76, and 389-390, subsequences thereof, and variants thereof. In some embodiments, the FLT3 binding protein comprises at least 60%-95% or more identity to a sequence selected from SEQ ID Nos. 1-76, and 389-390, subsequences thereof, and variants thereof. In some embodiments, the FLT3 binding protein comprises at least 60%, 61%, 62%, 63%, 63%, 65%, 66%, 67%, 68%, 69%, 70%, 75%, 80%, 85%, 90%, 95%, 96%, 97%, 98%, 99%, or more identity to a sequence selected from SEQ ID Nos. 1-76, and 389-390, subsequences thereof, and variants thereof.

In some embodiments, the CDR1 comprises the amino acid sequence selected from the group consisting of SEQ ID Nos. 77-108 or a sequence comprising one or more amino acid substitutions in a sequence selected from the group consisting of SEQ ID Nos. 77-108. In some embodiments, the CDR2 comprises the amino acid sequence selected from the group consisting of SEQ ID Nos. 109-154, and 393-394 or a sequence comprising one or more amino acid substitutions in a sequence selected from the group consisting of SEQ ID Nos. 109-154, and 393-394. In some embodiments, the CDR3 comprises the amino acid sequence selected from the group consisting of SEQ ID Nos. 155-195 or a sequence comprising one or more amino acid substitutions in a sequence selected from the group consisting of SEQ ID Nos. 155-195. In some embodiments, the CDR1 comprises the amino acid sequence selected from the group consisting of SEQ ID Nos. 89, 91, 92, 93, and 100 or a sequence comprising one or more amino acid substitutions in a sequence selected from the group consisting of SEQ ID Nos. 89, 91, 92, 93, and 100. In some embodiments, the CDR2 comprises the amino acid sequence selected from the group consisting of SEQ ID Nos. 149, 150, 151, 152, 153, 154, 393 and 394, or a sequence comprising one or more amino acid substitutions in a sequence selected from the group consisting of SEQ ID Nos. 149, 150, 151, 152, 153, 154, 393 and 394. In some embodiments, the CDR3 comprises the amino acid sequence selected from the group consisting of SEQ ID Nos. 173, 186 or 195 or a sequence comprising one or more amino acid substitutions in a sequence selected from the group consisting of SEQ ID Nos. 173, 196 or 195.

In various embodiments, the FLT3 binding domain of the present disclosure is at least about 60%, about 61%, at least about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 1-76, and 389-390.

In various embodiments, the FLT3 binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos.1-76, and 389-390.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in any one of SEQ ID Nos. 77-108.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID Nos. 109-154, and 393-394.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID Nos. 155-195.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in any one of SEQ ID Nos. 89, 91, 92, 93, and 100, and wherein the FLT3 binding domain comprises a humanized FLT3 binding domain.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in any one of SEQ ID Nos. 149, 150, 151, 152, 153, and 154, and wherein the FLT3 binding domain comprises a humanized FLT3 binding domain.

In various embodiments, a complementarity determining region of the FLT3 binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in any one of SEQ ID Nos. 173, 186 and 195, and wherein the FLT3 binding domain comprises a humanized FLT3 binding domain.

In some embodiments, the FLT3 binding domains of this disclosure comprises a set of three CDR sequences, as provided in Table 1.

TABLE 1

CDR sequences of exemplary FLT3 binding domains of this disclosure

| FLT3 Binder | CDR1 | CDR2 | CDR3 |
|---|---|---|---|
| FLL101 | 77 | 109 | 155 |
| FLL103 | 78 | 109 | 155 |
| FLL116 | 77 | 109 | 155 |
| FLL125 | 79 | 110 | 156 |
| FLL129 | 80 | 111 | 155 |
| FLL137 | 81 | 112 | 155 |
| FLL14 | 77 | 109 | 155 |
| FLL146 | 77 | 113 | 157 |
| FLL158 | 82 | 110 | 156 |
| FLL179 | 77 | 114 | 158 |
| FLL181 | 80 | 111 | 155 |
| FLL187 | 77 | 109 | 155 |
| FLL32 | 83 | 115 | 155 |
| FLL51 | 84 | 111 | 155 |
| FLL55 | 79 | 116 | 156 |
| FLL77 | 85 | 111 | 155 |
| FLL97 | 77 | 109 | 155 |
| FLL21 | 79 | 110 | 156 |
| FLL57 | 86 | 110 | 156 |
| FLL62 | 87 | 110 | 156 |
| FLL79 | 79 | 110 | 156 |
| FLL86 | 79 | 110 | 156 |
| FLL112 | 88 | 117 | 159 |
| FLL142 | 88 | 118 | 160 |
| FLL143 | 88 | 119 | 161 |
| FLL154 | 88 | 120 | 162 |
| FLL168 | 88 | 121 | 163 |
| FLL170 | 88 | 122 | 164 |
| FLL188 | 88 | 121 | 165 |
| FLL40 | 88 | 122 | 164 |
| FLL6 | 88 | 121 | 166 |
| FLL75 | 88 | 122 | 167 |
| FLL83 | 88 | 122 | 168 |
| FLL94 | 88 | 121 | 169 |
| FLL99 | 88 | 118 | 165 |
| FLL38 | 88 | 123 | 170 |
| FLL53 | 88 | 124 | 171 |
| FLL553 | 88 | 122 | 167 |
| FLL74 | 88 | 117 | 172 |
| FLL102 | 89 | 125 | 173 |
| FLL122 | 89 | 125 | 173 |
| FLL134 | 90 | 126 | 174 |
| FLL153 | 90 | 127 | 175 |
| FLL41 | 90 | 125 | 176 |
| FLL67 | 90 | 125 | 176 |
| FLL92 | 89 | 125 | 173 |
| FLL71 | 90 | 128 | 175 |
| FLL8 | 90 | 128 | 177 |
| FLL84 | 90 | 125 | 176 |
| FLL107 | 91 | 129 | 178 |
| FLL141 | 91 | 130 | 178 |
| FLL34 | 92 | 131 | 178 |
| FLL4 | 93 | 132 | 178 |
| FLL61 | 94 | 133 | 179 |
| FLL78 | 91 | 134 | 178 |
| FLL1 | 95 | 135 | 180 |
| FLL26 | 96 | 136 | 181 |
| FLL160 | 97 | 137 | 182 |
| FLL173 | 97 | 138 | 183 |
| FLL178 | 98 | 139 | 184 |
| FLL27 | 99 | 139 | 185 |
| FLL190 | 100 | 140 | 186 |
| FLL43 | 101 | 141 | 187 |
| FLL15 | 102 | 142 | 188 |
| FLL45 | 103 | 143 | 189 |
| FLL39 | 104 | 144 | 190 |
| FLL177 | 105 | 145 | 191 |
| FLL823 | 106 | 146 | 192 |
| FLL76 | 107 | 147 | 193 |
| FLL822 | 108 | 148 | 194 |
| FLH107 | 91 | 149 | 195 |
| FLH141 | 91 | 150 | 195 |
| FLH19C | 100 | 151 | 186 |
| FLH34 | 92 | 152 | 195 |
| FLH4 | 93 | 153 | 195 |
| FLH78 | 91 | 154 | 195 |
| FLH92a | 89 | 393 | 173 |
| FLH92b | 89 | 394 | 173 |

In some embodiments, the FLT3 binding domain is cross-reactive with human cynomolgus (cyno) and mouse FLT3. In some embodiments, the FLT3 binding domain is specific for human FLT3. In certain embodiments, the FLT3 binding domains disclosed herein bind to human FLT3 with a human Kd (hKd). In certain embodiments, the FLT3 binding domains disclosed herein bind to cynomolgus FLT3 with a cyno Kd (cKd). In certain embodiments, the FLT3 binding domains disclosed herein bind to cynomolgus FLT3 with a mouse Kd (mKd). In certain embodiments, the FLT3 binding domains disclosed herein bind to both cynomolgus FLT3 and a human FLT3, with a cyno Kd (cKd) and a human Kd (hKd), respectively. In certain embodiments, the FLT3 binding domains disclosed herein bind to cynomolgus FLT3, mouse FLT3, and a human FLT3, with a cyno Kd (cKd), mouse Kd (mKd), and a human Kd (hKd), respectively. In some embodiments, the FLT3 binding protein binds to human, mouse and cynomolgus FLT3 with comparable binding affinities (i.e., hKd, mKd and cKd values do not differ by more than ±10%). In some embodiments, the hKd, mKd and the cKd range from about 0.1 nM to about 500 nM. In some embodiments, the hKd, mKd and the cKd range from about 0.1 nM to about 450 nM. In some embodiments, the hKd, mKd and the cKd range from about 0.1 nM to about 400 nM. In some embodiments, the hKd, mKd and the cKd range from about 0.1 nM to about 350 nM. In some embodiments, the hKd, mKd and the cKd range from about 0.1 nM to about 300 nM. In some embodiments, the hKd, mKd and the cKd range from about 0.1 nM to about 250 nM. In some embodiments, the hKd, mKd and the cKd range from about 0.1 nM to about 200 nM. In some embodiments, the hKd, mKd and the cKd range from about 0.1 nM to about 150 nM. In some embodiments, the hKd, mKd and the cKd range from about 0.1 nM to about 100 nM. In some embodiments, the hKd, mKd and the cKd range from about 0.1 nM to about 90 nM. In some embodiments, the hKd, mKd and the cKd range from about 0.2 nM to about 80 nM. In some embodiments, the hKd, mKd and the cKd range from about 0.3 nM to about 70 nM. In some embodiments, the hKd, mKd and the cKd range from about 0.4 nM to about 50 nM. In some embodiments, the hKd, mKd and the cKd range from about 0.5 nM to about 30 nM. In some embodiments, the hKd, mKd and the cKd range from about 0.6 nM to about 10 nM. In some embodiments, the hKd, mKd and the cKd range from about 0.7 nM to about 8 nM. In some embodiments, the hKd, mKd and the cKd range from about 0.8 nM to about 6 nM. In some embodiments, the hKd, mKd and the cKd range from about 0.9 nM to about 4 nM. In some embodiments, the hKd, mKd and the cKd range from about 1 nM to about 2 nM.

In some embodiments, any of the foregoing FLT3 binding domains (e.g., anti-FLT3 single domain antibodies of SEQ ID Nos. 1-76, and 389-390) are affinity peptide tagged for ease of purification. In some embodiments, the affinity peptide tag is six consecutive histidine residues, also referred to as 6x-his (SEQ ID No. 374). In certain embodiments, the FLT3 binding domains of the present disclosure preferentially bind membrane bound FLT3 over soluble FLT3 Membrane bound FLT3 refers to the presence of FLT3 in or on the cell membrane surface of a cell that expresses FLT3. Soluble FLT3 refers to FLT3 that is no longer on in or on the cell membrane surface of a cell that expresses or expressed FLT3. In certain instances, the soluble FLT3 is present in the blood and/or lymphatic circulation in a subject. In one embodiment, the FLT3 binding domains bind membrane-bound FLT3 at least 5 fold, 10 fold, 15 fold, 20 fold, 25 fold, 30 fold, 40 fold, 50 fold, 100 fold, 500 fold, or 1000 fold greater than soluble FLT3. In one embodiment, the FLT3 binding proteins of the present disclosure preferentially bind membrane-bound FLT3 30 fold greater than soluble FLT3. Determining the preferential binding of an antigen binding protein to membrane bound FLT3 over soluble FLT3 can be readily determined using binding assays.

It is contemplated that in some embodiments the FLT3 binding protein is fairly small and no more than 25 kDa, no more than 20 kDa, no more than 15 kDa, or no more than 10 kDa in some embodiments. In certain instances, the FLT3 binding protein is 5 kDa or less if it is a peptide or small molecule entity.

In other embodiments, the FLT3 binding proteins described herein comprise small molecule entity (SME) binders for FLT3. SME binders are small molecules averaging about 500 to 2000 Da in size and are attached to the FLT3 binding proteins by known methods, such as sortase ligation or conjugation. In these instances, the FLT3 binding protein comprises a domain comprising a sortase recognition sequence, e.g., LPETG (SEQ ID No. 376). To attach a SME binder to FLT3 binding protein comprising a sortase recognition sequence, the protein is incubated with a sortase and a SME binder whereby the sortase attaches the SME binder to the recognition sequence. In yet other embodiments, the FLT3 binding proteins described herein comprise a knottin peptide for binding FLT3. Knottins are disulfide-stabilized peptides with a cysteine knot scaffold and have average sizes about 3.5 kDa. Knottins have been contemplated for binding to certain tumor molecules such as FLT3. In further embodiments, the FLT3 binding proteins described herein comprise a natural FLT3 ligand.

In some embodiments, the FLT3 binding protein comprises more than one domain and are of a single-polypeptide design with flexible linkage of the domains. This allows for facile production and manufacturing of the FLT3 binding proteins as they can be encoded by single cDNA molecule to be easily incorporated into a vector. Further, in some embodiments where the FLT3 binding proteins described herein are a monomeric single polypeptide chain, there are no chain pairing issues or a requirement for dimerization. It is contemplated that, in such embodiments, the FLT3 binding proteins described herein have a reduced tendency to aggregate.

In the FLT3 binding proteins comprising more than one domain, the domains are linked by one or more internal linker. In certain embodiments, the internal linkers are "short," i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, the internal linkers are "long," i.e., consist of 15, 20 or 25 amino acid residues. In some embodiments, the internal linkers consist of about 3 to about 15, for example 8, 9 or 10 contiguous amino acid residues. Regarding the amino acid composition of the internal linkers, peptides are selected with properties that confer flexibility to the FLT3 binding proteins, do not interfere with the binding domains as well as resist cleavage from proteases. For example, glycine and serine residues generally provide protease resistance. Examples of internal linkers suitable for linking the domains in the FLT3 binding proteins include but are not limited to (GS)n (SEQ ID No. 377), (GGS)n (SEQ ID No. 378), (GGGS)n (SEQ ID No. 379), (GGSG)n (SEQ ID No. 380), (GGSGG)n (SEQ ID No. 381), (GGGGS)n (SEQ ID No. 382), (GGGGG)n (SEQ ID No. 383), or (GGG)n (SEQ ID No. 384), wherein n is 1, 2, 3, 4, 5, 6, 7, 8, 9, or 10. In one embodiment, the linker is (GGGGSGGGGSGGGGSGGGGS) (SEQ ID No. 385), (GGGGSGGGGSGGGGS) (SEQ ID No. 386), or (GGGGSGGGS) (SEQ ID No. 387).

In some cases, where the FLT3 binding protein comprises more than one domain, the domains within the FLT3 binding proteins are conjugated using an enzymatic site-specific conjugation method which involves the use of a mammalian or bacterial transglutaminase enzyme. Microbial transglutaminases (mTGs) are versatile tools in modern research and biotechnology. The availability of large quantities of relatively pure enzymes, ease of use, and lack of regulation by calcium and guanosine-5'-triphosphate (GTP) has propelled mTG to be the main cross-linking enzyme used in both the food industry and biotechnology. Currently, mTGs are used in many applications to attach proteins and peptides to small molecules, polymers, surfaces, DNA, as well as to other proteins. See e.g., Pavel Strp, Veracity of microbial transglutaminase, Bioconjugate Chem. 25, 5, 855-862.

In some examples are provided FLT3 binding proteins comprising more than one domain, wherein one of the domains comprises an acceptor glutamine in a constant region, which can then be conjugated to another domain via a lysine-based linker (e.g., any primary amine chain which is a substrate for TGase, e.g. comprising an alkylamine, oxoamine) wherein the conjugation occurs exclusively on one or more acceptor glutamine residues present in the targeting moiety outside of the antigen combining site (e.g., outside a variable region, in a constant region). Conjugation thus does not occur on a glutamine, e.g. an at least partly surface exposed glutamine, within the variable region. The FLT3 binding protein, in some examples, is formed by reacting one of the domains with a lysine-based linker in the presence of a TGase.

In some embodiments, where one or more domains within the FLT3 binding proteins are directly joined, a hybrid vector is made where the DNA encoding the directly joined domains are themselves directly ligated to each other. In some embodiments, where linkers are used, a hybrid vector is made where the DNA encoding one domain is ligated to the DNA encoding one end of a linker moiety and the DNA encoding another domain is ligated to the other end of the linker moiety.

In some embodiments, the FLT3 binding protein is a single chain variable fragments (scFv), single-domain antibody such as a heavy chain variable domain (VH), a light chain variable domain (VL) and a variable domain (VHH) of camelid derived single domain antibody. In other embodiments, the FLT3 binding protein is a non-Ig binding domain, i.e., an antibody mimetic, such as anticalins, affilins, affibody molecules, affimers, affitins, alphabodies, avimers, DARPins, fynomers, kunitz domain peptides, and monobodies. In further embodiments, the FLT3 binding protein is a ligand or peptide that binds to or associates with FLT3. In yet further embodiments, the FLT3 binding protein is a knottin. In yet further embodiments, the binding domain to FLT3 is a small molecular entity.

In certain embodiments, the FLT3 binding proteins according to the present disclosure may be incorporated into FLT3 targeting trispecific proteins. In some embodiments, the trispecific proteins comprise a CD3 binding domain, a half-life extension domain, and an FLT3 binding domain according to this disclosure. In some embodiments, the FLT3 binding trispecific protein comprises a trispecific antibody.

Multispecific FLT3 Targeting Proteins, Such as FLT3 Targeting Trispecific Proteins (Also Referred to Herein as FLT3 Targeting TriTAC™ Proteins or Molecules)

In one aspect is described herein a multispecific or a multivalent protein comprising an FLT3 binding protein according to the present disclosure. In some embodiments, the multispecific protein further comprises a domain which specifically binds to a CD3. In some embodiments, the multispecific protein further comprises a domain which specifically binds to human CD3. In some embodiments, the multispecific protein further comprises a domain which specifically binds to CD3-gamma. In some embodiments, the multispecific protein further comprises a domain which specifically binds to CD3-delta. In some embodiments, the multispecific protein further comprises a domain which specifically binds to CD3-epsilon.

In additional embodiments, the multispecific protein further comprises a domain which specifically binds to the T cell receptor (TCR). In some embodiments, the multispecific protein further comprises a domain which specifically binds the alpha chain of the TCR. In some embodiments, the multispecific protein further comprises a domain which specifically binds the beta chain of the TCR.

In certain embodiments, the CD3 binding domain of the multispecific proteins exhibits not only potent CD3 binding affinities with human CD3, but shows excellent cross reactivity with the respective cynomolgus monkey CD3 proteins. In some instances, the CD3 binding domain of the multispecific proteins are cross-reactive with CD3 from cynomolgus monkey. In certain instances, human:cynomolgous KD (hKd: cKd) ratios for CD3 binding are between 20:1 and 1:2.

In some embodiments, the CD3 binding domain of the multispecific protein is any domain that binds to CD3 including but not limited to domains from a monoclonal antibody, a polyclonal antibody, a recombinant antibody, a human antibody, a humanized antibody, or antigen binding fragments of the CD3 binding antibodies, such as single domain antibodies (sdAb), Fab, F(ab')2, and Fv fragments, fragments comprised of one or more CDRs, single-chain antibodies (e.g., single chain Fv fragments (scFv), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some instances, it is beneficial for the CD3 binding domain to be derived from the same species in which the multispecific protein comprising a single domain serum albumin binding protein described herein will ultimately be used in. For example, for use in humans, it may be beneficial for the CD3 binding domain of the multispecific protein comprising an FLT3 binding protein described herein to comprise human or humanized residues from the antigen binding domain of an antibody or antibody fragment. Exemplary amino acid sequence for the CD3 binding domain of a multispecific (e.g., trispecific) FLT3 targeting protein of this disclosure is provided as SEQ ID No. 373.

In some embodiments, the serum albumin binding domain (also referred to herein as the half-life extension domain) of a multispecific protein comprising an FLT3 binding protein as described herein can be any domain that binds to serum albumin including but not limited to domains from a monoclonal antibody, a polyclonal antibody, a recombinant antibody, a human antibody, a humanized antibody. In some embodiments, the serum albumin binding domain is a single chain variable fragments (scFv), single-domain antibody such as a heavy chain variable domain (VH), a light chain variable domain (VL) and a variable domain (VHH) of camelid derived sdAb, or antigen binding fragments of the HSA binding antibodies, such as Fab, F(ab')2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain, peptide, ligand or small molecule entity specific for serum albumin. In certain embodiments, the HSA binding domain is a single-domain antibody. In other embodiments, the serum albumin binding domain is a peptide. In further embodiments, the serum albumin binding domain is a small molecule. It is contemplated that the serum albumin binding domain of the multispecific binding protein comprising a single chain variable fragment CD3 binding protein is fairly small and no more than 25 kD, no more than 20 kD, no more than 15 kD, or no more than 10 kD in some embodiments. In certain instances, the serum albumin binding is 5 kD or less if it is a peptide or small molecule entity. Exemplary amino acid sequence for a serum albumin binding domain of a multispecific (e.g., trispecific) FLT3 targeting protein of this disclosure is provided as SEQ ID No. 372.

The half-life extension domain of a multispecific binding protein as described herein, comprising a single chain variable fragment CD3 binding protein provides for altered pharmacodynamics and pharmacokinetics of the single chain variable fragment CD3 binding protein itself. As above, the half-life extension domain extends the elimination half-time. The half-life extension domain also alters pharmacodynamic properties including alteration of tissue distribution, penetration, and diffusion of the single chain variable fragment CD3 binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the multispecific binding protein comprising a single chain variable fragment CD3 binding protein, resulting in reduced side effects, such as reduced off-target, such as non-tumor cell cytotoxicity.

The half-life extension domain of a multispecific binding protein as described herein, comprising an FLT3 binding domain provides for altered pharmacodynamics and pharmacokinetics of FLT3 binding domain itself. As above, the half-life extension domain extends the elimination half-time. The half-life extension domain also alters pharmacodynamic properties including alteration of tissue distribution, penetration, and diffusion of the FLT3 binding domain. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the multispecific binding protein comprising an FLT3 binding domain, resulting in reduced side effects, such as reduced off-target, such as non-tumor cell cytotoxicity.

Further, the binding affinity of the half-life extension domain, in some embodiments, is selected so as to target a specific elimination half-time in a multispecific binding protein comprising an FLT3 binding protein as described herein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include $K_d$ of 10 nM or less (high), between 10 nM and 100 nM (medium), and greater than 100 nM (low). As above, binding affinities to serum albumin are determined by known methods such as Surface Plasmon Resonance (SPR).

An FLT3 targeting multispecific protein of this disclosure, in certain embodiments, comprises (A) a first domain which binds to a CD3; (B) a second domain which is an half-life extension domain; and (C) a third domain which is an FLT3 binding protein as described herein. In certain embodiments, the first domain comprises an scFv that specifically binds the CD3. The CD3 protein comprises, for instance, a human CD3 protein. In certain embodiments, the second domain comprises an sdAb that specifically binds a bulk serum protein. In some instances, the bulk serum protein is albumin, such as, a serum albumin, such as, a human serum albumin.

The domains (A), (B), and (C), are, in some embodiments, linked via linkers L1 and L2, in any one of the following orientations: $H_2N$-(A)-L1-(C)-L2-(B)-COOH, $H_2N$-(B)-L1-(A)-L2-(C)-COOH, $H_2N$-(C)-L1-(B)-L2-(A)-COOH, $H_2N$-(C)-L1-(A)-L2-(B)-COOH, $H_2N$-(A)-L1-(B)-(C)-L2-COOH, or $H_2N$-(B)-(C)-(A)-COOH.

An FLT3 targeting multispecific protein of this disclosure, in some embodiments, comprises an amino acid sequence that is at least about 70% to at least about 100% identical to a sequence selected from the group consisting of SEQ ID Nos. 196-272, and 391-392. In some embodiments, an FLT3 targeting multispecific protein of this disclosure, in some embodiments, comprises an amino acid sequence that is at least about 70%, at least about 75%, at least about 76%, at least about 77%, about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, to at least about 100% identical to a sequence selected from the group consisting of SEQ ID Nos. 196-272, and 391-392.

An FLT3 targeting multispecific protein of this disclosure, in some embodiments, comprises an $EC_{50}$ of about 0.5 pM to about 6000 pM, such as such as an $EC_{50}$ from about 0.5 pM to about 1500 pM, about 1 pM to about 4000 pM, about 10 pM to about 2000 pM, about 20 pM to about 1000 pM, about 30 pM to about 40 pM to about 500 pM, or about 50 pM to about 100 pM, in a T cell dependent cellular cytotoxicity (TDCC) assay that measures the potency of the multispecific protein in T cell mediated killing of cells, such as leukemia or lymphoma cells (see, e.g., TDCC $EC_{50}$ values provided in Table 5 and Table 6). In some embodiments, the $EC_{50}$ in the TDCC assay is from about 0.5 pM to about 6000 pM, such as from about 0.5 pM to about 35 pM.

Conditionally Active Multispecific FLT3 Targeting Proteins, Such as Conditionally Active FLT3 Targeting Trispecific Proteins (Also Referred to Herein as FLT3 Targeting ProTriTAC™ or Protrispecific Proteins or Molecules)

Figure 28:
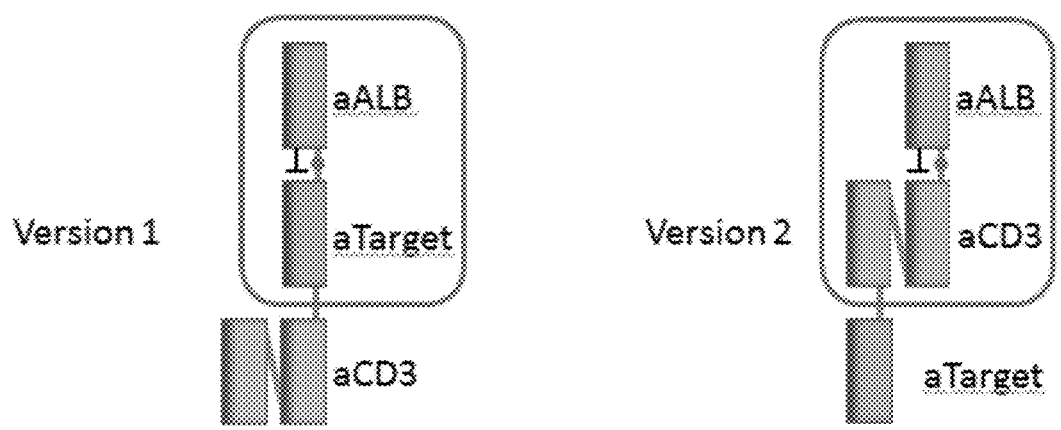
FIG. 28 provides exemplary arrangements of various domains of an FLT3 targeting conditionally active binding protein of this disclosure. The aTarget domain depicted in FIG. 28 Version 1 and Version 2 corresponds to an FLT3 binding domain as described herein.

One embodiment of this disclosure provides a conditionally active multispecific protein comprising an FLT3 binding domain as disclosed herein (for example, in some embodiment this disclosure provides an FLT3 targeting protrispecific/ProTriTAC™ protein comprising an FLT3 binding domain of this disclosure). Examples are illustrated in FIG. 28. In some embodiments, the conditionally active multispecific protein further comprises a domain which specifically binds to a CD3 and a binding moiety which specifically binds to a bulk serum protein, such as a human serum albumin. In some embodiments, the binding moiety is capable of masking the interaction of the FLT3 binding domain or the CD3 binding domain, to their targets. In some embodiments, a binding moiety of this disclosure comprises a masking moiety and a cleavable linker, such as a protease cleavable linker. In some embodiments, the masking moiety comprises a modified non-CDR loop sequence and a non-cleavable linker. The binding moiety is capable of synergistically expanding a therapeutic window of a conditionally active FLT3 targeting protrispecific protein, by both steric masking and specific masking. In some embodiments, the binding moiety combines both steric masking (for example, via binding to a bulk serum albumin) and specific masking (for example, via non-CDR loops binding to the CDRs of an anti-FLT3 domain or an anti-CD3 scFv domain). In some cases, modifying the non-CDR loops within the binding moiety does not affect albumin binding. The protease cleavable linker, in some cases, enables activation of an FLT3 targeting protrispecific protein in a single proteolytic event, thereby allowing more efficient conversion of the protrispecific molecule in tumor microenvironment. Further, tumor-associated proteolytic activation, in some cases, reveals active T cell engager with minimal off-tumor activity after activation. The present disclosure, in some embodiments, provides a half-life extended T cell engager format (ProTriTAC™) comprising an FLT3 binding moiety as described herein, which in some cases represents a new and improved approach to engineer conditionally active T cell engagers.

The half-life of the FLT3 binding domain in a conditionally active protrispecific format is, in some embodiments, extended in systemic circulation by using the binding moiety as described above which acts as a safety switch that keeps the multispecific protein in the pro format in an inert state until it reaches the tumor microenvironment where it is conditionally activated by cleavage of the linker and is able to bind its target antigen(s). The safety switch, in certain instances, provides several advantages: some examples including (i) expanding the therapeutic window of the conditionally active FLT3 targeting protein; (ii) reducing target-mediated drug disposition by maintaining the conditionally active FLT3 targeting protein in systemic circulation; (iii) reducing the concentration of undesirable activated protein in systemic circulation, thereby minimizing the spread of chemistry, manufacturing, and controls related impurities, e.g., pre-activated drug product, endogenous viruses, host-cell proteins, DNA, leachables, anti-foam, antibiotics, toxins, solvents, heavy metals; (iv) reducing the concentration of undesirable activated proteins in systemic circulation, thereby minimizing the spread of product related impurities, aggregates, breakdown products, product variants due to: oxidation, deamidation, denaturation, loss of C-term Lys in MAbs; (v) preventing aberrant activation in circulation; (vi) reducing the toxicities associated with the leakage of activated species from diseased tissue or other pathophysiological conditions, e.g., tumors, autoimmune diseases, inflammations, viral infections, tissue remodeling events (such as myocardial infarction, skin wound healing), or external injury (such as X-ray, CT scan, UV exposure); and (vii) reducing non-specific binding of the conditionally active FLT3 targeting protein. Furthermore, post-activation, or in other words post breaking of the safety switch, the conditionally active FLT3 targeting protein is separated from the safety switch which provided extended half-life, and thus is cleared from circulation.

In some embodiments, the conditionally active FLT3 targeting protein format gives the FLT3 binding domain a significantly longer serum half-life and reduces the likelihood of its undesirable activation in circulation, thereby producing a "biobetter" version.

A binding moiety as described herein comprises at least one non-CDR loop. In some embodiments, a non-CDR loop provides a binding site for binding of the binding moiety to an FLT3 binding domain of this disclosure. In some cases, the binding moiety masks binding of the FLT3 binding domain to its target antigen, e.g., via steric occlusion, via specific intermolecular interactions, or a combination of both.

Figure 29:
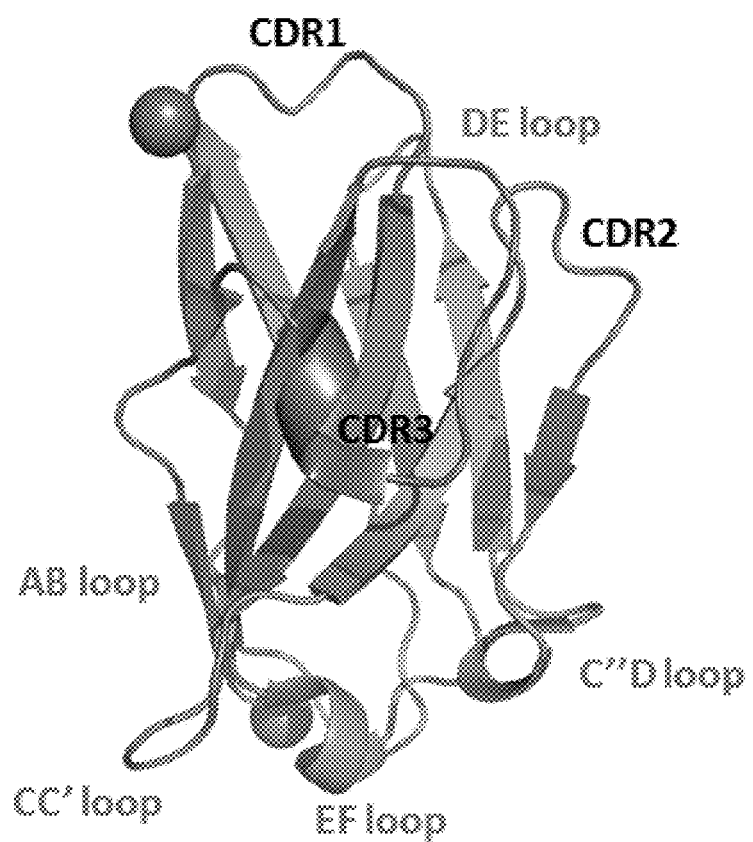
FIG. 29 illustrates a variable domain of an exemplary immunoglobulin domain, comprising complementarity determining regions (CDR1, CDR2, and CDR3), and non-CDR loops connecting the beta strand (AB, CC', C" D, EF, and DE).

In some embodiments, a binding moiety as described herein further comprise complementarity determining regions (CDRs), for instance, specific for binding a bulk serum protein (e.g., a human serum albumin). In some instances, a binding moiety of this disclosure is a domain derived from an immunoglobulin molecule (Ig molecule). The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. As shown in FIG. 29, a variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CHL CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I(Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain.

In some embodiments, the non-CDR loop is modified to generate an antigen binding site specific for a bulk serum protein, such as albumin. It is contemplated that various techniques can be used for modifying the non-CDR loop, e.g., site-directed mutagenesis, random mutagenesis, insertion of at least one amino acid that is foreign to the non-CDR loop amino acid sequence, amino acid substitution. An antigen peptide is inserted into a non-CDR loop, in some examples. In some examples, an antigenic peptide is substituted for the non-CDR loop. The modification, to generate an antigen binding site, is in some cases in only one non-CDR loop. In other instances, more than one non-CDR loop are modified. For instance, the modification is in any one of the non-CDR loops shown in FIG. 29, i.e., AB, CC', C" D, EF, and D-E. In some cases, the modification is in the DE loop. In other cases the modifications are in all four of AB, CC', C"-D, E-F loops. In certain examples, the binding moieties described herein are bound to the FLT3 binding domain via their AB, CC', C" D, or EF loop and are bound to a bulk-serum protein, such as albumin, via their B-C, C'-C", or F-G loop. In certain examples, the binding moiety is bound to the FLT3 binding domain via its AB, CC', C" D, and EF loop and is bound to a bulk-serum protein, such as albumin, via its BC, C'C", and FG loop. In certain examples, the binding moiety is bound to the FLT3 binding domain via one or more of AB, CC', C" D, and E-F loop and is bound to a bulk-serum protein, such as albumin, via one or more of BC, C'C", and FG loop. In certain examples, the binding moiety is bound to a bulk serum protein, such as albumin, via its AB, CC', C" D, or EF loop and is bound to the FLT3 binding domain via its BC, C'C", or FG loop. In certain examples, the binding moiety is bound to a bulk serum protein, such as albumin, via its AB, CC', C" D, and EF loop and is bound to the FLT3 binding domain via its BC, C'C", and FG loop. In certain examples, the binding moiety of the first embodiment is bound to a bulk serum protein, such as albumin, via one or more of AB, CC', C" D, and E-F loop and is bound to the FLT3 binding protein, via one or more of BC, C'C", and FG loop.

The bulk serum protein comprises, for example, albumin, fibrinogen, or a globulin. In some embodiments, the binding moieties are engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the binding moieties comprise a binding site for the bulk serum protein. In some embodiments, the CDRs within the binding moieties provide a binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the binding moieties comprise a binding site for an immunoglobulin light chain. In some embodiments, the CDRs provide a binding site for the immunoglobulin light chain. The immunoglobulin light chain is, in some examples, an Igκ free light chain or an Igλ free light chain.

The binding moieties are any kinds of polypeptides. For example, in certain instances the binding moieties are natural peptides, synthetic peptides, or fibronectin scaffolds, or engineered bulk serum proteins. In some examples, the binding moieties comprise any type of binding domain, including but not limited to, domains from a monoclonal antibody, a polyclonal antibody, a recombinant antibody, a human antibody, a humanized antibody. In some embodiments, the binding moiety is a single chain variable fragment (scFv), a soluble TCR fragment, a single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

Integration into Chimeric Antigen Receptors (CAR)

The FLT3 binding proteins of the present disclosure can, in certain examples, be incorporated into a chimeric antigen receptor (CAR). An engineered immune effector cell, e.g., a T cell or NK cell, can be used to express a CAR that includes an FLT3 binding protein containing, for example, an anti-FLT3 single domain antibody as described herein. In one embodiment, the CAR including the FLT3 binding protein as described herein is connected to a transmembrane domain via a hinge region, and further a costimulatory domain, e.g., a functional signaling domain obtained from OX40, CD27, CD28, CD5, ICAM-1, LFA-1 (CD11a/CD18), ICOS (CD278), or 4-1BB. In some embodiments, the CAR further comprises a sequence encoding an intracellular signaling domain, such as 4-1BB and/or CD3 zeta.

FLT3 Binding Protein Modifications

The FLT3 binding proteins described herein, including FLT3 binding domains (e.g., an FLT3 binding sdAb of this disclosure) and FLT3 targeting multispecific proteins (e.g., an FLT3 targeting trispecific protein as described herein) encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in the FLT3 binding proteins described herein, including the peptide backbone, the amino acid side-chains, and the amino or carboxyl termini. Certain common peptide modifications that are useful for modification of the FLT3 binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

In some embodiments, derivatives of the FLT3 binding proteins as described herein comprise immunoreactive modulator derivatives and antigen binding molecules comprising one or more modifications.

In some embodiments, the FLT3 binding proteins of the disclosure are monovalent or multivalent bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen).

In some embodiments, the FLT3 binding proteins as set forth above are fused to an Fc region from any species, including but not limited to, human immunoglobulin, such as human IgG1, a human IgG2, a human IgG3, human IgG4, to generate Fc-fusion FLT3 binding proteins. In some embodiments, the Fc-fusion FLT3 binding proteins of this disclosure have extended half-life compared to an otherwise identical FLT3 binding protein. In some embodiments, the Fc-fusion FLT3 binding proteins of this disclosure contain inter alia one or more additional amino acid residue substitutions, mutations and/or modifications, e.g., in the Fc region. which result in a binding protein with preferred characteristics including, but not limited to: altered pharmacokinetics, extended serum half-life.

In some embodiments, such Fc-fused FLT3 binding proteins provide extended half-lives in a mammal, such as in a human, of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-life, in some cases, results in a higher serum titer which thus reduces the frequency of the administration of the FLT3 binding proteins and/or reduces the concentration of the antibodies to be administered. Binding to human FcRn in vivo and serum half-life of human FcRn high affinity binding polypeptides is assayed, in some examples, in transgenic mice or transfected human cell lines expressing human FcRn, or in primates to which the polypeptides with a variant Fc region are administered.

The FLT3 binding proteins, in some cases, are differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications are carried out by techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Various post-translational modifications of the FLT3 binding proteins also encompassed by the disclosure include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the FLT3 binding proteins are, in some cases, modified with a detectable label, such as an enzymatic, fluorescent, radioisotopic or affinity label to allow for detection and isolation of the modulator.

Polynucleotides Encoding FLT3 Binding Proteins

Also provided, in some embodiments, are polynucleotide molecules encoding FLT3 binding proteins described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding a single domain FLT3 binding protein or gene encoding various domains of FLT3 binding proteins comprising more than one domain. In some embodiments, the gene encoding the domains are either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide coding for an FLT3 binding protein as described herein is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described FLT3 binding protein. Examples of expression vectors for expression in *E. coli* are pSKK (Le Gall et al., J Immunol Methods. (2004) 285(1): 111-27) or pcDNA5 (Invitrogen) for expression in mammalian cells.

Thus, the FLT3 binding proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising an anti-FLT3 binding protein described herein, a vector comprising the polynucleotide encoding the polypeptide of the FLT3 binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described FLT3 binding proteins packaged in lyophilized form, or packaged in an aqueous medium.

In some embodiments of the pharmaceutical compositions, the FLT3 binding proteins described herein are encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the FLT3 binding protein is attached to liposomes. In some instances, the FLT3 binding proteins are conjugated to the surface of liposomes. In some instances, the FLT3 binding proteins are encapsulated within the shell of a liposome. In some instances, the liposome is a cationic liposome.

The FLT3 binding proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the FLT3 binding proteins of this disclosure are administered at a dosage of up to 10 mg/kg at a frequency of once a week. In some cases, the dosage ranges from about 1 ng/kg to about 10 mg/kg, for example about 1 ng/kg to about 70 ng/kg, about 1 ng/kg to about 160 ng/kg, about 1 ng/kg to about 200 ng/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 µg/kg, about 0.5 µg/kg to about 5 µg/kg, about 2 µg/kg to about 10 µg/kg, about 7 µg/kg to about 15 µg/kg, about 12 µg/kg to about 25 µg/kg, about 20 µg/kg to about 50 µg/kg, about 35 µg/kg to about 70 µg/kg, about 45 µg/kg to about 80 µg/kg, about 65 µg/kg to about 90 µg/kg, about 85 µg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatment

Also provided in certain embodiments are methods of treating a condition associated with malignant cells expressing FLT3 in a subject comprising administering to a subject in need thereof an effective amount of an FLT3 binding domains or multispecific proteins (including conditionally active multispecific proteins) comprising an FLT3 binding domain of this disclosure, or a CAR comprising an FLT3 binding protein as described herein, or a pharmaceutical composition comprising the same. In some embodiments, the condition is a cancer. In some embodiment the condition is a hematologic malignancy derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), myeloid leukemia, chronic lymphocytic leukemia (CLL), and chronic myelogenous leukemia (CML), chronic myelomonocytic leukemia, undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, marginal zone lymphoma, nodal marginal zone B cell lymphoma, splenic marginal zone lymphoma, follicular lymphoma, diffuse histiocytic lymphoma (DHL), mucosa-associated lymphatic tissue lymphoma, small cell lymphocytic lymphoma, immunoblastic large cell lymphoma, precursor B-lymphoblastic lymphoma, cutaneous T-cell lymphoma (CTLC) (also called mycosis fungoides or Sezary syndrome), intravascular large B-cell lymphoma, lymphomatoid granulomatosis, T cell/histiocyte-rich large B-cell lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphomalymphoplasmactyic lymphoma, and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers.

In some embodiments, the condition is Myelodysplastic syndrome ("MDS") which refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production.

In another aspect, the disclosure provides a method of inhibiting tumor growth or progression in a subject who has malignant cells expressing FLT3, comprising administering to the subject in need thereof an effective amount of an FLT3 binding domains or multispecific proteins comprising an FLT3 binding domain of this disclosure, or a CAR comprising an FLT3 binding protein as described herein, or a pharmaceutical composition comprising the same. In another aspect, the disclosure provides a method of inhibiting metastasis of malignant cells expressing FLT3 in a subject, comprising administering to the subject in need thereof an effective amount of an FLT3 binding domains or multispecific proteins comprising an FLT3 binding domain of this disclosure, or a pharmaceutical composition comprising the same. In another aspect, the disclosure provides a method of inducing tumor regression in a subject who has malignant cells expressing FLT3, comprising administering to the subject in need thereof an effective amount of an FLT3 binding domains or multi specific proteins comprising an FLT3 binding domain of this disclosure, or a pharmaceutical composition comprising the same. In some embodiments, the methods as described herein further comprise administering an effective amount of a second therapeutic agent. In some embodiments, the second therapeutic agent is a biotherapeutic agent, for example, an antibody. In some embodiments, the second therapeutic agent is a cytokine, TNFa (Tumor Necrosis Factor alpha), a PAP (phosphatidic acid phosphatase) inhibitor, an oncolytic virus, a kinase inhibitor, an IDO (Indoleamine-pyrrole 2,3-dioxygenase) inhibitor, a glutaminase GLS1 inhibitor, a CAR (Chimeric Antigen Receptor)-T cell or T cell therapy, a TLR (Toll-Like Receptor) Agonist (e.g., TLR3, TLR4, TLR5, TLR7, TLR9), or a tumor vaccine.

In some embodiments, the FLT3 binding protein of this disclosure or a pharmaceutical composition comprising the same, reduces the growth of tumor cells in vivo when administered to a subject who has tumor cells that express FLT3. Measurement of the reduction of the growth of tumor cells can be determined by multiple different methodologies well known in the art. Nonlimiting examples include direct measurement of tumor dimension, measurement of excised tumor mass and comparison to control subjects, measurement via imaging techniques (e.g., CT or Mill) that may or may not use isotopes or luminescent molecules (e.g., luciferase) for enhanced analysis, and the like. In specific embodiments, administration of the FLT3 binding proteins of the disclosure or a pharmaceutical composition comprising the same results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the FLT3 binding proteins of the disclosure or a pharmaceutical composition comprising the same results in a reduction of in vivo growth of tumor cells as compared to a control antigen binding agent by about 50-100%, about 75-100% or about 90-100%. In further embodiments, administration of the FLT3 binding proteins of the disclosure or a pharmaceutical composition comprising the same results in a reduction of in vivo growth of tumor cells as compared to a control antigen binding agent by about 50-60%, about 60-70%, about 70-80%, about 80-90%, or about 90-100%.

In some embodiments, the FLT3 binding proteins of the present disclosure are administered to treat a neoplastic condition. Neoplastic conditions, in some embodiments, are benign or malignant; solid tumors or other blood neoplasia; and, in some embodiments, are selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer including triple negative breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterior unveal melanoma, rare hematologic disorders, renal metastatic cancer, rhabdoid tumor, rhabdomyosarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In certain embodiments the FLT3 binding proteins of the present disclosure are used as a front line therapy and administered to subjects who have not previously been treated for the cancerous condition. In other embodiments the FLT3 binding proteins of the present disclosure are used to treat subjects that have previously been treated (with an FLT3 binding protein of this disclosure or with other anticancer agent) and have relapsed or determined to be refractory to the previous treatment. In some embodiments the FLT3 binding proteins of the present disclosure are used to treat subjects that have recurrent tumors. In some aspects, the FLT3 binding proteins of the present disclosure are administered to treat a proliferative disorder comprising a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In some embodiments, the FLT3 binding proteins of the present disclosure are administered to a subject suffering from melanoma. In some embodiments, the FLT3 binding proteins of the present disclosure are used to diagnose, monitor, treat or prevent melanoma. The term "melanoma," as used herein, includes all types of melanoma including, but not limited to, primary melanoma, malignant melanoma, cutaneous melanoma, extracutaneous melanoma, superficial spreading melanoma, polypoid melanoma, melanocarcinomas, melano epitheliomas, melano sarcomas, melanoma in situ, nodular malignant melanoma, lentigo maligna melanoma, lentiginous melanoma, lentiginous malignant melanoma, mucosal lentiginous melanoma, mucosal melanoma, acral lentiginous melanoma, soft tissue melanoma, ocular melanoma, invasive melanoma, familial atypical mole and melanoma (FAM-M) syndrome, desmoplastic malignant melanoma or uveal melanoma. In some embodiments, possible indications for administration of the FLT3 binding proteins of this disclosure or pharmaceutical compositions comprising the same are tumorous diseases especially epithelial cancers/carcinomas such as breast cancer, colon cancer, prostate cancer, head and neck cancer, skin cancer, cancers of the genito-urinary tract, e.g., ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivatory glands and cancer of the thyroid gland. In some embodiments, the administration of the FLT3 binding proteins of this disclosure or pharmaceutical compositions comprising the same is indicated for minimal residual disease, such as early solid tumor, advanced solid tumor or metastatic solid tumor, which is characterized by the local and non-local reoccurrence of the tumor caused by the survival of single cells.

In selected aspects an FLT3 binding proteins of the disclosure is incorporated into a chimeric antigen receptors (CAR) and the FLT3 CAR is administered in a CAR based therapy effective at treating a cancer, such as: a hematologic malignancy derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., AML; epithelial cancers/carcinomas such as breast cancer; colon cancer, prostate cancer; head and neck cancer; skin cancer; cancers of the genito-urinary tract, e.g., ovarian cancer, endometrial cancer, cervix cancer and kidney cancer; lung cancer; gastric cancer; cancer of the small intestine; liver cancer; pancreas cancer; gall bladder cancer; cancers of the bile duct; esophagus cancer; cancer of the salivatory glands and cancer of the thyroid gland; small cell lung cancer; non-small cell lung cancer (e.g., squamous cell non-small cell lung cancer or squamous cell small cell lung cancer) and large cell neuroendocrine carcinoma (LCNEC).

A chimeric antigen receptor is generally an artificially constructed hybrid protein or polypeptide containing or comprising an antigen binding domain of an antibody linked to a signaling domain (e.g., T-cell signaling or T-cell activation domains). In some embodiments, CARs comprising the FLT3 binding proteins of the present disclosure have the ability to redirect the specificity and reactivity of sensitized lymphocytes (e.g., T-cells) toward FLT3 positive target cells in a non-WIC-restricted manner by exploiting the antigen-binding properties of antibodies or antigen binding fragments thereof. The non-WIC-restricted antigen recognition gives T-cells expressing FLT3 CARs the ability to recognize tumorigenic FLT3 independent of antigen processing, thus bypassing a major mechanism of tumor escape. Moreover, when expressed in T-cells, CARs advantageously do not dimerize with endogenous T cell receptor (TCR) alpha and beta chains. In some embodiments the disclosed FLT3 binding proteins are administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g., carboplatin, cisplatin, oxaliplatin) and/or a taxane (e.g., docetaxel, paclitaxel, larotaxel or cabazitaxel). In another embodiment the disclosed FLT3 CAR treatments are effective at treating ovarian cancer, including ovarian-serous carcinoma and ovarian-papillary serous carcinoma.

In another embodiment the FLT3 binding proteins of the disclosure, the FLT3 CAR, or the FLT3 sensitized lymphocytes, or any combination thereof are used in maintenance therapy to reduce or eliminate the chance of tumor recurrence following the initial presentation of the disease. In some cases, the disorder has been treated and the initial tumor mass eliminated, reduced or otherwise ameliorated so the patient is asymptomatic or in remission. At such time the subject is administered pharmaceutically effective amounts of the disclosed the FLT3 binding proteins of the disclosure, the FLT3 CAR, or the FLT3 sensitized lymphocytes, or any combination thereof one or more times regardless of if there is little or no indication of disease using standard diagnostic procedures. In some embodiments, the FLT3 binding proteins of the disclosure, the FLT3 CAR, or the FLT3 sensitized lymphocytes, or any combination thereof is administered on a regular schedule over a period of time, such as weekly, every two weeks, monthly, every six weeks, every two months, every three months every six months or annually, for example, to reduce the potential of disease recurrence. Moreover such treatments are in some embodiments continued for a period of weeks, months, years or even indefinitely depending on the patient response and clinical and diagnostic parameters.

In yet another embodiment, the FLT3 binding proteins of the disclosure, the FLT3 CAR, or the FLT3 sensitized lymphocytes, or any combination thereof are used to prophylactically or as an adjuvant therapy to prevent or reduce the possibility of tumor metastasis following a debulking procedure." As used in the present disclosure a "debulking procedure," is means any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. In some embodiments, at appropriate times, the FLT3 binding proteins of the disclosure, the FLT3 CAR, or the FLT3 sensitized lymphocytes, or any combination thereof are administered as suggested by clinical, diagnostic or theranostic procedures to reduce tumor metastasis. In some embodiments, the dosing regimen is accompanied by appropriate diagnostic or monitoring techniques that allow it to be modified.

Yet other embodiments of the disclosure comprise administering the FLT3 binding protein of the disclosure, the FLT3 CAR, or the FLT3 sensitized lymphocytes, or any combination thereof to subjects that are asymptomatic but at risk of developing a proliferative disorder. That is, in some embodiments, the FLT3 binding protein of the disclosure, the FLT3 CAR, or the FLT3 sensitized lymphocytes, or any combination thereof are used in preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical observation or through accepted clinical practices.

In some embodiments of the methods described herein, the FLT3 binding proteins, or compositions as described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (y-rays, X-rays, and/or the directed delivery of radioisotopes, microwaves, UV radiation and the like), gene therapies (e.g., antisense, retroviral therapy and the like) and other immunotherapies. In some embodiments, an FLT3 binding protein as described herein is administered in combination with anti-diarrheal agents, anti-emetic agents, analgesics, opioids and/or non-steroidal anti-inflammatory agents. In some embodiments, an FLT3 binding protein as described herein is administered in combination with anti-cancer agents. Nonlimiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, the FLT3 binding protein of the present disclosure is used in combination with gemcitabine. In some embodiments, the FLT3 binding protein as described herein is administered before, during, or after surgery.

The modality of administration of an FLT3 binding protein as described herein (e.g., an FLT3 targeting trispecific protein) or a pharmaceutical composition comprising the same, is, in some embodiment, in accord with known methods, e.g., injection or infusion by subcutaneous, intravenous, intraperitoneal, intracerebral, intradermic, intramuscular, intraocular, intraarterial, intrathecal, or intralesional routes, or by inhalation or by sustained release systems. In some embodiments the an FLT3 binding protein as described herein (e.g., an FLT3 targeting trispecific protein) or a pharmaceutical composition comprising the same is administered by infusion or by bolus injection. In some embodiments an FLT3 binding protein as described herein (e.g., an FLT3 targeting trispecific protein) or a pharmaceutical composition comprising the same is administered through the nose or lung, e.g., as a liquid or powder aerosol (lyophilized). In some embodiments an FLT3 binding protein as described herein (e.g., an FLT3 targeting trispecific protein) or a pharmaceutical composition comprising the same is administered intravenously, parenterally or subcutaneously as desired. When administered systemically, a pharmaceutical composition comprising an FLT3 binding protein as described herein (e.g., an FLT3 targeting trispecific protein) is for instance sterile, pyrogen-free and in a parenterally acceptable solution having due regard for pH, isotonicity, and stability.

Methods of Detection of FLT3 Expression and Diagnosis of FLT3 Associated Cancer

According to another embodiment of the disclosure, kits for detecting expression of FLT3 in vitro or in vivo are provided. The kits include the foregoing FLT3 binding protein (e.g., an FLT3 binding protein containing a labeled anti-FLT3 single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, FLT3 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with an anti-FLT3 single domain antibody as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-FLT3 single domain antibody as disclosed herein; and detecting binding of the antibody to the sample. An increase in binding of the antibody to the sample as compared to binding of the antibody to a control sample confirms the diagnosis of cancer in the subject.

In some examples of the disclosed methods, the FLT3 single domain antibody is directly labeled. In some examples, the methods further include contacting a second antibody that specifically binds the anti-FLT3 single domain antibody with the sample; and detecting the binding of the second antibody. An increase in binding of the second antibody to the sample as compared to binding of the second antibody to a control sample detects a condition in the subject or confirms the diagnosis of cancer in the subject. In some cases, the condition is a hematologic malignancy derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., AML. In some embodiments, the cancer is a neuroendocrine cancer, prostate cancer, lung cancer, stomach cancer, squamous cell carcinoma, pancreatic cancer, cholangiocarcinoma, triple negative breast cancer or ovarian cancer (such as epithelial ovarian carcinoma), or any other type of cancer that expresses FLT3. In some examples, the control sample is a sample from a subject without cancer. In particular examples, the sample is a blood or tissue sample.

In some cases, the antibody that binds (for example specifically binds) FLT3 is directly labeled with a detectable label. In another embodiment, the antibody that binds (for example, specifically binds) FLT3 (the first antibody) is unlabeled and a second antibody or other molecule that can bind the antibody that specifically binds FLT3 is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferon, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, FLT3 can be assayed in a biological sample by a competition immunoassay utilizing FLT3 standards labeled with a detectable substance and an unlabeled antibody that specifically binds FLT3. In this assay, the biological sample, the labeled FLT3 standards and the antibody that specifically bind FLT3 are combined and the amount of labeled FLT3 standard bound to the unlabeled antibody is determined. The amount of FLT3 in the biological sample is inversely proportional to the amount of labeled FLT3 standard bound to the antibody that specifically binds FLT3.

The immunoassays and method disclosed herein can be used for a number of purposes. In one embodiment, the antibody that specifically binds FLT3 may be used to detect the production of FLT3 in cells in cell culture. In another embodiment, the antibody can be used to detect the amount of FLT3 in a biological sample, such as a tissue sample, or a blood or serum sample. In some examples, the FLT3 is cell-surface FLT3. In other examples, the FLT3 is soluble FLT3 (e.g., FLT3 in a cell culture supernatant or soluble FLT3 in a body fluid sample, such as a blood or serum sample).

In one embodiment, a kit is provided for detecting FLT3 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble FLT3 protein or fragment. Kits for detecting a polypeptide will typically comprise a single domain antibody, according to the present disclosure, that specifically binds FLT3. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds FLT3. The instructional materials may be written, in an electronic form (such as a computer diskette or compact disk), may be visual (such as video files), or provided through an electronic network, for example, over the internet, World Wide Web, an intranet, or other network. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting FLT3 in a biological sample generally includes the steps of contacting the biological sample with an antibody which specifically reacts, under immunologically reactive conditions, to an FLT3 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells. See U.S. Pat. No. 5,061,620). Any of the single domain antibodies that bind FLT3, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

Example 1: Screening of Phage Display Library for Identification of FLT3 Binding Domains Llamas were immunized with purified FLT3 protein expressed in Expi293 cells. A phage display library for expression of heavy variable antibody domains was constructed from circulating B cells isolated from the immunized llamas (See van der Linden, de Geus, Stok, Bos, van Wassenaar, Verrips, and Frenken. 2000. J Immunol Methods 240:185-195). Phage clones were screened for binding to FLT3 by expressing llama anti-FLT3 proteins in *E. coli*, preparing periplasmic extracts, and performing colorimetric ELISAs. Seventy unique heavy chain only sequences were identified (SEQ ID Nos. 1-70) that produced a signal in the ELISA screening with human FLT3 protein (data provided in Table 2) relative to control wells that lacked FLT3 protein. The CDR1, CDR2, and CDR3 sequences for these heavy variable domains are listed in Table 1, above.

TABLE 2

Binding of Llama Anti-Human FLT3 Antibodies to Human FLT3 in an ELISA Assay (The numerical values in Table 2 represent the absorbance readings for the colorimetric ELISA)

| Sequence name | ELISA FLT3 | ELISA control | FLT3/control |
|---|---|---|---|
| FLL101 | 1.7 | 0.5 | 3 |
| FLL103 | 3.8 | 0.1 | 28 |
| FLL116 | 1.1 | 0.2 | 5 |
| FLL125 | 2.1 | 0.1 | 17 |
| FLL129 | 2.6 | 0.3 | 9 |
| FLL137 | 1.8 | 0.2 | 8 |
| FLL14 | 1.8 | 0.4 | 5 |
| FLL146 | 0.9 | 0.2 | 4 |
| FLL158 | 2.1 | 0.1 | 17 |
| FLL179 | 3.7 | 0.2 | 17 |
| FLL181 | 3.2 | 0.6 | 5 |
| FLL187 | 1.9 | 0.1 | 18 |
| FLL32 | 1.6 | 0.3 | 5 |
| FLL51 | 2.9 | 0.2 | 16 |
| FLL55 | 2.0 | 0.3 | 6 |
| FLL77 | 4.0 | 0.2 | 22 |
| FLL97 | 1.4 | 0.2 | 7 |
| FLL21 | 3.3 | 0.2 | 20 |
| FLL57 | 1.4 | 0.2 | 9 |
| FLL62 | 0.5 | 0.1 | 5 |
| FLL79 | 0.6 | 0.1 | 4 |
| FLL86 | 1.9 | 0.1 | 15 |
| FLL112 | 3.6 | 0.1 | 34 |
| FLL142 | 4.0 | 0.3 | 15 |
| FLL143 | 4.0 | 0.1 | 47 |
| FLL154 | 4.0 | 0.5 | 8 |
| FLL168 | 4.0 | 0.1 | 28 |
| FLL170 | 4.0 | 0.1 | 38 |
| FLL188 | 4.0 | 0.1 | 51 |
| FLL40 | 4.0 | 0.2 | 21 |
| FLL6 | 3.8 | 0.2 | 16 |
| FLL75 | 4.0 | 0.2 | 19 |
| FLL83 | 3.8 | 0.1 | 35 |
| FLL94 | 4.0 | 0.8 | 5 |
| FLL99 | 3.7 | 0.3 | 13 |
| FLL38 | 4.0 | 0.1 | 45 |
| FLL53 | 3.9 | 0.2 | 17 |
| FLL553 | 3.7 | 0.1 | 37 |
| FLL74 | 3.9 | 0.7 | 6 |
| FLL102 | 3.7 | 0.1 | 37 |
| FLL122 | 4.0 | 0.2 | 26 |
| FLL134 | 1.3 | 0.1 | 15 |
| FLL153 | 1.4 | 0.1 | 15 |
| FLL41 | 0.8 | 0.2 | 5 |
| FLL67 | 2.7 | 0.2 | 12 |
| FLL92 | 4.0 | 0.2 | 25 |
| FLL71 | 1.9 | 0.2 | 9 |
| FLL8 | 3.3 | 0.2 | 14 |
| FLL84 | 1.3 | 0.3 | 4 |
| FLL107 | 3.8 | 0.3 | 11 |
| FLL141 | 4.0 | 0.1 | 28 |
| FLL34 | 4.0 | 0.1 | 39 |
| FLL4 | 3.7 | 0.1 | 43 |
| FLL61 | 3.9 | 0.2 | 25 |
| FLL78 | 4.0 | 0.1 | 27 |
| FLL1 | 3.4 | 0.3 | 11 |
| FLL26 | 2.9 | 0.8 | 4 |
| FLL160 | 0.7 | 0.1 | 9 |
| FLL173 | 0.5 | 0.1 | 6 |
| FLL178 | 4.0 | 0.1 | 48 |
| FLL27 | 4.0 | 0.4 | 10 |
| FLL190 | 4.0 | 0.1 | 43 |
| FLL43 | 2.0 | 0.2 | 12 |
| FLL15 | 2.5 | 0.1 | 31 |
| FLL45 | 4.0 | 0.1 | 28 |
| FLL39 | 1.9 | 0.2 | 12 |
| FLL177 | 4.0 | 0.1 | 54 |
| FLL823 | 3.6 | 0.9 | 4 |
| FLL76 | 0.5 | 0.1 | 5 |
| FLL822 | 4.0 | 0.2 | 17 |

Example 2: Incorporation of FLT3 Binding Heavy Chain Only Single Domain Antibodies into FLT3 Targeting Multispecific Proteins and T Cell Dependent Cellular Cytotoxicity Assays The anti-FLT3 antibody sequences were cloned into DNA constructs for expression of recombinant multispecific proteins (SEQ ID Nos. 196-266). The coding sequences of the multispecific proteins contained a signal peptide for secreted cell expression, one of the anti-FLT3 antibody variable domains (SEQ ID Nos. 1-70), a humanized single domain anti-albumin antibody variable domain (SEQ ID No. 372), a humanized anti-CD3 antibody scFv fragment (SEQ ID No. 373), and a repeat of six histidine sequences (SEQ ID No. 374). A linker sequence was inserted at the junctions between the antibody domains (SEQ ID No. 375). These anti-FLT3/anti-albumin/anti-CD3 multispecific protein constructs were transfected into Expi293 cells (Life Technologies). The amount of multispecific protein in the conditioned media from the transfected Expi293 cells was quantitated using by using an Octet instrument with Protein A tips using a multispecific protein of similar molecular weight to the anti-FLT3/anti-albumin/anti-CD3 proteins as a standard.

The conditioned media were tested in a T-cell dependent cellular cytotoxicity assay (See Nazarian A A, Archibeque I L, Nguyen Y H, Wang P, Sinclair A M, Powers D A. 2015. J Biomol Screen. 20:519-27). In this assay, luciferase labelled MV-4-11 cells (biphenotypic B myelomonocytic leukemia cell line, ATCC® CRL-9591™), which express FLT3, were combined with purified human T cells and a titration of anti-FLT3/anti-albumin/anti-CD3 multispecific protein. If a multispecific protein directs T cells to kill the MV-4-11 cells, the signal in a luciferase assay performed at 48 hours after starting the experiment should decrease. FIGS. 1-11 show graphs of TDCC viability results. $EC_{50}$ values from the TDCC assay are listed in Tables 3 and 4. The most potent molecule had an $EC_{50}$ value of 3 pM. A negative control for the TDCC assays was an anti-GFP/anti-albumin/anti-CD3 protein, and this protein did not direct the T cells to kills the MV-4-11 cells except for slight activity at the highest concentration tested (e.g., FIGS. 10 and 21). As the multispecific proteins contain an anti-albumin domain, TDCC assay were also performed in the presence of 15 mg/ml human serum albumin (HSA) to measure directed T cell killing while bound to albumin (FIGS. 12-21). For all of the FLT3-targeting multispecific proteins tested, the $EC_{50}$ values for directed T cell killing increased in the presence of HSA (Table 3), and also relative to $EC_{50}$ values for directed T cell killing in the presence of bovine serum albumin (BSA) (FIGS. 1-11 and Tables 3 and 4). The anti-albumin domain in the multispecific proteins does not bind to BSA (data not shown).

TABLE 3

$EC_{50}$ Values for Redirected T Cell Killing of MV-4-11 Cells by Anti-FLT3/Anti-Albumin/Anti-CD3 Multispecific Proteins Containing Llama Anti-FLT3 Sequences (n/a indicates insufficient activity to calculate an $EC_{50}$ using the protein concentrations tested)

| FLT3 Binder | $EC_{50}$ (pM) | $EC_{50}$ with HSA (pM) |
|---|---|---|
| FLL21 | 169 | 1182 |
| FLL57 | 384 | 3119 |
| FLL62 | 619 | 6816 |
| FLL1 | 56 | 888 |
| FLL103 | 141 | 1355 |

TABLE 3-continued $EC_{50}$ Values for Redirected T Cell Killing of MV-4-11 Cells by Anti-FLT3/Anti-Albumin/Anti-CD3 Multispecific Proteins Containing Llama Anti-FLT3 Sequences (n/a indicates insufficient activity to calculate an $EC_{50}$ using the protein concentrations tested)

| FLT3 Binder | $EC_{50}$ (pM) | $EC_{50}$ with HSA (pM) |
|---|---|---|
| FLL107 | 11 | 85 |
| FLL112 | 136 | 1330 |
| FLL125 | 330 | 1717 |
| FLL129 | 1168 | n/a |
| FLL137 | 705 | n/a |
| FLL14 | 257 | 1147 |
| FLL141 | 16 | 77 |
| FLL142 | 233 | 984 |
| FLL143 | 70 | 345 |
| FLL146 | 989 | 5678 |
| FLL15 | 108 | 613 |
| FLL154 | 152 | 818 |
| FLL158 | 546 | 1973 |
| FLL160 | n/a | n/a |
| FLL168 | 77 | 383 |
| FLL173 | n/a | n/a |
| FLL177 | n/a | n/a |
| FLL178 | n/a | n/a |
| FLL179 | 176 | 1162 |
| FLL190 | 37 | 239 |
| FLL26 | 136 | 1186 |
| FLL32 | 175 | 1172 |
| FLL34 | 17 | 170 |
| FLL38 | 104 | 814 |
| FLL39 | 1387 | n/a |
| FLL4 | 21 | 181 |
| FLL40 | 69 | 601 |
| FLL43 | 223 | 1478 |
| FLL45 | 407 | n/a |
| FLL51 | 906 | 4649 |
| FLL53 | n/a | n/a |
| FLL55 | 192 | 1077 |
| FLL6 | 201 | 1859 |
| FLL61 | 39 | 424 |
| FLL75 | 224 | 2102 |
| FLL76 | n/a | n/a |
| FLL77 | 224 | 1582 |
| FLL78 | 21 | 194 |
| FLL82 | 1185 | n/a |
| FLL822 | n/a | n/a |
| FLL83 | 134 | 1274 |
| FLL94 | 202 | 2836 |
| FLL99 | 202 | 1746 |

TABLE 4

$EC_{50}$ Values for Redirected T Cell Killing of MV-4-11 Cells by Anti-FLT3/Anti-Albumin/Anti-CD3 Multispecific Proteins Containing Llama Anti-FLT3 Sequences

| FLT3 Binder | $EC_{50}$ with BSA (pM) | $EC_{50}$ with HSA (pM) |
|---|---|---|
| FLL8 | 26 | 680 |
| FLL41 | 380 | 2200 |
| FLL71 | 83 | 1900 |
| FLL92 | 3 | 53 |
| FLL134 | 66 | 1700 |
| FLL153 | 150 | 3000 |

Figure 23:
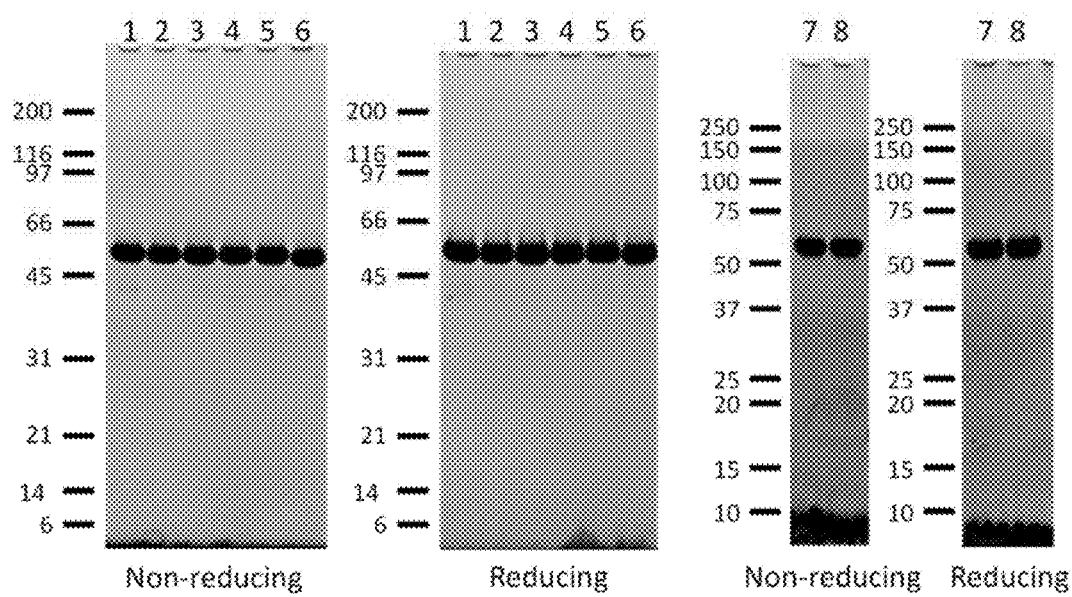
FIG. 23 illustrates an SDS-PAGE of purified humanized anti-FLT3/anti-albumin/anti-CD3 Multispecific Proteins under non-reducing (first and third panels) and reducing (second and fourth panels) conditions. Lanes 1-8 in order: FLH141, FLH107, FLH34, FLH4, FLH78, FLH19C, FLH92a, FLH92b. The migration of molecular weight standards (in kDa) is indicated by the horizontal lines and the numbers to the left of each gel image.
Figure 24:
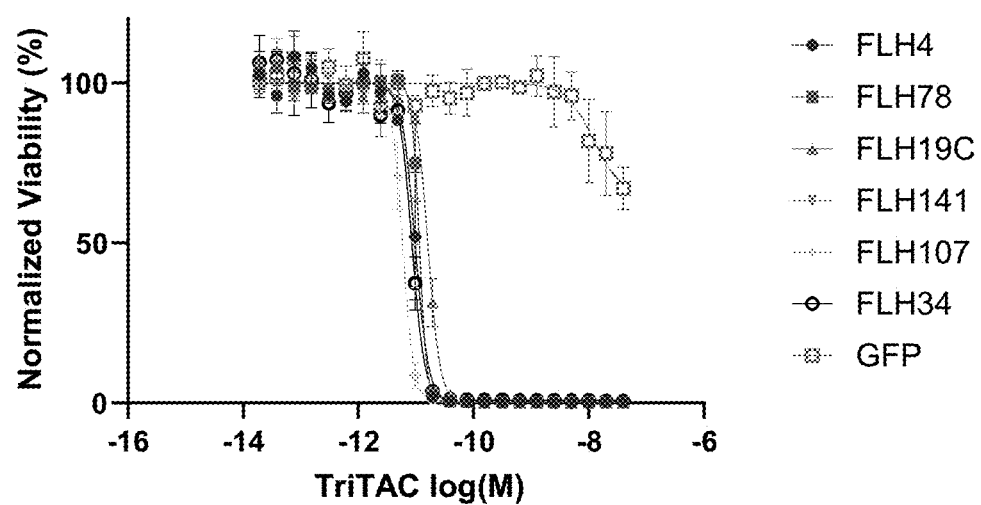
FIG. 24 illustrates the results of a TDCC Assay with MV-4-11 Cells and Anti-CD3/Anti-FLT3 Multispecific Proteins Containing Humanized Anti-FLT3 Sequences FLH4, FLH78, FLH19C, FLH141, FLH107, and FLH34 and with a negative control molecule targeting GFP, ran in the presence of 15 mg/ml BSA. The y-axis shows the normalized percentage of viability of the cancer cells.
Figure 25:
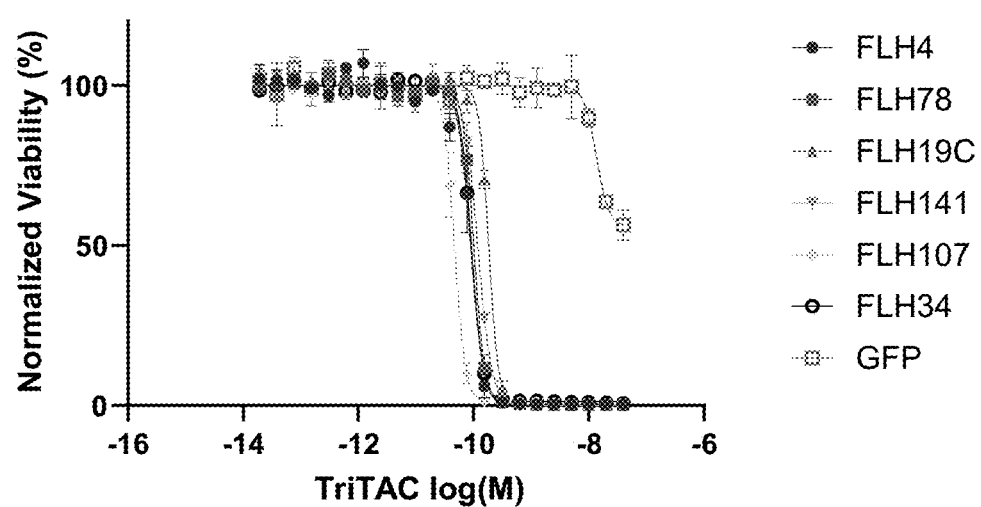
FIG. 25 illustrates the results of a TDCC Assay with MV-4-11 Cells and Anti-CD3/Anti-FLT3 Multispecific Proteins Containing Humanized Anti-FLT3 Sequences FLH4, FLH78, FLH19C, FLH141, FLH107, and FLH34 and with a negative control molecule targeting GFP, ran in the presence of 15 mg/ml HSA.
Figure 26:
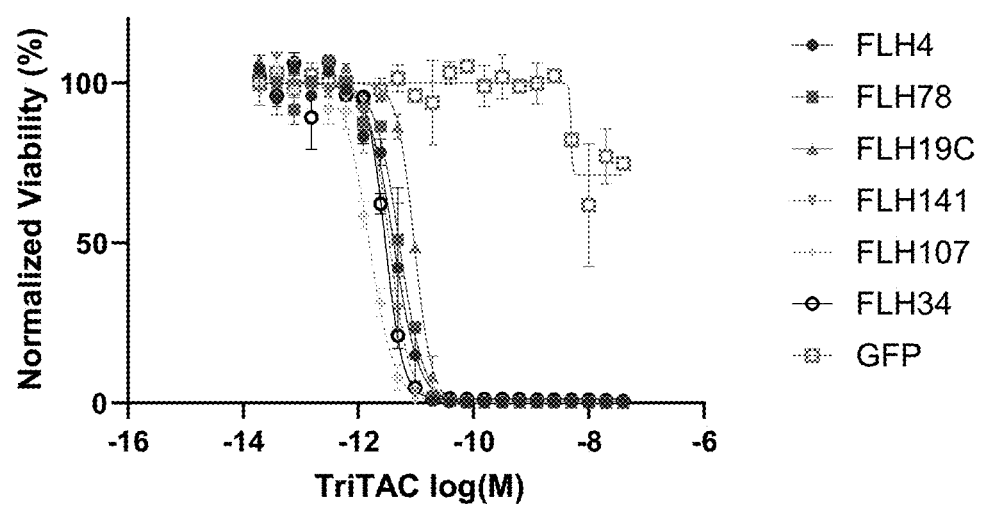
FIG. 26 illustrates the results of a TDCC Assay with EOL1 Cells and Anti-CD3/Anti-FLT3 Multispecific Proteins Containing Humanized Anti-FLT3 Sequences FLH4, FLH78, FLH19C, FLH141, FLH107, and FLH34 and with a negative control molecule targeting GFP, ran in the presence of 15 mg/ml BSA.
Figure 27:
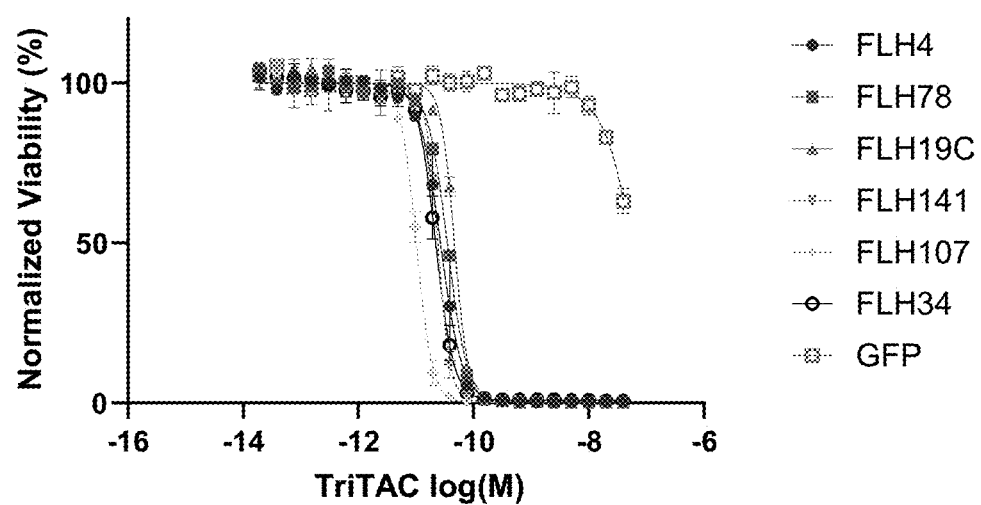
FIG. 27 illustrates the results of a TDCC Assay with EOL1 Cells and Anti-CD3/Anti-FLT3 Multispecific Proteins Containing Humanized Anti-FLT3 Sequences FLH4, FLH78, FLH19C, FLH141, FLH107, and FLH34 and with a negative control molecule targeting GFP. The assay was run in the presence of 15 mg/ml HSA.
Figure 30:
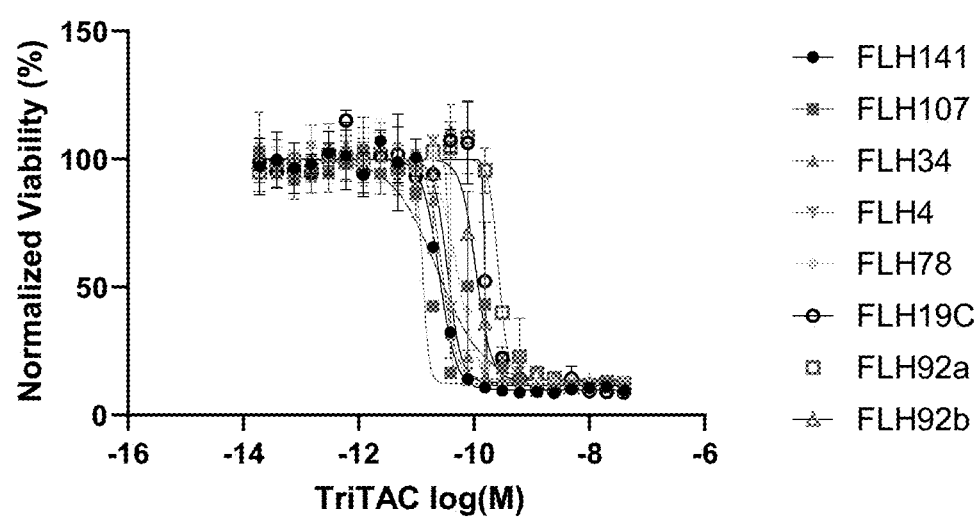
FIG. 30 illustrates the results of a TDCC Assay with THP1 Cells and Anti-CD3/Anti-FLT3 Multispecific Proteins Containing Humanized Anti-FLT3 Sequences FLH141, FLH107, FLH34, FLH4, FLH78, FLH19C, FLH92a, FLH92b, without the addition of any type of albumin.
Figure 31:
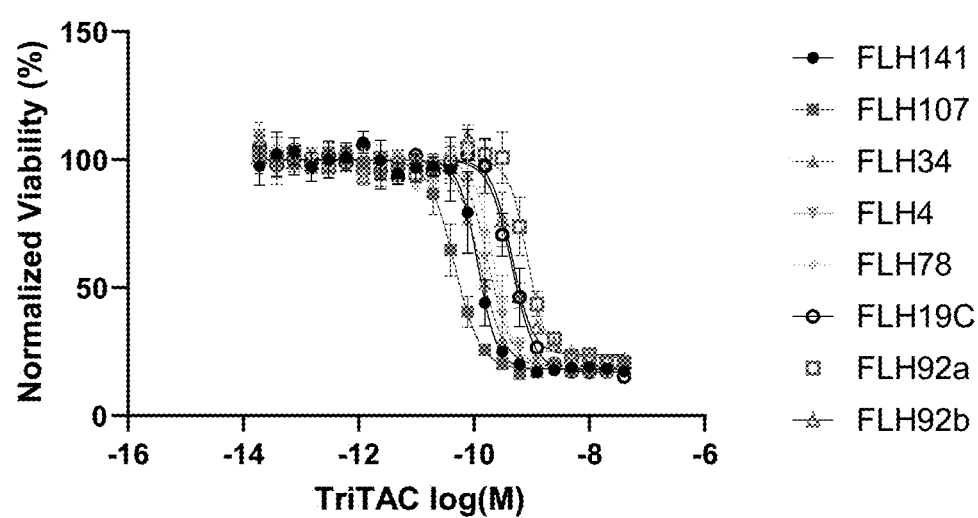
FIG. 31 illustrates the results of a TDCC Assay with THP1 Cells and Anti-CD3/Anti-FLT3 Multispecific Proteins Containing Humanized Anti-FLT3 Sequences FLH141, FLH107, FLH34, FLH4, FLH78, FLH19C, FLH92a, FLH92b, ran in the presence of 15 mg/ml HSA.
Figure 32:
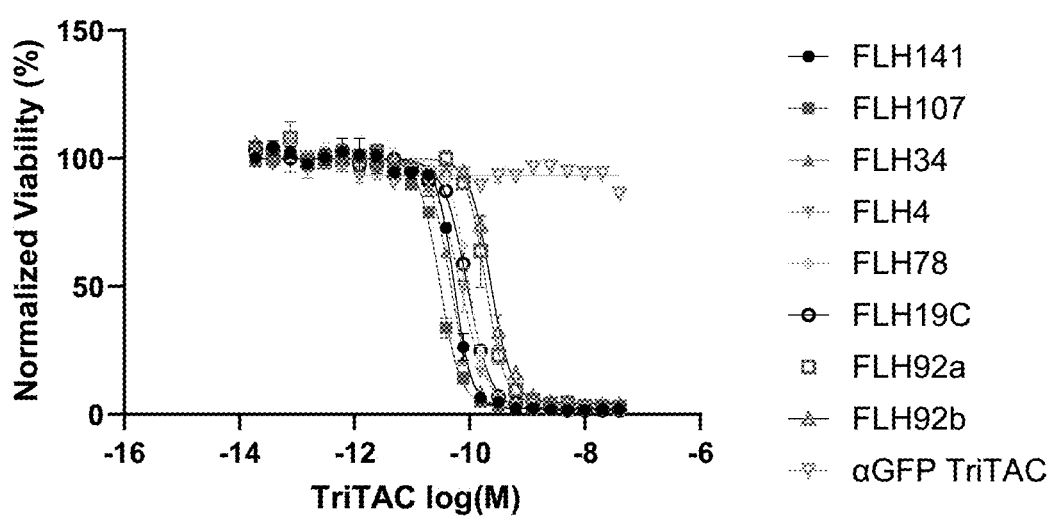
FIG. 32 illustrates the results of a TDCC Assay with MOLM13 Cells and Anti-CD3/Anti-FLT3 Multispecific Proteins Containing Humanized Anti-FLT3 Sequences FLH141, FLH107, FLH34, FLH4, FLH78, FLH19C, FLH92a, FLH92b, and with a negative control molecule targeting GFP, ran in the presence of 15 mg/ml HSA.
Figure 33:
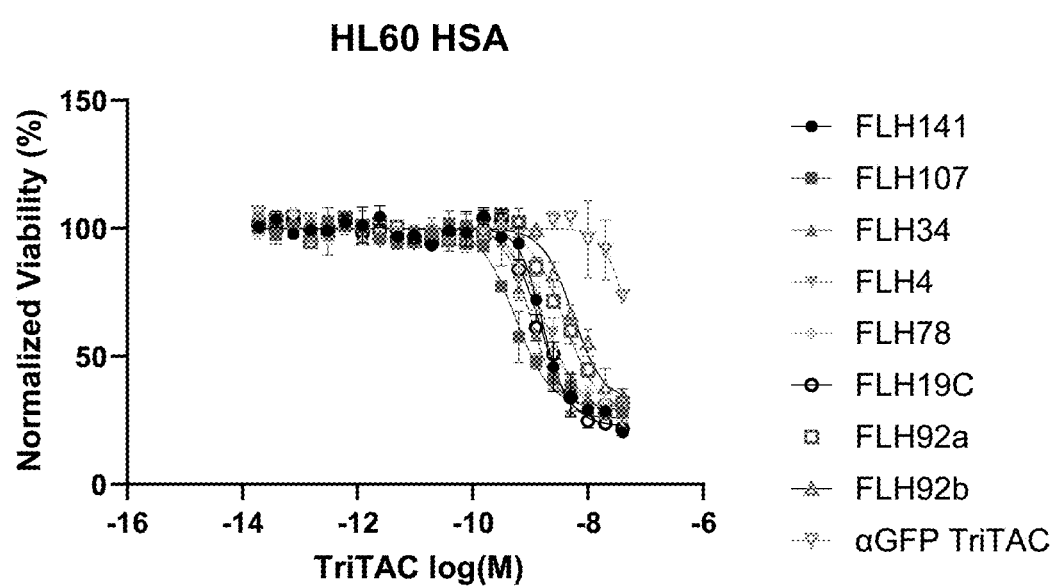
FIG. 33 illustrates the results of a TDCC Assay with HL60 Cells and Anti-CD3/Anti-FLT3 Multispecific Proteins Containing Humanized Anti-FLT3 Sequences FLH141, FLH107, FLH34, FLH4, FLH78, FLH19C, FLH92a, FLH92b, and with a negative control molecule targeting GFP, ran in the presence of 15 mg/ml HSA.

Example 3: Humanized Anti-FLT3 Binding Heavy Chain Only Single Domain Antibodies and Multispecific Proteins Containing the Same Seven of the llama anti-FLT3 antibody sequences were humanized by grafting their CDR sequences onto human germline sequences, while retaining some llama framework sequences to ensure the antibodies did not lose activity (SEQ ID Nos. 71-76; 389-390). These eight humanized sequences were cloned into expression constructs for expression of anti-FLT3/anti-albumin/anti-CD3 multispecific proteins (SEQ ID Nos. 267-272; 391-392) in CHO cells. The constructs were stably transfected into CHO cells, and pools of stable transfectants were used to express the multispecific proteins. Affinity and multi modal chromatography were used to purify the multispecific proteins from the CHO conditioned media. An SDS-PAGE of the purified proteins (FIG. 23) shows the proteins were purified to greater than 95% purity. The purified proteins were also analyzed by analytical size exclusion chromatography and were found to be 99% monomer (data not shown). These purified proteins were tested in a TDCC assay as described in Example 2 using FLT3-expressing MV-4-11 (acute myeloid leukemia cell line) and EOL1 cells (acute myeloid (eosinophilic) leukemia cell line). The assays were run in the presence 15 mg/ml BSA or 15 mg/ml HSA to measure directed cell killing while bound to albumin. Because the anti-albumin domain in these multispecific proteins does not measurably bind to BSA, BSA served as a negative control for the addition of HSA. The results of these TDCC assays are plotted in FIGS. 24-27 and FIGS. 38-39, and the $EC_{50}$ values for directed T cell killing are listed in Table 5 and Table 6. The MV-4-11 data in FIGS. 24-25 and FIGS. 38-39 and the corresponding $EC_{50}$ values in Tables 5 and 6 represent the results of assays performed using T cells isolated from two different T cell donors. Potent directed T cell killing was observed with both cell lines in the absence of HSA, with $EC_{50}$ values ranging from 1.6 pM to 22 pM. With addition of HSA, the $EC_{50}$ values increased, ranging from 10 pM to 408 pM. The purified proteins were also tested in a TDCC assay with FLT3-expression THP1 cells (acute monocytic leukemia) in the absence or presence of 15 mg/ml HSA (FIGS. 30 and 31) with FLT3-expressing MOLM13 (acute myeloid leukemia) and HL60 (human leukemia) cells (FIGS. 32 and 33) in the presence of 15 mg/ml HSA. The $EC_{50}$ values calculated from these TDCC assay data are also listed in Table 5. With the THP1 cells, $EC_{50}$ values ranged from 23 pM to 268 pM in the absence of HSA and 46 pM to 856 pM in the presence of HSA. With the MOLM13 cells in the presence of HSA the $EC_{50}$ values ranged from 30 pM to 229 pM, and with HL60 cells in the presence of HSA the $EC_{50}$ values ranged from 551 pM to 5478 pM. Compared to all of the other cell lines, the potency of FLT3 TriTAC directed T cell killing with HL60 cells was less potent. It is expected that if viability of the HL60 cells had been measured at a later time point, for example 72 or 96 hours, that the magnitude of killing would have been greater and that killing would have been more potent. A negative control anti-GFP/anti-albumin/anti-CD3 protein had no activity in these TDCC assays except for a minor amount of killing at the highest concentrations tested (>10 nM).

TABLE 5

$EC_{50}$ Values for Redirected T Cell Killing of MV-4-11, EOL1, THP1, MOLM13, and HL60 Cells by Purified Anti-FLT3/Anti-Albumin/Anti-CD3 Multispecific Proteins Containing Humanized Anti-FLT3 Sequences

| FLT3 Binder | EOL1 $EC_{50}$ (pM) | EOL1 + HSA $EC_{50}$ (pM) | MV-4-11 $EC_{50}$ (pM) | MV-4-11 + HSA $EC_{50}$ (pM) | THP1 $EC_{50}$ (pM) | THP1 + HSA $EC_{50}$ (pM) | MOLM-13 + HSA $EC_{50}$ (pM) | HL60 + HSA $EC_{50}$ (pM) |
|---|---|---|---|---|---|---|---|---|
| FLH107 | 1.6 | 10 | 5.9 | 47 | 23 | 46 | 30 | 551 |
| FLH141 | 3.5 | 24 | 9.6 | 119 | 25 | 118 | 54 | 1634 |
| FLH19C | 9.4 | 47 | 16 | 184 | 155 | 458 | 90 | 1518 |
| FLH34 | 3 | 22 | 8.5 | 91 | 28 | 127 | 47 | 1027 |
| FLH4 | 4.2 | 27 | 9.7 | 90 | 38 | 179 | 69 | 1828 |
| FLH78 | 5.2 | 35 | 12 | 101 | 51 | 221 | 97 | 1702 |
| FLH92a | not tested | not tested | not tested | not tested | 268 | 856 | 188 | 3876 |
| FLH92b | not tested | not tested | not tested | not tested | 109 | 461 | 229 | 5478 |

TABLE 6

$EC_{50}$ Values for Redirected T Cell Killing of MV-4-11 Cells by Purified Anti-FLT3/Anti-Albumin/Anti-CD3 Multispecific Proteins Containing Humanized Anti-FLT3 Sequences

| FLT3 Binder | MV-4-11 $EC_{50}$ (pM) | MV-4-11 + HSA $EC_{50}$ (pM) |
|---|---|---|
| FLH107 | 2.4 | 90 |
| FLH141 | 1.7 | 45 |
| FLH19C | 6.9 | 224 |
| FLH34 | 2 | 124 |
| FLH4 | 1.9 | 92 |
| FLH78 | 2.2 | 104 |
| FLH92a | 22 | 408 |
| FLH92b | 17 | 390 |

Example 4: Affinity Determinations for Anti-FLT3 Multispecific Proteins

The affinities of the purified multispecific proteins for human and cynomolgus FLT3 were measured with an Octet instrument with streptavidin tips were loaded with biotinylated human or cynomolgus FLT3 protein. The tips were then incubated with solutions containing 50, 16.7, 5.6, or 1.9 nM of the multispecific protein. Affinities ($K_D$), listed in Table 7, were calculated by measuring the on rate and off rate of binding of anti-FLT3/anti-albumin/anti-CD3 multispecific proteins to the captured biotinylated FLT3 proteins. The multispecific proteins bound to human FLT3 with affinities ranging from 0.7 to 8.1 nM, and they bound to cynomolgus FLT3 with affinities ranging from 2.7 to 214 nM.

TABLE 7

Affinities of Purified Anti-FLT3/Anti-Albumin/Anti-CD3
Multispecific Proteins Containing Humanized Anti-FLT3
Sequences for Human or Cynomolgus Monkey FLT3

| FLT3 Binder | Human $K_D$ (nM) | Cynomolgus $K_D$ (nM) | Cyno/human (fold change) |
|---|---|---|---|
| FLH107 | 0.7 | 10 | 14.3 |
| FLH19C | 1.9 | 2.7 | 1.4 |
| FLH141 | 1.9 | 35 | 18.4 |
| FLH34 | 2.1 | 19 | 9.0 |
| FLH4 | 3.7 | 214 | 57.8 |
| FLH78 | 4.1 | 161 | 39.3 |
| FLH92a | 8.1 | 11.8 | 1.5 |
| FLH92b | 4.9 | 7.8 | 1.6 |

Additional affinity determinations were performed using conditioned media from Example 2 with known concentrations of anti-FLT3/anti-CD3 multispecific proteins. The multispecific proteins tested contain llama anti-FLT3 sequences FLL8, FLL41, FLL71, FLL92, FLL134, or FLL153. An Octet instrument with streptavidin tips were loaded with biotinylated human or cynomolgus FLT3 protein, and $K_D$ values for binding FLT3 were calculated by measuring the on rate and off rate of binding of anti-FLT3/anti-CD3 multispecific proteins to the biotinylated FLT3 proteins. The affinity measurements were made using a single 50 nM concentration of anti-FLT3/anti-CD3 multispecific proteins, which allowed for rank ordering potency. The measured relative affinities are listed in Table 8. The multispecific proteins bound to human FLT3 with $K_D$ values ranging from 1.4 to 41 nM to cynomolgus FLT3 with $K_D$ values ranging from 2 to 102 nM.

TABLE 8

Relative affinities of Purified Anti-FLT3/Anti-Albumin/
Anti-CD3 Multispecific Proteins Containing Llama Anti-
FLT3 Sequences for Human or Cynomolgus Monkey FLT3

| FLT3 Binder | Human $K_D$ (nM) | Cynomolgus $K_D$ (nM) | Cyno/human (fold change) |
|---|---|---|---|
| FLL8 | 9.3 | 18 | 1.9 |
| FLL41 | 31 | 34 | 1.1 |
| FLL71 | 18 | 26 | 1.4 |
| FLL92 | 1.4 | 2 | 1.4 |
| FLL134 | 18 | 24 | 1.3 |
| FLL153 | 41 | 102 | 2.5 |

Example 5: Tumor Regression and Inhibition in an Orthotopic EOL1 Xenograft Model In vivo efficacy study of an exemplary FLT3 targeted multispecific protein of this disclosure is performed with EOL1, expressing luciferase and GFP, orthotopic model. EOL1 LucGFP cells are injected intravenously through the tail vein into 6-8 weeks old female Nod/Scid/IL2Rg−/− (NSG) animals. Intraperitoneal injection of D-luciferin, followed by anesthesia with isofluorane and subsequent whole body bioluminescence imaging (BLI) is to enable monitoring of tumor burden. Bioluminescent signals emitted by the interaction between luciferase expressed by the tumor cells and luciferin are captured by imaging and quantified as total flux (photons/sec) using. When the total flux reaches an average of 15E6 for all animals, the animals are injected through bolus tail vein with expanded T cells from PBMC. Briefly, pan-T cells are activated with a suitable human T Cell Activation/Expansion Kit. After three days, IL2 is added every two days until day 11. Cells are harvested, activation/expansion beads are magnetically removed, and cells are washed and resuspended in PBS. 2-days post T cell injection, mice are imaged as described above and animals are randomized into groups.

Three days post T-cell implant, a single dose of an FLT3 targeted multispecific protein of this disclosure and a negative control GFP targeted multispecific protein is administered via bolus tail vein injection. Animals are sacrificed when they exhibit hindlimb paralysis, an endpoint for AML orthotopic model. It is expected that the FLT3 targeted multispecific protein will result in tumor regression in a dose-dependent manner.

Figure 34:
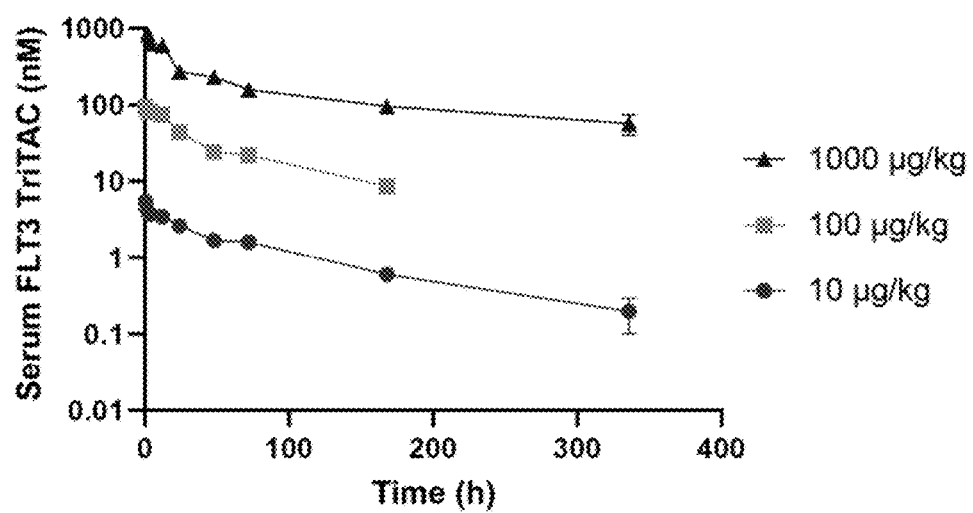
FIG. 34 illustrates the pharmacokinetics of a FLT3 Multispecific Protein Containing Humanized Anti-FLT3 Sequence FLH19C, in cynomolgus monkeys after single i.v. doses of 10 μg/kg, 100 μg/kg, and 1000 μg/kg. Plotted are mean values measured in samples collected from two test subjects per dose group.

Example 6: Phamacokinetics and Pharmacodynamics of FLT3 TriTACs in Cynomolgus Monkeys A FLT3 TriTAC (SEQ ID NO: 269, containing the FLT3 binder FLH19C, SEQ ID NO: 73) was administered at doses of 10, 100, and 1000 µg/kg single i.v. bolus doses to cynomolgus monkeys, with two test subjects per dose group. This FLT3 TriTAC binds to cynomolgus FLT3 (see Table 7) and binds to cynomolgus CD3 and cynomolgus serum albumin, with affinities of 3.3 nM and 4.4 nM, respectively, as determined using biolayer interferometry (data not shown). The amount of FLT3 TriTAC present in serum samples collected at different time points after dosing was measured using an electrochemiluminescent ELISA assay using labeled antibodies recognizing the anti-ALB and anti-CD3 domains of the FLT3 TriTAC molecule as capture and detection reagents. The measured serum concentrations versus time and dose are plotted in FIG. 34. The pharmacokinetic properties calculated from these data are listed in Table 9.

TABLE 9

Pharmacokinetic Properties of a FLT3 TriTAC Dosed in Cynomolgus Monkeys

| Dose | $T_{max}$ (h) | $C_{max}$ (nM) | $AUC_{168}$ (h*nM) | $AUC_{INF}$ (h*nM) | Half-life (h) | Cl (µg/(h*nM)) | Vz (ug/(nM)) |
|---|---|---|---|---|---|---|---|
| 10 µg/kg | 0.5 | 5.44 | 279 | 373 | 85.9 | 0.0805 | 10.0 |
| 100 µg/kg | 0.5 | 94.1 | 4520 | 5450 | 75.4 | 0.0555 | 6.06 |
| 1,000 µg/kg | 2 | 846 | 35600 | 61200 | 147 | 0.0493 | 10.4 |

Figure 35:
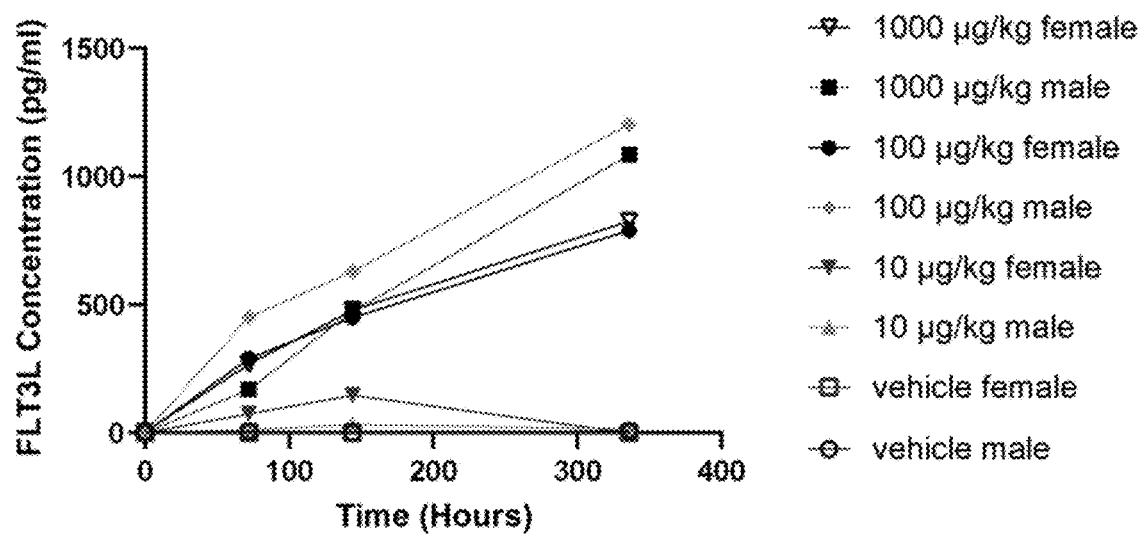
FIG. 35 illustrates the amount of soluble FLT3L present in serum samples collected from cynomolgus monkeys after single i.v. doses of 10 μg/kg, 100 μg/kg, and 1000 m/kg of a FLT3 Multispecific Protein Containing Humanized Anti-FLT3 Sequence FLH19C. Plotted are mean values measured in samples collected from two test subjects per dose group.
Figure 36:
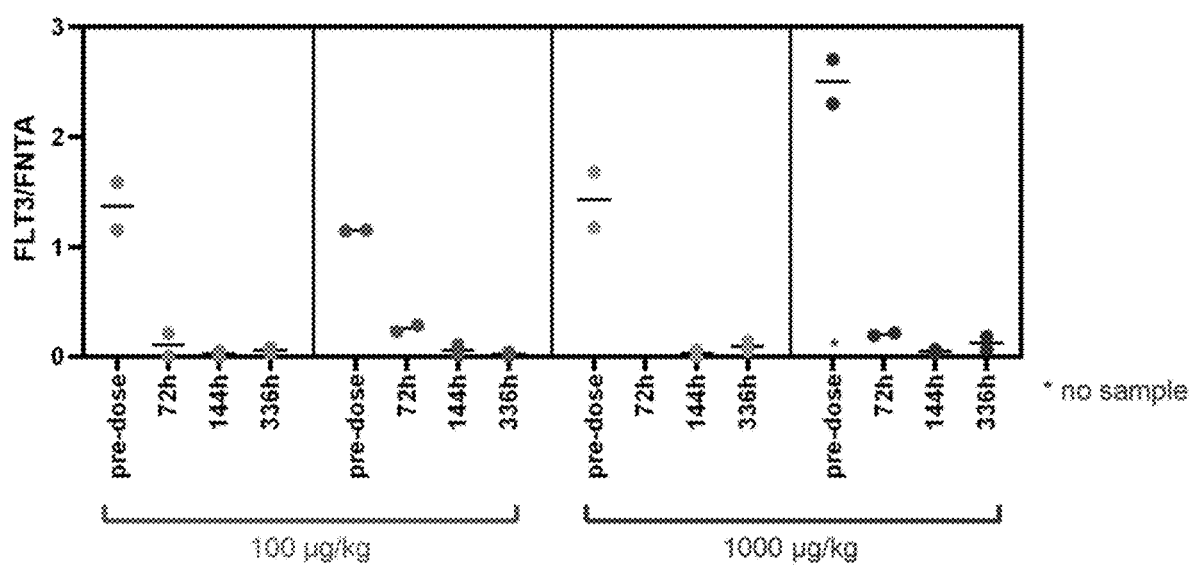
FIG. 36 illustrates the amount of FLT3 transcript present in RNA prepared from whole blood collected from cynomolgus monkeys after single i.v. doses of 100 μg/kg and 1000 m/kg of a FLT3 Multispecific Protein Containing Humanized Anti-FLT3 Sequence FLH19C. Plotted are technical replicates. Data are plotted each individual test subject in each dose group.
Figure 37:
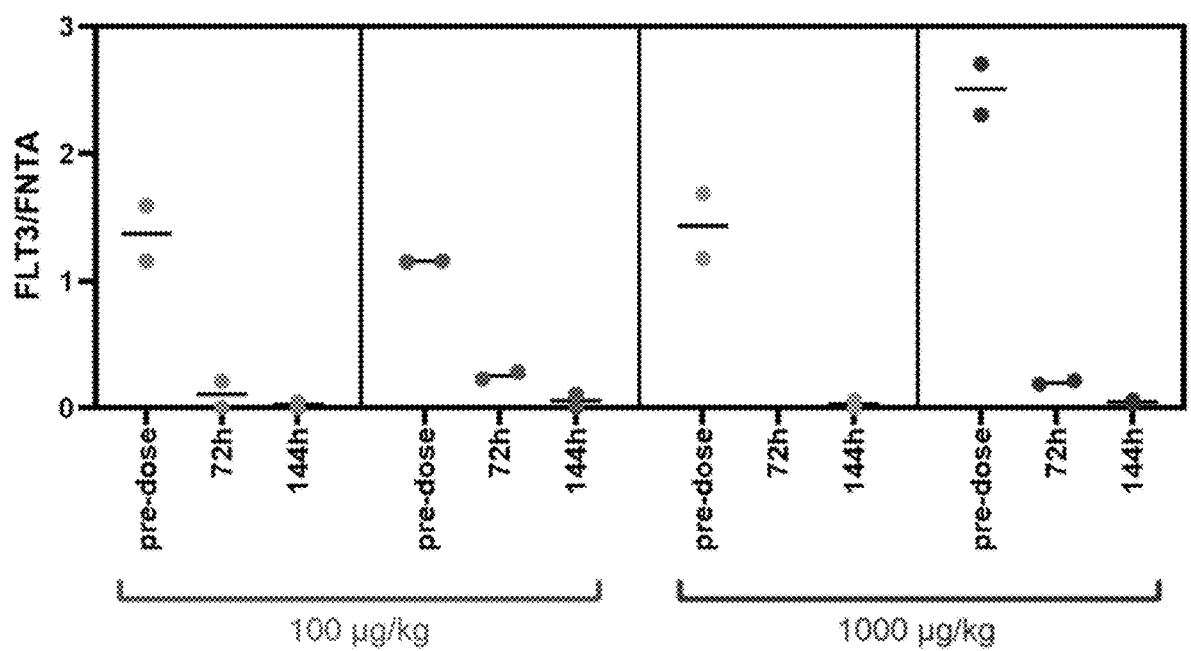
FIG. 37 illustrates the amount of FLT3 transcript present in RNA prepared from bone marrow collected from cynomolgus monkeys after single i.v. doses of 100 μg/kg and 1000 m/kg of a FLT3 Multispecific Protein Containing Humanized Anti-FLT3 Sequence FLH19C. Plotted are technical replicates. Data are plotted for each individual test subject in each dose group.
Figure 38:
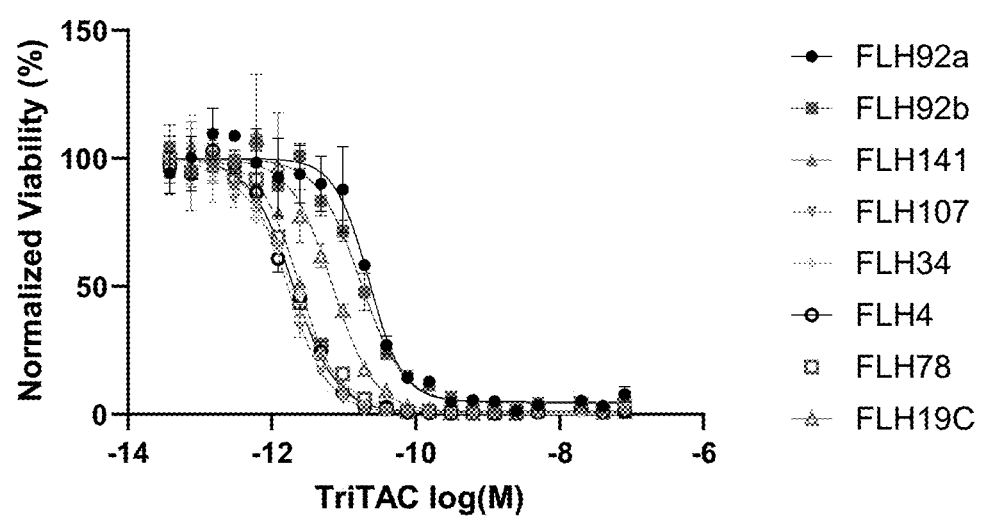
FIG. 38 illustrates the results of a TDCC Assay with MV-4-11 Cells and Anti-CD3/Anti-FLT3 Multispecific Proteins Containing Humanized Anti-FLT3 Sequences FLH4, FLH78, FLH19C, FLH141, FLH107, FLH34, FLH92a, and FLH92b, ran in the presence of 15 mg/ml BSA. The y-axis shows the normalized percentage of viability of the cancer cells. The T cells in this assay were obtained from a different donor compared to the assay FIG. 24.
Figure 39:
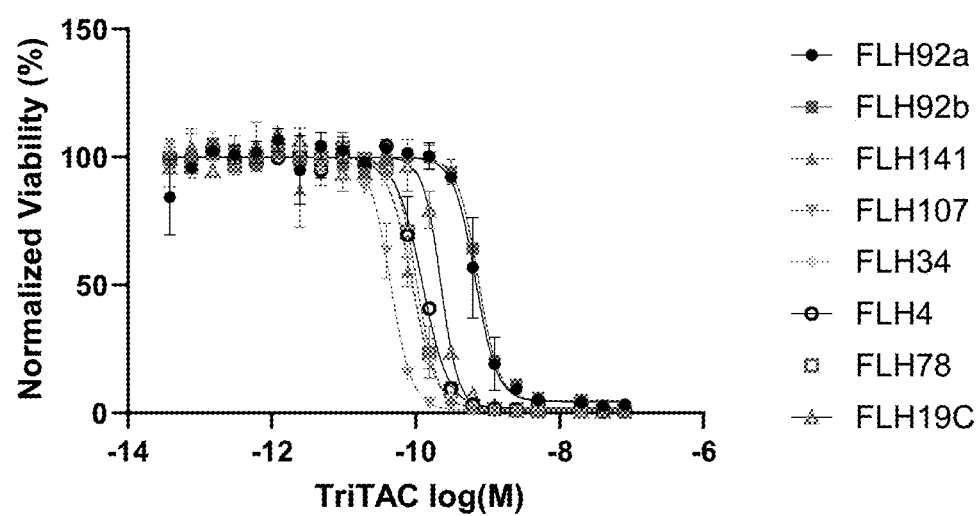
FIG. 39 illustrates the results of a TDCC Assay with MV-4-11 Cells and Anti-CD3/Anti-FLT3 Multispecific Proteins Containing Humanized Anti-FLT3 Sequences FLH4, FLH78, FLH19C, FLH141, FLH107, FLH34, FLH92a, and FLH92b, ran in the presence of 15 mg/ml HSA. The y-axis shows the normalized percentage of viability of the cancer cells. The T cells in this assay were obtained from a different donor compared to the assay in FIG. 25.

To determine if the FLT3 TriTAC directed cynomolgus T cells to kill endogenous cynomolgus FLT3-expressing cells, soluble FLT3L in serum and FLT3 RNA in whole blood were measured in sample collected from the pharmacokinetic study described above. Depletion of FLT3-expressing cells was expected to result in an increase in soluble FLT3L (see Brauchle et al. Mol Cancer Ther 2020; 19:1875-88). An electrochemiluminescent ELISA specific for Non-Human Primate FLT3L (Meso Scale Discovery) was used to measure the levels of FLT3L in serum samples collected at different time points (FIG. 35). With the 100 and 1,000 µg/kg dose groups, the soluble FLT3L increased over the time course of the study. One of the two subjects in the 10 µg/kg dose group had a slight increase in FLT3L at the 72 and 144 hour times points that returned to pre-dose levels at the 336 hour time point. If FLT3 expressing cells are depleted from whole blood or bone marrow, then FLT3 transcripts were expected to be depleted from RNA purified from whole blood or bone marrow. RNA was purified from whole blood or bone marrow using kits (Qiagen), cDNA was prepared by a reverse transcriptase reaction, and qPCR was used to measure the amount of FLT3 present using a standard curve qPCR method. FNTA was used as a house keeping gene for the qPCR reactions. Plotted in FIG. 36 are FTL3 RNA levels normalized to FNTA for blood samples isolated from the 100 and 1,000 µg/kg groups. Plotted in FIG. 37 are FTL3 RNA levels normalized to FNTA for bone marrow samples isolated from the 100 and 1,000 µg/kg groups. Compared to samples collected prior to dosing, FLT3 RNA is greatly reduced at all time points measured. The combined FLT3L and FLT3 RNA data indicate that the FLT3 TriTAC, when dosed at 100 and 1,000 µg/kg, eliminated FLT3 expressing cells in cynomolgus monkeys.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCES

| SEQ ID NO. | Sequence descriptor | Seq. name | Amino acid sequence |
|---|---|---|---|
| 1 | FLT3 antibody variable domain | FLL101 | QVQLQESGGGLVQAGGSLRLSCAASGVTFSINYIDWYRQAPGKQREWVAQITRDSNSFYADSVKGRFAISRDNAKNTVYLQMNNLKPEDTAVYYCRVLSYWGQGTQVTVSS |
| 2 | FLT3 antibody variable domain | FLL103 | QVQLQESGGGLVQAGGSLRLSCEASGPTFSINYIDWYRQAPGKQREWVAQITRDSNSFYADSVKGRFAVSRDNAKNTVYLQMNSLKPEDTAVYYCRVLSYWGQGTQVTVSS |
| 3 | FLT3 antibody variable domain | FLL116 | QVQLQESGGGLVQAGGSLRLSCAASGVTFSINYIDWYRQAPGKQREWVAQITRDSNSFYADSVKGRFAISRDNAKNTVYLQMNSLKPEDTAVYYCRVLSYWGQGTQVTVSS |
| 4 | FLT3 antibody variable domain | FLL125 | QVQLQESGGGLVQAGGSLRLSCAASGSTFSRNYIDWYRQAPGKQREWVAQITSGGNTHYEPSLKGRFTISRDNAKNTAYLQMNSLKPEDTAVYYCRILDYWGQGTQVTVSS |
| 5 | FLT3 antibody variable domain | FLL129 | QVQLQESGGGLVQAGGSLRLSCAASGVTFSASYIDWYRQAPGNEREWVAQITRGGDSFYADSVKGRFAISRDNAKNTVYLQMNSLKPEDTAVYYCRVLSYWGQGTQVTVSS |
| 6 | FLT3 antibody variable domain | FLL137 | QVQLQESGGGLVQAGGSLRLSCAASGSTFNNYAMDWFRQAPGKQREWVAQITRDSSSFYADSVKGRFAISRDNAKNTVYLQMNSLKPEDTAVYYCRVLSYWGQGTQVTVSS |
| 7 | FLT3 antibody variable domain | FLL14 | QVQLQESGGGLVQAGGSLRLSCAASGVTFSINYIDWYRQAPGKQREWVAQITRDSNSFYADSVKGRFAISRDNAKNTVYLQMNSLKPEDTAVYYCRLLSYWGQGTQVTVSS |
| 8 | FLT3 antibody variable domain | FLL146 | QVQLQESGGGLVQAGGSLRLSCAASGVTFSINYIDWYRQAPGKQREWVAQITRDDTSFYADSVKGRFAISRDNAKNTVYLQMNNLRPEDTAVYYCRLLSFWGQGTQVTVSS |
| 9 | FLT3 antibody variable domain | FLL158 | QVQLQESGGGLVQPGGSLRLSCAASGSTFGRNYIDWYRQAPGKQREWVAQITSGGNTHYEPSLKGRFTISRDNAKNTAYLQMNSLKPEDTAVYYCRILDYWGQGTQVTVSS |
| 10 | FLT3 antibody variable domain | FLL179 | QVQLQESGGGLVQAGGSLRLSCKASGVTFSINYIDWYRQAPGKQREWVAQITRDGSSFYADSVKGRFAISRDNAKNTVYLQMNSLKPEDTAVYYCRILSDWGQGTQVTVSS |
| 11 | FLT3 antibody variable domain | FLL181 | QVQLQESGGGLVQAGDSLRLSCAASGVTFSASYIDWYRQAPGNEREWVAQITRGGDSFYADSVKGRFAISRDNAKNTVYLQMNSLKPEDTAVYYCRVLSYWGQGTQVTVSS |
| 12 | FLT3 antibody variable domain | FLL187 | QVQLQESGGGLVQPGGSLRLSCAASGVTFSINYIDWYRQAPGKQREWVAQITRDSNSFYADSVKGRFAISRENAKNTVYLQMNSLKPEDTAVYYCRVLSYWGQGTQVTVSS |
| 13 | FLT3 antibody variable domain | FLL32 | QVQLQESGGGLVQAGGSLRLSCQASGVTFNINYIDWYRQAPGRQREWVAQITRDSTRFYADSVKGRFAISRDNAKNMVYLQLNSLKPEDTAVYYCRILSYWGQGTQVTVSS |
| 14 | FLT3 antibody variable domain | FLL51 | QVQLQESGGGLVQPGGSLRLSCAASGFDFSISYIDWYRQAPGNEREWVAQITRGGDSFYADSVKGRFAISRDNAKNTVYLQMNSLKPEDTAVYYCRILSYWGQGTQVTVSS |
| 15 | FLT3 antibody variable domain | FLL55 | QVQLQESGGGLVQAGGSLRLSCAASGSTFSRNYIDWYRQAPGKQREWVAQITSAGNTHYEPSLKGRFTISRDNAKNTAYLQMNSLKPEDTAVYYCRILDYWGQGTQVTVSS |
| 16 | FLT3 antibody variable domain | FLL77 | QVQLQESGGGLVQPGGSLRLSCAASGVTFSISYIDWYRQAPGNEREWVAQITRGGDSFYADSVKGRFAISRDNAKNTVYLQMNSLKPEDTAVYYCRILSYWGQGTQVTVSS |
| 17 | FLT3 antibody variable domain | FLL97 | QVQLQESGGGLVQAGGSLRLSCAASGVTFSINYIDWYRQAPGKQREWVAQITRDSNSFYADSVKGRFAVSRDNAKNTVYLQMNSLKPEDTAVYYCRVLSYWGQGTQVTVSS |

-continued

SEQUENCES

| SEQ ID NO. | Sequence descriptor | Seq. name | Amino acid sequence |
|---|---|---|---|
| 18 | FLT3 antibody variable domain | FLL21 | QVQLQESGGGLVQPGGSLTLSCAASGSTFSRNYIDWYRQAPGKQREWVAQITSGGNTHYEPSLKGRFTISRDNAKNTAYLQMNSLKPEDTAVYYCRILDYWGQGTQVTVSS |
| 19 | FLT3 antibody variable domain | FLL57 | QVQLQESGGGLVQAGGSLRLSCAASGSTFSKNYIDWYRQAPGKQREWVAQITSGGNTHYEPSLKGRFTISRDNAKNTAYLQMNSLKPEDTAVYYCRILDYWGQGTQVTVSS |
| 20 | FLT3 antibody variable domain | FLL62 | QVQLQESGGGLVQAGGSLRLSCAASGSTSSRNYIDWYRQAPGKQREWVAQITSGGNTHYEPSLKGRFTISRDNAKNTAYLQMNSLKPEDTAVYYCRILDYWGQGTQVTVSS |
| 21 | FLT3 antibody variable domain | FLL79 | QVQLQESGGGLVQAGGSLRLSCSASGSTFSRNYIDWYRQAPGKQREWVAQITSGGNTHYEPSLKGRFTISRDNAKNTAYLQMNSLKPEDTAVYYCRILDYWGQGTQVTVSS |
| 22 | FLT3 antibody variable domain | FLL86 | QVQLQESGGGLVQPGDPLRLSCAASGSTFSRNYIDWYRQAPGKQREWVAQITSGGNTHYEPSLKGRFTISRDNAKNTAYLQMNSLKPEDTAVYYCRILDYWGQGTQVTVSS |
| 23 | FLT3 antibody variable domain | FLL112 | QVQLQESGGGLVQAGGSLRLSCAVSGRTFSGFGTGWFRQAPGKEREFVAAISWAGGRTHYEDSVKGRFTIHRDNAKNTVYLQMNSLKPEDTAVYYCAAQVSRAYDGIWYSGGDYWGQGTQVTVSS |
| 24 | FLT3 antibody variable domain | FLL142 | QVQLQESGGGLVQAGGSLRLSCAVSGRTFSGFGTGWFRQAPGKEREFVAAISWDGGRTHYADFVKGRFTISRDNAKNTVYLQMNSLKPEDTAVYYCAAQVARAYDSKWYSGGDYWGQGTQVTVSS |
| 25 | FLT3 antibody variable domain | FLL143 | QVQLQESGGGLVQAGGSLRLSCAVSGRTFSGFGTGWFRQAPGKEREFVAAISWVGGRTHYADSVKGRFTISRDNAKNTVYLQMNSLKPEDTAVYYCAAQVARAYDGNWYSGGDYWGQGTQVTVSS |
| 26 | FLT3 antibody variable domain | FLL154 | QVQLQESGGGLVQAGGSLRLSCAVSGRTFSGFGTGWFRQAPGKEREFVAAISWSGGRTHYADSVKGRFTISRDNAKNTVYLQMNSLKPEDTAVYYCAGQVARAYDGNWYSRGDYWGQGTQVTVSS |
| 27 | FLT3 antibody variable domain | FLL168 | QVQLQESGGGSVQAGGSLRLSCAFSGRTFSGFGTGWFRQAPEKEREFVAAISWDGGRTHYADSVKGRFTISRDNAKNTVYLQMDSLKPEDTAIYYCAAQVSRAYDGRWYSAVDYWGRGTQVTVSS |
| 28 | FLT3 antibody variable domain | FLL170 | QVQLQESGGGLVQAGGSLRLSCAVSGRTFSGFGTGWFRQAPGKEREFVAAISWSGGTTHYADSVKGRFTISRDNAKNTVYLQMNSLKPEDTAVYYCAGQVARAYDSSWYSRGDYWGQGTQVTVSS |
| 29 | FLT3 antibody variable domain | FLL188 | QVQLQESGGGLVQAGGSLGLSCAVSGRTFSGFGTGWFRQPPEKEREFVAAISWDGGRTHYADSVKGRFTISRDNAKNTVFLQMNSLKPEDTAVYYCAAQVARAYDSRWYSGGDYWGQGTQVTVSS |
| 30 | FLT3 antibody variable domain | FLL40 | QVQLQESGGGLVQAGGSLRLSCAVSGRTFSGFGTGWFRQAPGKEREFVAAISWSGGTTHYADSVKGRFTISRDNAKNTVSLVYLQMNSLKPDDTAVYYCAGQVARAYDSSWYSRGDYLGQGTQVTVSS |
| 31 | FLT3 antibody variable domain | FLL6 | QVQLQESGGGLVQAGGSLRLSCAVSGRTFSGFGTGWFRQAPGKEREFVAAISWDGGRTHYADSVKGRFTISRDNAANTVYLQMNSLKPEDTAVYYCAGQVSRAYDSMWYGRDDYWGQGTQVTVSS |
| 32 | FLT3 antibody variable domain | FLL75 | QVQLQESGGGLVQAGGSLRLSCAVSGRTFSGFGTGWFRQAPGKEREFVAAISWSGGTTHYADSVKGRFTISRDNAKNTVNLVYLQMNDLRPEDTAVYYCAGQVARAYDSNWYSRGDYWGQGTQVTVSS |
| 33 | FLT3 antibody variable domain | FLL83 | QVQLQESGGGLVQAGGSLRLSCAVSGRTFSGFGTGWFRQAPGKEREFVAAISWSGGTTHYADSVKGRFTISRDNAENTVYLEMNSLKPEDTAVYICAGQVSRAYDSNWYSRDDYWGQGTQVTVSS |
| 34 | FLT3 antibody variable domain | FLL94 | QVQLQESGGGLVQAGGSLRLSCAVSGRTFSGFGTGWFRQAPEKEREFVAAISWDGGRTHYADSVKGRFTISRDNAKNTVYLQMNSLKPEDTAIYYCAGQVARAYDTRWYSRGDYWGQGTQVTVSS |
| 35 | FLT3 antibody variable domain | FLL99 | QVQLQESGGGLVQAGGSLRLSCAVSGRTFSGFGTGWFRQAPGKEREFVAAISWDGGRTHYADFVKGRFTISRDNAKNTVYLQMNSLKPEDTAVYYCAAQVARAYDSRWYSGGDYWGQGTQVTVSS |
| 36 | FLT3 antibody variable domain | FLL38 | QVQLQESGGGLVQAGGSLRLSCAVSGRTFSGFGTGWFRQAPGKEREFVAAVSWSGGTTEIADSVKGRFTISRDNAKNTVYLQMSSLKPGDTAVYYCAGQVARAYDSRWYSRGDYWGQGTQVTVSS |

-continued

SEQUENCES

| SEQ ID NO. | Sequence descriptor | Seq. name | Amino acid sequence |
|---|---|---|---|
| 37 | FLT3 antibody variable domain | FLL53 | QVQLQESGGGLVQAGDSLRLSCAVSGRTFSGFGTGWFRQAPGKEREFVAAVSQSGGTTHYADSVKGRFTISRDNAKNTETLVYLQMNSLKPEDTAVYYCAGQVARAYDSSWYARGDYWGQGTQVTVSS |
| 38 | FLT3 antibody variable domain | FLL553 | QVQLQESGGGLVQAGGSLRLSCAVSGRTFSGFGTGWFRQAPGKEREFVAAISWSGGTTHYADSVKGRFTISRDNAKNTVNLVYLQMNSLRPEDTAVYYCAGQVARAYDSNWYSRGDYWGQGTQVTVSS |
| 39 | FLT3 antibody variable domain | FLL74 | QVQLQESGGGLVQAGGSLRLSCRFSGRTFSGFGTGWFRQAPGKEREFVAAISWAGGRTHYEDSVKGRFTISRDNAKNTVYLQMNSLKPEDTAVYYCAVQVSRAYDGIWYSGGDYWGQGTQVTVSS |
| 40 | FLT3 antibody variable domain | FLL102 | QVQLQESGGGLVQAGGSLMVSCAASGGTWSSYATGWFRQVPGKERKLIAGISRSGGRTYYAESVKGRFTISRDNAKNTVYLQMNTLKPDDTAVYYCAAARYFTSSVVYTSGNDYDYWGQGTQVTVSS |
| 41 | FLT3 antibody variable domain | FLL122 | QVQLQESGGGLVQAGGSLMVSCAASGGTWSSYATGWFRQVPGKERELIAGISRSGGRTYYAESVKGRFTISRDNAKNTVYLQMNTLKPDDTAVYYCAAARYFTSSVVYTSGNDYDYWGQGTQVTVSS |
| 42 | FLT3 antibody variable domain | FLL134 | QVQLQESGGGLVQPGGSLRLSCAASGGTFSSYATGWFRQVPGKEREFIAGISRNSGRTYAESVKGRFTISRDNAKNTVYLQMNTLRPDDTAVYYCAAARYFTRDAIYTSGDDYDYWGQGTQVTASS |
| 43 | FLT3 antibody variable domain | FLL153 | QVQLQESGGGLVQVGGSLMVSCAASGGTFSSYATGWFRQVPGKEREFIAGVSRNSGRTYYAESVKGRFTISRDNAKNTVYLQMNTLKPDDTGVYYCAAARYFTRDAVYTSGDDYDYWGQGTQVTVSS |
| 44 | FLT3 antibody variable domain | FLL41 | QVQLQESGGGLVQLGDSLMVSCAASGGTFSSYATGWFRQVPGREREFIAGISRSGGRTYYAESVKGRFTISRDNAKNTVYLQMNTLKPDDTAVYYCAAARYFTTSVVYTSGDDYDYWGQGTQVTVSS |
| 45 | FLT3 antibody variable domain | FLL67 | QVQLQESGGGLVQLGDSLMVSCAASGGTFSSYATGWFRQVPGKEREFIAGISRSGGRTYYAESVKGRFTISRDNAKNTVYLQMNTLKPDDTAVYYCAAARYFTTSVVYTSGDDYDYWGQGTQVTVSS |
| 46 | FLT3 antibody variable domain | FLL92 | QVQLQESGGGLVQAGGSLMVSCAASGGTWSSYATGWFRQVPGKERELIAGISRSGGRTYYAESVKGRFTISRDNAKNTVYLQMNTLKSDDTAVYYCAAARYFTSSVVYTSGNDYDYWGQGTQVTVSS |
| 47 | FLT3 antibody variable domain | FLL71 | QVQLQESGGGLVQVGGSLMVSCAASGGTFSSYATGWFRQVPGKEREFIAGISRNSGRTYYAESVKGRFTISRDNAKNTVYLQMNTLKPDDTAVYYCAAARYFTRDAVYTSGDDYDYWGQGTQVTVSS |
| 48 | FLT3 antibody variable domain | FLL8 | QVQLQESGGGLVQVGGSLMVSCAASGGTFSSYATGWFRQVPGKEREFIAGISRNSGRTYYAESVKGRFTISRDNAKNTVYLQMNTLKPDDTAVYYCAAARYFTRDVVYTSGDDYDYWGQGTQVTVSS |
| 49 | FLT3 antibody variable domain | FLL84 | QVQLQESGGGLVQAGGSLMVSCAASGGTFSSYATGWFRQVPGKEREFIAGISRSGGRTYYAESVKGRFTISRDNAKNTVYLQMNTLKPDDTAVYYCAAARYFTSSVVYTSGDDYDYWGQGTQVTVSS |
| 50 | FLT3 antibody variable domain | FLL107 | QVQLQESGGGLVQAGGSLRLSCAASGRTFSSYAMGWFRQAPGKEREFVAAISWSGSNTYYADSVKGRFTISRDNAKNTVYLQMDSLKPEDTAVYYCAAGGSTRVVVTTTPVVKYWGQGTQVTVSS |
| 51 | FLT3 antibody variable domain | FLL141 | QVQLQESGGGLVQAGGSLRLSCAASGRTFSSYAMGWFRQAPGMEREFVAAISWSGYSTYYADSVKGRFTISRDDAKNTVYLQMDSLKPEDTAVYYCAAGGSTRVVVTTTPVVKYWGQGTQVTVSS |
| 52 | FLT3 antibody variable domain | FLL34 | QVQLQESGGGLVQAGGSLRLSCAASGRTFSSYALGWFRQAPGKEREFVAAISWSGGNTYYADSVKGRFTISRDDAKNTVYLQMDSLKPEDTAVYYCAAGGSTRVVVTTTPVVKYWGQGTQVTVSS |
| 53 | FLT3 antibody variable domain | FLL4 | QVQLQESGGGLVQAGGSLRLSCAASERTFSSYTMGWFRQAPGKEREFVAAMSWSGGSTYYADSVKGRFTISRDNAKNTVYLQMDSLKPEDTAVYYCAAGGSTRVVVTTTPVVKYWGQGTQVTVSS |
| 54 | FLT3 antibody variable domain | FLL61 | QVQLQESGGGLVQAGGSLRLSCAASERTFSSYAMGWFRQAPGKEREFVAAISWSGGSTYYADSVKGRFTISRDNAKNTVYLQMDSLKPEDTAVYYCAAGGSTRVVVTTTPIVKYWGQGTQVTVSS |

SEQUENCES

| SEQ ID NO. | Sequence descriptor | Seq. name | Amino acid sequence |
|---|---|---|---|
| 55 | FLT3 antibody variable domain | FLL78 | QVQLQESGGGWVQAGGSLRLSCAASGRTFSSYAMGWFRQAPGKEREFVAAISWSGSSTYYADSVKGRFTISRDNAKNTVYLLMDSLKPEDTAVYYCAAGGSTRVVVTTTPVVKYWGQGTQVTVSS |
| 56 | FLT3 antibody variable domain | FLL1 | QVQLQESGGGLVQAGGSLRLSCAASGRTFSTLTVAWFRQAPGKEREFVVASIPSGSNTGYAESVKGRFTISRDIAKNTVYLQMNSLKPEDTAMYFCAARIYFGSSRGYDYWGQGTQVTVSS |
| 57 | FLT3 antibody variable domain | FLL26 | QVQLQESGGGLVQAGGSLRLSCAASGRTFTTYTVAWFRQAPGKEREFLVASIPTGSNTAYAESVKGRFTISRGNAKNTVYLQMNSLKPEDTAMYYCAARTYFGSSRGYDYWGQGTQVTVSS |
| 58 | FLT3 antibody variable domain | FLL160 | QVQLQESGGGLVQAGDSLRLSCATSGRTFNLYRVGWFRQAPGKEREFVARITWSADITQYADSVKGRFTISRDNAKNTVYLQMNSLKPEDTAIYYCATTLRKSSGIYHVDDYDDWGQGTQVTVSS |
| 59 | FLT3 antibody variable domain | FLL173 | QVQLQESGGGLVQAGGSLRLSCATSGRTFNLYRVGWFRQAPGKEREFVARITWSADITQYTDSVKGRFTISRDNAKNTVYLQMNSLKPEDTAIYYCATTLRKSSGIYHTDDYDYWGQGTQVTVSS |
| 60 | FLT3 antibody variable domain | FLL178 | QVQLQESGGGLVQPGGSLRLSCAASGFTFSDYAMSWVRQAPGKGLEWVSGISSGGYKIGYTDSTKGRFTISRDNAKNTLYLQMNSLTAEDTAVYYCAKGTQWSWSLRDNTSRGQGTQVTVSS |
| 61 | FLT3 antibody variable domain | FLL27 | QVQLQESGGGLVQPGGSLRLSCKASGFTFSSYAMSWVRQAPGKGLEWVSGISSGGYKIGYTDSTKGRFTISRDNAKNTLYLQMNSLNAEDTAVYYCAKGTQWSWALRDSTSRGQGTQVTVSS |
| 62 | FLT3 antibody variable domain | FLL190 | QVQLQESGGGLVQAGGSLTLSCTASGSTFSINHFSWYRQAPGKQRELVAFISSDGVSIDVESVKGRFTISGDNDKNTAYLQMNGLKPEDTAVYYCYYRGFWGQGTQVTVSS |
| 63 | FLT3 antibody variable domain | FLL43 | QVQLQESGGGLVQPGGSLTLSCTASGSTFSINHFAWYRQAPGKQRELVAFISSDGRSTDVESVKGRFTISGDNDKNTAYLQMNGLKPEDTAVYYCYYRGSWGQGTQVTVSS |
| 64 | FLT3 antibody variable domain | FLL15 | QVQLQESGGGLVQAGGSLSLSCAASEGTISHAAMGWFRQAPGKERQFVAYDTWTGGSTNYADSVKDRFTITGDHAKNTVYLQMNSLKPEDTGVYYCAVRGRYSASYTYTNPASYKYWGQGTQVTVSS |
| 65 | FLT3 antibody variable domain | FLL45 | QVQLQESGGGLVQAGGSLRLSCAASGGTFSSSAMGWFRQAPGKEREFVATITQNDVPTYYTHSVKGRFTISRDNAKNTMYLQMNSLKPEDTAVYYCAQRVAQASGWRTTIKDYGYWGQGTQVTVSS |
| 66 | FLT3 antibody variable domain | FLL39 | QVQLQESGGGLVQAGGSLRLSCAASGLTSSTYRMAWFRQAPGKEREFAAGISYSADSGGSTNYADSVKGRFTISRDNAKNTVYLQMSSLKPEDTAVYYCAAGRYSGTYNSPYSSSYVYWGQGTQVTVSS |
| 67 | FLT3 antibody variable domain | FLL177 | QVQLQESGGGLVQTGGSLRLSCAASGSTFSRNTMGWFRQAPGKERVFVLGISWSGIRSYYLDSAKARFTISRDNAKNTVYLQMNSLRPEDTAVYYCAAQEGSSPGPYKYWGQGTQVTVSS |
| 68 | FLT3 antibody variable domain | FLL823 | QVQLQESGGGVVQVGGSLRLSCAASGGTFGYYAVGWFRQAPGKEREFVAAVTWNGAYLYSDPVKGRFTISRDNAKNTVYLQMNSLKSEDTAVYYCGLDRWSAVVESTPSTRGQGTQVTVSS |
| 69 | FLT3 antibody variable domain | FLL76 | QVQLQESGGGLVQAGGSLRLSCAASGGAFSSYVMGWFRQAPGKEREFVAAVISWSGRITDYADSVKGRFSISRDNAKSTVYLQMNNLKPEDTAVYYCAAKTGMYIDLRTSTFDYWGQGTQVTVSS |
| 70 | FLT3 antibody variable domain | FLL822 | QVQLQESGGGSVQAGGSLRLSCTASGRTFTDYTMGWFRQAPGKEREFMLGISSNGYRRYYTGSMKDRFTISRDNVKKTVYLQMNDLKPEDTAVYYCAASEDHGAPRYDYWGQGTQVTVSS |
| 71 | FLT3 antibody variable domain | FLH107 | EVQLLESGGGLVQPGGSLTLSCAASGRTFSSYAMGWFRQAPGKEREFVAAISWSGSNTYYADSVKGRFTISRDNSKNTLYLQMNSLRAEDTAVYYCAAGGSTRVVVTTTPVVKYWGQGTLVTVSS |
| 72 | FLT3 antibody variable domain | FLH141 | EVQLLESGGGLVQPGGSLTLSCAASGRTFSSYAMGWFRQAPGMEREFVAAISWSGYSTYYADSVKGRFTISRDNSKNTLYLQMNSLRAEDTAVYYCAAGGSTRVVVTTTPVVKYWGQGTLVTVSS |
| 73 | FLT3 antibody variable domain | FLH19C | EVQLVESGGGLVQPGGSLTLSCAASGSTFSINHFSWYRQAPGKQRELVAFISSDGVSIDVESVKGRFTISGDNSKNTAYLQMNSLRAEDTAVYYCYYRGFWGQGTLVTVSS |

-continued

| SEQ ID NO. | Sequence descriptor | Seq. name | Amino acid sequence |
|---|---|---|---|
| 74 | FLT3 antibody variable domain | FLH34 | EVQLLESGGGLVQPGGSLTLSCAASGRTFSSYALGWF RQAPGKEREFVAAISWSGGNTYYADSVKGRFTISRDN SKNTLYLQMNSLRAEDTAVYYCAAGGSTRVVVTTTPV VKYWGQGTLVTVSS |
| 75 | FLT3 antibody variable domain | FLH4 | EVQLLESGGGLVQPGGSLTLSCAASERTFSSYTMGWF RQAPGKEREFVAAMSWSGGSTYYADSVKGRFTISRDN SKNTLYLQMNSLRAEDTAVYYCAAGGSTRVVVTTTPV VKYWGQGTLVTVSS |
| 76 | FLT3 antibody variable domain | FLH78 | EVQLLESGGGLVQPGGSLTLSCAASGRTFSSYAMGWF RQAPGKEREFVAAISWSGSSTYYADSVKGRFTISRDN SKNTLYLQMNSLRAEDTAVYYCAAGGSTRVVVTTTPV VKYWGQGTLVTVSS |
| 77 | CDR1 | FLL101 | GVTFSINYID |
| 78 | CDR1 | FLL103 | GPTFSINYID |
| 77 | CDR1 | FLL116 | GVTFSINYID |
| 79 | CDR1 | FLL125 | GSTFSRNYID |
| 80 | CDR1 | FLL129 | GVTFSASYID |
| 81 | CDR1 | FLL137 | GSTFNNYAMD |
| 77 | CDR1 | FLL14 | GVTFSINYID |
| 77 | CDR1 | FLL146 | GVTFSINYID |
| 82 | CDR1 | FLL158 | GSTFGRNYID |
| 77 | CDR1 | FLL179 | GVTFSINYID |
| 80 | CDR1 | FLL181 | GVTFSASYID |
| 77 | CDR1 | FLL187 | GVTFSINYID |
| 83 | CDR1 | FLL32 | GVTFNINYID |
| 84 | CDR1 | FLL51 | GFDFSISYID |
| 79 | CDR1 | FLL55 | GSTFSRNYID |
| 85 | CDR1 | FLL77 | GVTFSISYID |
| 77 | CDR1 | FLL97 | GVTFSINYID |
| 79 | CDR1 | FLL21 | GSTFSRNYID |
| 86 | CDR1 | FLL57 | GSTFSKNYID |
| 87 | CDR1 | FLL62 | GSTSSRNYID |
| 79 | CDR1 | FLL79 | GSTFSRNYID |
| 79 | CDR1 | FLL86 | GSTFSRNYID |
| 88 | CDR1 | FLL112 | GRTFSGFGTG |
| 88 | CDR1 | FLL142 | GRTFSGFGTG |
| 88 | CDR1 | FLL143 | GRTFSGFGTG |
| 88 | CDR1 | FLL154 | GRTFSGFGTG |
| 88 | CDR1 | FLL168 | GRTFSGFGTG |
| 88 | CDR1 | FLL170 | GRTFSGFGTG |
| 88 | CDR1 | FLL188 | GRTFSGFGTG |
| 88 | CDR1 | FLL40 | GRTFSGFGTG |
| 88 | CDR1 | FLL6 | GRTFSGFGTG |
| 88 | CDR1 | FLL75 | GRTFSGFGTG |
| 88 | CDR1 | FLL83 | GRTFSGFGTG |
| 88 | CDR1 | FLL94 | GRTFSGFGTG |
| 88 | CDR1 | FLL99 | GRTFSGFGTG |
| 88 | CDR1 | FLL38 | GRTFSGFGTG |
| 88 | CDR1 | FLL53 | GRTFSGFGTG |
| 88 | CDR1 | FLL553 | GRTFSGFGTG |
| 88 | CDR1 | FLL74 | GRTFSGFGTG |
| 89 | CDR1 | FLL102 | GGTWSSYATG |
| 89 | CDR1 | FLL122 | GGTWSSYATG |
| 90 | CDR1 | FLL134 | GGTFSSYATG |
| 90 | CDR1 | FLL153 | GGTFSSYATG |
| 90 | CDR1 | FLL41 | GGTFSSYATG |
| 90 | CDR1 | FLL67 | GGTFSSYATG |
| 89 | CDR1 | FLL92 | GGTWSSYATG |
| 90 | CDR1 | FLL71 | GGTFSSYATG |
| 90 | CDR1 | FLL8 | GGTFSSYATG |
| 90 | CDR1 | FLL84 | GGTFSSYATG |
| 91 | CDR1 | FLL107 | GRTFSSYAMG |
| 91 | CDR1 | FLL141 | GRTFSSYAMG |
| 92 | CDR1 | FLL34 | GRTFSSYALG |
| 93 | CDR1 | FLL4 | ERTFSSYTMG |
| 94 | CDR1 | FLL61 | ERTFSSYAMG |
| 91 | CDR1 | FLL78 | GRT FS SYAMG |
| 95 | CDR1 | FLL1 | GRTFSTLTVA |
| 96 | CDR1 | FLL26 | GRTFTTYTVA |
| 97 | CDR1 | FLL160 | GRTFNLYRVG |
| 97 | CDR1 | FLL173 | GRTFNLYRVG |
| 98 | CDR1 | FLL178 | GFT FS DYAMS |
| 99 | CDR1 | FLL27 | GFTFSSYAMS |
| 100 | CDR1 | FLL190 | GSTFSINHFS |

-continued

SEQUENCES

| SEQ ID NO. | Sequence descriptor | Seq. name | Amino acid sequence |
|---|---|---|---|
| 101 | CDR1 | FLL43 | GSTFSINHFA |
| 102 | CDR1 | FLL15 | EGTISHAAMG |
| 103 | CDR1 | FLL45 | GGTFSSSAMG |
| 104 | CDR1 | FLL39 | GLTSSTYRMA |
| 105 | CDR1 | FLL177 | GSTFSRNTMG |
| 106 | CDR1 | FLL823 | GGTFGYYAVG |
| 107 | CDR1 | FLL76 | GGAFSSYVMG |
| 108 | CDR1 | FLL822 | GRTFTDYTMG |
| 91 | CDR1 | FLH107 | GRTFSSYAMG |
| 91 | CDR1 | FLH141 | GRTFSSYAMG |
| 100 | CDR1 | FLH19C | GSTFSINHFS |
| 92 | CDR1 | FLH34 | GRTFSSYALG |
| 93 | CDR1 | FLH4 | ERTFSSYTMG |
| 91 | CDR1 | FLH78 | GRTFSSYAMG |
| 109 | CDR2 | FLL101 | QITRDSNSFYADSVKG |
| 109 | CDR2 | FLL103 | QITRDSNSFYADSVKG |
| 109 | CDR2 | FLL116 | QITRDSNSFYADSVKG |
| 110 | CDR2 | FLL125 | QITSGGNTHYEPSLKG |
| 111 | CDR2 | FLL129 | QITRGGDSFYADSVKG |
| 112 | CDR2 | FLL137 | QITRDSSSFYADSVKG |
| 109 | CDR2 | FLL14 | QITRDSNSFYADSVKG |
| 113 | CDR2 | FLL146 | QITRDDTSFYADSVKG |
| 110 | CDR2 | FLL158 | QITSGGNTHYEPSLKG |
| 114 | CDR2 | FLL179 | QITRDGSSFYADSVKG |
| 111 | CDR2 | FLL181 | QITRGGDSFYADSVKG |
| 109 | CDR2 | FLL187 | QITRDSNSFYADSVKG |
| 115 | CDR2 | FLL32 | QITRDSTRFYADSVKG |
| 111 | CDR2 | FLL51 | QITRGGDSFYADSVKG |
| 116 | CDR2 | FLL55 | QITSAGNTHYEPSLKG |
| 111 | CDR2 | FLL77 | QITRGGDSFYADSVKG |
| 109 | CDR2 | FLL97 | QITRDSNSFYADSVKG |
| 110 | CDR2 | FLL21 | QITSGGNTHYEPSLKG |
| 110 | CDR2 | FLL57 | QITSGGNTHYEPSLKG |
| 110 | CDR2 | FLL62 | QITSGGNTHYEPSLKG |
| 110 | CDR2 | FLL79 | QITSGGNTHYEPSLKG |
| 110 | CDR2 | FLL86 | QITSGGNTHYEPSLKG |
| 117 | CDR2 | FLL112 | AISWAGGRTHYEDSVKG |
| 118 | CDR2 | FLL142 | AISWDGGRTHYADFVKG |
| 119 | CDR2 | FLL143 | AISWVGGRTHYADSVKG |
| 120 | CDR2 | FLL154 | AISWSGGRTHYADSVKG |
| 121 | CDR2 | FLL168 | AISWDGGRTHYADSVKG |
| 122 | CDR2 | FLL170 | AISWSGGTTHYADSVKG |
| 121 | CDR2 | FLL188 | AISWDGGRTHYADSVKG |
| 122 | CDR2 | FLL40 | AISWSGGTTHYADSVKG |
| 121 | CDR2 | FLL6 | AISWDGGRTHYADSVKG |
| 122 | CDR2 | FLL75 | AISWSGGTTHYADSVKG |
| 122 | CDR2 | FLL83 | AISWSGGTTHYADSVKG |
| 121 | CDR2 | FLL94 | AISWDGGRTHYADSVKG |
| 118 | CDR2 | FLL99 | AISWDGGRTHYADFVKG |
| 123 | CDR2 | FLL38 | AVSWSGGTTEIADSVKG |
| 124 | CDR2 | FLL53 | AVSQSGGTTHYADSVKG |
| 122 | CDR2 | FLL553 | AISWSGGTTHYADSVKG |
| 117 | CDR2 | FLL74 | AISWAGGRTHYEDSVKG |
| 125 | CDR2 | FLL102 | GISRSGGRTYYAESVKG |
| 125 | CDR2 | FLL122 | GISRSGGRTYYAESVKG |
| 126 | CDR2 | FLL134 | GISRNSGRTYAESVKG |
| 127 | CDR2 | FLL153 | GVSRNSGRTYYAESVKG |
| 125 | CDR2 | FLL41 | GISRSGGRTYYAESVKG |
| 125 | CDR2 | FLL67 | GISRSGGRTYYAESVKG |
| 125 | CDR2 | FLL92 | GISRSGGRTYYAESVKG |
| 128 | CDR2 | FLL71 | GISRNSGRTYYAESVKG |
| 128 | CDR2 | FLL8 | GISRNSGRTYYAESVKG |
| 125 | CDR2 | FLL84 | GISRSGGRTYYAESVKG |
| 129 | CDR2 | FLL107 | AISWSGSNTYYADSVKG |
| 130 | CDR2 | FLL141 | AISWSGYSTYYADSVKG |
| 131 | CDR2 | FLL34 | AISWSGGNTYYADSVKG |
| 132 | CDR2 | FLL4 | AMSWSGGSTYYADSVKG |
| 133 | CDR2 | FLL61 | AISWSGGSTYYADSVKG |
| 134 | CDR2 | FLL78 | AISWSGSSTYYADSVKG |
| 135 | CDR2 | FLL1 | ASIPSGSNTGYAESVKG |
| 136 | CDR2 | FLL26 | ASIPTGSNTAYAESVKG |
| 137 | CDR2 | FLL160 | RITWSADITQYADSVKG |
| 138 | CDR2 | FLL173 | RITWSADITQYTDSVKG |
| 139 | CDR2 | FLL178 | GISSGGYKIGYTDSTKG |

-continued

SEQUENCES

| SEQ ID NO. | Sequence descriptor | Seq. name | Amino acid sequence |
|---|---|---|---|
| 139 | CDR2 | FLL27 | GISSGGYKIGYTDSTKG |
| 140 | CDR2 | FLL190 | FISSDGVSIDVESVKG |
| 141 | CDR2 | FLL43 | FISSDGRSTDVESVKG |
| 142 | CDR2 | FLL15 | YDTWTGGSTNYADSVKD |
| 143 | CDR2 | FLL45 | TITQNDVPTYYTHSVKG |
| 144 | CDR2 | FLL39 | AGISYSADSGGSTNYADSVKG |
| 145 | CDR2 | FLL177 | GISWSGIRSYYLDSAKA |
| 146 | CDR2 | FLL823 | AVTWNGAYLYSDPVKG |
| 147 | CDR2 | FLL76 | AVISWSGRITDYADSVKG |
| 148 | CDR2 | FLL822 | GISSNGYRRYYTGSMKD |
| 149 | CDR2 | FLH107 | ISWSGSNTYYADSVKG |
| 150 | CDR2 | FLH141 | ISWSGYSTYYADSVKG |
| 151 | CDR2 | FLH19C | ISSDGVSIDVESVKG |
| 152 | CDR2 | FLH34 | ISWSGGNTYYADSVKG |
| 153 | CDR2 | FLH4 | MSWSGGSTYYADSVKG |
| 154 | CDR2 | FLH78 | ISWSGSSTYYADSVKG |
| 155 | CDR3 | FLL101 | LSY |
| 155 | CDR3 | FLL103 | LSY |
| 155 | CDR3 | FLL116 | LSY |
| 156 | CDR3 | FLL125 | LDY |
| 155 | CDR3 | FLL129 | LSY |
| 155 | CDR3 | FLL137 | LSY |
| 155 | CDR3 | FLL14 | LSY |
| 157 | CDR3 | FLL146 | LSF |
| 156 | CDR3 | FLL158 | LDY |
| 158 | CDR3 | FLL179 | LSD |
| 155 | CDR3 | FLL181 | LSY |
| 155 | CDR3 | FLL187 | LSY |
| 155 | CDR3 | FLL32 | LSY |
| 155 | CDR3 | FLL51 | LSY |
| 156 | CDR3 | FLL55 | LDY |
| 155 | CDR3 | FLL77 | LSY |
| 155 | CDR3 | FLL97 | LSY |
| 156 | CDR3 | FLL21 | LDY |
| 156 | CDR3 | FLL57 | LDY |
| 156 | CDR3 | FLL62 | LDY |
| 156 | CDR3 | FLL79 | LDY |
| 156 | CDR3 | FLL86 | LDY |
| 159 | CDR3 | FLL112 | AQVSRAYDGIWYSGGDY |
| 160 | CDR3 | FLL142 | AQVARAYDSKWYSGGDY |
| 161 | CDR3 | FLL143 | AQVARAYDGNWYSGGDY |
| 162 | CDR3 | FLL154 | GQVARAYDGNWYSRGDY |
| 163 | CDR3 | FLL168 | AQVSRAYDGRWYSAVDY |
| 164 | CDR3 | FLL170 | GQVARAYDSSWYSRGDY |
| 165 | CDR3 | FLL188 | AQVARAYDSRWYSGGDY |
| 164 | CDR3 | FLL40 | GQVARAYDSSWYSRGDY |
| 166 | CDR3 | FLL6 | GQVSRAYDSMWYGRDDY |
| 167 | CDR3 | FLL75 | GQVARAYDSNWYSRGDY |
| 168 | CDR3 | FLL83 | GQVSRAYDSNWYSRDDY |
| 169 | CDR3 | FLL94 | GQVARAYDTRWYSRGDY |
| 165 | CDR3 | FLL99 | AQVARAYDSRWYSGGDY |
| 170 | CDR3 | FLL38 | GQVARAYDSRWYSRGDY |
| 171 | CDR3 | FLL53 | GQVARAYDSSWYARGDY |
| 167 | CDR3 | FLL553 | GQVARAYDSNWYSRGDY |
| 172 | CDR3 | FLL74 | VQVSRAYDGIWYSGGDY |
| 173 | CDR3 | FLL102 | ARYFTSSVVYTSGNDYDY |
| 173 | CDR3 | FLL122 | ARYFTSSVVYTSGNDYDY |
| 174 | CDR3 | FLL134 | ARYFTRDAIYTSGDDYDY |
| 175 | CDR3 | FLL153 | ARYFTRDAVYTSGDDYDY |
| 176 | CDR3 | FLL41 | ARYFTTSVVYTSGDDYDY |
| 176 | CDR3 | FLL67 | ARYFTTSVVYTSGDDYDY |
| 173 | CDR3 | FLL92 | ARYFTSSVVYTSGNDYDY |
| 175 | CDR3 | FLL71 | ARYFTRDAVYTSGDDYDY |
| 177 | CDR3 | FLL8 | ARYFTRDVVYTSGDDYDY |
| 176 | CDR3 | FLL84 | ARYFTTSVVYTSGDDYDY |
| 178 | CDR3 | FLL107 | AGGSTRVVVTTTPVVKY |
| 178 | CDR3 | FLL141 | AGGSTRVVVTTTPVVKY |
| 178 | CDR3 | FLL34 | AGGSTRVVVTTTPVVKY |
| 178 | CDR3 | FLL4 | AGGSTRVVVTTTPVVKY |
| 179 | CDR3 | FLL61 | AGGSTRVVVTTTPIVKY |
| 178 | CDR3 | FLL78 | AGGSTRVVVTTTPVVKY |
| 180 | CDR3 | FLL1 | RIYFGSSRGYDY |
| 181 | CDR3 | FLL26 | RTYFGSSRGYDY |
| 182 | CDR3 | FLL160 | TLRKSSGIYHVDDYDD |

-continued

SEQUENCES

| SEQ ID NO. | Sequence descriptor | Seq. name | Amino acid sequence |
|---|---|---|---|
| 183 | CDR3 | FLL173 | TLRKSSGIYHTDDYDY |
| 184 | CDR3 | FLL178 | GTQWSWSLRDNTS |
| 185 | CDR3 | FLL27 | GTQWSWALRDSTS |
| 186 | CDR3 | FLL190 | RGF |
| 187 | CDR3 | FLL43 | RGS |
| 188 | CDR3 | FLL15 | RGRYSASYTYTNPASYKY |
| 189 | CDR3 | FLL45 | RVAQASGWRTTIKDYGY |
| 190 | CDR3 | FLL39 | GRYSGTYNSPYSSSYVY |
| 191 | CDR3 | FLL177 | AQEGSSPGPYKY |
| 192 | CDR3 | FLL823 | DRWSAVVESTPST |
| 193 | CDR3 | FLL76 | AKTGMYIDLRTSTFDY |
| 194 | CDR3 | FLL822 | SEDHGAPRYDY |
| 195 | CDR3 | FLH107 | GGSTRVVVTTTPVVKY |
| 195 | CDR3 | FLH141 | GGSTRVVVTTTPVVKY |
| 186 | CDR3 | FLH19C | RGF |
| 195 | CDR3 | FLH34 | GGSTRVVVTTTPVVKY |
| 195 | CDR3 | FLH4 | GGSTRVVVTTTPVVKY |
| 195 | CDR3 | FLH78 | GGSTRVVVTTTPVVKY |
| 273 | framework 1 | FLL101 | QVQLQESGGGLVQAGGSLRLSCAAS |
| 274 | framework 1 | FLL103 | QVQLQESGGGLVQAGGSLRLSCEAS |
| 273 | framework 1 | FLL116 | QVQLQESGGGLVQAGGSLRLSCAAS |
| 273 | framework 1 | FLL125 | QVQLQESGGGLVQAGGSLRLSCAAS |
| 273 | framework 1 | FLL129 | QVQLQESGGGLVQAGGSLRLSCAAS |
| 273 | framework 1 | FLL137 | QVQLQESGGGLVQAGGSLRLSCAAS |
| 273 | framework 1 | FLL14 | QVQLQESGGGLVQAGGSLRLSCAAS |
| 273 | framework 1 | FLL146 | QVQLQESGGGLVQAGGSLRLSCAAS |
| 275 | framework 1 | FLL158 | QVQLQESGGGLVQPGGSLRLSCAAS |
| 276 | framework 1 | FLL179 | QVQLQESGGGLVQAGGSLRLSCKAS |
| 277 | framework 1 | FLL181 | QVQLQESGGGLVQAGDSLRLSCAAS |
| 275 | framework 1 | FLL187 | QVQLQESGGGLVQPGGSLRLSCAAS |
| 278 | framework 1 | FLL32 | QVQLQESGGGLVQAGGSLRLSCQAS |
| 275 | framework 1 | FLL51 | QVQLQESGGGLVQPGGSLRLSCAAS |
| 273 | framework 1 | FLL55 | QVQLQESGGGLVQAGGSLRLSCAAS |
| 275 | framework 1 | FLL77 | QVQLQESGGGLVQPGGSLRLSCAAS |
| 273 | framework 1 | FLL97 | QVQLQESGGGLVQAGGSLRLSCAAS |
| 279 | framework 1 | FLL21 | QVQLQESGGGLVQPGGSLTLSCAAS |
| 273 | framework 1 | FLL57 | QVQLQESGGGLVQAGGSLRLSCAAS |
| 273 | framework 1 | FLL62 | QVQLQESGGGLVQAGGSLRLSCAAS |
| 280 | framework 1 | FLL79 | QVQLQESGGGLVQAGGSLRLSCSAS |
| 281 | framework 1 | FLL86 | QVQLQESGGGLVQPGDPLRLSCAAS |
| 282 | framework 1 | FLL112 | QVQLQESGGGLVQAGGSLRLSCAVS |
| 282 | framework 1 | FLL142 | QVQLQESGGGLVQAGGSLRLSCAVS |
| 282 | framework 1 | FLL143 | QVQLQESGGGLVQAGGSLRLSCAVS |
| 282 | framework 1 | FLL154 | QVQLQESGGGLVQAGGSLRLSCAVS |
| 283 | framework 1 | FLL168 | QVQLQESGGGSVQAGGSLRLSCAFS |
| 282 | framework 1 | FLL170 | QVQLQESGGGLVQAGGSLRLSCAVS |
| 284 | framework 1 | FLL188 | QVQLQESGGGLVQAGGSLGLSCAVS |
| 282 | framework 1 | FLL40 | QVQLQESGGGLVQAGGSLRLSCAVS |
| 282 | framework 1 | FLL6 | QVQLQESGGGLVQAGGSLRLSCAVS |
| 282 | framework 1 | FLL75 | QVQLQESGGGLVQAGGSLRLSCAVS |
| 282 | framework 1 | FLL83 | QVQLQESGGGLVQAGGSLRLSCAVS |
| 282 | framework 1 | FLL94 | QVQLQESGGGLVQAGGSLRLSCAVS |
| 282 | framework 1 | FLL99 | QVQLQESGGGLVQAGGSLRLSCAVS |
| 282 | framework 1 | FLL38 | QVQLQESGGGLVQAGGSLRLSCAVS |
| 285 | framework 1 | FLL53 | QVQLQESGGGLVQAGDSLRLSCAVS |
| 282 | framework 1 | FLL553 | QVQLQESGGGLVQAGGSLRLSCAVS |
| 286 | framework 1 | FLL74 | QVQLQESGGGLVQAGGSLRLSCRFS |
| 287 | framework 1 | FLL102 | QVQLQESGGGLVQAGGSLMVSCAAS |
| 287 | framework 1 | FLL122 | QVQLQESGGGLVQAGGSLMVSCAAS |
| 275 | framework 1 | FLL134 | QVQLQESGGGLVQPGGSLRLSCAAS |
| 288 | framework 1 | FLL153 | QVQLQESGGGLVQVGGSLMVSCAAS |
| 289 | framework 1 | FLL41 | QVQLQESGGGLVQLGDSLMVSCAAS |
| 289 | framework 1 | FLL67 | QVQLQESGGGLVQLGDSLMVSCAAS |
| 287 | framework 1 | FLL92 | QVQLQESGGGLVQAGGSLMVSCAAS |
| 288 | framework 1 | FLL71 | QVQLQESGGGLVQVGGSLMVSCAAS |
| 288 | framework 1 | FLL8 | QVQLQESGGGLVQVGGSLMVSCAAS |
| 287 | framework 1 | FLL84 | QVQLQESGGGLVQAGGSLMVSCAAS |
| 273 | framework 1 | FLL107 | QVQLQESGGGLVQAGGSLRLSCAAS |
| 273 | framework 1 | FLL141 | QVQLQESGGGLVQAGGSLRLSCAAS |
| 273 | framework 1 | FLL34 | QVQLQESGGGLVQAGGSLRLSCAAS |
| 273 | framework 1 | FLL4 | QVQLQESGGGLVQAGGSLRLSCAAS |
| 273 | framework 1 | FLL61 | QVQLQESGGGLVQAGGSLRLSCAAS |
| 290 | framework 1 | FLL78 | QVQLQESGGGWVQAGGSLRLSCAAS |
| 273 | framework 1 | FLL1 | QVQLQESGGGLVQAGGSLRLSCAAS |

SEQUENCES

| SEQ ID NO. | Sequence descriptor | Seq. name | Amino acid sequence |
|---|---|---|---|
| 273 | framework 1 | FLL26 | QVQLQESGGGLVQAGGSLRLSCAAS |
| 291 | framework 1 | FLL160 | QVQLQESGGGLVQAGDSLRLS CAT S |
| 292 | framework 1 | FLL173 | QVQLQESGGGLVQAGGSLRLS CAT S |
| 275 | framework 1 | FLL178 | QVQLQESGGGLVQPGGSLRLSCAAS |
| 293 | framework 1 | FLL27 | QVQLQESGGGLVQPGGSLRLSCKAS |
| 294 | framework 1 | FLL190 | QVQLQESGGGLVQAGGSLTLSCTAS |
| 295 | framework 1 | FLL43 | QVQLQESGGGLVQPGGSLTLSCTAS |
| 296 | framework 1 | FLL15 | QVQLQES GGGLVQAGGSLSLSCAAS |
| 273 | framework 1 | FLL45 | QVQLQESGGGLVQAGGSLRLSCAAS |
| 273 | framework 1 | FLL39 | QVQLQESGGGLVQAGGSLRLSCAAS |
| 297 | framework 1 | FLL177 | QVQLQESGGGLVQTGGSLRLSCAAS |
| 298 | framework 1 | FLL823 | QVQLQESGGGVVQVGGSLRLSCAAS |
| 273 | framework 1 | FLL76 | QVQLQESGGGLVQAGGSLRLSCAAS |
| 299 | framework 1 | FLL822 | QVQLQESGGGSVQAGGSLRLSCTAS |
| 300 | framework 1 | FLH107 | EVQLLESGGGLVQPGGSLTLSCAAS |
| 300 | framework 1 | FLH141 | EVQLLESGGGLVQPGGSLTLSCAAS |
| 301 | framework 1 | FLH19C | EVQLVESGGGLVQPGGSLTLSCAAS |
| 300 | framework 1 | FLH34 | EVQLLESGGGLVQPGGSLTLSCAAS |
| 300 | framework 1 | FLH4 | EVQLLESGGGLVQPGGSLTLSCAAS |
| 300 | framework 1 | FLH78 | EVQLLESGGGLVQPGGSLTLSCAAS |
| 302 | framework 2 | FLL101 | WYRQAPGKQREWVA |
| 302 | framework 2 | FLL103 | WYRQAPGKQREWVA |
| 302 | framework 2 | FLL116 | WYRQAPGKQREWVA |
| 302 | framework 2 | FLL125 | WYRQAPGKQREWVA |
| 303 | framework 2 | FLL129 | WYRQAPGNEREWVA |
| 304 | framework 2 | FLL137 | WFRQAPGKQREWVA |
| 302 | framework 2 | FLL14 | WYRQAPGKQREWVA |
| 302 | framework 2 | FLL146 | WYRQAPGKQREWVA |
| 302 | framework 2 | FLL158 | WYRQAPGKQREWVA |
| 302 | framework 2 | FLL179 | WYRQAPGKQREWVA |
| 303 | framework 2 | FLL181 | WYRQAPGNEREWVA |
| 302 | framework 2 | FLL187 | WYRQAPGKQREWVA |
| 305 | framework 2 | FLL32 | WYRQAPGRQREWVA |
| 303 | framework 2 | FLL51 | WYRQAPGNEREWVA |
| 302 | framework 2 | FLL55 | WYRQAPGKQREWVA |
| 303 | framework 2 | FLL77 | WYRQAPGNEREWVA |
| 302 | framework 2 | FLL97 | WYRQAPGKQREWVA |
| 302 | framework 2 | FLL21 | WYRQAPGKQREWVA |
| 302 | framework 2 | FLL57 | WYRQAPGKQREWVA |
| 302 | framework 2 | FLL62 | WYRQAPGKQREWVA |
| 302 | framework 2 | FLL79 | WYRQAPGKQREWVA |
| 302 | framework 2 | FLL86 | WYRQAPGKQREWVA |
| 306 | framework 2 | FLL112 | WFRQAPGKEREFVA |
| 306 | framework 2 | FLL142 | WFRQAPGKEREFVA |
| 306 | framework 2 | FLL143 | WFRQAPGKEREFVA |
| 306 | framework 2 | FLL154 | WFRQAPGKEREFVA |
| 307 | framework 2 | FLL168 | WFRQAPEKEREFVA |
| 306 | framework 2 | FLL170 | WFRQAPGKEREFVA |
| 308 | framework 2 | FLL188 | WFRQPPEKEREFVA |
| 306 | framework 2 | FLL40 | WFRQAPGKEREFVA |
| 306 | framework 2 | FLL6 | WFRQAPGKEREFVA |
| 306 | framework 2 | FLL75 | WFRQAPGKEREFVA |
| 306 | framework 2 | FLL83 | WFRQAPGKEREFVA |
| 307 | framework 2 | FLL94 | WFRQAPEKEREFVA |
| 306 | framework 2 | FLL99 | WFRQAPGKEREFVA |
| 306 | framework 2 | FLL38 | WFRQAPGKEREFVA |
| 306 | framework 2 | FLL53 | WFRQAPGKEREFVA |
| 306 | framework 2 | FLL553 | WFRQAPGKEREFVA |
| 306 | framework 2 | FLL74 | WFRQAPGKEREFVA |
| 406 | framework 2 | FLL102 | WFRQVPGKERKLIA |
| 309 | framework 2 | FLL122 | WFRQVPGKERELIA |
| 310 | framework 2 | FLL134 | WFRQVPGKEREFIA |
| 310 | framework 2 | FLL153 | WFRQVPGKEREFIA |
| 311 | framework 2 | FLL41 | WFRQVPGREREFIA |
| 310 | framework 2 | FLL67 | WFRQVPGKEREFIA |
| 309 | framework 2 | FLL92 | WFRQVPGKERELIA |
| 310 | framework 2 | FLL71 | WFRQVPGKEREFIA |
| 310 | framework 2 | FLL8 | WFRQVPGKEREFIA |
| 310 | framework 2 | FLL84 | WFRQVPGKEREFIA |
| 306 | framework 2 | FLL107 | WFRQAPGKEREFVA |
| 312 | framework 2 | FLL141 | WFRQAPGMEREFVA |
| 306 | framework 2 | FLL34 | WFRQAPGKEREFVA |
| 306 | framework 2 | FLL4 | WFRQAPGKEREFVA |
| 306 | framework 2 | FLL61 | WFRQAPGKEREFVA |

-continued

SEQUENCES

| SEQ ID NO. | Sequence descriptor | Seq. name | Amino acid sequence |
|---|---|---|---|
| 306 | framework 2 | FLL78 | WFRQAPGKEREFVA |
| 313 | framework 2 | FLL1 | WFRQAPGKEREFVV |
| 314 | framework 2 | FLL26 | WFRQAPGKEREFLV |
| 306 | framework 2 | FLL160 | WFRQAPGKEREFVA |
| 306 | framework 2 | FLL173 | WFRQAPGKEREFVA |
| 315 | framework 2 | FLL178 | WVRQAPGKGLEWVS |
| 315 | framework 2 | FLL27 | WVRQAPGKGLEWVS |
| 316 | framework 2 | FLL190 | WYRQAPGKQRELVA |
| 316 | framework 2 | FLL43 | WYRQAPGKQRELVA |
| 317 | framework 2 | FLL15 | WFRQAPGKERQFVA |
| 306 | framework 2 | FLL45 | WFRQAPGKEREFVA |
| 318 | framework 2 | FLL39 | WFRQAPGKEREFA |
| 319 | framework 2 | FLL177 | WFRQAPGKERVFVL |
| 306 | framework 2 | FLL823 | WFRQAPGKEREFVA |
| 306 | framework 2 | FLL76 | WFRQAPGKEREFVA |
| 320 | framework 2 | FLL822 | WFRQAPGKEREFML |
| 321 | framework 2 | FLH107 | WFRQAPGKEREFVAA |
| 322 | framework 2 | FLH141 | WFRQAPGMEREFVAA |
| 407 | framework 2 | FLH19C | WYRQAPGKQRELVAF |
| 321 | framework 2 | FLH34 | WFRQAPGKEREFVAA |
| 321 | framework 2 | FLH4 | WFRQAPGKEREFVAA |
| 321 | framework 2 | FLH78 | WFRQAPGKEREFVAA |
| 323 | framework 3 | FLL101 | RFAISRDNAKNTVYLQMNNLKPEDTAVYYCRV |
| 324 | framework 3 | FLL103 | RFAVSRDNAKNTVYLQMNSLKPEDTAVYYCRV |
| 325 | framework 3 | FLL116 | RFAISRDNAKNTVYLQMNSLKPEDTAVYYCRV |
| 326 | framework 3 | FLL125 | RFTISRDNAKNTAYLQMNSLKPEDTAVYYCRI |
| 325 | framework 3 | FLL129 | RFAISRDNAKNTVYLQMNSLKPEDTAVYYCRV |
| 325 | framework 3 | FLL137 | RFAISRDNAKNTVYLQMNSLKPEDTAVYYCRV |
| 327 | framework 3 | FLL14 | RFAISRDNAKNTVYLQMNSLKPEDTAVYYCRL |
| 328 | framework 3 | FLL146 | RFAISRDNAKNTVYLQMNNLRPEDTAVYYCRL |
| 326 | framework 3 | FLL158 | RFTISRDNAKNTAYLQMNSLKPEDTAVYYCRI |
| 329 | framework 3 | FLL179 | RFAISRDNAKNTVYLQMNSLKPEDTAVYYCRI |
| 325 | framework 3 | FLL181 | RFAISRDNAKNTVYLQMNSLKPEDTAVYYCRV |
| 330 | framework 3 | FLL187 | RFAISRENAKNTVYLQMNSLKPEDTAVYYCRV |
| 331 | framework 3 | FLL32 | RFAISRDNAKNMVYLQLNSLKPEDTAVYYCRI |
| 329 | framework 3 | FLL51 | RFAISRDNAKNTVYLQMNSLKPEDTAVYYCRI |
| 326 | framework 3 | FLL55 | RFTISRDNAKNTAYLQMNSLKPEDTAVYYCRI |
| 329 | framework 3 | FLL77 | RFAISRDNAKNTVYLQMNSLKPEDTAVYYCRI |
| 324 | framework 3 | FLL97 | RFAVSRDNAKNTVYLQMNSLKPEDTAVYYCRV |
| 326 | framework 3 | FLL21 | RFTISRDNAKNTAYLQMNSLKPEDTAVYYCRI |
| 326 | framework 3 | FLL57 | RFTISRDNAKNTAYLQMNSLKPEDTAVYYCRI |
| 326 | framework 3 | FLL62 | RFTISRDNAKNTAYLQMNSLKPEDTAVYYCRI |
| 326 | framework 3 | FLL79 | RFTISRDNAKNTAYLQMNSLKPEDTAVYYCRI |
| 326 | framework 3 | FLL86 | RFTISRDNAKNTAYLQMNSLKPEDTAVYYCRI |
| 332 | framework 3 | FLL112 | RFTIHRDNAKNTVYLQMNSLKPEDTAVYYCA |
| 333 | framework 3 | FLL142 | RFTISRDNAKNTVYLQMNSLKPEDTAVYYCA |
| 333 | framework 3 | FLL143 | RFTISRDNAKNTVYLQMNSLKPEDTAVYYCA |
| 333 | framework 3 | FLL154 | RFTISRDNAKNTVYLQMNSLKPEDTAVYYCA |
| 334 | framework 3 | FLL168 | RFTISRDNAKNTVYLQMDSLKPEDTAIYYCA |
| 333 | framework 3 | FLL170 | RFTISRDNAKNTVYLQMNSLKPEDTAVYYCA |
| 335 | framework 3 | FLL188 | RFTISRDNAKNTVFLQMNS LKPEDTAVYYCA |
| 336 | framework 3 | FLL40 | RFTISRDNAKNTVSLVYLQMNSLKPDDTAVYYCA |
| 337 | framework 3 | FLL6 | RFTISRDNAANTVYLQMNSLKPEDTAVYYCA |
| 338 | framework 3 | FLL75 | RFTISRDNAKNTVNLVYLQMNDLRPEDTAVYYCA |
| 339 | framework 3 | FLL83 | RFTISRDNAENTVYLEMNSLKPEDTAVYICA |
| 340 | framework 3 | FLL94 | RFTISRDNAKNTVYLQMNSLKPEDTAIYYCA |
| 333 | framework 3 | FLL99 | RFTISRDNAKNTVYLQMNSLKP EDTAVYYCA |
| 341 | framework 3 | FLL38 | RFTISRDNAKNTVYLQMSSLKPGDTAVYYCA |
| 342 | framework 3 | FLL53 | RFTISRDNAKNTETLVYLQMNSLKPEDTAVYYCA |
| 343 | framework 3 | FLL553 | RFTISRDNAKNTVNLVYLQMNSLRPEDTAVYYCA |
| 333 | framework 3 | FLL74 | RFTISRDNAKNTVYLQMNSLKPEDTAVYYCA |
| 344 | framework 3 | FLL102 | RFTISRDNAKNTVYLQMNTLKPDDTAVYYCAA |
| 344 | framework 3 | FLL122 | RFTISRDNAKNTVYLQMNTLKPDDTAVYYCAA |
| 345 | framework 3 | FLL134 | RFTISRDNAKNTVYLQMNTLRPDDTAVYYCAA |
| 346 | framework 3 | FLL153 | RFTISRDNAKNTVYLQMNTLKPDDTGVYYCAA |
| 344 | framework 3 | FLL41 | RFTISRDNAKNTVYLQMNTLKPDDTAVYYCAA |
| 344 | framework 3 | FLL67 | RFTISRDNAKNTVYLQMNTLKPDDTAVYYCAA |
| 347 | framework 3 | FLL92 | RFTISRDNAKNTVYLQMNTLKSDDTAVYYCAA |
| 344 | framework 3 | FLL71 | RFTISRDNAKNTVYLQMNTLKPDDTAVYYCAA |
| 344 | framework 3 | FLL8 | RFTISRDNAKNTVYLQMNTLKPDDTAVYYCAA |
| 344 | framework 3 | FLL84 | RFTISRDNAKNTVYLQMNTLKPDDTAVYYCAA |
| 348 | framework 3 | FLL107 | RFTISRDNAKNTVYLQMDSLKP EDTAVYYCA |
| 349 | framework 3 | FLL141 | RFTISRDDAKNTVYLQMDSLKPEDTAVYYCA |
| 349 | framework 3 | FLL34 | RFTISRDDAKNTVYLQMDSLKPEDTAVYYCA |

-continued

SEQUENCES

| SEQ ID NO. | Sequence descriptor | Seq. name | Amino acid sequence |
|---|---|---|---|
| 348 | framework 3 | FLL4 | RFTISRDNAKNTVYLQMDSLKPEDTAVYYCA |
| 348 | framework 3 | FLL61 | RFTISRDNAKNTVYLQMDSLKPEDTAVYYCA |
| 350 | framework 3 | FLL78 | RFTISRDNAKNTVYLLMDSLKPEDTAVYYCA |
| 351 | framework 3 | FLL1 | RFTISRDIAKNTVYLQMNSLKPEDTAMYFCAA |
| 352 | framework 3 | FLL26 | RFTISRGNAKNTVYLQMNSLKPEDTAMYYCAA |
| 353 | framework 3 | FLL160 | RFTISRDNAKNTVYLQMNSLKPEDTAIYYCAT |
| 353 | framework 3 | FLL173 | RFTISRDNAKNTVYLQMNSLKPEDTAIYYCAT |
| 354 | framework 3 | FLL178 | RFTISRDNAKNTLYLQMNSLTAEDTAVYYCAK |
| 355 | framework 3 | FLL27 | RFTISRDNAKNTLYLQMNSLNAEDTAVYYCAK |
| 356 | framework 3 | FLL190 | RFTISGDNDKNTAYLQMNGLKPEDTAVYYCYY |
| 356 | framework 3 | FLL43 | RFTISGDNDKNTAYLQMNGLKPEDTAVYYCYY |
| 357 | framework 3 | FLL15 | RFTITGDHAKNTVYLQMNSLKPEDTGVYYCAV |
| 358 | framework 3 | FLL45 | RFTISRDNAKNTMYLQMNSLKPEDTAVYYCAQ |
| 359 | framework 3 | FLL39 | RFTISRDNAKNTVYLQMSSLKPEDTAVYYCAA |
| 360 | framework 3 | FLL177 | RFTISRDNAKNTVYLQMNSLRPEDTAVYYCA |
| 361 | framework 3 | FLL823 | RFTISRDNAKNTVYLQMNSLKSEDTAVYYCGL |
| 362 | framework 3 | FLL76 | RFSISRDNAKSTVYLQMNNLKPEDTAVYYCA |
| 363 | framework 3 | FLL822 | RFTISRDNVKKTVYLQMNDLKPEDTAVYYCAA |
| 364 | framework 3 | FLH107 | RFTISRDNSKNTLYLQMNSLRAEDTAVYYCAA |
| 364 | framework 3 | FLH141 | RFTISRDNSKNTLYLQMNSLRAEDTAVYYCAA |
| 365 | framework 3 | FLH19C | RFTISGDNSKNTAYLQMNSLRAEDTAVYYCYY |
| 364 | framework 3 | FLH34 | RFTISRDNSKNTLYLQMNSLRAEDTAVYYCAA |
| 364 | framework 3 | FLH4 | RFTISRDNSKNTLYLQMNSLRAEDTAVYYCAA |
| 364 | framework 3 | FLH78 | RFTISRDNSKNTLYLQMNSLRAEDTAVYYCAA |
| 366 | framework 4 | FLL101 | WGQGTQVTVSS |
| 366 | framework 4 | FLL103 | WGQGTQVTVSS |
| 366 | framework 4 | FLL116 | WGQGTQVTVSS |
| 366 | framework 4 | FLL125 | WGQGTQVTVSS |
| 366 | framework 4 | FLL129 | WGQGTQVTVSS |
| 366 | framework 4 | FLL137 | WGQGTQVTVSS |
| 366 | framework 4 | FLL14 | WGQGTQVTVSS |
| 366 | framework 4 | FLL146 | WGQGTQVTVSS |
| 366 | framework 4 | FLL158 | WGQGTQVTVSS |
| 366 | framework 4 | FLL179 | WGQGTQVTVSS |
| 366 | framework 4 | FLL181 | WGQGTQVTVSS |
| 366 | framework 4 | FLL187 | WGQGTQVTVSS |
| 366 | framework 4 | FLL32 | WGQGTQVTVSS |
| 366 | framework 4 | FLL51 | WGQGTQVTVSS |
| 366 | framework 4 | FLL55 | WGQGTQVTVSS |
| 366 | framework 4 | FLL77 | WGQGTQVTVSS |
| 366 | framework 4 | FLL97 | WGQGTQVTVSS |
| 366 | framework 4 | FLL21 | WGQGTQVTVSS |
| 366 | framework 4 | FLL57 | WGQGTQVTVSS |
| 366 | framework 4 | FLL62 | WGQGTQVTVSS |
| 366 | framework 4 | FLL79 | WGQGTQVTVSS |
| 366 | framework 4 | FLL86 | WGQGTQVTVSS |
| 366 | framework 4 | FLL112 | WGQGTQVTVSS |
| 366 | framework 4 | FLL142 | WGQGTQVTVSS |
| 366 | framework 4 | FLL143 | WGQGTQVTVSS |
| 366 | framework 4 | FLL154 | WGQGTQVTVSS |
| 367 | framework 4 | FLL168 | WGRGTQVTVSS |
| 366 | framework 4 | FLL170 | WGQGTQVTVSS |
| 366 | framework 4 | FLL188 | WGQGTQVTVSS |
| 368 | framework 4 | FLL40 | LGQGTQVTVSS |
| 366 | framework 4 | FLL6 | WGQGTQVTVSS |
| 366 | framework 4 | FLL75 | WGQGTQVTVSS |
| 366 | framework 4 | FLL83 | WGQGTQVTVSS |
| 366 | framework 4 | FLL94 | WGQGTQVTVSS |
| 366 | framework 4 | FLL99 | WGQGTQVTVSS |
| 366 | framework 4 | FLL38 | WGQGTQVTVSS |
| 366 | framework 4 | FLL53 | WGQGTQVTVSS |
| 366 | framework 4 | FLL553 | WGQGTQVTVSS |
| 366 | framework 4 | FLL74 | WGQGTQVTVSS |
| 366 | framework 4 | FLL102 | WGQGTQVTVSS |
| 366 | framework 4 | FLL122 | WGQGTQVTVSS |
| 369 | framework 4 | FLL134 | WGQGTQVTASS |
| 366 | framework 4 | FLL153 | WGQGTQVTVSS |
| 366 | framework 4 | FLL41 | WGQGTQVTVSS |
| 366 | framework 4 | FLL67 | WGQGTQVTVSS |
| 366 | framework 4 | FLL92 | WGQGTQVTVSS |
| 366 | framework 4 | FLL71 | WGQGTQVTVSS |
| 366 | framework 4 | FLL8 | WGQGTQVTVSS |
| 366 | framework 4 | FLL84 | WGQGTQVTVSS |
| 366 | framework 4 | FLL107 | WGQGTQVTVSS |

SEQUENCES

| SEQ ID NO. | Sequence descriptor | Seq. name | Amino acid sequence |
|---|---|---|---|
| 366 | framework 4 | FLL141 | WGQGTQVTVSS |
| 366 | framework 4 | FLL34 | WGQGTQVTVSS |
| 366 | framework 4 | FLL4 | WGQGTQVTVSS |
| 366 | framework 4 | FLL61 | WGQGTQVTVSS |
| 366 | framework 4 | FLL78 | WGQGTQVTVSS |
| 366 | framework 4 | FLL1 | WGQGTQVTVSS |
| 366 | framework 4 | FLL26 | WGQGTQVTVSS |
| 366 | framework 4 | FLL160 | WGQGTQVTVSS |
| 366 | framework 4 | FLL173 | WGQGTQVTVSS |
| 370 | framework 4 | FLL178 | RGQGTQVTVSS |
| 370 | framework 4 | FLL27 | RGQGTQVTVSS |
| 366 | framework 4 | FLL190 | WGQGTQVTVSS |
| 366 | framework 4 | FLL43 | WGQGTQVTVSS |
| 366 | framework 4 | FLL15 | WGQGTQVTVSS |
| 366 | framework 4 | FLL45 | WGQGTQVTVSS |
| 366 | framework 4 | FLL39 | WGQGTQVTVSS |
| 366 | framework 4 | FLL177 | WGQGTQVTVSS |
| 370 | framework 4 | FLL823 | RGQGTQVTVSS |
| 366 | framework 4 | FLL76 | WGQGTQVTVSS |
| 366 | framework 4 | FLL822 | WGQGTQVTVSS |
| 371 | framework 4 | FLH107 | WGQGTLVTVSS |
| 371 | framework 4 | FLH141 | WGQGTLVTVSS |
| 371 | framework 4 | FLH19C | WGQGTLVTVSS |
| 371 | framework 4 | FLH34 | WGQGTLVTVSS |
| 371 | framework 4 | FLH4 | WGQGTLVTVSS |
| 371 | framework 4 | FLH78 | WGQGTLVTVSS |
| 196 | anti-FLT3/anti-HSA/anti-CD3 fusion protein | FLL101 | QVQLQESGGGLVQAGGSLRLSCAASGVTFSINYIDWY RQAPGKQREWVAQITRDSNSFYADSVKGRFAISRDNA KNTVYLQMNNLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 197 | anti-FLT3/anti-HSA/anti-CD3 fusion protein | FLL103 | QVQLQESGGGLVQAGGSLRLSCEASGPTFSINYIDWY RQAPGKQREWVAQITRDSNSFYADSVKGRFAVSRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 198 | anti-FLT3/anti-HSA/anti-CD3 fusion protein | FLL116 | QVQLQESGGGLVQAGGSLRLSCAASGVTFSINYIDWY RQAPGKQREWVAQITRDSNSFYADSVKGRFAISRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 199 | anti-FLT3/anti-HSA/anti-CD3 fusion protein | FLL125 | QVQLQESGGGLVQAGGSLRLSCAASGSTFSRNYIDWY RQAPGKQREWVAQITSGGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL |

-continued

| SEQ ID NO. | Sequence descriptor | Seq. name | Amino acid sequence |
|---|---|---|---|
| | | | SVSSQGTLVTVSSGGGGSGGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 200 | anti-FLT3/anti-HSA/anti-CD3 fusion protein | FLL129 | QVQLQESGGGLVQAGGSLRLSCAASGVTFSASYIDWY RQAPGNEREWVAQITRGGDSFYADSVKGRFAISRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 201 | anti-FLT3/anti-HSA/anti-CD3 fusion protein | FLL137 | QVQLQESGGGLVQAGGSLRLSCAASGSTFNNYAMDWF RQAPGKQREWVAQITRDSSSFYADSVKGRFAISRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 202 | anti-FLT3/anti-HSA/anti-CD3 fusion protein | FLL14 | QVQLQESGGGLVQAGGSLRLSCAASGVTFSINYIDWY RQAPGKQREWVAQITRDSNSFYADSVKGRFAISRDNA KNTVYLQMNSLKPEDTAVYYCRLLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 203 | anti-FLT3/anti-HSA/anti-CD3 fusion protein | FLL146 | QVQLQESGGGLVQAGGSLRLSCAASGVTFSINYIDWY RQAPGKQREWVAQITRDDTSFYADSVKGRFAISRDNA KNTVYLQMNNLRPEDTAVYYCRLLSFWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 204 | anti-FLT3/anti-HSA/anti-CD3 fusion protein | FLL158 | QVQLQESGGGLVQPGGSLRLSCAASGSTFGRNYIDWY RQAPGKQREWVAQITSGGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG |

| SEQ ID NO. | Sequence descriptor | Seq. name | Amino acid sequence |
|---|---|---|---|
| | | | GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 205 | anti-FLT3/anti-HSA/anti-CD3 fusion protein | FLL179 | QVQLQESGGGLVQAGGSLRLSCKASGVTFSINYIDWY RQAPGKQREWVAQITRDGSSFYADSVKGRFAISRDNA KNTVYLQMNSLKPEDTAVYYCRILSDWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 206 | anti-FLT3/anti-HSA/anti-CD3 fusion protein | FLL181 | QVQLQESGGGLVQAGDSLRLSCAASGVTFSASYIDWY RQAPGNEREWVAQITRGGDSFYADSVKGRFAISRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 207 | anti-FLT3/anti-HSA/anti-CD3 fusion protein | FLL187 | QVQLQESGGGLVQPGGSLRLSCAASGVTFSINYIDWY RQAPGKQREWVAQITRDSNSFYADSVKGRFAISRENA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 208 | anti-FLT3/anti-HSA/anti-CD3 fusion protein | FLL32 | QVQLQESGGGLVQAGGSLRLSCQASGVTFNINYIDWY RQAPGRQREWVAQITRDSTRFYADSVKGRFAISRDNA KNMVYLQLNSLKPEDTAVYYCRILSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 209 | anti-FLT3/anti-HSA/anti-CD3 fusion protein | FLL51 | QVQLQESGGGLVQPGGSLRLSCAASGFDFSISYIDWY RQAPGNEREWVAQITRGGDSFYADSVKGRFAISRDNA KNTVYLQMNSLKPEDTAVYYCRILSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |

-continued

SEQUENCES

| SEQ ID NO. | Sequence descriptor | Seq. name | Amino acid sequence |
|---|---|---|---|
| 210 | anti-FLT3/anti-HSA/anti-CD3 fusion protein | FLL55 | QVQLQESGGGLVQAGGSLRLSCAASGSTFSRNYIDWY RQAPGKQREWVAQITSAGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 211 | anti-FLT3/anti-HSA/anti-CD3 fusion protein | FLL77 | QVQLQESGGGLVQPGGSLRLSCAASGVTFSISYIDWY RQAPGNEREWVAQITRGGDSFYADSVKGRFAISRDNA KNTVYLQMNSLKPEDTAVYYCRILSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 212 | anti-FLT3/anti-HSA/anti-CD3 fusion protein | FLL97 | QVQLQESGGGLVQAGGSLRLSCAASGVTFSINYIDWY RQAPGKQREWVAQITRDSNSFYADSVKGRFAVSRDNA KNTVYLQMNSLKPEDTAVYYCRVLSYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 213 | anti-FLT3/anti-HSA/anti-CD3 fusion protein | FLL21 | QVQLQESGGGLVQPGGSLTLSCAASGSTFSRNYIDWY RQAPGKQREWVAQITSGGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 214 | anti-FLT3/anti-HSA/anti-CD3 fusion protein | FLL57 | QVQLQESGGGLVQAGGSLRLSCAASGSTFSKNYIDWY RQAPGKQREWVAQITSGGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGSGGGGSQTVVTQEPSLTVSPGGTVTLTCA SSTGAVTSGNYPNWVQQKPGQAPRGLIGGTKFLVPGT PARFSGSLLGGKAALTLSGVQPEDEAEYYCTLWYSNR WVFGGGTKLTVLHHHHHH |
| 215 | anti-FLT3/anti-HSA/anti-CD3 fusion protein | FLL62 | QVQLQESGGGLVQAGGSLRLSCAASGSTSSRNYIDWY RQAPGKQREWVAQITSGGNTHYEPSLKGRFTISRDNA KNTAYLQMNSLKPEDTAVYYCRILDYWGQGTQVTVSS GGGGSGGGSEVQLVESGGGLVQPGNSLRLSCAASGFT |

SEQUENCES

| SEQ ID NO. | Sequence descriptor | Seq. name | Amino acid sequence |
|---|---|---|---|
| | | | FSKFGMSWVRQAPGKGLEWVSSISGSGRDTLYADSVK<br>GRFTISRDNAKTTLYLQMNSLRPEDTAVYYCTIGGSL<br>SVSSQGTLVTVSSGGGGSGGGGSEVQLVESGGGLVQPG<br>GSLKLSCAASGFTFNKYAINWVRQAPGKGLEWVARIR<br>SKYNNYATYYADQVKDRFTISRDDSKNTAYLQMNNLK<br>TEDTAVYYCVRHANFGNSYISYWAYWGQGTLVTVSSG<br>GGGSGGGGSGGGGSQTVVTQEPSLTVSPGGTVTLTCA<br>SSTGAVTSGNYPNWVQQKPGQAPRGLIGGTKFLVPGT<br>PARFSGSLLGGKAALTLSGVQPEDEAEYYCTLWYSNR<br>WVFGGGTKLTVLHHHHHH |
| 216 | anti-FLT3/anti-HSA/anti-CD3 fusion protein | FLL79 | QVQLQESGGGLVQAGGSLRLSCSASGSTFSRNYIDWY<br>RQAPGKQREWVAQITSGGNTHYEPSLKGRFTISRDNA<br>KNTAYLQMNSLKPEDTAVYYCRILDYWGQGTQVTVSS<br>GGGGSGGGSEVQLVESGGGLVQPGNSLRLSCAASGFT<br>FSKFGMSWVRQAPGKGLEWVSSISGSGRDTLYADSVK<br>GRFTISRDNAKTTLYLQMNSLRPEDTAVYYCTIGGSL<br>SVSSQGTLVTVSSGGGGSGGGGSEVQLVESGGGLVQPG<br>GSLKLSCAASGFTFNKYAINWVRQAPGKGLEWVARIR<br>SKYNNYATYYADQVKDRFTISRDDSKNTAYLQMNNLK<br>TEDTAVYYCVRHANFGNSYISYWAYWGQGTLVTVSSG<br>GGGSGGGGSGGGGSQTVVTQEPSLTVSPGGTVTLTCA<br>SSTGAVTSGNYPNWVQQKPGQAPRGLIGGTKFLVPGT<br>PARFSGSLLGGKAALTLSGVQPEDEAEYYCTLWYSNR<br>WVFGGGTKLTVLHHHHHH |
| 217 | anti-FLT3/anti-HSA/anti-CD3 fusion protein | FLL86 | QVQLQESGGGLVQPGDPLRLSCAASGSTFSRNYIDWY<br>RQAPGKQREWVAQITSGGNTHYEPSLKGRFTISRDNA<br>KNTAYLQMNSLKPEDTAVYYCRILDYWGQGTQVTVSS<br>GGGGSGGGSEVQLVESGGGLVQPGNSLRLSCAASGFT<br>FSKFGMSWVRQAPGKGLEWVSSISGSGRDTLYADSVK<br>GRFTISRDNAKTTLYLQMNSLRPEDTAVYYCTIGGSL<br>SVSSQGTLVTVSSGGGGSGGGGSEVQLVESGGGLVQPG<br>GSLKLSCAASGFTFNKYAINWVRQAPGKGLEWVARIR<br>SKYNNYATYYADQVKDRFTISRDDSKNTAYLQMNNLK<br>TEDTAVYYCVRHANFGNSYISYWAYWGQGTLVTVSSG<br>GGGSGGGGSGGGGSQTVVTQEPSLTVSPGGTVTLTCA<br>SSTGAVTSGNYPNWVQQKPGQAPRGLIGGTKFLVPGT<br>PARFSGSLLGGKAALTLSGVQPEDEAEYYCTLWYSNR<br>WVFGGGTKLTVLHHHHHH |
| 218 | anti-FLT3/anti-HSA/anti-CD3 fusion protein | FLL112 | QVQLQESGGGLVQAGGSLRLSCAVSGRTFSGFGTGWF<br>RQAPGKEREFVAAISWAGGRTHYEDSVKGRFTIHRDN<br>AKNTVYLQMNSLKPEDTAVYYCAAQVSRAYDGIWYSG<br>GDYWGQGTQVTVSSGGGGSGGGGSEVQLVESGGGLVQP<br>GNSLRLSCAASGFTFSKFGMSWVRQAPGKGLEWVSSI<br>SGSGRDTLYADSVKGRFTISRDNAKTTLYLQMNSLRP<br>EDTAVYYCTIGGSLSVSSQGTLVTVSSGGGGSGGGSE<br>VQLVESGGGLVQPGGSLKLSCAASGFTFNKYAINWVR<br>QAPGKGLEWVARIRSKYNNYATYYADQVKDRFTISRD<br>DSKNTAYLQMNNLKTEDTAVYYCVRHANFGNSYISYW<br>AYWGQGTLVTVSSGGGGSGGGGSGGGGSQTVVTQEPS<br>LTVSPGGTVTLTCASSTGAVTSGNYPNWVQQKPGQAP<br>RGLIGGTKFLVPGTPARFSGSLLGGKAALTLSGVQPE<br>DEAEYYCTLWYSNRWVFGGGTKLTVLHHHHHH |
| 219 | anti-FLT3/anti-HSA/anti-CD3 fusion protein | FLL142 | QVQLQESGGGLVQAGGSLRLSCAVSGRTFSGFGTGWF<br>RQAPGKEREFVAAISWDGGRTHYADFVKGRFTISRDN<br>AKNTVYLQMNSLKPEDTAVYYCAAQVARAYDSKWYSG<br>GDYWGQGTQVTVSSGGGGSGGGGSEVQLVESGGGLVQP<br>GNSLRLSCAASGFTFSKFGMSWVRQAPGKGLEWVSSI<br>SGSGRDTLYADSVKGRFTISRDNAKTTLYLQMNSLRP<br>EDTAVYYCTIGGSLSVSSQGTLVTVSSGGGGSGGGSE<br>VQLVESGGGLVQPGGSLKLSCAASGFTFNKYAINWVR<br>QAPGKGLEWVARIRSKYNNYATYYADQVKDRFTISRD<br>DSKNTAYLQMNNLKTEDTAVYYCVRHANFGNSYISYW<br>AYWGQGTLVTVSSGGGGSGGGGSGGGGSQTVVTQEPS<br>LTVSPGGTVTLTCASSTGAVTSGNYPNWVQQKPGQAP<br>RGLIGGTKFLVPGTPARFSGSLLGGKAALTLSGVQPE<br>DEAEYYCTLWYSNRWVFGGGTKLTVLHHHHHH |
| 220 | anti-FLT3/anti-HSA/anti-CD3 fusion protein | FLL143 | QVQLQESGGGLVQAGGSLRLSCAVSGRTFSGFGTGWF<br>RQAPGKEREFVAAISWVGGRTHYADSVKGRFTISRDN<br>AKNTVYLQMNSLKPEDTAVYYCAAQVARAYDGNWYSG<br>GDYWGQGTQVTVSSGGGGSGGGGSEVQLVESGGGLVQP<br>GNSLRLSCAASGFTFSKFGMSWVRQAPGKGLEWVSSI<br>SGSGRDTLYADSVKGRFTISRDNAKTTLYLQMNSLRP<br>EDTAVYYCTIGGSLSVSSQGTLVTVSSGGGGSGGGSE<br>VQLVESGGGLVQPGGSLKLSCAASGFTFNKYAINWVR |

SEQUENCES

| SEQ ID NO. | Sequence descriptor | Seq. name | Amino acid sequence |
|---|---|---|---|
| | | | QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 221 | anti-FLT3/anti-HSA/anti-CD3 fusion protein | FLL154 | QVQLQESGGGLVQAGGSLRLSCAVSGRTFSGFGTGWF RQAPGKEREFVAAISWSGGRTHYADSVKGRFTISRDN AKNTVYLQMNSLKPEDTAVYYCAGQVARAYDGNWYSR GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 222 | anti-FLT3/anti-HSA/anti-CD3 fusion protein | FLL168 | QVQLQESGGGSVQAGGSLRLSCAFSGRTFSGFGTGWF RQAPEKEREFVAAISWDGGRTHYADSVKGRFTISRDN AKNTVYLQMDSLKPEDTAIYYCAAQVSRAYDGRWYSA VDYWGRGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 223 | anti-FLT3/anti-HSA/anti-CD3 fusion protein | FLL170 | QVQLQESGGGLVQAGGSLRLSCAVSGRTFSGFGTGWF RQAPGKEREFVAAISWSGGTTHYADSVKGRFTISRDN AKNTVYLQMNSLKPEDTAVYYCAGQVARAYDSSWYSR GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 224 | anti-FLT3/anti-HSA/anti-CD3 fusion protein | FLL188 | QVQLQESGGGLVQAGGSLGLSCAVSGRTFSGFGTGWF RQPPEKEREFVAAISWDGGRTHYADSVKGRFTISRDN AKNTVFLQMNSLKPEDTAVYYCAAQVARAYDSRWYSG GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 225 | anti-FLT3/anti-HSA/anti-CD3 fusion protein | FLL40 | QVQLQESGGGLVQAGGSLRLSCAVSGRTFSGFGTGWF RQAPGKEREFVAAISWSGGTTHYADSVKGRFTISRDN AKNTVSLVYLQMNSLKPDDTAVYYCAGQVARAYDSSW YSRGDYLGQGTQVTVSSGGGGSGGGSEVQLVESGGGL VQPGNSLRLSCAASGFTFSKFGMSWVRQAPGKGLEWV SSISGSGRDTLYADSVKGRFTISRDNAKTTLYLQMNS LRPEDTAVYYCTIGGSLSVSSQGTLVTVSSGGGGSGG GSEVQLVESGGGLVQPGGSLKLSCAASGFTFNKYAIN WVRQAPGKGLEWVARIRSKYNNYATYYADQVKDRFTI SRDDSKNTAYLQMNNLKTEDTAVYYCVRHANFGNSYI SYWAYWGQGTLVTVSSGGGGSGGGGSGGGGSQTVVTQ EPSLTVSPGGTVTLTCASSTGAVTSGNYPNWVQQKPG |

-continued

SEQUENCES

| SEQ ID NO. | Sequence descriptor | Seq. name | Amino acid sequence |
|---|---|---|---|
| 226 | anti-FLT3/anti-HSA/anti-CD3 fusion protein | FLL6 | QAPRGLIGGTKFLVPGTPARFSGSLLGGKAALTLSGV QPEDEAEYYCTLWYSNRWVFGGGTKLTVLHHHHHH QVQLQESGGGLVQAGGSLRLSCAVSGRTFSGFGTGWF RQAPGKEREFVAAISWDGGRTHYADSVKGRFTISRDN AANTVYLQMNSLKPEDTAVYYCAGQVSRAYDSMWYGR DDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 227 | anti-FLT3/anti-HSA/anti-CD3 fusion protein | FLL75 | QVQLQESGGGLVQAGGSLRLSCAVSGRTFSGFGTGWF RQAPGKEREFVAAISWSGGTTHYADSVKGRFTISRDN AKNTVNLVYLQMNDLRPEDTAVYYCAGQVARAYDSNW YSRGDYWGQGTQVTVSSGGGGSGGGSEVQLVESGGGL VQPGNSLRLSCAASGFTFSKFGMSWVRQAPGKGLEWV SSISGSGRDTLYADSVKGRFTISRDNAKTTLYLQMNS LRPEDTAVYYCTIGGSLSVSSQGTLVTVSSGGGGSGG GSEVQLVESGGGLVQPGGSLKLSCAASGFTFNKYAIN WVRQAPGKGLEWVARIRSKYNNYATYYADQVKDRFTI SRDDSKNTAYLQMNNLKTEDTAVYYCVRHANFGNSYI SYWAYWGQGTLVTVSSGGGGSGGGGSGGGGSQTVVTQ EPSLTVSPGGTVTLTCASSTGAVTSGNYPNWVQQKPG QAPRGLIGGTKFLVPGTPARFSGSLLGGKAALTLSGV QPEDEAEYYCTLWYSNRWVFGGGTKLTVLHHHHHH |
| 228 | anti-FLT3/anti-HSA/anti-CD3 fusion protein | FLL83 | QVQLQESGGGLVQAGGSLRLSCAVSGRTFSGFGTGWF RQAPGKEREFVAAISWSGGTTHYADSVKGRFTISRDN AENTVYLEMNSLKPEDTAVYICAGQVSRAYDSNWYSR DDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 229 | anti-FLT3/anti-HSA/anti-CD3 fusion protein | FLL94 | QVQLQESGGGLVQAGGSLRLSCAVSGRTFSGFGTGWF RQAPEKEREFVAAISWDGGRTHYADSVKGRFTISRDN AKNTVYLQMNSLKPEDTAIYYCAGQVARAYDTRWYSR GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 230 | anti-FLT3/anti-HSA/anti-CD3 fusion protein | FLL99 | QVQLQESGGGLVQAGGSLRLSCAVSGRTFSGFGTGWF RQAPGKEREFVAAISWDGGRTHYADFVKGRFTISRDN AKNTVYLQMNSLKPEDTAVYYCAAQVARAYDSRWYSG GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |

SEQUENCES

| SEQ ID NO. | Sequence descriptor | Seq. name | Amino acid sequence |
|---|---|---|---|
| 231 | anti-FLT3/anti-HSA/anti-CD3 fusion protein | FLL38 | QVQLQESGGGLVQAGGSLRLSCAVSGRTFSGFGTGWF RQAPGKEREFVAAVSWSGGTTEIADSVKGRFTISRDN AKNTVYLQMSSLKPGDTAVYYCAGQVARAYDSRWYSR GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 232 | anti-FLT3/anti-HSA/anti-CD3 fusion protein | FLL53 | QVQLQESGGGLVQAGDSLRLSCAVSGRTFSGFGTGWF RQAPGKEREFVAAVSQSGGTTHYADSVKGRFTISRDN AKNTETLVYLQMNSLKPEDTAVYYCAGQVARAYDSSW YARGDYWGQGTQVTVSSGGGGSGGGSEVQLVESGGGL VQPGNSLRLSCAASGFTFSKFGMSWVRQAPGKGLEWV SSISGSGRDTLYADSVKGRFTISRDNAKTTLYLQMNS LRPEDTAVYYCTIGGSLSVSSQGTLVTVSSGGGGSGG GSEVQLVESGGGLVQPGGSLKLSCAASGFTFNKYAIN WVRQAPGKGLEWVARIRSKYNNYATYYADQVKDRFTI SRDDSKNTAYLQMNNLKTEDTAVYYCVRHANFGNSYI SYWAYWGQGTLVTVSSGGGGSGGGGSGGGGSQTVVTQ EPSLTVSPGGTVTLTCASSTGAVTSGNYPNWVQQKPG QAPRGLIGGTKFLVPGTPARFSGSLLGGKAALTLSGV QPEDEAEYYCTLWYSNRWVFGGGTKLTVLHHHHHH |
| 233 | anti-FLT3/anti-HSA/anti-CD3 fusion protein | FLL553 | QVQLQESGGGLVQAGGSLRLSCAVSGRTFSGFGTGWF RQAPGKEREFVAAISWSGGTTHYADSVKGRFTISRDN AKNTVNLVYLQMNSLRPEDTAVYYCAGQVARAYDSNW YSRGDYWGQGTQVTVSSGGGGSGGGSEVQLVESGGGL VQPGNSLRLSCAASGFTESKFGMSWVRQAPGKGLEWV SSISGSGRDTLYADSVKGRFTISRDNAKTTLYLQMNS LRPEDTAVYYCTIGGSLSVSSQGTLVTVSSGGGGSGG GSEVQLVESGGGLVQPGGSLKLSCAASGFTFNKYAIN WVRQAPGKGLEWVARIRSKYNNYATYYADQVKDRFTI SRDDSKNTAYLQMNNLKTEDTAVYYCVRHANFGNSYI SYWAYWGQGTLVTVSSGGGGSGGGGSGGGGSQTVVTQ EPSLTVSPGGTVTLTCASSTGAVTSGNYPNWVQQKPG QAPRGLIGGTKFLVPGTPARFSGSLLGGKAALTLSGV QPEDEAEYYCTLWYSNRWVFGGGTKLTVLHHHHHH |
| 234 | anti-FLT3/anti-HSA/anti-CD3 fusion protein | FLL74 | QVQLQESGGGLVQAGGSLRLSCRFSGRTFSGFGTGWF RQAPGKEREFVAAISWAGGRTHYEDSVKGRFTISRDN AKNTVYLQMNSLKPEDTAVYYCAVQVSRAYDGIWYSG GDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 235 | anti-FLT3/anti-HSA/anti-CD3 fusion protein | FLL102 | QVQLQESGGGLVQAGGSLMVSCAASGGTWSSYATGWF RQVPGKERKLIAGISRSGGRTYYAESVKGRFTISRDN AKNTVYLQMNTLKPDDTAVYYCAAARYFTSSVVYTSG NDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 236 | anti-FLT3/anti-HSA/anti-CD3 fusion protein | FLL122 | QVQLQESGGGLVQAGGSLMVSCAASGGTWSSYATGWF RQVPGKERELIAGISRSGGRTYYAESVKGRFTISRDN AKNTVYLQMNTLKPDDTAVYYCAAARYFTSSVVYTSG NDYDYWGQGTQVTVSSGGGGSGGGSEVQLVESGGGLV |

SEQUENCES

| SEQ ID NO. | Sequence descriptor | Seq. name | Amino acid sequence |
|---|---|---|---|
| | | | QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 237 | anti-FLT3/anti-HSA/anti-CD3 fusion protein | FLL134 | QVQLQESGGGLVQPGGSLRLSCAASGGTFSSYATGWF RQVPGKEREFIAGISRNSGRTYYAESVKGRFTISRDNA KNTVYLQMNTLRPDDTAVYYCAAARYFTRDAIYTSGD DYDYWGQGTQVTASSGGGGSGGGSEVQLVESGGGLVQ PGNSLRLSCAASGFTESKFGMSWVRQAPGKGLEWVSS ISGSGRDTLYADSVKGRFTISRDNAKTTLYLQMNSLR PEDTAVYYCTIGGSLSVSSQGTLVTVSSGGGGSGGGS EVQLVESGGGLVQPGGSLKLSCAASGFTFNKYAINWV RQAPGKGLEWVARIRSKYNNYATYYADQVKDRFTISR DDSKNTAYLQMNNLKTEDTAVYYCVRHANFGNSYISY WAYWGQGTLVTVSSGGGGSGGGGSGGGGSQTVVTQEP SLTVSPGGTVTLTCASSTGAVTSGNYPNWVQQKPGQA PRGLIGGTKFLVPGTPARFSGSLLGGKAALTLSGVQP EDEAEYYCTLWYSNRWVFGGGTKLTVLHHHHHH |
| 238 | anti-FLT3/anti-HSA/anti-CD3 fusion protein | FLL153 | QVQLQESGGGLVQVGGSLMVSCAASGGTESSYATGWF RQVPGKEREFIAGVSRNSGRTYYAESVKGRFTISRDN AKNTVYLQMNTLKPDDTGVYYCAAARYFTRDAVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 239 | anti-FLT3/anti-HSA/anti-CD3 fusion protein | FLL41 | QVQLQESGGGLVQLGDSLMVSCAASGGTESSYATGWF RQVPGREREFIAGISRSGGRTYYAESVKGRFTISRDN AKNTVYLQMNTLKPDDTAVYYCAAARYFTTSVVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 240 | anti-FLT3/anti-HSA/anti-CD3 fusion protein | FLL67 | QVQLQESGGGLVQLGDSLMVSCAASGGTESSYATGWF RQVPGKEREFIAGISRSGGRTYYAESVKGRFTISRDN AKNTVYLQMNTLKPDDTAVYYCAAARYFTTSVVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 241 | anti-FLT3/anti-HSA/anti-CD3 fusion protein | FLL92 | QVQLQESGGGLVQAGGSLMVSCAASGGTWSSYATGWF RQVPGKERELIAGISRSGGRTYYAESVKGRFTISRDN AKNTVYLQMNTLKSDDTAVYYCAAARYFTSSVVYTSG NDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW |

-continued

| SEQ ID NO. | Sequence descriptor | Seq. name | Amino acid sequence |
|---|---|---|---|
| 243 | anti-FLT3/anti-HSA/anti-CD3 fusion protein | FLL71 | VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH QVQLQESGGGLVQVGGSLMVSCAASGGTESSYATGWF RQVPGKEREFIAGISRNSGRTYYAESVKGRFTISRDN AKNTVYLQMNTLKPDDTAVYYCAAARYFTRDAVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 244 | anti-FLT3/anti-HSA/anti-CD3 fusion protein | FLL8 | QVQLQESGGGLVQVGGSLMVSCAASGGTESSYATGWF RQVPGKEREFIAGISRNSGRTYYAESVKGRFTISRDN AKNTVYLQMNTLKPDDTAVYYCAAARYFTRDVVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 245 | anti-FLT3/anti-HSA/anti-CD3 fusion protein | FLL84 | QVQLQESGGGLVQAGGSLMVSCAASGGTESSYATGWF RQVPGKEREFIAGISRSGGRTYYAESVKGRFTISRDN AKNTVYLQMNTLKPDDTAVYYCAAARYFTTSVVYTSG DDYDYWGQGTQVTVSSGGGGSGGGSEVQLVESGGGLV QPGNSLRLSCAASGFTESKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 246 | anti-FLT3/anti-HSA/anti-CD3 fusion protein | FLL107 | QVQLQESGGGLVQAGGSLRLSCAASGRTFSSYAMGWF RQAPGKEREFVAAISWSGSNTYYADSVKGRFTISRDN AKNTVYLQMDSLKPEDTAVYYCAAGGSTRVVVTTTPV VKYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 247 | anti-FLT3/anti-HSA/anti-CD3 fusion protein | FLL141 | QVQLQESGGGLVQAGGSLRLSCAASGRTFSSYAMGWF RQAPGMEREFVAAISWSGYSTYYADSVKGRFTISRDD AKNTVYLQMDSLKPEDTAVYYCAAGGSTRVVVTTTPV VKYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW |

-continued

SEQUENCES

| SEQ ID NO. | Sequence descriptor | Seq. name | Amino acid sequence |
|---|---|---|---|
| 248 | anti-FLT3/anti-HSA/anti-CD3 fusion protein | FLL34 | AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH QVQLQESGGGLVQAGGSLRLSCAASGRTFSSYALGWF RQAPGKEREFVAAISWSGGNTYYADSVKGRFTISRDD AKNTVYLQMDSLKPEDTAVYYCAAGGSTRVVVTTTPV VKYWGQGTQVTVSSGGGGSGGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 249 | anti-FLT3/anti-HSA/anti-CD3 fusion protein | FLL4 | QVQLQESGGGLVQAGGSLRLSCAASERTFSSYTMGWF RQAPGKEREFVAAMSWSGGSTYYADSVKGRFTISRDN AKNTVYLQMDSLKPEDTAVYYCAAGGSTRVVVTTTPV VKYWGQGTQVTVSSGGGGSGGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 250 | anti-FLT3/anti-HSA/anti-CD3 fusion protein | FLL61 | QVQLQESGGGLVQAGGSLRLSCAASERTFSSYAMGWF RQAPGKEREFVAAISWSGGSTYYADSVKGRFTISRDN AKNTVYLQMDSLKPEDTAVYYCAAGGSTRVVVTTTPI VKYWGQGTQVTVSSGGGGSGGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 251 | anti-FLT3/anti-HSA/anti-CD3 fusion protein | FLL78 | QVQLQESGGGWVQAGGSLRLSCAASGRTFSSYAMGWF RQAPGKEREFVAAISWSGSSTYYADSVKGRFTISRDN AKNTVYLLMDSLKPEDTAVYYCAAGGSTRVVVTTTPV VKYWGQGTQVTVSSGGGGSGGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 252 | anti-FLT3/anti-HSA/anti-CD3 fusion protein | FLL1 | QVQLQESGGGLVQAGGSLRLSCAASGRTFSTLTVAWF RQAPGKEREFVVASIPSGSNTGYAESVKGRFTISRDI AKNTVYLQMNSLKPEDTAMYFCAARIYFGSSRGYDYW GQGTQVTVSSGGGGSGGGGSEVQLVESGGGLVQPGNSL RLSCAASGFTFSKFGMSWVRQAPGKGLEWVSSISGSG RDTLYADSVKGRFTISRDNAKTTLYLQMNSLRPEDTA VYYCTIGGSLSVSSQGTLVTVSSGGGGSGGGGSEVQLV ESGGGLVQPGGSLKLSCAASGFTFNKYAINWVRQAPG KGLEWVARIRSKYNNYATYYADQVKDRFTISRDDSKN TAYLQMNNLKTEDTAVYYCVRHANFGNSYISYWAYWG QGTLVTVSSGGGGSGGGGSGGGGSQTVVTQEPSLTVS PGGTVTLTCASSTGAVTSGNYPNWVQQKPGQAPRGLI GGTKFLVPGTPARFSGSLLGGKAALTLSGVQPEDEAE YYCTLWYSNRWVFGGGTKLTVLHHHHHH |

SEQUENCES

| SEQ ID NO. | Sequence descriptor | Seq. name | Amino acid sequence |
|---|---|---|---|
| 253 | anti-FLT3/anti-HSA/anti-CD3 fusion protein | FLL26 | QVQLQESGGGLVQAGGSLRLSCAASGRTFTTYTVAWF RQAPGKEREFLVASIPTGSNTAYAESVKGRFTISRGN AKNTVYLQMNSLKPEDTAMYYCAARTYFGSSRGYDYW GQGTQVTVSSGGGGSGGGSEVQLVESGGGLVQPGNSL RLSCAASGFTFSKFGMSWVRQAPGKGLEWVSSISGSG RDTLYADSVKGRFTISRDNAKTTLYLQMNSLRPEDTA VYYCTIGGSLSVSSQGTLVTVSSGGGGSGGGSEVQLV ESGGGLVQPGGSLKLSCAASGFTFNKYAINWVRQAPG KGLEWVARIRSKYNNYATYYADQVKDRFTISRDDSKN TAYLQMNNLKTEDTAVYYCVRHANFGNSYISYWAYWG QGTLVTVSSGGGGSGGGGSGGGGSQTVVTQEPSLTVS PGGTVTLTCASSTGAVTSGNYPNWVQQKPGQAPRGLI GGTKFLVPGTPARFSGSLLGGKAALTLSGVQPEDEAE YYCTLWYSNRWVFGGGTKLTVLHHHHHH |
| 254 | anti-FLT3/anti-HSA/anti-CD3 fusion protein | FLL160 | QVQLQESGGGLVQAGDSLRLSCATSGRTFNLYRVGWF RQAPGKEREFVARITWSADITQYADSVKGRFTISRDN AKNTVYLQMNSLKPEDTAIYYCATTLRKSSGIYHVDD YDDWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 255 | anti-FLT3/anti-HSA/anti-CD3 fusion protein | FLL173 | QVQLQESGGGLVQAGGSLRLSCATSGRTFNLYRVGWF RQAPGKEREFVARITWSADITQYTDSVKGRFTISRDN AKNTVYLQMNSLKPEDTAIYYCATTLRKSSGIYHTDD YDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 256 | anti-FLT3/anti-HSA/anti-CD3 fusion protein | FLL178 | QVQLQESGGGLVQPGGSLRLSCAASGFTFSDYAMSWV RQAPGKGLEWVSGISSSGGYKIGYTDSTKGRFTISRDN AKNTLYLQMNSLTAEDTAVYYCAKGTQWSWSLRDNTS RGQGTQVTVSSGGGGSGGGSEVQLVESGGGLVQPGNS LRLSCAASGFTFSKFGMSWVRQAPGKGLEWVSSI SGS GRDTLYADSVKGRFTISRDNAKTTLYLQMNSLRPEDT AVYYCTIGGSLSVSSQGTLVTVSSGGGGSGGGSEVQL VESGGGLVQPGGSLKLSCAASGFTFNKYAINWVRQAP GKGLEWVARIRSKYNNYATYYADQVKDRFTISRDDSK NTAYLQMNNLKTEDTAVYYCVRHANFGNSYISYWAYW GQGTLVTVSSGGGGSGGGGSGGGGSQTVVTQEPSLTV SPGGTVTLTCASSTGAVTSGNYPNWVQQKPGQAPRGL IGGTKFLVPGTPARFSGSLLGGKAALTLSGVQPEDEA EYYCTLWYSNRWVFGGGTKLTVLHHHHHH |
| 257 | anti-FLT3/anti-HSA/anti-CD3 fusion protein | FLL27 | QVQLQESGGGLVQPGGSLRLSCKASGFTFSSYAMSWV RQAPGKGLEWVSGISSGGYKIGYTDSTKGRFTISRDN AKNTLYLQMNSLNAEDTAVYYCAKGTQWSWALRDSTS RGQGTQVTVSSGGGGSGGGSEVQLVESGGGLVQPGNS LRLSCAASGFTFSKFGMSWVRQAPGKGLEWVSSI SGS GRDTLYADSVKGRFTISRDNAKTTLYLQMNSLRPEDT AVYYCTIGGSLSVSSQGTLVTVSSGGGGSGGGSEVQL VESGGGLVQPGGSLKLSCAASGFTFNKYAINWVRQAP GKGLEWVARIRSKYNNYATYYADQVKDRFTISRDDSK NTAYLQMNNLKTEDTAVYYCVRHANFGNSYISYWAYW GQGTLVTVSSGGGGSGGGGSGGGGSQTVVTQEPSLTV SPGGTVTLTCASSTGAVTSGNYPNWVQQKPGQAPRGL IGGTKFLVPGTPARFSGSLLGGKAALTLSGVQPEDEA EYYCTLWYSNRWVFGGGTKLTVLHHHHHH |
| 258 | anti-FLT3/anti-HSA/anti-CD3 fusion protein | FLL190 | QVQLQESGGGLVQAGGSLTLSCTASGSTFSINHFSWY RQAPGKQRELVAFISSDGVSIDVESVKGRFTISGDND KNTAYLQMNGLKPEDTAVYYCYYRGFWGQGTQVTVSS GGGGSGGGSEVQLVESGGGLVQPGNSLRLSCAASGFT |

SEQUENCES

| SEQ ID NO. | Sequence descriptor | Seq. name | Amino acid sequence |
|---|---|---|---|
| | | | FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT RARFSGSLLGGKAALTLSGVQPEDEAEYYCTLWYSNR WVFGGGTKLTVLHHHHHH |
| 259 | anti-FLT3/anti-HSA/anti-CD3 fusion protein | FLL43 | QVQLQESGGGLVQPGGSLTLSCTASGSTFSINHFAWY RQAPGKQRELVAFISSDGRSTDVESVKGRFTISGDND KNTAYLQMNGLKPEDTAVYYCYYRGSWGQGTQVTVSS GGGGSGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT RARFSGSLLGGKAALTLSGVQPEDEAEYYCTLWYSNR WVFGGGTKLTVLHHHHHH |
| 260 | anti-FLT3/anti-HSA/anti-CD3 fusion protein | FLL15 | QVQLQESGGGLVQAGGSLSLSCAASEGTISHAAMGWF RQAPGKERQFVAYDTWTGGSTNYADSVKDRFTITGDH AKNTVYLQMNSLKPEDTGVYYCAVRGRYSASYTYTNP ASYKYWGQGTQVTVSSGGGGSGGGSEVQLVESGGGLV QPGNSLRLSCAASGFTFSKFGMSWVRQAPGKGLEWVS SISGSGRDTLYADSVKGRFTISRDNAKTTLYLQMNSL RPEDTAVYYCTIGGSLSVSSQGTLVTVSSGGGGSGGG SEVQLVESGGGLVQPGGSLKLSCAASGFTFNKYAINW VRQAPGKGLEWVARIRSKYNNYATYYADQVKDRFTIS RDDSKNTAYLQMNNLKTEDTAVYYCVRHANFGNSYIS YWAYWGQGTLVTVSSGGGGSGGGGSGGGGSQTVVTQE PSLTVSPGGTVTLTCASSTGAVTSGNYPNWVQQKPGQ APRGLIGGTKFLVPGTPARFSGSLLGGKAALTLSGVQ PEDEAEYYCTLWYSNRWVFGGGTKLTVLHHHHHH |
| 261 | anti-FLT3/anti-HSA/anti-CD3 fusion protein | FLL45 | QVQLQESGGGLVQAGGSLRLSCAASGGTFSSSAMGWF RQAPGKEREFVATITQNDVPTYYTHSVKGRFTISRDN AKNTMYLQMNSLKPEDTAVYYCAQRVAQASGWRTTIK DYGYWGQGTQVTVSSGGGGSGGGSEVQLVESGGGLVQ PGNSLRLSCAASGFTFSKFGMSWVRQAPGKGLEWVSS ISGSGRDTLYADSVKGRFTISRDNAKTTLYLQMNSLR PEDTAVYYCTIGGSLSVSSQGTLVTVSSGGGGSGGGS EVQLVESGGGLVQPGGSLKLSCAASGFTFNKYAINWV RQAPGKGLEWVARIRSKYNNYATYYADQVKDRFTISR DDSKNTAYLQMNNLKTEDTAVYYCVRHANFGNSYISY WAYWGQGTLVTVSSGGGGSGGGGSGGGGSQTVVTQEP SLTVSPGGTVTLTCASSTGAVTSGNYPNWVQQKPGQA PRGLIGGTKFLVPGTPARFSGSLLGGKAALTLSGVQP EDEAEYYCTLWYSNRWVFGGGTKLTVLHHHHHH |
| 262 | anti-FLT3/anti-HSA/anti-CD3 fusion protein | FLL39 | QVQLQESGGGLVQAGGSLRLSCAASGLTSSTYRMAWF RQAPGKEREFAAGISYSADSGGSTNYADSVKGRFTIS RDNAKNTVYLQMSSLKPEDTAVYYCAAGRYSGTYNSP YSSSYVYWGQGTQVTVSSGGGGSGGGSEVQLVESGGG LVQPGNSLRLSCAASGFTFSKFGMSWVRQAPGKGLEW VSSISGSGRDTLYADSVKGRFTISRDNAKTTLYLQMN SLRPEDTAVYYCTIGGSLSVSSQGTLVTVSSGGGGSG GGSEVQLVESGGGLVQPGGSLKLSCAASGFTFNKYAI NWVRQAPGKGLEWVARIRSKYNNYATYYADQVKDRFT ISRDDSKNTAYLQMNNLKTEDTAVYYCVRHANFGNSY ISYWAYWGQGTLVTVSSGGGGSGGGGSGGGGSQTVVT QEPSLTVSPGGTVTLTCASSTGAVTSGNYPNWVQQKP GQAPRGLIGGTKFLVPGTPARFSGSLLGGKAALTLSG VQPEDEAEYYCTLWYSNRWVFGGGTKLTVLHHHHHH |
| 263 | anti-FLT3/anti-HSA/anti-CD3 fusion protein | FLL177 | QVQLQESGGGLVQTGGSLRLSCAASGSTFSRNTMGWF RQAPGKERVFVLGISWSGIRSYYLDSAKARFTISRDN AKNTVYLQMNSLRPEDTAVYYCAAQEGSSPGPYKYWG QGTQVTVSSGGGGSGGGSEVQLVESGGGLVQPGNSLR LSCAASGFTFSKFGMSWVRQAPGKGLEWVSSISGSGR DTLYADSVKGRFTISRDNAKTTLYLQMNSLRPEDTAV YYCTIGGSLSVSSQGTLVTVSSGGGGSGGGSEVQLVE SGGGLVQPGGSLKLSCAASGFTFNKYAINWVRQAPGK |

| SEQ ID NO. | Sequence descriptor | Seq. name | Amino acid sequence |
|---|---|---|---|
| | | | GLEWVARIRSKYNNYATYYADQVKDRFTISRDDSKNT AYLQMNNLKTEDTAVYYCVRHANFGNSYISYWAYWGQ GTLVTVSSGGGGSGGGGSGGGGSQTVVTQEPSLTVSP GGTVTLTCASSTGAVTSGNYPNWVQQKPGQAPRGLIG GTKFLVPGTPARFSGSLLGGKAALTLSGVQPEDEAEY YCTLWYSNRWVFGGGTKLTVLHHHHHH |
| 264 | anti-FLT3/anti-HSA/anti-CD3 fusion protein | FLL823 | QVQLQESGGGVVQVGGSLRLSCAASGGTFGYYAVGWF RQAPGKEREFVAAVTWNGAYLYSDPVKGRFTISRDNA KNTVYLQMNSLKSEDTAVYYCGLDRWSAVVESTPSTR GQGTQVTVSSGGGGSGGGSEVQLVESGGGLVQPGNSL RLSCAASGFTFSKFGMSWVRQAPGKGLEWVSSISGSG RDTLYADSVKGRFTISRDNAKTTLYLQMNSLRPEDTA VYYCTIGGSLSVSSQGTLVTVSSGGGGSGGGSEVQLV ESGGGLVQPGGSLKLSCAASGFTFNKYAINWVRQAPG KGLEWVARIRSKYNNYATYYADQVKDRFTISRDDSKN TAYLQMNNLKTEDTAVYYCVRHANFGNSYISYWAYWG QGTLVTVSSGGGGSGGGGSGGGGSQTVVTQEPSLTVS PGGTVTLTCASSTGAVTSGNYPNWVQQKPGQAPRGLI GGTKFLVPGTPARFSGSLLGGKAALTLSGVQPEDEAE YYCTLWYSNRWVFGGGTKLTVLHHHHHH |
| 265 | anti-FLT3/anti-HSA/anti-CD3 fusion protein | FLL76 | QVQLQESGGGLVQAGGSLRLSCAASGGAFSSYVMGWF RQAPGKEREFVAAVISWSGRITDYADSVKGRFSISRD NAKSTVYLQMNNLKPEDTAVYYCAAKTGMYIDLRTST FDYWGQGTQVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 266 | anti-FLT3/anti-HSA/anti-CD3 fusion protein | FLL822 | QVQLQESGGGSVQAGGSLRLSCTASGRTFTDYTMGWF RQAPGKEREFMLGISSNGYRRYYTGSMKDRFTISRDN VKKTVYLQMNDLKPEDTAVYYCAASEDHGAPRYDYWG QGTQVTVSSGGGGSGGGSEVQLVESGGGLVQPGNSLR LSCAASGFTFSKFGMSWVRQAPGKGLEWVSSISGSGR DTLYADSVKGRFTISRDNAKTTLYLQMNSLRPEDTAV YYCTIGGSLSVSSQGTLVTVSSGGGGSGGGSEVQLVE SGGGLVQPGGSLKLSCAASGFTFNKYAINWVRQAPGK GLEWVARIRSKYNNYATYYADQVKDRFTISRDDSKNT AYLQMNNLKTEDTAVYYCVRHANFGNSYISYWAYWGQ GTLVTVSSGGGGSGGGGSGGGGSQTVVTQEPSLTVSP GGTVTLTCASSTGAVTSGNYPNWVQQKPGQAPRGLIG GTKFLVPGTPARFSGSLLGGKAALTLSGVQPEDEAEY YCTLWYSNRWVFGGGTKLTVLHHHHHH |
| 267 | anti-FLT3/anti-HSA/anti-CD3 fusion protein | FLH107 | EVQLLESGGGLVQPGGSLTLSCAASGRTFSSYAMGWF RQAPGKEREFVAAISWSGSNTYYADSVKGRFTISRDN SKNTLYLQMNSLRAEDTAVYYCAAGGSTRVVVTTPV VKYWGQGTLVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 268 | anti-FLT3/anti-HSA/anti-CD3 fusion protein | FLH141 | EVQLLESGGGLVQPGGSLTLSCAASGRTFSSYAMGWF RQAPGMEREFVAAISWSGYSTYYADSVKGRFTISRDN SKNTLYLQMNSLRAEDTAVYYCAAGGSTRVVVTTPV VKYWGQGTLVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW |

-continued

| SEQ ID NO. | Sequence descriptor | Seq. name | Amino acid sequence |
|---|---|---|---|
| 269 | anti-FLT3/anti-HSA/anti-CD3 fusion protein | FLH19C | AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH EVQLVESGGGLVQPGGSLTLSCAASGSTFSINHFSWY RQAPGKQRELVAFISSDGVSIDVESVKGRFTISGDNS KNTAYLQMNSLRAEDTAVYYCYYRGFWGQGTLVTVSS GGGGSGGGGSEVQLVESGGGLVQPGNSLRLSCAASGFT FSKFGMSWVRQAPGKGLEWVSSISGSGRDTLYADSVK GRFTISRDNAKTTLYLQMNSLRPEDTAVYYCTIGGSL SVSSQGTLVTVSSGGGGSGGGSEVQLVESGGGLVQPG GSLKLSCAASGFTFNKYAINWVRQAPGKGLEWVARIR SKYNNYATYYADQVKDRFTISRDDSKNTAYLQMNNLK TEDTAVYYCVRHANFGNSYISYWAYWGQGTLVTVSSG GGGSGGGGSGGGGSQTVVTQEPSLTVSPGGTVTLTCA SSTGAVTSGNYPNWVQQKPGQAPRGLIGGTKFLVPGT RARFSGSLLGGKAALTLSGVQPEDEAEYYCTLWYSNR WVFGGGTKLTVLHHHHHH |
| 270 | anti-FLT3/anti-HSA/anti-CD3 fusion protein | FLH34 | EVQLLESGGGLVQPGGSLTLSCAASGRTFSSYALGWF RQAPGKEREFVAAISWSGGNTYYADSVKGRFTISRDN SKNTLYLQMNSLRAEDTAVYYCAAGGSTRVVVTTTPV VKYWGQGTLVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 271 | anti-FLT3/anti-HSA/anti-CD3 fusion protein | FLH4 | EVQLLESGGGLVQPGGSLTLSCAASERTFSSYTMGWF RQAPGKEREFVAAMSWSGGSTYYADSVKGRFTISRDN SKNTLYLQMNSLRAEDTAVYYCAAGGSTRVVVTTTPV VKYWGQGTLVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 272 | anti-FLT3/anti-HSA/anti-CD3 fusion protein | FLH78 | EVQLLESGGGLVQPGGSLTLSCAASGRTESSYAMGWF RQAPGKEREFVAAISWSGSSTYYADSVKGRFTISRDN SKNTLYLQMNSLRAEDTAVYYCAAGGSTRVVVTTTPV VKYWGQGTLVTVSSGGGGSGGGSEVQLVESGGGLVQP GNSLRLSCAASGFTFSKFGMSWVRQAPGKGLEWVSSI SGSGRDTLYADSVKGRFTISRDNAKTTLYLQMNSLRP EDTAVYYCTIGGSLSVSSQGTLVTVSSGGGGSGGGSE VQLVESGGGLVQPGGSLKLSCAASGFTFNKYAINWVR QAPGKGLEWVARIRSKYNNYATYYADQVKDRFTISRD DSKNTAYLQMNNLKTEDTAVYYCVRHANFGNSYISYW AYWGQGTLVTVSSGGGGSGGGGSGGGGSQTVVTQEPS LTVSPGGTVTLTCASSTGAVTSGNYPNWVQQKPGQAP RGLIGGTKFLVPGTPARFSGSLLGGKAALTLSGVQPE DEAEYYCTLWYSNRWVFGGGTKLTVLHHHHHH |
| 372 | sdAb | Anti-albumin | EVQLVESGGGLVQPGNSLRLSCAASGFTESKFGMSWV RQAPGKGLEWVSSISGSGRDTLYADSVKGRFTISRDN AKTTLYLQMNSLRPEDTAVYYCTIGGSLSVSSQGTLV TVSS |
| 373 | scFv- | Anti-CD3 | EVQLVESGGGLVQPGGSLKLSCAASGFTFNKYAINWV RQAPGKGLEWVARIRSKYNNYATYYADQVKDRFTISR DDSKNTAYLQMNNLKTEDTAVYYCVRHANFGNSYISY WAYWGQGTLVTVSSGGGGSGGGGSGGGGSQTVVTQEP SLTVSPGGTVTLTCASSTGAVTSGNYPNWVQQKPGQA PRGLIGGTKFLVPGTPARFSGSLLGGKAALTLSGVQP EDEAEYYCTLWYSNRWVFGGGTKLTVL |
| 374 | Tag | 6x-His | HHHHHH |
| 375 | linker | G45G35 | GGGGSGGGS |
| 376 | Sortase | | LPETG |

-continued

SEQUENCES

| SEQ ID NO. | Sequence descriptor | Seq. name | Amino acid sequence |
|---|---|---|---|
| 377 | linker | (GS)$_n$ | (GS)$_n$ |
| 378 | linker | (GGS)$_n$ | (GGS)$_n$ |
| 379 | linker | (GGGS)$_n$ | (GGGS)$_n$ |
| 380 | linker | (GGSG)$_n$ | (GGSG)$_n$ |
| 381 | linker | (GGSGG)$_n$ | (GGSGG)$_n$ |
| 382 | linker | (GGGGS)$_n$ | (GGGGS)$_n$ |
| 383 | linker | (GGGGG)$_n$ | (GGGGG)$_n$ |
| 384 | linker | (GGG)$_n$ | (GGG)$_n$ |
| 385 | linker | | GGGGSGGGGSGGGGSGGGGS |
| 386 | linker | | GGGGSGGGGSGGGGS |
| 387 | linker | | GGGGSGGGS |
| 388 | P36888 | | MPALARDGGQLPLLVVFSAMIFGTITNQDLPVIKCVL INHKNNDSSVGKSSSYPMVSESPEDLGCALRPQSSGT VYEAAAVEVDVSASITLQVLVDAPGNISCLWVFKHSS LNCQPHFDLQNRGVVSMVILKMTETQAGEYLLFIQSE ATNYTILFTVSIRNTLLYTLRRPYFRKMENQDALVCI SESVPEPIVEWVLCDSQGESCKEESPAVVKKEEKVLH ELFGTDIRCCARNELGRECTRLFTIDLNQTPQTTLPQ LFLKVGEPLWIRCKAVHVNHGFGLTWELENKALEEGN YFEMSTYSTNRTMIRILFAFVSSVARNDTGYYTCSSS KHPSQSALVTIVEKGFINATNSSEDYEIDQYEEFCFS VRFKAYPQIRCTWTFSRKSFPCEQKGLDNGYSISKFC NHKHQPGEYI FHAENDDAQFTKMFTLNIRRKPQVLAE ASASQASCFSDGYPLPSWTWKKCSDKSPNCTEEITE GVWNRKANRKVEGQWVSSSTLNMSEAIKGFLVKCCAY NSLGTSCETILLNSPGPFPFIQDNISFYATIGVCLLF IVVLTLLICHKYKKQFRYESQLQMVQVTGSSDNEYFY VDFREYEYDLKWEFPRENLEFGKVLGSGAFGKVMNAT AYGISKTGVSIQVAVKMLKEKADSSEREALMSELKMM TQLGSHENIVNLLGACTLSGPIYLIFEYCCYGDLLNY LRSKREKFHRTWTEIFKEHNFSFYPTFQSHPNSSMPG SREVQIHPDSDQISGLHGNSFHSEDEIEYENQKRLEE EEDLNVLTFEDLLCFAYQVAKGMEFLEFKSCVHRDLA ARNVLVTHGKVVKICDFGLARDIMSDSNYVVRGNARL PVKWMAPESLFEGIYTIKSDVWSYGILLWEIFSLGVN PYPGIPVDANFYKLIQNGFKMDQPFYATEEIYIIMQS CWAFDSRKRPSFPNLTSFLGCQLADAEEAMYQNVDG RVSECPHTYQNRRPFSREMDLGLLSPQAQVEDS |
| 389 | FLT3 antibody variable domain | FLH92a | EVQLLESGGGLVQPGGSLTLSCAASGGTWSSYA TGWFRQAPGKERELIAGISRSGGRTYYADSVKG RFTISRDNSKNTLYLQMNSLRAEDTAVYYCAAA RYFTSSVVYTSGNDYDYWGQGTLVTVSS |
| 390 | FLT3 antibody variable domain | FLH92b | EVQLLESGGGLVQPGGSLTLSCAASGGTWSSYA TGWFRQAPGKERELIAGISRSGGRTYYADSVKG RFTISRDNSKNIVYLQMNSLRAEDTAVYYCAKA RYFTSSVVYTSGNDYDYWGQGTLVTVSS |
| 391 | anti-FLT3/anti-HSA/anti-CD3 fusion protein | FLH92a | EVQLLESGGGLVQPGGSLTLSCAASGGTWSSYA TGWFRQAPGKERELIAGISRSGGRTYYADSVKG RFTISRDNSKNTLYLQMNSLRAEDTAVYYCAAA RYFTSSVVYTSGNDYDYWGQGTLVTVSSGGGGS GGGSEVQLVESGGGLVQPGNSLRLSCAASGFTF SKFGMSWVRQAPGKGLEWVSSISGSGRDTLYAD SVKGRFTISRDNAKTTLYLQMNSLRPEDTAVYY CTIGGSLSVSSQGTLVTVSSGGGGSGGGSEVQL VESGGGLVQPGGSLKLSCAASGFTFNKYAINWV RQAPGKGLEWVARIRSKYNNYATYYADQVKDRF TISRDDSKNTAYLQMNNLKTEDTAVYYCVRHAN FGNSYISYWAYWGQGTLVTVSSGGGGSGGGGSG GGGSQTVVTQEPSLTVSPGGTVTLTCASSTGAV TSGNYPNWVQQKPGQAPRGLIGGTKFLVPGTPA RFSGSLLGGKAALTLSGVQPEDEAEYYCTLWYS NRWVFGGGTKLTVLHHHHHH |
| 392 | anti-FLT3/anti-HSA/anti-CD3 fusion protein | FLH92b | EVQLLESGGGLVQPGGSLTLSCAASGGTWSSYA TGWFRQAPGKERELIAGISRSGGRTYYADSVKG RFTISRDNSKNIVYLQMNSLRAEDTAVYYCAKA RYFTSSVVYTSGNDYDYWGQGTLVTVSSGGGGS GGGSEVQLVESGGGLVQPGNSLRLSCAASGFTF SKFGMSWVRQAPGKGLEWVSSISGSGRDTLYAD SVKGRFTISRDNAKTTLYLQMNSLRPEDTAVYY CTIGGSLSVSSQGTLVTVSSGGGGSGGGSEVQL VESGGGLVQPGGSLKLSCAASGFTFNKYAINWV RQAPGKGLEWVARIRSKYNNYATYYADQVKDRF TISRDDSKNTAYLQMNNLKTEDTAVYYCVRHAN FGNSYISYWAYWGQGTLVTVSSGGGGSGGGGSG |

-continued

| SEQ ID NO. | Sequence descriptor | Seq. name | Amino acid sequence |
|---|---|---|---|
| | | | GGGSQTVVTQEPSLTVSPGGTVTLTCASSTGAV |
| | | | TSGNYPNWVQQKPGQAPRGLIGGTKFLVPGTPA |
| | | | RFSGSLLGGKAALTLSGVQPEDEAEYYCTLWYS |
| | | | NRWVFGGGTKLTVLHHHHHH |
| 89 | CDR1 | FLH92a | GGTWSSYATG |
| 89 | CDR1 | FLH92b | GGTWSSYATG |
| 393 | CDR2 | FLH92a | GISRSGGRTYYADSVKG |
| 394 | CDR2 | FLH92b | GISRSGGRTYYADSVKG |
| 173 | CDR3 | FLH92a | ARYFTSSVVYTSGNDYDY |
| 173 | CDR3 | FLH92b | ARYFTSSVVYTSGNDYDY |
| 300 | framework 1 | FLH92a | EVQLLESGGGLVQPGGSLTLSCAAS |
| 300 | framework 1 | FLH92b | EVQLLESGGGLVQPGGSLTLSCAAS |
| 395 | framework 2 | FLH92a | WFRQAPGKERELIA |
| 395 | framework 2 | FLH92b | WFRQAPGKERELIA |
| 364 | framework 3 | FLH92a | RFTISRDNSKNTLYLQMNSLRAEDTAVYYCAA |
| 396 | framework 3 | FLH92b | RFTISRDNSKNTVYLQMNSLRAEDTAVYYCAK |
| 371 | framework 4 | FLH92a | WGQGTLVTVSS |
| 371 | framework 4 | FLH92b | WGQGTLVTVSS |
| 397 | CD3 binder exemplary HC CDR1 (heavy chain CDR1) | | GFTFNKYAIN |
| 398 | CD3 binder exemplary HC CDR2 | | RIRSKYNNYATYYADQVK |
| 399 | CD3 binder exemplary HC CDR3 | | HANFGNSYISYWAY |
| 400 | CD3 binder exemplary LC CDR1 (light chain CDR1) | | ASSTGAVTSGNYPN |
| 401 | CD3 binder exemplary LC CDR2 | | GTKFLVP |
| 402 | CD3 binder exemplary LC CDR3 | | TLWYSNRWV |
| 403 | HSA binder exemplary CDR1 | | GFTFSKFGMS |
| 404 | HSA binder exemplary CDR2 | | SISGSGRDTLYADSVK |
| 405 | HSA binder exemplary CDR3 | | GGSLSV |

What is claimed is:

1. A FLT3 binding domain comprising at least three complementarity determining regions (a CDR1, a CDR2, and a CDR3), wherein
the CDR1 comprises SEQ ID NO: 91
the CDR2 comprises SEQ ID NO: 149; and
the CDR3 comprises SEQ ID NO: 195.

2. The FLT3 binding domain of claim 1, comprising an amino acid sequence that is at least 80% identical to SEQ ID NO: 71.

3. The FLT3 binding domain of claim 1, comprising SEQ ID NO: 71.

4. The FLT3 binding domain of claim 1, wherein the FLT3 binding domain is part of a bispecific antibody.

5. The FLT3 binding domain of claim 4, wherein the bispecific antibody comprises a CD3 binding domain.

6. The FLT3 binding domain of claim 5, wherein the CD3 binding domain is a single chain variable fragment (scFv).

7. The FLT3 binding domain of claim 6, wherein the CD3 is a human CD3.

8. The FLT3 binding domain of claim 1, wherein the FLT3 binding domain is part of a multispecific antibody.

9. A multispecific antibody comprising the FLT3 binding domain of claim 1, a CD3 binding domain and an albumin binding domain.

10. The multispecific antibody of claim 9, wherein the CD3 binding domain is an scFv.

11. The multispecific antibody of claim 10, wherein the CD3 binding domain comprises the amino acid sequence of SEQ ID No. 373.

12. The multispecific antibody of claim 9, wherein the CD3 is a human CD3.

13. The multispecific antibody of claim 9, wherein the albumin binding domain is a single domain antibody (sdAb).

14. The multispecific antibody of claim 9, wherein the albumin binding domain comprises the amino acid sequence of SEQ ID No. 372.

15. The multispecific antibody of claim 9, wherein the albumin is a human serum albumin.

16. The multispecific antibody of claim 9, wherein the multispecific antibody is a single chain polypeptide and the FLT3 binding domain, the CD3 binding domain, and the albumin binding domain are joined in any order from N-terminus to C-terminus.

17. The multispecific antibody of claim 9, wherein multispecific antibody comprises SEQ ID NO: 267.

18. The FLT3 binding domain of claim 1, wherein the FLT3 binding domain binds to human FLT3.

19. An FLT3 targeting trispecific protein comprising
(A) a first domain that binds a human CD3;
(B) a second domain that binds a human serum albumin protein; and
(C) a third domain that binds a human FLT3,
wherein the third domain that binds to a human FLT3 comprises a CDR1 comprising SEQ ID NO: 91, a CDR2 comprising SEQ ID NO: 149 and a CDR3 comprising SEQ ID NO: 195.

20. The FLT3 targeting trispecific protein of claim 19, wherein the first domain is an scFv that comprises a heavy chain comprising HC CDR1, HC CDR2, HC CDR3, and a light chain comprising LC CDR1, LC CDR2, or LC CDR3, wherein the HC CDR1 comprises the amino acid sequence of SEQ ID NO: 397; the HC CDR2 comprises the amino acid sequence of SEQ ID NO: 398; the HC CDR3 comprises the amino acid sequence of SEQ ID NO: 399; the LC CDR1 comprises the amino acid sequence of SEQ ID NO: 400; the LC CDR2 comprises the amino acid sequence of SEQ ID NO: 401; and the LC CDR3 comprises the amino acid sequence of SEQ ID NO: 402.

21. The FLT3 targeting trispecific protein of claim 20, wherein the first domain comprises an amino acid sequence that is at least 90% identical to the sequence set forth in SEQ ID No. 373.

22. The FLT3 targeting trispecific protein of claim 19, wherein the second domain is an sdAb that comprises a CDR1, a CDR2, and a CDR3, wherein the CDR1 comprises the amino acid sequence of SEQ ID NO: 403 the CDR2 comprises the amino acid sequence of SEQ ID NO: 404; and the CDR3 comprises the amino acid sequence of SEQ ID NO: 405.

23. The FLT3 targeting trispecific protein of claim 22, wherein the second domain comprises an amino acid sequence that is at least 90% identical to the sequence set forth in SEQ ID No. 372.

24. A method of treating a hematologic malignancy in a subject, the method comprising administering to the subject a FLT3 targeting trispecific protein according to claim 19.

25. The method of claim 24, wherein the third domain that binds to a human FLT3 comprises an amino acid sequence that is at least 80% identical to SEQ ID NO: 71.

26. The method of claim 24, wherein the trispecific protein comprises SEQ ID NO: 267.

27. The method of claim 24, wherein the hematologic malignancy is an acute myeloid leukemia (AML), a myelodysplastic syndrome, or a chronic myelomonocytic leukemia.

* * * * *

SEQUENCE LISTING

<160> NUMBER OF SEQ ID NOS: 407

<210> SEQ ID NO 1
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Ser Asn Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Arg
            85                  90                  95

Val Leu Ser Tyr Trp Gly Gln Gly Thr Gln Val Thr Val Ser Ser
            100                 105                 110

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Leu Val Gln Ala Gly Gly
1               5                   10                  15

Ser Leu Arg Leu Ser Cys Glu Ala Ser Gly Pro Thr Phe Ser Ile Asn
            20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
        50                  55                  60

Gly Arg Phe Ala Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
            85                  90                  95

Val Leu Ser Tyr Trp Gly Gln Gly Thr Gln Val Thr Val Ser Ser
            100                 105                 110

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
        50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
            85                  90                  95

Val Leu Ser Tyr Trp Gly Gln Gly Thr Gln Val Thr Val Ser Ser
            100                 105                 110

<210> SEQ ID NO 4
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 5
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ala Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Asn Asn Tyr
            20                  25                  30

Ala Met Asp Trp Phe Arg Gln Ala Pro Gly Lys Gln Arg Glu Trp Val
        35                  40                  45

Ala Gln Ile Thr Arg Asp Ser Ser Phe Tyr Ala Asp Ser Val Lys
    50                  55                  60

Gly Arg Phe Ala Ile Ser Arg Asp Asn Ala Lys Asn Thr Val Tyr Leu

```
            65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser
            100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
        50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Leu Leu Ser Tyr Trp Gly Gln Gly Thr Gln Val Thr Val Ser Ser
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
            35                  40                  45

Ala Gln Ile Thr Arg Asp Asp Thr Ser Phe Tyr Ala Asp Ser Val Lys
        50                  55                  60

Gly Arg Phe Ala Ile Ser Arg Asp Asn Ala Lys Asn Thr Val Tyr Leu
65                  70                  75                  80

Gln Met Asn Asn Leu Arg Pro Glu Asp Thr Ala Val Tyr Tyr Cys Arg
                85                  90                  95

Leu Leu Ser Phe Trp Gly Gln Gly Thr Gln Val Thr Val Ser Ser
            100                 105                 110

<210> SEQ ID NO 9
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Phe Gly Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Lys Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Gly Ser Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Ile Leu Ser Asp Trp Gly Gln Gly Thr Gln Val Thr Val Ser Ser
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Leu Val Gln Ala Gly Asp
1               5                   10                  15

Ser Leu Arg Leu Ser Cys Ala Ala Ser Gly Val Thr Phe Ser Ala Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Ser Asn Ser Phe Tyr Ala Asp Ser Val Lys
    50                  55                  60

Gly Arg Phe Ala Ile Ser Arg Glu Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Gln Ala Ser Gly Val Thr Phe Asn Ile Asn
            20                  25                  30

Tyr Ile Asp Trp Tyr Arg Gln Ala Pro Gly Arg Gln Arg Glu Trp Val
        35                  40                  45

Ala Gln Ile Thr Arg Asp Ser Thr Arg Phe Tyr Ala Asp Ser Val Lys
    50                  55                  60

Gly Arg Phe Ala Ile Ser Arg Asp Asn Ala Lys Asn Met Val Tyr Leu
65                  70                  75                  80

Gln Leu Asn Ser Leu Lys Pro Glu Asp Thr Ala Val Tyr Tyr Cys Arg
                85                  90                  95

Ile Leu Ser Tyr Trp Gly Gln Gly Thr Gln Val Thr Val Ser Ser
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asp Phe Ser Ile Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Ile Leu Ser Tyr Trp Gly Gln Gly Thr Gln Val Thr Val Ser Ser
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Ala Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Thr Phe Ser Ile Ser
            20                  25                  30

Tyr Ile Asp Trp Tyr Arg Gln Ala Pro Gly Asn Glu Arg Glu Trp Val
        35                  40                  45

```
Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Ile Leu Ser Tyr Trp Gly Gln Gly Thr Gln Val Thr Val Ser Ser
            100                 105                 110

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Ser Asn Ser Phe Tyr Ala Asp Ser Val Lys
    50                  55                  60

Gly Arg Phe Ala Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Gly Gly Leu Val Gln Pro Gly Gly
1               5                   10                  15

Ser Leu Thr Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 19
<211> LENGTH: 111
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Lys Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Ser Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 21
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ser Ala Ser Gly Ser Thr Phe Ser Arg Asn
            20                  25                  30

Tyr Ile Asp Trp Tyr Arg Gln Ala Pro Gly Lys Gln Arg Glu Trp Val

```
                35                  40                  45

Ala Gln Ile Thr Ser Gly Gly Asn Thr His Tyr Glu Pro Ser Leu Lys
            50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Leu Val Gln Pro Gly Asp
1               5                   10                  15

Pro Leu Arg Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser
            100                 105                 110

<210> SEQ ID NO 23
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ala Gly Gly Arg Thr His Tyr Glu Asp Ser Val
    50                  55                  60

Lys Gly Arg Phe Thr Ile His Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ser Arg Ala Tyr Asp Gly Ile Trp Tyr Ser Gly Gly
            100                 105                 110

Asp Tyr Trp Gly Gln Gly Thr Gln Val Thr Val Ser Ser
```

<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Asp Gly Arg Thr His Tyr Ala Asp Phe Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Ser Lys Trp Tyr Ser Gly Gly
            100                 105                 110

Asp Tyr Trp Gly Gln Gly Thr Gln Val Thr Val Ser Ser
        115                 120                 125

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Val Gly Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Gly Asn Trp Tyr Ser Gly Gly
            100                 105                 110

Asp Tyr Trp Gly Gln Gly Thr Gln Val Thr Val Ser Ser
        115                 120                 125

<210> SEQ ID NO 26
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ser Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gln Val Ala Arg Ala Tyr Asp Gly Asn Trp Tyr Ser Arg Gly
            100                 105                 110

Asp Tyr Trp Gly Gln Gly Thr Gln Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Glu Ser Gly Gly Gly Ser Val Gln Ala Gly Gly
1               5                   10                  15

Ser Leu Arg Leu Ser Cys Ala Phe Ser Gly Arg Thr Phe Ser Gly Phe
            20                  25                  30

Gly Thr Gly Trp Phe Arg Gln Ala Pro Glu Lys Glu Arg Glu Phe Val
        35                  40                  45

Ala Ala Ile Ser Trp Asp Gly Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Ile Tyr Tyr Cys
                85                  90                  95

Ala Ala Gln Val Ser Arg Ala Tyr Asp Gly Arg Trp Tyr Ser Ala Val
            100                 105                 110

Asp Tyr Trp Gly Arg Gly Thr Gln Val Thr Val Ser Ser
        115                 120                 125

<210> SEQ ID NO 28
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gln Val Ala Arg Ala Tyr Asp Ser Ser Trp Tyr Ser Arg Gly
            100                 105                 110

Asp Tyr Trp Gly Gln Gly Thr Gln Val Thr Val Ser Ser
        115                 120                 125

<210> SEQ ID NO 29
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Leu Val Gln Ala Gly Gly
1               5                   10                  15

Ser Leu Gly Leu Ser Cys Ala Val Ser Gly Arg Thr Phe Ser Gly Phe
            20                  25                  30

Gly Thr Gly Trp Phe Arg Gln Pro Pro Glu Lys Glu Arg Glu Phe Val
            35                  40                  45

Ala Ala Ile Ser Trp Asp Gly Arg Thr His Tyr Ala Asp Ser Val
        50                  55                  60

Lys Gly Arg Phe Thr Ile Ser Arg Asp Asn Ala Lys Asn Thr Val Phe
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Ser Arg Trp Tyr Ser Gly Gly
            100                 105                 110

Asp Tyr Trp Gly Gln Gly Thr Gln Val Thr Val Ser Ser
        115                 120                 125

<210> SEQ ID NO 30
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
        50                  55                  60

Lys Gly Arg Phe Thr Ile Ser Arg Asp Asn Ala Lys Asn Thr Val Ser
65                  70                  75                  80

```
Leu Val Tyr Leu Gln Met Asn Ser Leu Lys Pro Asp Thr Ala Val
                85                  90                  95

Tyr Tyr Cys Ala Gly Gln Val Ala Arg Ala Tyr Asp Ser Ser Trp Tyr
            100                 105                 110

Ser Arg Gly Asp Tyr Leu Gly Gln Gly Thr Gln Val Thr Val Ser Ser
            115                 120                 125
```

<210> SEQ ID NO 31
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Asp Gly Arg Thr His Tyr Ala Asp Ser Val
    50                  55                  60

Lys Gly Arg Phe Thr Ile Ser Arg Asp Asn Ala Ala Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gln Val Ser Arg Ala Tyr Asp Ser Met Trp Tyr Gly Arg Asp
            100                 105                 110

Asp Tyr Trp Gly Gln Gly Thr Gln Val Thr Val Ser Ser
            115                 120                 125
```

<210> SEQ ID NO 32
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ser Gly Gly Thr Thr His Tyr Ala Asp Ser Val
    50                  55                  60

Lys Gly Arg Phe Thr Ile Ser Arg Asp Asn Ala Lys Asn Thr Val Asn
65                  70                  75                  80

Leu Val Tyr Leu Gln Met Asn Asp Leu Arg Pro Glu Asp Thr Ala Val
                85                  90                  95

Tyr Tyr Cys Ala Gly Gln Val Ala Arg Ala Tyr Asp Ser Asn Trp Tyr
            100                 105                 110

Ser Arg Gly Asp Tyr Trp Gly Gln Gly Thr Gln Val Thr Val Ser Ser
            115                 120                 125
```

<210> SEQ ID NO 33
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ser Gly Thr Thr His Tyr Ala Asp Ser Val
    50                  55                  60

Lys Gly Arg Phe Thr Ile Ser Arg Asp Asn Ala Glu Asn Thr Val Tyr
65                  70                  75                  80

Leu Glu Met Asn Ser Leu Lys Pro Glu Asp Thr Ala Val Tyr Ile Cys
                85                  90                  95

Ala Gly Gln Val Ser Arg Ala Tyr Asp Ser Asn Trp Tyr Ser Arg Asp
            100                 105                 110

Asp Tyr Trp Gly Gln Gly Thr Gln Val Thr Val Ser Ser
        115                 120                 125
```

<210> SEQ ID NO 34
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Glu Lys Glu Arg Glu Phe Val
        35                  40                  45

Ala Ala Ile Ser Trp Asp Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Gln Val Ala Arg Ala Tyr Asp Thr Arg Trp Tyr Ser Arg Gly
            100                 105                 110

Asp Tyr Trp Gly Gln Gly Thr Gln Val Thr Val Ser Ser
        115                 120                 125
```

<210> SEQ ID NO 35
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Asp Gly Arg Thr His Tyr Ala Asp Phe Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Ser Arg Trp Tyr Ser Gly Gly
            100                 105                 110

Asp Tyr Trp Gly Gln Gly Thr Gln Val Thr Val Ser Ser
        115                 120                 125

<210> SEQ ID NO 36
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Val Ser Trp Ser Gly Gly Thr Thr Glu Ile Ala Asp Ser Val
50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Gly Asp Thr Ala Val Tyr Tyr Cys
                85                  90                  95

Ala Gly Gln Val Ala Arg Ala Tyr Asp Ser Arg Trp Tyr Ser Arg Gly
            100                 105                 110

Asp Tyr Trp Gly Gln Gly Thr Gln Val Thr Val Ser Ser
        115                 120                 125

<210> SEQ ID NO 37
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Glu Ser Gly Gly Gly Leu Val Gln Ala Gly Asp
1               5                   10                  15

Ser Leu Arg Leu Ser Cys Ala Val Ser Gly Arg Thr Phe Ser Gly Phe
            20                  25                  30

```
Gly Thr Gly Trp Phe Arg Gln Ala Pro Gly Lys Glu Arg Glu Phe Val
            35                  40                  45

Ala Ala Val Ser Gln Ser Gly Gly Thr Thr His Tyr Ala Asp Ser Val
 50                  55                  60

Lys Gly Arg Phe Thr Ile Ser Arg Asp Asn Ala Lys Asn Thr Glu Thr
 65                  70                  75                  80

Leu Val Tyr Leu Gln Met Asn Ser Leu Lys Pro Glu Asp Thr Ala Val
                 85                  90                  95

Tyr Tyr Cys Ala Gly Gln Val Ala Arg Ala Tyr Asp Ser Ser Trp Tyr
                100                 105                 110

Ala Arg Gly Asp Tyr Trp Gly Gln Gly Thr Gln Val Thr Val Ser Ser
            115                 120                 125
```

<210> SEQ ID NO 38
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Gln Val Gln Leu Gln Glu Ser Gly Gly Gly Leu Val Gln Ala Gly Gly
 1               5                  10                  15

Ser Leu Arg Leu Ser Cys Ala Val Ser Gly Arg Thr Phe Ser Gly Phe
             20                  25                  30

Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
 50                  55                  60

Lys Gly Arg Phe Thr Ile Ser Arg Asp Asn Ala Lys Asn Thr Val Asn
 65                  70                  75                  80

Leu Val Tyr Leu Gln Met Asn Ser Leu Arg Pro Glu Asp Thr Ala Val
                 85                  90                  95

Tyr Tyr Cys Ala Gly Gln Val Ala Arg Ala Tyr Asp Ser Asn Trp Tyr
                100                 105                 110

Ser Arg Gly Asp Tyr Trp Gly Gln Gly Thr Gln Val Thr Val Ser Ser
            115                 120                 125
```

<210> SEQ ID NO 39
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Val Gln Leu Gln Glu Ser Gly Gly Gly Leu Val Gln Ala Gly Gly
 1               5                  10                  15

Ser Leu Arg Leu Ser Cys Arg Phe Ser Gly Arg Thr Phe Ser Gly Phe
             20                  25                  30

Gly Thr Gly Trp Phe Arg Gln Ala Pro Gly Lys Glu Arg Glu Phe Val
            35                  40                  45

Ala Ala Ile Ser Trp Ala Gly Gly Arg Thr His Tyr Glu Asp Ser Val
 50                  55                  60

Lys Gly Arg Phe Thr Ile Ser Arg Asp Asn Ala Lys Asn Thr Val Tyr
 65                  70                  75                  80
```

Leu Gln Met Asn Ser Leu Lys Pro Glu Asp Thr Ala Val Tyr Tyr Cys
                85                  90                  95

Ala Val Gln Val Ser Arg Ala Tyr Asp Gly Ile Trp Tyr Ser Gly Gly
            100                 105                 110

Asp Tyr Trp Gly Gln Gly Thr Gln Val Thr Val Ser Ser
        115                 120                 125

<210> SEQ ID NO 40
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
            20                  25                  30

Ala Thr Gly Trp Phe Arg Gln Val Pro Gly Lys Glu Arg Lys Leu Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Ser Ser Val Val Tyr Thr Ser Gly Asn
            100                 105                 110

Asp Tyr Asp Tyr Trp Gly Gln Gly Thr Gln Val Thr Val Ser Ser
        115                 120                 125

<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
            20                  25                  30

Ala Thr Gly Trp Phe Arg Gln Val Pro Gly Lys Glu Arg Glu Leu Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Ser Ser Val Val Tyr Thr Ser Gly Asn
            100                 105                 110

Asp Tyr Asp Tyr Trp Gly Gln Gly Thr Gln Val Thr Val Ser Ser
        115                 120                 125

<210> SEQ ID NO 42
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Asn Ser Gly Arg Thr Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Pro Asp Asp Thr Ala Val Tyr Tyr Cys Ala
                85                  90                  95

Ala Ala Arg Tyr Phe Thr Arg Asp Ala Ile Tyr Thr Ser Gly Asp Asp
            100                 105                 110

Tyr Asp Tyr Trp Gly Gln Gly Thr Gln Val Thr Ala Ser Ser
        115                 120                 125
```

<210> SEQ ID NO 43
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Gln Val Gln Leu Gln Glu Ser Gly Gly Gly Leu Val Gln Val Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Val Ser Arg Asn Ser Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Gly Val Tyr Tyr Cys
                85                  90                  95

Ala Ala Ala Arg Tyr Phe Thr Arg Asp Ala Val Tyr Thr Ser Gly Asp
            100                 105                 110

Asp Tyr Asp Tyr Trp Gly Gln Gly Thr Gln Val Thr Val Ser Ser
        115                 120                 125
```

<210> SEQ ID NO 44
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 44

Gln Val Gln Leu Gln Glu Ser Gly Gly Gly Leu Val Gln Leu Gly Asp
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Arg Glu Arg Glu Phe Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Thr Ser Val Val Tyr Thr Ser Gly Asp
            100                 105                 110

Asp Tyr Asp Tyr Trp Gly Gln Gly Thr Gln Val Thr Val Ser Ser
        115                 120                 125

<210> SEQ ID NO 45
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Gly Gly Leu Val Gln Leu Gly Asp
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Thr Ser Val Val Tyr Thr Ser Gly Asp
            100                 105                 110

Asp Tyr Asp Tyr Trp Gly Gln Gly Thr Gln Val Thr Val Ser Ser
        115                 120                 125

<210> SEQ ID NO 46
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
            20                  25                  30

Ala Thr Gly Trp Phe Arg Gln Val Pro Gly Lys Glu Arg Glu Leu Ile
```

```
                    35                  40                  45
Ala Gly Ile Ser Arg Ser Gly Gly Arg Thr Tyr Tyr Ala Glu Ser Val
            50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Ser Asp Asp Thr Ala Val Tyr Tyr Cys
                    85                  90                  95

Ala Ala Ala Arg Tyr Phe Thr Ser Ser Val Val Tyr Thr Ser Gly Asn
               100                 105                 110

Asp Tyr Asp Tyr Trp Gly Gln Gly Thr Gln Val Thr Val Ser Ser
           115                 120                 125

<210> SEQ ID NO 47
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Glu Ser Gly Gly Gly Leu Val Gln Val Gly Gly
 1               5                  10                  15

Ser Leu Met Val Ser Cys Ala Ala Ser Gly Gly Thr Phe Ser Ser Tyr
                20                  25                  30

Ala Thr Gly Trp Phe Arg Gln Val Pro Gly Lys Glu Arg Glu Phe Ile
            35                  40                  45

Ala Gly Ile Ser Arg Asn Ser Gly Arg Thr Tyr Tyr Ala Glu Ser Val
            50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Pro Asp Asp Thr Ala Val Tyr Tyr Cys
                    85                  90                  95

Ala Ala Ala Arg Tyr Phe Thr Arg Asp Ala Val Tyr Thr Ser Gly Asp
               100                 105                 110

Asp Tyr Asp Tyr Trp Gly Gln Gly Thr Gln Val Thr Val Ser Ser
           115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Gln Glu Ser Gly Gly Gly Leu Val Gln Val Gly Gly
 1               5                  10                  15

Ser Leu Met Val Ser Cys Ala Ala Ser Gly Gly Thr Phe Ser Ser Tyr
                20                  25                  30

Ala Thr Gly Trp Phe Arg Gln Val Pro Gly Lys Glu Arg Glu Phe Ile
            35                  40                  45

Ala Gly Ile Ser Arg Asn Ser Gly Arg Thr Tyr Tyr Ala Glu Ser Val
            50                  55                  60

Lys Gly Arg Phe Thr Ile Ser Arg Asp Asn Ala Lys Asn Thr Val Tyr
 65                  70                  75                  80

Leu Gln Met Asn Thr Leu Lys Pro Asp Asp Thr Ala Val Tyr Tyr Cys
```

```
                        85                  90                  95

Ala Ala Ala Arg Tyr Phe Thr Arg Asp Val Val Tyr Thr Ser Gly Asp
                       100                 105                 110

Asp Tyr Asp Tyr Trp Gly Gln Gly Thr Gln Val Thr Val Ser Ser
            115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Ser Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Thr Ser Val Val Tyr Thr Ser Gly Asp
                       100                 105                 110

Asp Tyr Asp Tyr Trp Gly Gln Gly Thr Gln Val Thr Val Ser Ser
            115                 120                 125

<210> SEQ ID NO 50
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Thr Pro Val Val
                       100                 105                 110

Lys Tyr Trp Gly Gln Gly Thr Gln Val Thr Val Ser Ser
            115                 120                 125
```

```
<210> SEQ ID NO 51
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

| Gln | Val | Gln | Leu | Gln | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Arg | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Gly | Trp | Phe | Arg | Gln | Ala | Pro | Gly | Met | Glu | Arg | Glu | Phe | Val |
|---|---|---|---|---|---|---|---|---|---|---|---|---|---|---|---|
| | | 35 | | | | | 40 | | | | | 45 | | | |

| Ala | Ala | Ile | Ser | Trp | Ser | Gly | Tyr | Ser | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asp | Ala | Lys | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Lys | Pro | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Gly | Gly | Ser | Thr | Arg | Val | Val | Val | Thr | Thr | Thr | Pro | Val | Val |
|---|---|---|---|---|---|---|---|---|---|---|---|---|---|---|---|
| | | | 100 | | | | | 105 | | | | | 110 | | |

| Lys | Tyr | Trp | Gly | Gln | Gly | Thr | Gln | Val | Thr | Val | Ser | Ser |
|---|---|---|---|---|---|---|---|---|---|---|---|---|
| | | 115 | | | | | 120 | | | | | 125 |

```
<210> SEQ ID NO 52
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52
```

| Gln | Val | Gln | Leu | Gln | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Arg | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Leu | Gly | Trp | Phe | Arg | Gln | Ala | Pro | Gly | Lys | Glu | Arg | Glu | Phe | Val |
|---|---|---|---|---|---|---|---|---|---|---|---|---|---|---|---|
| | | 35 | | | | | 40 | | | | | 45 | | | |

| Ala | Ala | Ile | Ser | Trp | Ser | Gly | Gly | Asn | Thr | Tyr | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asp | Ala | Lys | Asn | Thr | Val | Tyr |
|---|---|---|---|---|---|---|---|---|---|---|---|---|---|---|---|
| 65 | | | | | 70 | | | | | 75 | | | | | 80 |

| Leu | Gln | Met | Asp | Ser | Leu | Lys | Pro | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Gly | Gly | Ser | Thr | Arg | Val | Val | Val | Thr | Thr | Thr | Pro | Val | Val |
|---|---|---|---|---|---|---|---|---|---|---|---|---|---|---|---|
| | | | 100 | | | | | 105 | | | | | 110 | | |

| Lys | Tyr | Trp | Gly | Gln | Gly | Thr | Gln | Val | Thr | Val | Ser | Ser |
|---|---|---|---|---|---|---|---|---|---|---|---|---|
| | | 115 | | | | | 120 | | | | | 125 |

```
<210> SEQ ID NO 53
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Met Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Gln Val Thr Val Ser Ser
            115                 120                 125

<210> SEQ ID NO 54
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Thr Pro Ile Val
            100                 105                 110

Lys Tyr Trp Gly Gln Gly Thr Gln Val Thr Val Ser Ser
            115                 120                 125

<210> SEQ ID NO 55
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Glu Ser Gly Gly Gly Trp Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

```
Ala Ala Ile Ser Trp Ser Gly Ser Ser Thr Tyr Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Leu Met Asp Ser Leu Lys Pro Glu Asp Thr Ala Val Tyr Tyr Cys
                 85                  90                  95

Ala Ala Gly Gly Ser Thr Arg Val Val Val Thr Thr Thr Pro Val Val
            100                 105                 110

Lys Tyr Trp Gly Gln Gly Thr Gln Val Thr Val Ser Ser
            115                 120                 125

<210> SEQ ID NO 56
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Ser Thr Leu
             20                  25                  30

Thr Val Ala Trp Phe Arg Gln Ala Pro Gly Lys Glu Arg Glu Phe Val
         35                  40                  45

Val Ala Ser Ile Pro Ser Gly Ser Asn Thr Gly Tyr Ala Glu Ser Val
     50                  55                  60

Lys Gly Arg Phe Thr Ile Ser Arg Asp Ile Ala Lys Asn Thr Val Tyr
 65                  70                  75                  80

Leu Gln Met Asn Ser Leu Lys Pro Glu Asp Thr Ala Met Tyr Phe Cys
                 85                  90                  95

Ala Ala Arg Ile Tyr Phe Gly Ser Ser Arg Gly Tyr Asp Tyr Trp Gly
            100                 105                 110

Gln Gly Thr Gln Val Thr Val Ser Ser
            115                 120

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Gly Gly Leu Val Gln Ala Gly Gly
 1               5                  10                  15

Ser Leu Arg Leu Ser Cys Ala Ala Ser Gly Arg Thr Phe Thr Thr Tyr
             20                  25                  30

Thr Val Ala Trp Phe Arg Gln Ala Pro Gly Lys Glu Arg Glu Phe Leu
         35                  40                  45

Val Ala Ser Ile Pro Thr Gly Ser Asn Thr Ala Tyr Ala Glu Ser Val
     50                  55                  60

Lys Gly Arg Phe Thr Ile Ser Arg Gly Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95
```

```
Ala Ala Arg Thr Tyr Phe Gly Ser Ser Arg Gly Tyr Asp Tyr Trp Gly
            100                 105                 110

Gln Gly Thr Gln Val Thr Val Ser Ser
        115                 120

<210> SEQ ID NO 58
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Gln Glu Ser Gly Gly Gly Leu Val Gln Ala Gly Asp
1               5                   10                  15

Ser Leu Arg Leu Ser Cys Ala Thr Ser Gly Arg Thr Phe Asn Leu Tyr
            20                  25                  30

Arg Val Gly Trp Phe Arg Gln Ala Pro Gly Lys Glu Arg Glu Phe Val
        35                  40                  45

Ala Arg Ile Thr Trp Ser Ala Asp Ile Thr Gln Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Thr Thr Leu Arg Lys Ser Ser Gly Ile Tyr His Val Asp Asp Tyr
            100                 105                 110

Asp Asp Trp Gly Gln Gly Thr Gln Val Thr Val Ser Ser
        115                 120                 125

<210> SEQ ID NO 59
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Ala Thr Ser Gly Arg Thr Phe Asn Leu Tyr
            20                  25                  30

Arg Val Gly Trp Phe Arg Gln Ala Pro Gly Lys Glu Arg Glu Phe Val
        35                  40                  45

Ala Arg Ile Thr Trp Ser Ala Asp Ile Thr Gln Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Thr Thr Leu Arg Lys Ser Ser Gly Ile Tyr His Thr Asp Asp Tyr
            100                 105                 110

Asp Tyr Trp Gly Gln Gly Thr Gln Val Thr Val Ser Ser
        115                 120                 125

<210> SEQ ID NO 60
```

<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Tyr Lys Ile Gly Tyr Thr Asp Ser Thr
    50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Gly Thr Gln Trp Ser Trp Ser Leu Arg Asp Asn Thr Ser Arg
            100                 105                 110

Gly Gln Gly Thr Gln Val Thr Val Ser Ser
        115                 120

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Gln Val Gln Leu Gln Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Tyr Lys Ile Gly Tyr Thr Asp Ser Thr
    50                  55                  60

Lys Gly Arg Phe Thr Ile Ser Arg Asp Asn Ala Lys Asn Thr Leu Tyr
65                  70                  75                  80

Leu Gln Met Asn Ser Leu Asn Ala Glu Asp Thr Ala Val Tyr Tyr Cys
                85                  90                  95

Ala Lys Gly Thr Gln Trp Ser Trp Ala Leu Arg Asp Ser Thr Ser Arg
            100                 105                 110

Gly Gln Gly Thr Gln Val Thr Val Ser Ser
        115                 120

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Gln Val Gln Leu Gln Glu Ser Gly Gly Gly Leu Val Gln Ala Gly Gly
1               5                   10                  15

Ser Leu Thr Leu Ser Cys Thr Ala Ser Gly Ser Thr Phe Ser Ile Asn
            20                  25                  30

His Phe Ser Trp Tyr Arg Gln Ala Pro Gly Lys Gln Arg Glu Leu Val
        35                  40                  45

Ala Phe Ile Ser Ser Asp Gly Val Ser Ile Asp Val Glu Ser Val Lys
    50                  55                  60

Gly Arg Phe Thr Ile Ser Gly Asp Asn Asp Lys Asn Thr Ala Tyr Leu
65                  70                  75                  80

Gln Met Asn Gly Leu Lys Pro Glu Asp Thr Ala Val Tyr Tyr Cys Tyr
                85                  90                  95

Tyr Arg Gly Phe Trp Gly Gln Gly Thr Gln Val Thr Val Ser Ser
                100                 105                 110

<210> SEQ ID NO 63
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Gly Gly Leu Val Gln Pro Gly Gly
1               5                   10                  15

Ser Leu Thr Leu Ser Cys Thr Ala Ser Gly Ser Thr Phe Ser Ile Asn
            20                  25                  30

His Phe Ala Trp Tyr Arg Gln Ala Pro Gly Lys Gln Arg Glu Leu Val
        35                  40                  45

Ala Phe Ile Ser Ser Asp Gly Arg Ser Thr Asp Val Glu Ser Val Lys
    50                  55                  60

Gly Arg Phe Thr Ile Ser Gly Asp Asn Asp Lys Asn Thr Ala Tyr Leu
65                  70                  75                  80

Gln Met Asn Gly Leu Lys Pro Glu Asp Thr Ala Val Tyr Tyr Cys Tyr
                85                  90                  95

Tyr Arg Gly Ser Trp Gly Gln Gly Thr Gln Val Thr Val Ser Ser
                100                 105                 110

<210> SEQ ID NO 64
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Gln Glu Ser Gly Gly Gly Leu Val Gln Ala Gly Gly
1               5                   10                  15

Ser Leu Ser Leu Ser Cys Ala Ala Ser Glu Gly Thr Ile Ser His Ala
            20                  25                  30

Ala Met Gly Trp Phe Arg Gln Ala Pro Gly Lys Glu Arg Gln Phe Val
        35                  40                  45

Ala Tyr Asp Thr Trp Thr Gly Gly Ser Thr Asn Tyr Ala Asp Ser Val
    50                  55                  60

Lys Asp Arg Phe Thr Ile Thr Gly Asp His Ala Lys Asn Thr Val Tyr
65                  70                  75                  80

-continued

Leu Gln Met Asn Ser Leu Lys Pro Glu Asp Thr Gly Val Tyr Tyr Cys
                85                  90                  95

Ala Val Arg Gly Arg Tyr Ser Ser Tyr Thr Tyr Thr Asn Pro Ala
            100                 105                 110

Ser Tyr Lys Tyr Trp Gly Gln Gly Thr Gln Val Thr Val Ser Ser
        115                 120                 125

<210> SEQ ID NO 65
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Thr Phe Ser Ser Ser
            20                  25                  30

Ala Met Gly Trp Phe Arg Gln Ala Pro Gly Lys Glu Arg Glu Phe Val
        35                  40                  45

Ala Thr Ile Thr Gln Asn Asp Val Pro Thr Tyr Tyr Thr His Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Gln Arg Val Ala Gln Ala Ser Gly Trp Arg Thr Thr Ile Lys Asp
            100                 105                 110

Tyr Gly Tyr Trp Gly Gln Gly Thr Gln Val Thr Val Ser Ser
        115                 120                 125

<210> SEQ ID NO 66
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Ser Ser Thr Tyr
            20                  25                  30

Arg Met Ala Trp Phe Arg Gln Ala Pro Gly Lys Glu Arg Glu Phe Ala
        35                  40                  45

Ala Gly Ile Ser Tyr Ser Ala Asp Ser Gly Ser Thr Asn Tyr Ala
    50                  55                  60

Asp Ser Val Lys Gly Arg Phe Thr Ile Ser Arg Asp Asn Ala Lys Asn
65                  70                  75                  80

Thr Val Tyr Leu Gln Met Ser Ser Leu Lys Pro Glu Asp Thr Ala Val
                85                  90                  95

Tyr Tyr Cys Ala Ala Gly Arg Tyr Ser Gly Thr Tyr Asn Ser Pro Tyr
            100                 105                 110

Ser Ser Ser Tyr Val Tyr Trp Gly Gln Gly Thr Gln Val Thr Val Ser
        115                 120                 125

Ser

<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Glu Ser Gly Gly Gly Leu Val Gln Thr Gly Gly
1               5                   10                  15

Ser Leu Arg Leu Ser Cys Ala Ala Ser Gly Ser Thr Phe Ser Arg Asn
            20                  25                  30

Thr Met Gly Trp Phe Arg Gln Ala Pro Gly Lys Glu Arg Val Phe Val
        35                  40                  45

Leu Gly Ile Ser Trp Ser Gly Ile Arg Ser Tyr Tyr Leu Asp Ser Ala
    50                  55                  60

Lys Ala Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gln Glu Gly Ser Ser Pro Gly Pro Tyr Lys Tyr Trp Gly Gln
            100                 105                 110

Gly Thr Gln Val Thr Val Ser Ser
        115                 120

<210> SEQ ID NO 68
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Gln Glu Ser Gly Gly Gly Val Val Gln Val Gly Gly
1               5                   10                  15

Ser Leu Arg Leu Ser Cys Ala Ala Ser Gly Gly Thr Phe Gly Tyr Tyr
            20                  25                  30

Ala Val Gly Trp Phe Arg Gln Ala Pro Gly Lys Glu Arg Glu Phe Val
        35                  40                  45

Ala Ala Val Thr Trp Asn Gly Ala Tyr Leu Tyr Ser Asp Pro Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Gly
                85                  90                  95

Leu Asp Arg Trp Ser Ala Val Val Glu Ser Pro Thr Arg Gly
            100                 105                 110

Gln Gly Thr Gln Val Thr Val Ser Ser
        115                 120

<210> SEQ ID NO 69
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Ala Phe Ser Ser Tyr
            20                  25                  30

Val Met Gly Trp Phe Arg Gln Ala Pro Gly Lys Glu Arg Glu Phe Val
        35                  40                  45

Ala Ala Val Ile Ser Trp Ser Gly Arg Ile Thr Asp Tyr Ala Asp Ser
    50                  55                  60

Val Lys Gly Arg Phe Ser Ile Ser Arg Asp Asn Ala Lys Ser Thr Val
65                  70                  75                  80

Tyr Leu Gln Met Asn Asn Leu Lys Pro Glu Asp Thr Ala Val Tyr Tyr
                85                  90                  95

Cys Ala Ala Lys Thr Gly Met Tyr Ile Asp Leu Arg Thr Ser Thr Phe
            100                 105                 110

Asp Tyr Trp Gly Gln Gly Thr Gln Val Thr Val Ser Ser
        115                 120                 125

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Gln Glu Ser Gly Gly Gly Ser Val Gln Ala Gly Gly
1               5                   10                  15

Ser Leu Arg Leu Ser Cys Thr Ala Ser Gly Arg Thr Phe Thr Asp Tyr
            20                  25                  30

Thr Met Gly Trp Phe Arg Gln Ala Pro Gly Lys Glu Arg Glu Phe Met
        35                  40                  45

Leu Gly Ile Ser Ser Asn Gly Tyr Arg Arg Tyr Tyr Thr Gly Ser Met
    50                  55                  60

Lys Asp Arg Phe Thr Ile Ser Arg Asp Asn Val Lys Lys Thr Val Tyr
65                  70                  75                  80

Leu Gln Met Asn Asp Leu Lys Pro Glu Asp Thr Ala Val Tyr Tyr Cys
                85                  90                  95

Ala Ala Ser Glu Asp His Gly Ala Pro Arg Tyr Asp Tyr Trp Gly Gln
            100                 105                 110

Gly Thr Gln Val Thr Val Ser Ser
        115                 120

<210> SEQ ID NO 71
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

```
Ala Met Gly Trp Phe Arg Gln Ala Pro Gly Lys Glu Arg Glu Phe Val
        35                  40                  45

Ala Ala Ile Ser Trp Ser Gly Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Gly Ser Thr Arg Val Val Val Thr Thr Pro Val Val
                100                 105                 110

Lys Tyr Trp Gly Gln Gly Thr Leu Val Thr Val Ser Ser
            115                 120                 125
```

<210> SEQ ID NO 72
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Glu Val Gln Leu Leu Glu Ser Gly Gly Gly Leu Val Gln Pro Gly Gly
 1               5                  10                  15

Ser Leu Thr Leu Ser Cys Ala Ala Ser Gly Arg Thr Phe Ser Ser Tyr
                 20                  25                  30

Ala Met Gly Trp Phe Arg Gln Ala Pro Gly Met Glu Arg Glu Phe Val
         35                  40                  45

Ala Ala Ile Ser Trp Ser Gly Tyr Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Gly Ser Thr Arg Val Val Val Thr Thr Pro Val Val
                100                 105                 110

Lys Tyr Trp Gly Gln Gly Thr Leu Val Thr Val Ser Ser
            115                 120                 125
```

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Val Glu Ser Gly Gly Gly Leu Val Gln Pro Gly Gly
 1               5                  10                  15

Ser Leu Thr Leu Ser Cys Ala Ala Ser Gly Ser Thr Phe Ser Ile Asn
                 20                  25                  30

His Phe Ser Trp Tyr Arg Gln Ala Pro Gly Lys Gln Arg Glu Leu Val
         35                  40                  45

Ala Phe Ile Ser Ser Asp Gly Val Ser Ile Asp Val Glu Ser Val Lys
 50                  55                  60

Gly Arg Phe Thr Ile Ser Gly Asp Asn Ser Lys Asn Thr Ala Tyr Leu
 65                  70                  75                  80
```

Gln Met Asn Ser Leu Arg Ala Glu Asp Thr Ala Val Tyr Tyr Cys Tyr
            85                  90                  95

Tyr Arg Gly Phe Trp Gly Gln Gly Thr Leu Val Thr Val Ser Ser
        100                 105                 110

<210> SEQ ID NO 74
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

Ala Leu Gly Trp Phe Arg Gln Ala Pro Gly Lys Glu Arg Glu Phe Val
        35                  40                  45

Ala Ala Ile Ser Trp Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Leu Val Thr Val Ser Ser
        115                 120                 125

<210> SEQ ID NO 75
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Leu Glu Ser Gly Gly Gly Leu Val Gln Pro Gly Gly
1               5                   10                  15

Ser Leu Thr Leu Ser Cys Ala Ala Ser Glu Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Met Ser Trp Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Leu Val Thr Val Ser Ser
        115                 120                 125

<210> SEQ ID NO 76

-continued

```
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Leu Val Thr Val Ser Ser
        115                 120                 125

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Val Thr Phe Ser Ile Asn Tyr Ile Asp
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Pro Thr Phe Ser Ile Asn Tyr Ile Asp
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ser Thr Phe Ser Arg Asn Tyr Ile Asp
1               5                   10

<210> SEQ ID NO 80
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 80

Gly Val Thr Phe Ser Ala Ser Tyr Ile Asp
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Thr Phe Asn Asn Tyr Ala Met Asp
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Thr Phe Gly Arg Asn Tyr Ile Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Val Thr Phe Asn Ile Asn Tyr Ile Asp
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Asp Phe Ser Ile Ser Tyr Ile Asp
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Val Thr Phe Ser Ile Ser Tyr Ile Asp
1               5                   10
```

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ser Thr Phe Ser Lys Asn Tyr Ile Asp
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ser Thr Ser Ser Arg Asn Tyr Ile Asp
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Arg Thr Phe Ser Gly Phe Gly Thr Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Thr Trp Ser Ser Tyr Ala Thr Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Thr Phe Ser Ser Tyr Ala Thr Gly
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Arg Thr Phe Ser Ser Tyr Ala Met Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Arg Thr Phe Ser Ser Tyr Ala Leu Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Arg Thr Phe Ser Ser Tyr Thr Met Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Arg Thr Phe Ser Ser Tyr Ala Met Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Arg Thr Phe Ser Thr Leu Thr Val Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Arg Thr Phe Thr Thr Tyr Thr Val Ala
1               5                   10

<210> SEQ ID NO 97
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Arg Thr Phe Asn Leu Tyr Arg Val Gly
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Thr Phe Ser Asp Tyr Ala Met Ser
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Thr Phe Ser Ser Tyr Ala Met Ser
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ser Thr Phe Ser Ile Asn His Phe Ser
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ser Thr Phe Ser Ile Asn His Phe Ala
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Gly Thr Ile Ser His Ala Ala Met Gly
```

```
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Thr Phe Ser Ser Ser Ala Met Gly
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Thr Ser Ser Thr Tyr Arg Met Ala
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Thr Phe Ser Arg Asn Thr Met Gly
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Thr Phe Gly Tyr Tyr Ala Val Gly
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Ala Phe Ser Ser Tyr Val Met Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                           peptide

<400> SEQUENCE: 108

Gly Arg Thr Phe Thr Asp Tyr Thr Met Gly
1               5                   10

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Ile Thr Arg Asp Ser Asn Ser Phe Tyr Ala Asp Ser Val Lys Gly
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ile Thr Ser Gly Gly Asn Thr His Tyr Glu Pro Ser Leu Lys Gly
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Ile Thr Arg Gly Gly Asp Ser Phe Tyr Ala Asp Ser Val Lys Gly
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Ile Thr Arg Asp Ser Ser Ser Phe Tyr Ala Asp Ser Val Lys Gly
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Ile Thr Arg Asp Asp Thr Ser Phe Tyr Ala Asp Ser Val Lys Gly
1               5                   10                  15

<210> SEQ ID NO 114
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Ile Thr Arg Asp Gly Ser Ser Phe Tyr Ala Asp Ser Val Lys Gly
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln Ile Thr Arg Asp Ser Thr Arg Phe Tyr Ala Asp Ser Val Lys Gly
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Ile Thr Ser Ala Gly Asn Thr His Tyr Glu Pro Ser Leu Lys Gly
1               5                   10                  15

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ala Ile Ser Trp Ala Gly Gly Arg Thr His Tyr Glu Asp Ser Val Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ile Ser Trp Asp Gly Gly Arg Thr His Tyr Ala Asp Phe Val Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 119

Ala Ile Ser Trp Val Gly Gly Arg Thr His Tyr Ala Asp Ser Val Lys
1               5                   10                  15

Gly

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ile Ser Trp Ser Gly Gly Arg Thr His Tyr Ala Asp Ser Val Lys
1               5                   10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Ile Ser Trp Asp Gly Gly Arg Thr His Tyr Ala Asp Ser Val Lys
1               5                   10                  15

Gly

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Ile Ser Trp Ser Gly Gly Thr Thr His Tyr Ala Asp Ser Val Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Val Ser Trp Ser Gly Gly Thr Thr Glu Ile Ala Asp Ser Val Lys
1               5                   10                  15

Gly

<210> SEQ ID NO 124
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 124

Ala Val Ser Gln Ser Gly Gly Thr Thr His Tyr Ala Asp Ser Val Lys
1               5                   10                  15

Gly

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Ile Ser Arg Ser Gly Gly Arg Thr Tyr Tyr Ala Glu Ser Val Lys
1               5                   10                  15

Gly

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ile Ser Arg Asn Ser Gly Arg Thr Tyr Ala Glu Ser Val Lys Gly
1               5                   10                  15

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Val Ser Arg Asn Ser Gly Arg Thr Tyr Tyr Ala Glu Ser Val Lys
1               5                   10                  15

Gly

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Ile Ser Arg Asn Ser Gly Arg Thr Tyr Tyr Ala Glu Ser Val Lys
1               5                   10                  15

Gly

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic

```
                       peptide

<400> SEQUENCE: 129

Ala Ile Ser Trp Ser Gly Ser Asn Thr Tyr Tyr Ala Asp Ser Val Lys
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Ile Ser Trp Ser Gly Tyr Ser Thr Tyr Tyr Ala Asp Ser Val Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ile Ser Trp Ser Gly Gly Asn Thr Tyr Tyr Ala Asp Ser Val Lys
1               5                   10                  15

Gly

<210> SEQ ID NO 132
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Met Ser Trp Ser Gly Gly Ser Thr Tyr Tyr Ala Asp Ser Val Lys
1               5                   10                  15

Gly

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile Ser Trp Ser Gly Gly Ser Thr Tyr Tyr Ala Asp Ser Val Lys
1               5                   10                  15

Gly

<210> SEQ ID NO 134
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 134

Ala Ile Ser Trp Ser Gly Ser Ser Thr Tyr Tyr Ala Asp Ser Val Lys
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ser Ile Pro Ser Gly Ser Asn Thr Gly Tyr Ala Glu Ser Val Lys
1               5                   10                  15

Gly

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ser Ile Pro Thr Gly Ser Asn Thr Ala Tyr Ala Glu Ser Val Lys
1               5                   10                  15

Gly

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Ile Thr Trp Ser Ala Asp Ile Thr Gln Tyr Ala Asp Ser Val Lys
1               5                   10                  15

Gly

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Ile Thr Trp Ser Ala Asp Ile Thr Gln Tyr Thr Asp Ser Val Lys
1               5                   10                  15

Gly

<210> SEQ ID NO 139
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 139

Gly Ile Ser Ser Gly Gly Tyr Lys Ile Gly Tyr Thr Asp Ser Thr Lys
1               5                   10                  15

Gly

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Phe Ile Ser Ser Asp Gly Val Ser Ile Asp Val Glu Ser Val Lys Gly
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Ile Ser Ser Asp Gly Arg Ser Thr Asp Val Glu Ser Val Lys Gly
1               5                   10                  15

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Asp Thr Trp Thr Gly Gly Ser Thr Asn Tyr Ala Asp Ser Val Lys
1               5                   10                  15

Asp

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Ile Thr Gln Asn Asp Val Pro Thr Tyr Tyr Thr His Ser Val Lys
1               5                   10                  15

Gly

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 144

Ala Gly Ile Ser Tyr Ser Ala Asp Ser Gly Gly Ser Thr Asn Tyr Ala
1               5                   10                  15

Asp Ser Val Lys Gly
            20

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Ile Ser Trp Ser Gly Ile Arg Ser Tyr Tyr Leu Asp Ser Ala Lys
1               5                   10                  15

Ala

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Val Thr Trp Asn Gly Ala Tyr Leu Tyr Ser Asp Pro Val Lys Gly
1               5                   10                  15

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Val Ile Ser Trp Ser Gly Arg Ile Thr Asp Tyr Ala Asp Ser Val
1               5                   10                  15

Lys Gly

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ile Ser Ser Asn Gly Tyr Arg Arg Tyr Tyr Thr Gly Ser Met Lys
1               5                   10                  15

Asp

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Ser Trp Ser Gly Ser Asn Thr Tyr Tyr Ala Asp Ser Val Lys Gly
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Ser Trp Ser Gly Tyr Ser Thr Tyr Tyr Ala Asp Ser Val Lys Gly
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Ser Ser Asp Gly Val Ser Ile Asp Val Glu Ser Val Lys Gly
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Ser Trp Ser Gly Gly Asn Thr Tyr Tyr Ala Asp Ser Val Lys Gly
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Met Ser Trp Ser Gly Gly Ser Thr Tyr Tyr Ala Asp Ser Val Lys Gly
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Ser Trp Ser Gly Ser Ser Thr Tyr Tyr Ala Asp Ser Val Lys Gly
1               5                   10                  15

<210> SEQ ID NO 155
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Ser Tyr
1

<210> SEQ ID NO 156
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Leu Asp Tyr
1

<210> SEQ ID NO 157
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Leu Ser Phe
1

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Leu Ser Asp
1

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Gln Val Ser Arg Ala Tyr Asp Gly Ile Trp Tyr Ser Gly Gly Asp
1               5                   10                  15

Tyr

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160
```

Ala Gln Val Ala Arg Ala Tyr Asp Ser Lys Trp Tyr Ser Gly Gly Asp
1               5                   10                  15

Tyr

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Gln Val Ala Arg Ala Tyr Asp Gly Asn Trp Tyr Ser Gly Gly Asp
1               5                   10                  15

Tyr

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gln Val Ala Arg Ala Tyr Asp Gly Asn Trp Tyr Ser Arg Gly Asp
1               5                   10                  15

Tyr

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Gln Val Ser Arg Ala Tyr Asp Gly Arg Trp Tyr Ser Ala Val Asp
1               5                   10                  15

Tyr

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Gln Val Ala Arg Ala Tyr Asp Ser Ser Trp Tyr Ser Arg Gly Asp
1               5                   10                  15

Tyr

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 165

Ala Gln Val Ala Arg Ala Tyr Asp Ser Arg Trp Tyr Ser Gly Gly Asp
1               5                   10                  15
Tyr

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Gln Val Ser Arg Ala Tyr Asp Ser Met Trp Tyr Gly Arg Asp Asp
1               5                   10                  15
Tyr

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Gln Val Ala Arg Ala Tyr Asp Ser Asn Trp Tyr Ser Arg Gly Asp
1               5                   10                  15
Tyr

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Gln Val Ser Arg Ala Tyr Asp Ser Asn Trp Tyr Ser Arg Asp Asp
1               5                   10                  15
Tyr

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Gln Val Ala Arg Ala Tyr Asp Thr Arg Trp Tyr Ser Arg Gly Asp
1               5                   10                  15
Tyr

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 170

Gly Gln Val Ala Arg Ala Tyr Asp Ser Arg Trp Tyr Ser Arg Gly Asp
1               5                   10                  15

Tyr

<210> SEQ ID NO 171
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Gln Val Ala Arg Ala Tyr Asp Ser Ser Trp Tyr Ala Arg Gly Asp
1               5                   10                  15

Tyr

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Gln Val Ser Arg Ala Tyr Asp Gly Ile Trp Tyr Ser Gly Gly Asp
1               5                   10                  15

Tyr

<210> SEQ ID NO 173
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Arg Tyr Phe Thr Ser Ser Val Val Tyr Thr Ser Gly Asn Asp Tyr
1               5                   10                  15

Asp Tyr

<210> SEQ ID NO 174
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Arg Tyr Phe Thr Arg Asp Ala Ile Tyr Thr Ser Gly Asp Asp Tyr
1               5                   10                  15

Asp Tyr

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 175

Ala Arg Tyr Phe Thr Arg Asp Ala Val Tyr Thr Ser Gly Asp Asp Tyr
1               5                   10                  15

Asp Tyr

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Arg Tyr Phe Thr Thr Ser Val Val Tyr Thr Ser Gly Asp Asp Tyr
1               5                   10                  15

Asp Tyr

<210> SEQ ID NO 177
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Arg Tyr Phe Thr Arg Asp Val Val Tyr Thr Ser Gly Asp Asp Tyr
1               5                   10                  15

Asp Tyr

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Gly Gly Ser Thr Arg Val Val Val Thr Thr Thr Pro Val Val Lys
1               5                   10                  15

Tyr

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Gly Gly Ser Thr Arg Val Val Val Thr Thr Thr Pro Ile Val Lys
1               5                   10                  15

Tyr

<210> SEQ ID NO 180
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 180

Arg Ile Tyr Phe Gly Ser Ser Arg Gly Tyr Asp Tyr
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Arg Thr Tyr Phe Gly Ser Ser Arg Gly Tyr Asp Tyr
1               5                   10

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Leu Arg Lys Ser Ser Gly Ile Tyr His Val Asp Asp Tyr Asp Asp
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Leu Arg Lys Ser Ser Gly Ile Tyr His Thr Asp Asp Tyr Asp Tyr
1               5                   10                  15

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Thr Gln Trp Ser Trp Ser Leu Arg Asp Asn Thr Ser
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Thr Gln Trp Ser Trp Ala Leu Arg Asp Ser Thr Ser
1               5                   10

-continued

```
<210> SEQ ID NO 186
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Gly Phe
1

<210> SEQ ID NO 187
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Gly Ser
1

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Gly Arg Tyr Ser Ala Ser Tyr Thr Tyr Thr Asn Pro Ala Ser Tyr
1               5                   10                  15

Lys Tyr

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Val Ala Gln Ala Ser Gly Trp Arg Thr Thr Ile Lys Asp Tyr Gly
1               5                   10                  15

Tyr

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Arg Tyr Ser Gly Thr Tyr Asn Ser Pro Tyr Ser Ser Ser Tyr Val
1               5                   10                  15

Tyr

<210> SEQ ID NO 191
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 191

Ala Gln Glu Gly Ser Ser Pro Gly Pro Tyr Lys Tyr
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Arg Trp Ser Ala Val Val Glu Ser Thr Pro Ser Thr
1               5                   10

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Lys Thr Gly Met Tyr Ile Asp Leu Arg Thr Ser Thr Phe Asp Tyr
1               5                   10                  15

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Glu Asp His Gly Ala Pro Arg Tyr Asp Tyr
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Gly Ser Thr Arg Val Val Val Thr Thr Pro Val Val Lys Tyr
1               5                   10                  15

<210> SEQ ID NO 196
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Gln Glu Ser Gly Gly Gly Leu Val Gln Ala Gly Gly
1               5                   10                  15
```

Ser Leu Arg Leu Ser Cys Ala Ala Ser Gly Val Thr Phe Ser Ile Asn
                20                  25                  30

Tyr Ile Asp Trp Tyr Arg Gln Ala Pro Gly Lys Gln Arg Glu Trp Val
                35                  40                  45

Ala Gln Ile Thr Arg Asp Ser Asn Ser Phe Tyr Ala Asp Ser Val Lys
 50                  55                  60

Gly Arg Phe Ala Ile Ser Arg Asp Asn Ala Lys Asn Thr Val Tyr Leu
 65                  70                  75                  80

Gln Met Asn Asn Leu Lys Pro Glu Asp Thr Ala Val Tyr Tyr Cys Arg
                 85                  90                  95

Val Leu Ser Tyr Trp Gly Gln Gly Thr Gln Val Thr Val Ser Ser Gly
                100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
        130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
                180                 185                 190

Asp Asn Ala Lys Thr Thr Leu Tyr Leu Gln Met Asn Ser Leu Arg Pro
            195                 200                 205

Glu Asp Thr Ala Val Tyr Tyr Cys Thr Ile Gly Gly Ser Leu Ser Val
            210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
                275                 280                 285

Leu Glu Trp Val Ala Arg Ile Arg Ser Lys Tyr Asn Asn Tyr Ala Thr
            290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
                355                 360                 365

Ser Gly Gly Gly Gly Ser Gly Gly Gly Gly Ser Gly Gly Gly Gly Ser
        370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
                420                 425                 430

```
Leu Ile Gly Gly Thr Lys Phe Leu Val Pro Gly Pro Ala Arg Phe
            435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Thr Lys Leu Thr Val Leu His His His
                485                 490                 495

His His His
```

<210> SEQ ID NO 197
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Gln Val Gln Leu Gln Glu Ser Gly Gly Gly Leu Val Gln Ala Gly Gly
1               5                   10                  15

Ser Leu Arg Leu Ser Cys Glu Ala Ser Gly Pro Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Ser Asn Ser Phe Tyr Ala Asp Ser Val Lys
    50                  55                  60

Gly Arg Phe Ala Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285
```

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
                420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 198
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
                20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
                100                 105                 110

Gly Gly Ser Gly Gly Gly Ser Glu Val Gln Leu Val Glu Ser Gly
            115                 120                 125

Gly Gly Leu Val Gln Pro Gly Asn Ser Leu Arg Leu Ser Cys Ala Ala
            130                 135                 140

```
Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
            165                 170                 175

Asp Thr Leu Tyr Ala Asp Ser Val Lys Gly Arg Phe Thr Ile Ser Arg
        180                 185                 190

Asp Asn Ala Lys Thr Thr Leu Tyr Leu Gln Met Asn Ser Leu Arg Pro
    195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
            245                 250                 255

Gln Pro Gly Gly Ser Leu Lys Leu Ser Cys Ala Ala Ser Gly Phe Thr
        260                 265                 270

Phe Asn Lys Tyr Ala Ile Asn Trp Val Arg Gln Ala Pro Gly Lys Gly
    275                 280                 285

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Ala Asn Phe Gly Asn Ser Tyr
        340                 345                 350

Ile Ser Tyr Trp Ala Tyr Trp Gly Gln Gly Thr Leu Val Thr Val Ser
    355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
            405                 410                 415

Asn Tyr Pro Asn Trp Val Gln Gln Lys Pro Gly Gln Ala Pro Arg Gly
        420                 425                 430

Leu Ile Gly Gly Thr Lys Phe Leu Val Pro Gly Thr Pro Ala Arg Phe
    435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
            485                 490                 495

His His His

<210> SEQ ID NO 199
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
            85                  90                  95

Ile Leu Asp Tyr Trp Gly Gln Gly Thr Gln Val Thr Val Ser Ser Gly
        100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
        165                 170                 175

Asp Thr Leu Tyr Ala Asp Ser Val Lys Gly Arg Phe Thr Ile Ser Arg
        180                 185                 190

Asp Asn Ala Lys Thr Thr Leu Tyr Leu Gln Met Asn Ser Leu Arg Pro
    195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
        245                 250                 255

Gln Pro Gly Gly Ser Leu Lys Leu Ser Cys Ala Ala Ser Gly Phe Thr
        260                 265                 270

Phe Asn Lys Tyr Ala Ile Asn Trp Val Arg Gln Ala Pro Gly Lys Gly
    275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
```

```
            420                 425                 430
Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

<210> SEQ ID NO 200
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ala Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
```

```
            275                 280                 285
Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

```
<210> SEQ ID NO 201
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Asn Asn Tyr
            20                  25                  30

Ala Met Asp Trp Phe Arg Gln Ala Pro Gly Lys Gln Arg Glu Trp Val
        35                  40                  45

Ala Gln Ile Thr Arg Asp Ser Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
```

```
                130                 135                 140
Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
                180                 185                 190

Asp Asn Ala Lys Thr Thr Leu Tyr Leu Gln Met Asn Ser Leu Arg Pro
                195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
                275                 280                 285

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
                355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
                420                 425                 430

Leu Ile Gly Gly Thr Lys Phe Leu Val Pro Gly Thr Pro Ala Arg Phe
                435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His

<210> SEQ ID NO 202
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 202

```
Gln Val Gln Leu Gln Glu Ser Gly Gly Gly Leu Val Gln Ala Gly Gly
1               5                   10                  15
Ser Leu Arg Leu Ser Cys Ala Ala Ser Gly Val Thr Phe Ser Ile Asn
            20                  25                  30
Tyr Ile Asp Trp Tyr Arg Gln Ala Pro Gly Lys Gln Arg Glu Trp Val
        35                  40                  45
Ala Gln Ile Thr Arg Asp Ser Asn Ser Phe Tyr Ala Asp Ser Val Lys
    50                  55                  60
Gly Arg Phe Ala Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Arg
                85                  90                  95
Leu Leu Ser Tyr Trp Gly Gln Gly Thr Gln Val Thr Val Ser Ser Gly
            100                 105                 110
Gly Gly Gly Ser Gly Gly Gly Ser Glu Val Gln Leu Val Glu Ser Gly
        115                 120                 125
Gly Gly Leu Val Gln Pro Gly Asn Ser Leu Arg Leu Ser Cys Ala Ala
    130                 135                 140
Ser Gly Phe Thr Phe Ser Lys Phe Gly Met Ser Trp Val Arg Gln Ala
145                 150                 155                 160
Pro Gly Lys Gly Leu Glu Trp Val Ser Ser Ile Ser Gly Ser Gly Arg
                165                 170                 175
Asp Thr Leu Tyr Ala Asp Ser Val Lys Gly Arg Phe Thr Ile Ser Arg
            180                 185                 190
Asp Asn Ala Lys Thr Thr Leu Tyr Leu Gln Met Asn Ser Leu Arg Pro
        195                 200                 205
Glu Asp Thr Ala Val Tyr Tyr Cys Thr Ile Gly Gly Ser Leu Ser Val
    210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Gly Leu Val
                245                 250                 255
Gln Pro Gly Gly Ser Leu Lys Leu Ser Cys Ala Ala Ser Gly Phe Thr
            260                 265                 270
Phe Asn Lys Tyr Ala Ile Asn Trp Val Arg Gln Ala Pro Gly Lys Gly
        275                 280                 285
Leu Glu Trp Val Ala Arg Ile Arg Ser Lys Tyr Asn Asn Tyr Ala Thr
    290                 295                 300
Tyr Tyr Ala Asp Gln Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Ala Asn Phe Gly Asn Ser Tyr
            340                 345                 350
Ile Ser Tyr Trp Ala Tyr Trp Gly Gln Gly Thr Leu Val Thr Val Ser
        355                 360                 365
Ser Gly Gly Gly Gly Ser Gly Gly Gly Ser Gly Gly Gly Gly Ser
370                 375                 380
Gln Thr Val Val Thr Gln Glu Pro Ser Leu Thr Val Ser Pro Gly Gly
        385                 390                 395                 400
Thr Val Thr Leu Thr Cys Ala Ser Ser Thr Gly Ala Val Thr Ser Gly
            405                 410                 415
```

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 203
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Asp Thr Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Asn Leu Arg Pro Glu Asp Thr Ala Val Tyr Tyr Cys Arg
                85                  90                  95

Leu Leu Ser Phe Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

```
Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Gly Ser Gly Gly Gly Gly Ser
            370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
            405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
            450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
            485                 490                 495

His His His
```

<210> SEQ ID NO 204
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Phe Gly Arg Asn
            20                  25                  30

Tyr Ile Asp Trp Tyr Arg Gln Ala Pro Gly Lys Gln Arg Glu Trp Val
            35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
            85                  90                  95

Ile Leu Asp Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
            115                 120                 125
```

Gly Gly Leu Val Gln Pro Gly Asn Ser Leu Arg Leu Ser Cys Ala Ala
            130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
        290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His

<210> SEQ ID NO 205
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Gln Val Gln Leu Gln Glu Ser Gly Gly Gly Leu Val Gln Ala Gly Gly
1               5                   10                  15

Ser Leu Arg Leu Ser Cys Lys Ala Ser Gly Val Thr Phe Ser Ile Asn
            20                  25                  30

Tyr Ile Asp Trp Tyr Arg Gln Ala Pro Gly Lys Gln Arg Glu Trp Val
        35                  40                  45

Ala Gln Ile Thr Arg Asp Gly Ser Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Ile Leu Ser Asp Trp Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                    405                 410                 415

Asn Tyr Pro Asn Trp Val Gln Gln Lys Pro Gly Gln Ala Pro Arg Gly
                420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
        450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 206
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gln Val Gln Leu Gln Glu Ser Gly Gly Leu Val Gln Ala Gly Asp
1               5                   10                  15

Ser Leu Arg Leu Ser Cys Ala Ala Ser Gly Val Thr Phe Ser Ala Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

```
Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
        290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

<210> SEQ ID NO 207
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Thr Phe Ser Ile Asn
                20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
        50                  55                  60

Gly Arg Phe Ala Ile Ser Arg Glu Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110
```

-continued

Gly Gly Gly Ser Gly Gly Gly Ser Glu Val Gln Leu Val Glu Ser Gly
          115                 120                 125
Gly Gly Leu Val Gln Pro Gly Asn Ser Leu Arg Leu Ser Cys Ala Ala
130                 135                 140
Ser Gly Phe Thr Phe Ser Lys Phe Gly Met Ser Trp Val Arg Gln Ala
145                 150                 155                 160
Pro Gly Lys Gly Leu Glu Trp Val Ser Ser Ile Ser Gly Ser Gly Arg
                165                 170                 175
Asp Thr Leu Tyr Ala Asp Ser Val Lys Gly Arg Phe Thr Ile Ser Arg
            180                 185                 190
Asp Asn Ala Lys Thr Thr Leu Tyr Leu Gln Met Asn Ser Leu Arg Pro
        195                 200                 205
Glu Asp Thr Ala Val Tyr Tyr Cys Thr Ile Gly Gly Ser Leu Ser Val
210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Gly Leu Val
                245                 250                 255
Gln Pro Gly Gly Ser Leu Lys Leu Ser Cys Ala Ala Ser Gly Phe Thr
            260                 265                 270
Phe Asn Lys Tyr Ala Ile Asn Trp Val Arg Gln Ala Pro Gly Lys Gly
        275                 280                 285
Leu Glu Trp Val Ala Arg Ile Arg Ser Lys Tyr Asn Asn Tyr Ala Thr
290                 295                 300
Tyr Tyr Ala Asp Gln Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Ala Asn Phe Gly Asn Ser Tyr
            340                 345                 350
Ile Ser Tyr Trp Ala Tyr Trp Gly Gln Gly Thr Leu Val Thr Val Ser
        355                 360                 365
Ser Gly Gly Gly Gly Ser Gly Gly Gly Ser Gly Gly Gly Gly Ser
370                 375                 380
Gln Thr Val Val Thr Gln Glu Pro Ser Leu Thr Val Ser Pro Gly Gly
385                 390                 395                 400
Thr Val Thr Leu Thr Cys Ala Ser Ser Thr Gly Ala Val Thr Ser Gly
                405                 410                 415
Asn Tyr Pro Asn Trp Val Gln Gln Lys Pro Gly Gln Ala Pro Arg Gly
            420                 425                 430
Leu Ile Gly Gly Thr Lys Phe Leu Val Pro Gly Thr Pro Ala Arg Phe
        435                 440                 445
Ser Gly Ser Leu Leu Gly Gly Lys Ala Ala Leu Thr Leu Ser Gly Val
450                 455                 460
Gln Pro Glu Asp Glu Ala Glu Tyr Tyr Cys Thr Leu Trp Tyr Ser Asn
465                 470                 475                 480
Arg Trp Val Phe Gly Gly Gly Thr Lys Leu Thr Val Leu His His His
                485                 490                 495
His His His

<210> SEQ ID NO 208
<211> LENGTH: 499
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 208

Gln Val Gln Leu Gln Glu Ser Gly Gly Gly Leu Val Gln Ala Gly Gly
1               5                   10                  15

Ser Leu Arg Leu Ser Cys Gln Ala Ser Gly Val Thr Phe Asn Ile Asn
            20                  25                  30

Tyr Ile Asp Trp Tyr Arg Gln Ala Pro Gly Arg Gln Arg Glu Trp Val
        35                  40                  45

Ala Gln Ile Thr Arg Asp Ser Thr Arg Phe Tyr Ala Asp Ser Val Lys
50                  55                  60

Gly Arg Phe Ala Ile Ser Arg Asp Asn Ala Lys Asn Met Val Tyr Leu
65                  70                  75                  80

Gln Leu Asn Ser Leu Lys Pro Glu Asp Thr Ala Val Tyr Tyr Cys Arg
                85                  90                  95

Ile Leu Ser Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
370                 375                 380

Gln Thr Val Val Thr Gln Glu Pro Ser Leu Thr Val Ser Pro Gly Gly
```

```
                385                 390                 395                 400
Thr Val Thr Leu Thr Cys Ala Ser Ser Thr Gly Ala Val Thr Ser Gly
                    405                 410                 415

Asn Tyr Pro Asn Trp Val Gln Gln Lys Pro Gly Gln Ala Pro Arg Gly
                    420                 425                 430

Leu Ile Gly Gly Thr Lys Phe Leu Val Pro Gly Thr Pro Ala Arg Phe
                    435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                    485                 490                 495

His His His
```

<210> SEQ ID NO 209
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asp Phe Ser Ile Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
            85                  90                  95

Ile Leu Ser Tyr Trp Gly Gln Gly Thr Gln Val Thr Val Ser Ser Gly
        100                 105                 110

Gly Gly Gly Ser Gly Gly Gly Ser Glu Val Gln Leu Val Glu Ser Gly
    115                 120                 125

Gly Gly Leu Val Gln Pro Gly Asn Ser Leu Arg Leu Ser Cys Ala Ala
130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
            165                 170                 175

Asp Thr Leu Tyr Ala Asp Ser Val Lys Gly Arg Phe Thr Ile Ser Arg
        180                 185                 190

Asp Asn Ala Lys Thr Thr Leu Tyr Leu Gln Met Asn Ser Leu Arg Pro
    195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
```

```
                        245                 250                 255
Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
            290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Gly Ser Gly Gly Gly Gly Ser
            370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
            405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
            450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
            485                 490                 495

His His His
```

```
<210> SEQ ID NO 210
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Ala Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser Gly
```

-continued

```
                100                 105                 110
Gly Gly Gly Ser Gly Gly Ser Glu Val Gln Leu Val Glu Ser Gly
            115                 120                 125
Gly Gly Leu Val Gln Pro Gly Asn Ser Leu Arg Leu Ser Cys Ala Ala
            130                 135                 140
Ser Gly Phe Thr Phe Ser Lys Phe Gly Met Ser Trp Val Arg Gln Ala
145                 150                 155                 160
Pro Gly Lys Gly Leu Glu Trp Val Ser Ile Ser Gly Ser Gly Arg
            165                 170                 175
Asp Thr Leu Tyr Ala Asp Ser Val Lys Gly Arg Phe Thr Ile Ser Arg
            180                 185                 190
Asp Asn Ala Lys Thr Thr Leu Tyr Leu Gln Met Asn Ser Leu Arg Pro
            195                 200                 205
Glu Asp Thr Ala Val Tyr Tyr Cys Thr Ile Gly Gly Ser Leu Ser Val
            210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Leu Val
            245                 250                 255
Gln Pro Gly Gly Ser Leu Lys Leu Ser Cys Ala Ala Ser Gly Phe Thr
            260                 265                 270
Phe Asn Lys Tyr Ala Ile Asn Trp Val Arg Gln Ala Pro Gly Lys Gly
            275                 280                 285
Leu Glu Trp Val Ala Arg Ile Arg Ser Lys Tyr Asn Asn Tyr Ala Thr
            290                 295                 300
Tyr Tyr Ala Asp Gln Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
            325                 330                 335
Thr Ala Val Tyr Tyr Cys Val Arg His Ala Asn Phe Gly Asn Ser Tyr
            340                 345                 350
Ile Ser Tyr Trp Ala Tyr Trp Gly Gln Gly Thr Leu Val Thr Val Ser
            355                 360                 365
Ser Gly Gly Gly Gly Ser Gly Gly Gly Ser Gly Gly Gly Gly Ser
            370                 375                 380
Gln Thr Val Val Thr Gln Glu Pro Ser Leu Thr Val Ser Pro Gly Gly
385                 390                 395                 400
Thr Val Thr Leu Thr Cys Ala Ser Ser Thr Gly Ala Val Thr Ser Gly
            405                 410                 415
Asn Tyr Pro Asn Trp Val Gln Gln Lys Pro Gly Gln Ala Pro Arg Gly
            420                 425                 430
Leu Ile Gly Gly Thr Lys Phe Leu Val Pro Gly Thr Pro Ala Arg Phe
            435                 440                 445
Ser Gly Ser Leu Leu Gly Gly Lys Ala Ala Leu Thr Leu Ser Gly Val
            450                 455                 460
Gln Pro Glu Asp Glu Ala Glu Tyr Tyr Cys Thr Leu Trp Tyr Ser Asn
465                 470                 475                 480
Arg Trp Val Phe Gly Gly Gly Thr Lys Leu Thr Val Leu His His
            485                 490                 495
His His His

<210> SEQ ID NO 211
<211> LENGTH: 499
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Val Gln Leu Gln Glu Ser Gly Gly Gly Leu Val Gln Pro Gly Gly
1               5                   10                  15

Ser Leu Arg Leu Ser Cys Ala Ala Ser Gly Val Thr Phe Ser Ile Ser
            20                  25                  30

Tyr Ile Asp Trp Tyr Arg Gln Ala Pro Gly Asn Glu Arg Glu Trp Val
        35                  40                  45

Ala Gln Ile Thr Arg Gly Gly Asp Ser Phe Tyr Ala Asp Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Ile Leu Ser Tyr Trp Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380
```

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 212
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Gln Glu Ser Gly Gly Gly Leu Val Gln Ala Gly Gly
1               5                   10                  15

Ser Leu Arg Leu Ser Cys Ala Ala Ser Gly Val Thr Phe Ser Ile Asn
                20                  25                  30

Tyr Ile Asp Trp Tyr Arg Gln Ala Pro Gly Lys Gln Arg Glu Trp Val
            35                  40                  45

Ala Gln Ile Thr Arg Asp Ser Asn Ser Phe Tyr Ala Asp Ser Val Lys
        50                  55                  60

Gly Arg Phe Ala Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Arg
                85                  90                  95

Val Leu Ser Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 213
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gln Val Gln Leu Gln Glu Ser Gly Gly Gly Leu Val Gln Pro Gly Gly
1               5                   10                  15

Ser Leu Thr Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

```
Ile Leu Asp Tyr Trp Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
        130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His
```

```
<210> SEQ ID NO 214
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Lys Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365
```

```
Ser Gly Gly Gly Gly Ser Gly Gly Gly Ser Gly Gly Gly Ser
    370                 375             380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

<210> SEQ ID NO 215
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Ser Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220
```

```
Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 216
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Gln Glu Ser Gly Gly Gly Leu Val Gln Ala Gly Gly
1               5                   10                  15

Ser Leu Arg Leu Ser Cys Ser Ala Ser Gly Ser Thr Phe Ser Arg Asn
                20                  25                  30

Tyr Ile Asp Trp Tyr Arg Gln Ala Pro Gly Lys Gln Arg Glu Trp Val
            35                  40                  45

Ala Gln Ile Thr Ser Gly Gly Asn Thr His Tyr Glu Pro Ser Leu Lys
        50                  55                  60

Gly Arg Phe Thr Ile Ser Arg Asp Asn Ala Lys Asn Thr Ala Tyr Leu
65                  70                  75                  80
```

-continued

```
Gln Met Asn Ser Leu Lys Pro Glu Asp Thr Ala Val Tyr Tyr Cys Arg
             85                  90                  95

Ile Leu Asp Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
            115                 120                 125

Gly Gly Leu Val Gln Pro Gly Asn Ser Leu Arg Leu Ser Cys Ala Ala
            130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
            195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
            245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
            290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Ser Gly Gly Gly Gly Ser
            370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
            450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

<210> SEQ ID NO 217
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

```
Gln Val Gln Leu Gln Glu Ser Gly Gly Gly Leu Val Gln Pro Gly Asp
1               5                   10                  15

Pro Leu Arg Leu Ser Cys Ala Ala Ser Gly Ser Thr Phe Ser Arg Asn
            20                  25                  30

Tyr Ile Asp Trp Tyr Arg Gln Ala Pro Gly Lys Gln Arg Glu Trp Val
        35                  40                  45

Ala Gln Ile Thr Ser Gly Gly Asn Thr His Tyr Glu Pro Ser Leu Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Arg
                85                  90                  95

Ile Leu Asp Tyr Trp Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
```

```
                355                 360                 365
Ser Gly Gly Gly Ser Gly Gly Gly Ser Gly Gly Gly Ser
        370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
        420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
        450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 218
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ala Gly Gly Arg Thr His Tyr Glu Asp Ser Val
    50                  55                  60

Lys Gly Arg Phe Thr Ile His Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ser Arg Ala Tyr Asp Gly Ile Trp Tyr Ser Gly Gly
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
```

```
                210                 215                 220
Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
                260                 265                 270

Gly Gly Ser Leu Lys Leu Ser Cys Ala Ala Ser Gly Phe Thr Phe Asn
                275                 280                 285

Lys Tyr Ala Ile Asn Trp Val Arg Gln Ala Pro Gly Lys Gly Leu Glu
                290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
                340                 345                 350

Val Tyr Tyr Cys Val Arg His Ala Asn Phe Gly Asn Ser Tyr Ile Ser
                355                 360                 365

Tyr Trp Ala Tyr Trp Gly Gln Gly Thr Leu Val Thr Val Ser Ser Gly
                370                 375                 380

Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
                420                 425                 430

Pro Asn Trp Val Gln Gln Lys Pro Gly Gln Ala Pro Arg Gly Leu Ile
                435                 440                 445

Gly Gly Thr Lys Phe Leu Val Pro Gly Thr Pro Ala Arg Phe Ser Gly
                450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
                500                 505                 510

His
```

<210> SEQ ID NO 219
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
                20                  25                  30

Gly Thr Gly Trp Phe Arg Gln Ala Pro Gly Lys Glu Arg Glu Phe Val
                35                  40                  45

Ala Ala Ile Ser Trp Asp Gly Gly Arg Thr His Tyr Ala Asp Phe Val
```

```
           50                  55                  60
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                     85                  90                  95

Ala Ala Gln Val Ala Arg Ala Tyr Asp Ser Lys Trp Tyr Ser Gly Gly
                100                 105                 110

Asp Tyr Trp Gly Gln Gly Thr Gln Val Thr Val Ser Ser Gly Gly Gly
                115                 120                 125

Gly Ser Gly Gly Gly Ser Glu Val Gln Leu Val Glu Ser Gly Gly Gly
                130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
                180                 185                 190

Leu Tyr Ala Asp Ser Val Lys Gly Arg Phe Thr Ile Ser Arg Asp Asn
                195                 200                 205

Ala Lys Thr Thr Leu Tyr Leu Gln Met Asn Ser Leu Arg Pro Glu Asp
                210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Leu Val Gln Pro
                260                 265                 270

Gly Gly Ser Leu Lys Leu Ser Cys Ala Ala Ser Gly Phe Thr Phe Asn
                275                 280                 285

Lys Tyr Ala Ile Asn Trp Val Arg Gln Ala Pro Gly Lys Gly Leu Glu
                290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
                340                 345                 350

Val Tyr Tyr Cys Val Arg His Ala Asn Phe Gly Asn Ser Tyr Ile Ser
                355                 360                 365

Tyr Trp Ala Tyr Trp Gly Gln Gly Thr Leu Val Thr Val Ser Ser Gly
                370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
                420                 425                 430

Pro Asn Trp Val Gln Gln Lys Pro Gly Gln Ala Pro Arg Gly Leu Ile
                435                 440                 445

Gly Gly Thr Lys Phe Leu Val Pro Gly Thr Pro Ala Arg Phe Ser Gly
                450                 455                 460

Ser Leu Leu Gly Gly Lys Ala Ala Leu Thr Leu Ser Gly Val Gln Pro
465                 470                 475                 480
```

```
Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
            500                 505                 510

His

<210> SEQ ID NO 220
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Val Gly Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Gly Asn Trp Tyr Ser Gly Gly
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320
```

```
Ala Asp Gln Val Lys Asp Arg Phe Thr Ile Ser Arg Asp Asp Ser Lys
            325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
            355                 360                 365

Tyr Trp Ala Tyr Trp Gly Gln Gly Thr Leu Val Thr Val Ser Ser Gly
            370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
            405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
            435                 440                 445

Gly Gly Thr Lys Phe Leu Val Pro Gly Thr Pro Ala Arg Phe Ser Gly
            450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
            485                 490                 495

Val Phe Gly Gly Gly Thr Lys Leu Thr Val Leu His His His His His
            500                 505                 510

His

<210> SEQ ID NO 221
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
            35                  40                  45

Ala Ala Ile Ser Trp Ser Gly Arg Thr His Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Gly Gln Val Ala Arg Ala Tyr Asp Gly Asn Trp Tyr Ser Arg Gly
            100                 105                 110

Asp Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
            130                 135                 140

Leu Val Gln Pro Gly Asn Ser Leu Arg Leu Ser Cys Ala Ala Ser Gly
145                 150                 155                 160
```

Phe Thr Phe Ser Lys Phe Gly Met Ser Trp Val Arg Gln Ala Pro Gly
            165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
            210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Gly Gly Gly Ser Gly Gly
            245                 250                 255

Gly Ser Glu Val Gln Leu Val Glu Ser Gly Gly Leu Val Gln Pro
            260                 265                 270

Gly Gly Ser Leu Lys Leu Ser Cys Ala Ala Ser Gly Phe Thr Phe Asn
            275                 280                 285

Lys Tyr Ala Ile Asn Trp Val Arg Gln Ala Pro Gly Lys Gly Leu Glu
            290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
            325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
            355                 360                 365

Tyr Trp Ala Tyr Trp Gly Gln Gly Thr Leu Val Thr Val Ser Ser Gly
            370                 375                 380

Gly Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
            405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
            435                 440                 445

Gly Gly Thr Lys Phe Leu Val Pro Gly Thr Pro Ala Arg Phe Ser Gly
            450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
            485                 490                 495

Val Phe Gly Gly Gly Thr Lys Leu Thr Val Leu His His His His
            500                 505                 510

His

<210> SEQ ID NO 222
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Gln Val Gln Leu Gln Glu Ser Gly Gly Gly Val Gln Ala Gly Gly
  1               5                  10                 15

Ser Leu Arg Leu Ser Cys Ala Phe Ser Gly Arg Thr Phe Ser Gly Phe
                 20                  25                 30

Gly Thr Gly Trp Phe Arg Gln Ala Pro Glu Lys Glu Arg Glu Phe Val
             35                  40                  45

Ala Ala Ile Ser Trp Asp Gly Arg Thr His Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asp Ser Leu Lys Pro Glu Asp Thr Ala Ile Tyr Tyr Cys
                 85                  90                  95

Ala Ala Gln Val Ser Arg Ala Tyr Asp Gly Arg Trp Tyr Ser Ala Val
             100                 105                 110

Asp Tyr Trp Gly Arg Gly Thr Gln Val Thr Val Ser Ser Gly Gly Gly
         115                 120                 125

Gly Ser Gly Gly Gly Ser Glu Val Gln Leu Val Glu Ser Gly Gly Gly
130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                 165                 170                 175

Lys Gly Leu Glu Trp Val Ser Ser Ile Ser Gly Ser Gly Arg Asp Thr
             180                 185                 190

Leu Tyr Ala Asp Ser Val Lys Gly Arg Phe Thr Ile Ser Arg Asp Asn
         195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
             245                 250                 255

Gly Ser Glu Val Gln Leu Val Glu Ser Gly Gly Gly Leu Val Gln Pro
             260                 265                 270

Gly Gly Ser Leu Lys Leu Ser Cys Ala Ala Ser Gly Phe Thr Phe Asn
             275                 280                 285

Lys Tyr Ala Ile Asn Trp Val Arg Gln Ala Pro Gly Lys Gly Leu Glu
290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
             325                 330                 335

Asn Thr Ala Tyr Leu Gln Met Asn Asn Leu Lys Thr Glu Asp Thr Ala
             340                 345                 350

Val Tyr Tyr Cys Val Arg His Ala Asn Phe Gly Asn Ser Tyr Ile Ser
             355                 360                 365

Tyr Trp Ala Tyr Trp Gly Gln Gly Thr Leu Val Thr Val Ser Ser Gly
         370                 375                 380

Gly Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
                 405                 410                 415
```

```
Thr Leu Thr Cys Ala Ser Ser Thr Gly Ala Val Ser Gly Asn Tyr
            420                 425                 430

Pro Asn Trp Val Gln Gln Lys Pro Gly Gln Ala Pro Arg Gly Leu Ile
            435                 440                 445

Gly Gly Thr Lys Phe Leu Val Pro Gly Thr Pro Ala Arg Phe Ser Gly
            450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
            500                 505                 510

His
```

<210> SEQ ID NO 223
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gln Val Ala Arg Ala Tyr Asp Ser Ser Trp Tyr Ser Arg Gly
            100                 105                 110

Asp Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
            130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
            210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Gly Ser Gly Gly
                245                 250                 255
```

Gly Ser Glu Val Gln Leu Val Glu Ser Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
            500                 505                 510

His

<210> SEQ ID NO 224
<211> LENGTH: 513
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 224

Gln Val Gln Leu Gln Glu Ser Gly Gly Gly Leu Val Gln Ala Gly Gly
1               5                   10                  15

Ser Leu Gly Leu Ser Cys Ala Val Ser Gly Arg Thr Phe Ser Gly Phe
            20                  25                  30

Gly Thr Gly Trp Phe Arg Gln Pro Pro Glu Lys Glu Arg Glu Phe Val
        35                  40                  45

Ala Ala Ile Ser Trp Asp Gly Arg Thr His Tyr Ala Asp Ser Val
    50                  55                  60

Lys Gly Arg Phe Thr Ile Ser Arg Asp Asn Ala Lys Asn Thr Val Phe
65                  70                  75                  80

Leu Gln Met Asn Ser Leu Lys Pro Glu Asp Thr Ala Val Tyr Tyr Cys
                85                  90                  95

```
Ala Ala Gln Val Ala Arg Ala Tyr Asp Ser Arg Trp Tyr Ser Gly Gly
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ile Ser Gly Ser Gly Arg Asp Thr
            180                 185                 190

Leu Tyr Ala Asp Ser Val Lys Gly Arg Phe Thr Ile Ser Arg Asp Asn
    195                 200                 205

Ala Lys Thr Thr Leu Tyr Leu Gln Met Asn Ser Leu Arg Pro Glu Asp
        210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
            245                 250                 255

Gly Ser Glu Val Gln Leu Val Glu Ser Gly Gly Gly Leu Val Gln Pro
    260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
            325                 330                 335

Asn Thr Ala Tyr Leu Gln Met Asn Asn Leu Lys Thr Glu Asp Thr Ala
        340                 345                 350

Val Tyr Tyr Cys Val Arg His Ala Asn Phe Gly Asn Ser Tyr Ile Ser
    355                 360                 365

Tyr Trp Ala Tyr Trp Gly Gln Gly Thr Leu Val Thr Val Ser Ser Gly
    370                 375                 380

Gly Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
            405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
        450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
            485                 490                 495

Val Phe Gly Gly Gly Thr Lys Leu Thr Val Leu His His His His
            500                 505                 510

His
```

<210> SEQ ID NO 225
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ser Gly Gly Thr Thr His Tyr Ala Asp Ser Val
    50                  55                  60

Lys Gly Arg Phe Thr Ile Ser Arg Asp Asn Ala Lys Asn Thr Val Ser
65                  70                  75                  80

Leu Val Tyr Leu Gln Met Asn Ser Leu Lys Pro Asp Asp Thr Ala Val
                85                  90                  95

Tyr Tyr Cys Ala Gly Gln Val Ala Arg Ala Tyr Asp Ser Ser Trp Tyr
            100                 105                 110

Ser Arg Gly Asp Tyr Leu Gly Gln Gly Thr Gln Val Thr Val Ser Ser
        115                 120                 125

Gly Gly Gly Gly Ser Gly Gly Gly Ser Glu Val Gln Leu Val Glu Ser
    130                 135                 140

Gly Gly Gly Leu Val Gln Pro Gly Asn Ser Leu Arg Leu Ser Cys Ala
145                 150                 155                 160

Ala Ser Gly Phe Thr Phe Ser Lys Phe Gly Met Ser Trp Val Arg Gln
                165                 170                 175

Ala Pro Gly Lys Gly Leu Glu Trp Val Ser Ser Ile Ser Gly Ser Gly
            180                 185                 190

Arg Asp Thr Leu Tyr Ala Asp Ser Val Lys Gly Arg Phe Thr Ile Ser
        195                 200                 205

Arg Asp Asn Ala Lys Thr Thr Leu Tyr Leu Gln Met Asn Ser Leu Arg
    210                 215                 220

Pro Glu Asp Thr Ala Val Tyr Tyr Cys Thr Ile Gly Gly Ser Leu Ser
225                 230                 235                 240

Val Ser Ser Gln Gly Thr Leu Val Thr Val Ser Ser Gly Gly Gly Gly
                245                 250                 255

Ser Gly Gly Gly Ser Glu Val Gln Leu Val Glu Ser Gly Gly Gly Leu
            260                 265                 270

Val Gln Pro Gly Gly Ser Leu Lys Leu Ser Cys Ala Ala Ser Gly Phe
        275                 280                 285

Thr Phe Asn Lys Tyr Ala Ile Asn Trp Val Arg Gln Ala Pro Gly Lys
    290                 295                 300

Gly Leu Glu Trp Val Ala Arg Ile Arg Ser Lys Tyr Asn Asn Tyr Ala
305                 310                 315                 320

Thr Tyr Tyr Ala Asp Gln Val Lys Asp Arg Phe Thr Ile Ser Arg Asp
                325                 330                 335

Asp Ser Lys Asn Thr Ala Tyr Leu Gln Met Asn Asn Leu Lys Thr Glu
            340                 345                 350

Asp Thr Ala Val Tyr Tyr Cys Val Arg His Ala Asn Phe Gly Asn Ser

```
                355                 360                 365
Tyr Ile Ser Tyr Trp Ala Tyr Trp Gly Gln Gly Thr Leu Val Thr Val
    370                 375                 380
Ser Ser Gly Gly Gly Ser Gly Gly Gly Ser Gly Gly Gly Gly
385                 390                 395                 400
Ser Gln Thr Val Val Thr Gln Glu Pro Ser Leu Thr Val Ser Pro Gly
                405                 410                 415
Gly Thr Val Thr Leu Thr Cys Ala Ser Ser Thr Gly Ala Val Thr Ser
                420                 425                 430
Gly Asn Tyr Pro Asn Trp Val Gln Gln Lys Pro Gly Gln Ala Pro Arg
            435                 440                 445
Gly Leu Ile Gly Gly Thr Lys Phe Leu Val Pro Gly Thr Pro Ala Arg
    450                 455                 460
Phe Ser Gly Ser Leu Leu Gly Gly Lys Ala Ala Leu Thr Leu Ser Gly
465                 470                 475                 480
Val Gln Pro Glu Asp Glu Ala Glu Tyr Tyr Cys Thr Leu Trp Tyr Ser
                485                 490                 495
Asn Arg Trp Val Phe Gly Gly Gly Thr Lys Leu Thr Val Leu His His
            500                 505                 510
His His His His
        515

<210> SEQ ID NO 226
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Gln Glu Ser Gly Gly Gly Leu Val Gln Ala Gly Gly
1               5                   10                  15
Ser Leu Arg Leu Ser Cys Ala Val Ser Gly Arg Thr Phe Ser Gly Phe
            20                  25                  30
Gly Thr Gly Trp Phe Arg Gln Ala Pro Gly Lys Glu Arg Glu Phe Val
        35                  40                  45
Ala Ala Ile Ser Trp Asp Gly Arg Thr His Tyr Ala Asp Ser Val
    50                  55                  60
Lys Gly Arg Phe Thr Ile Ser Arg Asp Asn Ala Ala Asn Thr Val Tyr
65                  70                  75                  80
Leu Gln Met Asn Ser Leu Lys Pro Glu Asp Thr Ala Val Tyr Tyr Cys
                85                  90                  95
Ala Gly Gln Val Ser Arg Ala Tyr Asp Ser Met Trp Tyr Gly Arg Asp
                100                 105                 110
Asp Tyr Trp Gly Gln Gly Thr Gln Val Thr Val Ser Ser Gly Gly Gly
            115                 120                 125
Gly Ser Gly Gly Gly Ser Glu Val Gln Leu Val Glu Ser Gly Gly Gly
        130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
            180                 185                 190
```

-continued

```
Leu Tyr Ala Asp Ser Val Lys Gly Arg Phe Thr Ile Ser Arg Asp Asn
            195                 200                 205
Ala Lys Thr Thr Leu Tyr Leu Gln Met Asn Ser Leu Arg Pro Glu Asp
210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Gly Leu Val Gln Pro
            260                 265                 270
Gly Gly Ser Leu Lys Leu Ser Cys Ala Ala Ser Gly Phe Thr Phe Asn
            275                 280                 285
Lys Tyr Ala Ile Asn Trp Val Arg Gln Ala Pro Gly Lys Gly Leu Glu
        290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
        355                 360                 365
Tyr Trp Ala Tyr Trp Gly Gln Gly Thr Leu Val Thr Val Ser Ser Gly
    370                 375                 380
Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
        435                 440                 445
Gly Gly Thr Lys Phe Leu Val Pro Gly Thr Pro Ala Arg Phe Ser Gly
    450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His
            500                 505                 510
His
```

```
<210> SEQ ID NO 227
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Gln Glu Ser Gly Gly Gly Leu Val Gln Ala Gly Gly
1               5                   10                  15
Ser Leu Arg Leu Ser Cys Ala Val Ser Gly Arg Thr Phe Ser Gly Phe
            20                  25                  30
```

```
Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
 50                  55                  60

Lys Gly Arg Phe Thr Ile Ser Arg Asp Asn Ala Lys Asn Thr Val Asn
 65                  70                  75                  80

Leu Val Tyr Leu Gln Met Asn Asp Leu Arg Pro Glu Asp Thr Ala Val
                    85                  90                  95

Tyr Tyr Cys Ala Gly Gln Val Ala Arg Ala Tyr Asp Ser Asn Trp Tyr
               100                 105                 110

Ser Arg Gly Asp Tyr Trp Gly Gln Gly Thr Gln Val Thr Val Ser Ser
           115                 120                 125

Gly Gly Gly Gly Ser Gly Gly Ser Glu Val Gln Leu Val Glu Ser
           130                 135                 140

Gly Gly Gly Leu Val Gln Pro Gly Asn Ser Leu Arg Leu Ser Cys Ala
 145                 150                 155                 160

Ala Ser Gly Phe Thr Phe Ser Lys Phe Gly Met Ser Trp Val Arg Gln
                165                 170                 175

Ala Pro Gly Lys Gly Leu Glu Trp Val Ser Ser Ile Ser Gly Ser Gly
            180                 185                 190

Arg Asp Thr Leu Tyr Ala Asp Ser Val Lys Gly Arg Phe Thr Ile Ser
            195                 200                 205

Arg Asp Asn Ala Lys Thr Thr Leu Tyr Leu Gln Met Asn Ser Leu Arg
 210                 215                 220

Pro Glu Asp Thr Ala Val Tyr Tyr Cys Thr Ile Gly Gly Ser Leu Ser
225                 230                 235                 240

Val Ser Ser Gln Gly Thr Leu Val Thr Val Ser Ser Gly Gly Gly Gly
            245                 250                 255

Ser Gly Gly Gly Ser Glu Val Gln Leu Val Glu Ser Gly Gly Gly Leu
            260                 265                 270

Val Gln Pro Gly Gly Ser Leu Lys Leu Ser Cys Ala Ala Ser Gly Phe
            275                 280                 285

Thr Phe Asn Lys Tyr Ala Ile Asn Trp Val Arg Gln Ala Pro Gly Lys
            290                 295                 300

Gly Leu Glu Trp Val Ala Arg Ile Arg Ser Lys Tyr Asn Asn Tyr Ala
305                 310                 315                 320

Thr Tyr Tyr Ala Asp Gln Val Lys Asp Arg Phe Thr Ile Ser Arg Asp
                325                 330                 335

Asp Ser Lys Asn Thr Ala Tyr Leu Gln Met Asn Asn Leu Lys Thr Glu
            340                 345                 350

Asp Thr Ala Val Tyr Tyr Cys Val Arg His Ala Asn Phe Gly Asn Ser
            355                 360                 365

Tyr Ile Ser Tyr Trp Ala Tyr Trp Gly Gln Gly Thr Leu Val Thr Val
            370                 375                 380

Ser Ser Gly Gly Gly Gly Ser Gly Gly Gly Ser Gly Gly Gly Gly
 385                 390                 395                 400

Ser Gln Thr Val Val Thr Gln Glu Pro Ser Leu Thr Val Ser Pro Gly
                405                 410                 415

Gly Thr Val Thr Leu Thr Cys Ala Ser Ser Thr Gly Ala Val Thr Ser
                420                 425                 430

Gly Asn Tyr Pro Asn Trp Val Gln Gln Lys Pro Gly Gln Ala Pro Arg
            435                 440                 445

Gly Leu Ile Gly Gly Thr Lys Phe Leu Val Pro Gly Thr Pro Ala Arg
```

450                 455                 460
Phe Ser Gly Ser Leu Leu Gly Gly Lys Ala Ala Leu Thr Leu Ser Gly
465                 470                 475                 480

Val Gln Pro Glu Asp Glu Ala Glu Tyr Tyr Cys Thr Leu Trp Tyr Ser
                485                 490                 495

Asn Arg Trp Val Phe Gly Gly Gly Thr Lys Leu Thr Val Leu His His
                500                 505                 510

His His His His
        515

<210> SEQ ID NO 228
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
                20                  25                  30

Gly Thr Gly Trp Phe Arg Gln Ala Pro Gly Lys Glu Arg Glu Phe Val
            35                  40                  45

Ala Ala Ile Ser Trp Ser Gly Gly Thr Thr His Tyr Ala Asp Ser Val
        50                  55                  60

Lys Gly Arg Phe Thr Ile Ser Arg Asp Asn Ala Glu Asn Thr Val Tyr
65                  70                  75                  80

Leu Glu Met Asn Ser Leu Lys Pro Glu Asp Thr Ala Val Tyr Ile Cys
                85                  90                  95

Ala Gly Gln Val Ser Arg Ala Tyr Asp Ser Asn Trp Tyr Ser Arg Asp
                100                 105                 110

Asp Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
                180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
        210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
            500                 505                 510
His

<210> SEQ ID NO 229
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Glu Lys Glu Arg Glu Phe Val
        35                  40                  45

Ala Ala Ile Ser Trp Asp Gly Arg Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Gly Gln Val Ala Arg Ala Tyr Asp Thr Arg Trp Tyr Ser Arg Gly
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
370                 375                 380

Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
            500                 505                 510

His

<210> SEQ ID NO 230
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Val Gln Leu Gln Glu Ser Gly Gly Gly Leu Val Gln Ala Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Asp Gly Arg Thr His Tyr Ala Asp Phe Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Val Ala Arg Ala Tyr Asp Ser Arg Trp Tyr Ser Gly Gly
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
    275                 280                 285

Lys Tyr Ala Ile Asn Trp Val Arg Gln Ala Pro Gly Lys Gly Leu Glu
290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Gly Ser Gly Gly Gly Gly Ser Gln Thr

```
           385                 390                 395                 400
Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
                420                 425                 430

Pro Asn Trp Val Gln Gln Lys Pro Gly Gln Ala Pro Arg Gly Leu Ile
                435                 440                 445

Gly Gly Thr Lys Phe Leu Val Pro Gly Thr Pro Ala Arg Phe Ser Gly
                450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
                500                 505                 510

His

<210> SEQ ID NO 231
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
                20                  25                  30

Gly Thr Gly Trp Phe Arg Gln Ala Pro Gly Lys Glu Arg Glu Phe Val
                35                  40                  45

Ala Ala Val Ser Trp Ser Gly Gly Thr Thr Glu Ile Ala Asp Ser Val
                50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Gly Asp Thr Ala Val Tyr Tyr Cys
                85                  90                  95

Ala Gly Gln Val Ala Arg Ala Tyr Asp Ser Arg Trp Tyr Ser Arg Gly
                100                 105                 110

Asp Tyr Trp Gly Gln Gly Thr Gln Val Thr Val Ser Ser Gly Gly Gly
                115                 120                 125

Gly Ser Gly Gly Gly Ser Glu Val Gln Leu Val Glu Ser Gly Gly Gly
                130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
                180                 185                 190

Leu Tyr Ala Asp Ser Val Lys Gly Arg Phe Thr Ile Ser Arg Asp Asn
                195                 200                 205

Ala Lys Thr Thr Leu Tyr Leu Gln Met Asn Ser Leu Arg Pro Glu Asp
                210                 215                 220

Thr Ala Val Tyr Tyr Cys Thr Ile Gly Gly Ser Leu Ser Val Ser Ser
```

```
            225                 230                 235                 240
        Gln Gly Thr Leu Val Thr Val Ser Ser Gly Gly Gly Ser Gly Gly
                        245                 250                 255
        Gly Ser Glu Val Gln Leu Val Glu Ser Gly Gly Leu Val Gln Pro
                        260                 265                 270
        Gly Gly Ser Leu Lys Leu Ser Cys Ala Ala Ser Gly Phe Thr Phe Asn
                        275                 280                 285
        Lys Tyr Ala Ile Asn Trp Val Arg Gln Ala Pro Gly Lys Gly Leu Glu
                        290                 295                 300
        Trp Val Ala Arg Ile Arg Ser Lys Tyr Asn Asn Tyr Ala Thr Tyr Tyr
        305                 310                 315                 320
        Ala Asp Gln Val Lys Asp Arg Phe Thr Ile Ser Arg Asp Asp Ser Lys
                        325                 330                 335
        Asn Thr Ala Tyr Leu Gln Met Asn Asn Leu Lys Thr Glu Asp Thr Ala
                        340                 345                 350
        Val Tyr Tyr Cys Val Arg His Ala Asn Phe Gly Asn Ser Tyr Ile Ser
                        355                 360                 365
        Tyr Trp Ala Tyr Trp Gly Gln Gly Thr Leu Val Thr Val Ser Ser Gly
                        370                 375                 380
        Gly Gly Gly Ser Gly Gly Gly Ser Gly Gly Gly Ser Gln Thr
        385                 390                 395                 400
        Val Val Thr Gln Glu Pro Ser Leu Thr Val Ser Pro Gly Gly Thr Val
                        405                 410                 415
        Thr Leu Thr Cys Ala Ser Ser Thr Gly Ala Val Thr Ser Gly Asn Tyr
                        420                 425                 430
        Pro Asn Trp Val Gln Gln Lys Pro Gly Gln Ala Pro Arg Gly Leu Ile
                        435                 440                 445
        Gly Gly Thr Lys Phe Leu Val Pro Gly Thr Pro Ala Arg Phe Ser Gly
                        450                 455                 460
        Ser Leu Leu Gly Gly Lys Ala Ala Leu Thr Leu Ser Gly Val Gln Pro
        465                 470                 475                 480
        Glu Asp Glu Ala Glu Tyr Tyr Cys Thr Leu Trp Tyr Ser Asn Arg Trp
                        485                 490                 495
        Val Phe Gly Gly Gly Thr Lys Leu Thr Val Leu His His His His
                        500                 505                 510
        His

<210> SEQ ID NO 232
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Gln Glu Ser Gly Gly Gly Leu Val Gln Ala Gly Asp
        1               5                   10                  15
        Ser Leu Arg Leu Ser Cys Ala Val Ser Gly Arg Thr Phe Ser Gly Phe
                        20                  25                  30
        Gly Thr Gly Trp Phe Arg Gln Ala Pro Gly Lys Glu Arg Glu Phe Val
                        35                  40                  45
        Ala Ala Val Ser Gln Ser Gly Gly Thr His Tyr Ala Asp Ser Val
                        50                  55                  60
        Lys Gly Arg Phe Thr Ile Ser Arg Asp Asn Ala Lys Asn Thr Glu Thr
```

-continued

```
             65                  70                  75                  80
Leu Val Tyr Leu Gln Met Asn Ser Leu Lys Pro Glu Asp Thr Ala Val
                 85                  90                  95
Tyr Tyr Cys Ala Gly Gln Val Ala Arg Ala Tyr Asp Ser Ser Trp Tyr
            100                 105                 110
Ala Arg Gly Asp Tyr Trp Gly Gln Gly Thr Gln Val Thr Val Ser Ser
            115                 120                 125
Gly Gly Gly Gly Ser Gly Gly Ser Glu Val Gln Leu Val Glu Ser
            130                 135                 140
Gly Gly Gly Leu Val Gln Pro Gly Asn Ser Leu Arg Leu Ser Cys Ala
145                 150                 155                 160
Ala Ser Gly Phe Thr Phe Ser Lys Phe Gly Met Ser Trp Val Arg Gln
                165                 170                 175
Ala Pro Gly Lys Gly Leu Glu Trp Val Ser Ser Ile Ser Gly Ser Gly
            180                 185                 190
Arg Asp Thr Leu Tyr Ala Asp Ser Val Lys Gly Arg Phe Thr Ile Ser
            195                 200                 205
Arg Asp Asn Ala Lys Thr Thr Leu Tyr Leu Gln Met Asn Ser Leu Arg
            210                 215                 220
Pro Glu Asp Thr Ala Val Tyr Tyr Cys Thr Ile Gly Gly Ser Leu Ser
225                 230                 235                 240
Val Ser Ser Gln Gly Thr Leu Val Thr Val Ser Ser Gly Gly Gly Gly
                245                 250                 255
Ser Gly Gly Gly Ser Glu Val Gln Leu Val Glu Ser Gly Gly Gly Leu
            260                 265                 270
Val Gln Pro Gly Gly Ser Leu Lys Leu Ser Cys Ala Ala Ser Gly Phe
            275                 280                 285
Thr Phe Asn Lys Tyr Ala Ile Asn Trp Val Arg Gln Ala Pro Gly Lys
            290                 295                 300
Gly Leu Glu Trp Val Ala Arg Ile Arg Ser Lys Tyr Asn Asn Tyr Ala
305                 310                 315                 320
Thr Tyr Tyr Ala Asp Gln Val Lys Asp Arg Phe Thr Ile Ser Arg Asp
                325                 330                 335
Asp Ser Lys Asn Thr Ala Tyr Leu Gln Met Asn Asn Leu Lys Thr Glu
            340                 345                 350
Asp Thr Ala Val Tyr Tyr Cys Val Arg His Ala Asn Phe Gly Asn Ser
            355                 360                 365
Tyr Ile Ser Tyr Trp Ala Tyr Trp Gly Gln Gly Thr Leu Val Thr Val
            370                 375                 380
Ser Ser Gly Gly Gly Gly Ser Gly Gly Gly Gly Ser Gly Gly Gly Gly
385                 390                 395                 400
Ser Gln Thr Val Val Thr Gln Glu Pro Ser Leu Thr Val Ser Pro Gly
                405                 410                 415
Gly Thr Val Thr Leu Thr Cys Ala Ser Ser Thr Gly Ala Val Thr Ser
            420                 425                 430
Gly Asn Tyr Pro Asn Trp Val Gln Gln Lys Pro Gly Gln Ala Pro Arg
            435                 440                 445
Gly Leu Ile Gly Gly Thr Lys Phe Leu Val Pro Gly Thr Pro Ala Arg
            450                 455                 460
Phe Ser Gly Ser Leu Leu Gly Gly Lys Ala Ala Leu Thr Leu Ser Gly
465                 470                 475                 480
Val Gln Pro Glu Asp Glu Ala Glu Tyr Tyr Cys Thr Leu Trp Tyr Ser
                485                 490                 495
```

```
Asn Arg Trp Val Phe Gly Gly Gly Thr Lys Leu Thr Val Leu His His
            500                 505                 510

His His His His
        515

<210> SEQ ID NO 233
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Gln Glu Ser Gly Gly Gly Leu Val Gln Ala Gly Gly
1               5                   10                  15

Ser Leu Arg Leu Ser Cys Ala Val Ser Gly Arg Thr Phe Ser Gly Phe
            20                  25                  30

Gly Thr Gly Trp Phe Arg Gln Ala Pro Gly Lys Glu Arg Glu Phe Val
        35                  40                  45

Ala Ala Ile Ser Trp Ser Gly Gly Thr Thr His Tyr Ala Asp Ser Val
50                  55                  60

Lys Gly Arg Phe Thr Ile Ser Arg Asp Asn Ala Lys Asn Thr Val Asn
65                  70                  75                  80

Leu Val Tyr Leu Gln Met Asn Ser Leu Arg Pro Glu Asp Thr Ala Val
                85                  90                  95

Tyr Tyr Cys Ala Gly Gln Val Ala Arg Ala Tyr Asp Ser Asn Trp Tyr
            100                 105                 110

Ser Arg Gly Asp Tyr Trp Gly Gln Gly Thr Gln Val Thr Val Ser Ser
        115                 120                 125

Gly Gly Gly Gly Ser Gly Gly Ser Glu Val Gln Leu Val Glu Ser
    130                 135                 140

Gly Gly Gly Leu Val Gln Pro Gly Asn Ser Leu Arg Leu Ser Cys Ala
145                 150                 155                 160

Ala Ser Gly Phe Thr Phe Ser Lys Phe Gly Met Ser Trp Val Arg Gln
                165                 170                 175

Ala Pro Gly Lys Gly Leu Glu Trp Val Ser Ser Ile Ser Gly Ser Gly
            180                 185                 190

Arg Asp Thr Leu Tyr Ala Asp Ser Val Lys Gly Arg Phe Thr Ile Ser
        195                 200                 205

Arg Asp Asn Ala Lys Thr Thr Leu Tyr Leu Gln Met Asn Ser Leu Arg
210                 215                 220

Pro Glu Asp Thr Ala Val Tyr Tyr Cys Thr Ile Gly Gly Ser Leu Ser
225                 230                 235                 240

Val Ser Ser Gln Gly Thr Leu Val Thr Val Ser Ser Gly Gly Gly Gly
                245                 250                 255

Ser Gly Gly Gly Ser Glu Val Gln Leu Val Glu Ser Gly Gly Gly Leu
            260                 265                 270

Val Gln Pro Gly Gly Ser Leu Lys Leu Ser Cys Ala Ala Ser Gly Phe
        275                 280                 285

Thr Phe Asn Lys Tyr Ala Ile Asn Trp Val Arg Gln Ala Pro Gly Lys
                290                 295                 300

Gly Leu Glu Trp Val Ala Arg Ile Arg Ser Lys Tyr Asn Asn Tyr Ala
305                 310                 315                 320

Thr Tyr Tyr Ala Asp Gln Val Lys Asp Arg Phe Thr Ile Ser Arg Asp
```

325                 330                 335
Asp Ser Lys Asn Thr Ala Tyr Leu Gln Met Asn Asn Leu Lys Thr Glu
            340                 345                 350

Asp Thr Ala Val Tyr Tyr Cys Val Arg His Ala Asn Phe Gly Asn Ser
            355                 360                 365

Tyr Ile Ser Tyr Trp Ala Tyr Trp Gly Gln Gly Thr Leu Val Thr Val
            370                 375                 380

Ser Ser Gly Gly Gly Gly Ser Gly Gly Gly Ser Gly Gly Gly Gly
385                 390                 395                 400

Ser Gln Thr Val Val Thr Gln Glu Pro Ser Leu Thr Val Ser Pro Gly
            405                 410                 415

Gly Thr Val Thr Leu Thr Cys Ala Ser Ser Thr Gly Ala Val Thr Ser
            420                 425                 430

Gly Asn Tyr Pro Asn Trp Val Gln Gln Lys Pro Gly Gln Ala Pro Arg
            435                 440                 445

Gly Leu Ile Gly Gly Thr Lys Phe Leu Val Pro Gly Thr Pro Ala Arg
            450                 455                 460

Phe Ser Gly Ser Leu Leu Gly Gly Lys Ala Ala Leu Thr Leu Ser Gly
465                 470                 475                 480

Val Gln Pro Glu Asp Glu Ala Glu Tyr Tyr Cys Thr Leu Trp Tyr Ser
            485                 490                 495

Asn Arg Trp Val Phe Gly Gly Gly Thr Lys Leu Thr Val Leu His His
            500                 505                 510

His His His His
        515

<210> SEQ ID NO 234
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Gln Glu Ser Gly Gly Gly Leu Val Gln Ala Gly Gly
1               5                   10                  15

Ser Leu Arg Leu Ser Cys Arg Phe Ser Gly Arg Thr Phe Ser Gly Phe
            20                  25                  30

Gly Thr Gly Trp Phe Arg Gln Ala Pro Gly Lys Glu Arg Glu Phe Val
            35                  40                  45

Ala Ala Ile Ser Trp Ala Gly Gly Arg Thr His Tyr Glu Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
            85                  90                  95

Ala Val Gln Val Ser Arg Ala Tyr Asp Gly Ile Trp Tyr Ser Gly Gly
            100                 105                 110

Asp Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

```
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Gly Leu Val Gln Pro
            260                 265                 270
Gly Gly Ser Leu Lys Leu Ser Cys Ala Ala Ser Gly Phe Thr Phe Asn
        275                 280                 285
Lys Tyr Ala Ile Asn Trp Val Arg Gln Ala Pro Gly Lys Gly Leu Glu
    290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
        355                 360                 365
Tyr Trp Ala Tyr Trp Gly Gln Gly Thr Leu Val Thr Val Ser Ser Gly
    370                 375                 380
Gly Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
        435                 440                 445
Gly Gly Thr Lys Phe Leu Val Pro Gly Thr Pro Ala Arg Phe Ser Gly
    450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His His
            500                 505                 510
His
```

<210> SEQ ID NO 235
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
            20                  25                  30

Ala Thr Gly Trp Phe Arg Gln Val Pro Gly Lys Glu Arg Lys Leu Ile
            35                  40                  45

Ala Gly Ile Ser Arg Ser Gly Arg Thr Tyr Tyr Ala Glu Ser Val
50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Ser Ser Val Val Tyr Thr Ser Gly Asn
            100                 105                 110

Asp Tyr Asp Tyr Trp Gly Gln Gly Thr Gln Val Thr Val Ser Ser Gly
            115                 120                 125

Gly Gly Gly Ser Gly Gly Gly Ser Glu Val Gln Leu Val Glu Ser Gly
            130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
            165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
            195                 200                 205

Asp Asn Ala Lys Thr Thr Leu Tyr Leu Gln Met Asn Ser Leu Arg Pro
            210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
            275                 280                 285

Phe Asn Lys Tyr Ala Ile Asn Trp Val Arg Gln Ala Pro Gly Lys Gly
            290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
            325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
            355                 360                 365

Ile Ser Tyr Trp Ala Tyr Trp Gly Gln Gly Thr Leu Val Thr Val Ser
            370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
            405                 410                 415

Thr Val Thr Leu Thr Cys Ala Ser Ser Thr Gly Ala Val Thr Ser Gly
```

```
            420                 425                 430
Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
    450                 455                 460

Ser Gly Ser Leu Leu Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 236
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
            20                  25                  30

Ala Thr Gly Trp Phe Arg Gln Val Pro Gly Lys Glu Arg Glu Leu Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Ser Val Val Tyr Thr Ser Gly Asn
            100                 105                 110

Asp Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255
```

```
Gly Gly Gly Ser Glu Val Gln Leu Val Glu Ser Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365

Ile Ser Tyr Trp Ala Tyr Trp Gly Gln Gly Thr Leu Val Thr Val Ser
    370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
    450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His
            500                 505                 510

His His His
        515

<210> SEQ ID NO 237
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Asn Ser Gly Arg Thr Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Pro Asp Asp Thr Ala Val Tyr Tyr Cys Ala
                85                  90                  95
```

Ala Ala Arg Tyr Phe Thr Arg Asp Ala Ile Tyr Ser Gly Asp Asp
        100                 105                 110

Tyr Asp Tyr Trp Gly Gln Gly Thr Gln Val Thr Ala Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Lys Phe Gly Met Ser Trp Val Arg Gln Ala Pro
                165                 170                 175

Gly Lys Gly Leu Glu Trp Val Ser Ser Ile Ser Gly Ser Gly Arg Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Val Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Lys Leu Ser Cys Ala Ala Ser Gly Phe Thr Phe
        275                 280                 285

Asn Lys Tyr Ala Ile Asn Trp Val Arg Gln Ala Pro Gly Lys Gly Leu
    290                 295                 300

Glu Trp Val Ala Arg Ile Arg Ser Lys Tyr Asn Asn Tyr Ala Thr Tyr
305                 310                 315                 320

Tyr Ala Asp Gln Val Lys Asp Arg Phe Thr Ile Ser Arg Asp Asp Ser
                325                 330                 335

Lys Asn Thr Ala Tyr Leu Gln Met Asn Asn Leu Lys Thr Glu Asp Thr
            340                 345                 350

Ala Val Tyr Tyr Cys Val Arg His Ala Asn Phe Gly Asn Ser Tyr Ile
        355                 360                 365

Ser Tyr Trp Ala Tyr Trp Gly Gln Gly Thr Leu Val Thr Val Ser Ser
    370                 375                 380

Gly Gly Gly Gly Ser Gly Gly Gly Ser Gly Gly Gly Ser Gln
385                 390                 395                 400

Thr Val Val Thr Gln Glu Pro Ser Leu Thr Val Ser Pro Gly Gly Thr
            405                 410                 415

Val Thr Leu Thr Cys Ala Ser Ser Thr Gly Ala Val Thr Ser Gly Asn
        420                 425                 430

Tyr Pro Asn Trp Val Gln Gln Lys Pro Gly Gln Ala Pro Arg Gly Leu
    435                 440                 445

Ile Gly Gly Thr Lys Phe Leu Val Pro Gly Thr Pro Ala Arg Phe Ser
    450                 455                 460

Gly Ser Leu Leu Gly Gly Lys Ala Ala Leu Thr Leu Ser Gly Val Gln
465                 470                 475                 480

Pro Glu Asp Glu Ala Glu Tyr Tyr Cys Thr Leu Trp Tyr Ser Asn Arg
                485                 490                 495

Trp Val Phe Gly Gly Gly Thr Lys Leu Thr Val Leu His His His
            500                 505                 510

His His

<210> SEQ ID NO 238
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Gln Val Gln Leu Gln Glu Ser Gly Gly Gly Leu Val Gln Val Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Val Ser Arg Asn Ser Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Gly Val Tyr Tyr Cys
                85                  90                  95

Ala Ala Ala Arg Tyr Phe Thr Arg Asp Ala Val Tyr Thr Ser Gly Asp
            100                 105                 110

Asp Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350
```

Thr Ala Val Tyr Tyr Cys Val Arg His Ala Asn Phe Gly Asn Ser Tyr
              355                 360                 365

Ile Ser Tyr Trp Ala Tyr Trp Gly Gln Gly Thr Leu Val Thr Val Ser
    370                 375                 380

Ser Gly Gly Gly Gly Ser Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
                420                 425                 430

Asn Tyr Pro Asn Trp Val Gln Gln Lys Pro Gly Gln Ala Pro Arg Gly
            435                 440                 445

Leu Ile Gly Gly Thr Lys Phe Leu Val Pro Gly Thr Pro Ala Arg Phe
    450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 239
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Gln Glu Ser Gly Gly Gly Leu Val Gln Leu Gly Asp
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Arg Glu Arg Glu Phe Ile
        35                  40                  45

Ala Gly Ile Ser Arg Ser Gly Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Thr Ser Val Val Tyr Thr Ser Gly Asp
            100                 105                 110

Asp Tyr Asp Tyr Trp Gly Gln Gly Thr Gln Val Thr Val Ser Ser Gly
        115                 120                 125

Gly Gly Gly Ser Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
    195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
                260                 265                 270

Gln Pro Gly Gly Ser Leu Lys Leu Ser Cys Ala Ala Ser Gly Phe Thr
                275                 280                 285

Phe Asn Lys Tyr Ala Ile Asn Trp Val Arg Gln Ala Pro Gly Lys Gly
                290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
                340                 345                 350

Thr Ala Val Tyr Tyr Cys Val Arg His Ala Asn Phe Gly Asn Ser Tyr
                355                 360                 365

Ile Ser Tyr Trp Ala Tyr Trp Gly Gln Gly Thr Leu Val Thr Val Ser
                370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
                420                 425                 430

Asn Tyr Pro Asn Trp Val Gln Gln Lys Pro Gly Gln Ala Pro Arg Gly
                435                 440                 445

Leu Ile Gly Gly Thr Lys Phe Leu Val Pro Gly Thr Pro Ala Arg Phe
                450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
                500                 505                 510

His His His
        515

<210> SEQ ID NO 240
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Gln Glu Ser Gly Gly Gly Leu Val Gln Leu Gly Asp
1               5                   10                  15

Ser Leu Met Val Ser Cys Ala Ala Ser Gly Gly Thr Phe Ser Ser Tyr

```
                20                  25                  30
Ala Thr Gly Trp Phe Arg Gln Val Pro Gly Lys Glu Arg Glu Phe Ile
            35                  40                  45

Ala Gly Ile Ser Arg Ser Gly Gly Arg Thr Tyr Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Thr Ser Val Val Tyr Thr Ser Gly Asp
            100                 105                 110

Asp Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
        130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365

Ile Ser Tyr Trp Ala Tyr Trp Gly Gln Gly Thr Leu Val Thr Val Ser
        370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445
```

```
Leu Ile Gly Gly Thr Lys Phe Leu Val Pro Gly Thr Pro Ala Arg Phe
    450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
                500                 505                 510

His His His
        515

<210> SEQ ID NO 241
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Trp Ser Ser Tyr
                20                  25                  30

Ala Thr Gly Trp Phe Arg Gln Val Pro Gly Lys Glu Arg Glu Leu Ile
            35                  40                  45

Ala Gly Ile Ser Arg Ser Gly Gly Arg Thr Tyr Tyr Ala Glu Ser Val
        50                  55                  60

Lys Gly Arg Phe Thr Ile Ser Arg Asp Asn Ala Lys Asn Thr Val Tyr
65                  70                  75                  80

Leu Gln Met Asn Thr Leu Lys Ser Asp Asp Thr Ala Val Tyr Tyr Cys
                85                  90                  95

Ala Ala Ala Arg Tyr Phe Thr Ser Val Val Tyr Thr Ser Gly Asn
                100                 105                 110

Asp Tyr Asp Tyr Trp Gly Gln Gly Thr Gln Val Thr Val Ser Ser Gly
            115                 120                 125

Gly Gly Gly Ser Gly Gly Ser Glu Val Gln Leu Val Glu Ser Gly
        130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
```

```
                275                 280                 285
Phe Asn Lys Tyr Ala Ile Asn Trp Val Arg Gln Ala Pro Gly Lys Gly
            290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
                355                 360                 365

Ile Ser Tyr Trp Ala Tyr Trp Gly Gln Gly Thr Leu Val Thr Val Ser
            370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
                420                 425                 430

Asn Tyr Pro Asn Trp Val Gln Gln Lys Pro Gly Gln Ala Pro Arg Gly
            435                 440                 445

Leu Ile Gly Gly Thr Lys Phe Leu Val Pro Gly Thr Pro Ala Arg Phe
450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
                500                 505                 510

His His His
        515

<210> SEQ ID NO 242

<400> SEQUENCE: 242

000

<210> SEQ ID NO 243
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Val Gln Leu Gln Glu Ser Gly Gly Gly Leu Val Gln Val Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Asn Ser Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Thr Leu Lys Pro Asp Asp Thr Ala Val Tyr Tyr Cys
                    85                  90                  95

Ala Ala Ala Arg Tyr Phe Thr Arg Asp Ala Val Tyr Thr Ser Gly Asp
            100                 105                 110

Asp Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365

Ile Ser Tyr Trp Ala Tyr Trp Gly Gln Gly Thr Leu Val Thr Val Ser
    370                 375                 380

Ser Gly Gly Gly Gly Ser Gly Gly Gly Ser Gly Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
    450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495
```

```
Arg Trp Val Phe Gly Gly Gly Thr Lys Leu Thr Val Leu His His
                500                 505                 510
His His His
        515

<210> SEQ ID NO 244
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Val Gln Leu Gln Glu Ser Gly Gly Gly Leu Val Gln Val Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
        35                  40                  45

Ala Gly Ile Ser Arg Asn Ser Gly Arg Thr Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Arg Asp Val Val Tyr Thr Ser Gly Asp
            100                 105                 110

Asp Tyr Asp Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335
```

```
Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
            355                 360                 365

Ile Ser Tyr Trp Ala Tyr Trp Gly Gln Gly Thr Leu Val Thr Val Ser
370                 375                 380

Ser Gly Gly Gly Gly Ser Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
            435                 440                 445

Leu Ile Gly Gly Thr Lys Phe Leu Val Pro Gly Thr Pro Ala Arg Phe
450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
                500                 505                 510

His His His
        515

<210> SEQ ID NO 245
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Gln Glu Ser Gly Gly Gly Leu Val Gln Ala Gly Gly
1               5                   10                  15

Ser Leu Met Val Ser Cys Ala Ala Ser Gly Gly Thr Phe Ser Ser Tyr
            20                  25                  30

Ala Thr Gly Trp Phe Arg Gln Val Pro Gly Lys Glu Arg Glu Phe Ile
            35                  40                  45

Ala Gly Ile Ser Arg Ser Gly Gly Arg Thr Tyr Tyr Ala Glu Ser Val
50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Asp Asp Thr Ala Val Tyr Tyr Cys
                85                  90                  95

Ala Ala Ala Arg Tyr Phe Thr Ser Val Val Tyr Thr Ser Gly Asp
            100                 105                 110

Asp Tyr Asp Tyr Trp Gly Gln Gly Thr Gln Val Thr Val Ser Ser Gly
            115                 120                 125

Gly Gly Gly Ser Gly Gly Ser Glu Val Gln Leu Val Glu Ser Gly
            130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
```

```
                165                 170                 175
Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
            195                 200                 205

Asp Asn Ala Lys Thr Thr Leu Tyr Leu Gln Met Asn Ser Leu Arg Pro
        210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
            275                 280                 285

Phe Asn Lys Tyr Ala Ile Asn Trp Val Arg Gln Ala Pro Gly Lys Gly
        290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
            355                 360                 365

Ile Ser Tyr Trp Ala Tyr Trp Gly Gln Gly Thr Leu Val Thr Val Ser
        370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
        450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His
            500                 505                 510

His His His
        515

<210> SEQ ID NO 246
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Asn Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Pro Val Val
                100                 105                 110

Lys Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
```

```
                420           425           430
Pro Asn Trp Val Gln Lys Pro Gly Gln Ala Pro Arg Gly Leu Ile
            435                 440                 445
Gly Gly Thr Lys Phe Leu Val Pro Gly Thr Pro Ala Arg Phe Ser Gly
        450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His His
                500                 505                 510
His
```

<210> SEQ ID NO 247
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

```
Gln Val Gln Leu Gln Glu Ser Gly Gly Gly Leu Val Gln Ala Gly Gly
1               5                   10                  15
Ser Leu Arg Leu Ser Cys Ala Ala Ser Gly Arg Thr Phe Ser Ser Tyr
            20                  25                  30
Ala Met Gly Trp Phe Arg Gln Ala Pro Gly Met Glu Arg Glu Phe Val
        35                  40                  45
Ala Ala Ile Ser Trp Ser Gly Tyr Ser Thr Tyr Tyr Ala Asp Ser Val
    50                  55                  60
Lys Gly Arg Phe Thr Ile Ser Arg Asp Asp Ala Lys Asn Thr Val Tyr
65                  70                  75                  80
Leu Gln Met Asp Ser Leu Lys Pro Glu Asp Thr Ala Val Tyr Tyr Cys
                85                  90                  95
Ala Ala Gly Gly Ser Thr Arg Val Val Val Thr Thr Thr Pro Val Val
            100                 105                 110
Lys Tyr Trp Gly Gln Gly Thr Gln Val Thr Val Ser Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Gly Ser Gly Gly
                245                 250                 255
Gly Ser Glu Val Gln Leu Val Glu Ser Gly Gly Gly Leu Val Gln Pro
```

```
            260                 265                 270
Gly Gly Ser Leu Lys Leu Ser Cys Ala Ala Ser Gly Phe Thr Phe Asn
            275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
        500                 505                 510

His

<210> SEQ ID NO 248
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Leu Gly Trp Phe Arg Gln Ala Pro Gly Lys Glu Arg Glu Phe Val
        35                  40                  45

Ala Ala Ile Ser Trp Ser Gly Gly Asn Thr Tyr Tyr Ala Asp Ser Val
    50                  55                  60

Lys Gly Arg Phe Thr Ile Ser Arg Asp Asp Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Pro Val Val
```

-continued

```
                100                 105                 110
Lys Tyr Trp Gly Gln Gly Thr Gln Val Thr Val Ser Ser Gly Gly Gly
            115                 120                 125
Gly Ser Gly Gly Gly Ser Glu Val Gln Leu Val Glu Ser Gly Gly Gly
            130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
            165                 170                 175
Lys Gly Leu Glu Trp Val Ser Ser Ile Ser Gly Ser Gly Arg Asp Thr
            180                 185                 190
Leu Tyr Ala Asp Ser Val Lys Gly Arg Phe Thr Ile Ser Arg Asp Asn
            195                 200                 205
Ala Lys Thr Thr Leu Tyr Leu Gln Met Asn Ser Leu Arg Pro Glu Asp
            210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
            245                 250                 255
Gly Ser Glu Val Gln Leu Val Glu Ser Gly Gly Leu Val Gln Pro
            260                 265                 270
Gly Gly Ser Leu Lys Leu Ser Cys Ala Ala Ser Gly Phe Thr Phe Asn
            275                 280                 285
Lys Tyr Ala Ile Asn Trp Val Arg Gln Ala Pro Gly Lys Gly Leu Glu
            290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
            325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
            355                 360                 365
Tyr Trp Ala Tyr Trp Gly Gln Gly Thr Leu Val Thr Val Ser Ser Gly
            370                 375                 380
Gly Gly Gly Ser Gly Gly Gly Ser Gly Gly Gly Ser Gln Thr
385                 390                 395                 400
Val Val Thr Gln Glu Pro Ser Leu Thr Val Ser Pro Gly Gly Thr Val
            405                 410                 415
Thr Leu Thr Cys Ala Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
            435                 440                 445
Gly Gly Thr Lys Phe Leu Val Pro Gly Thr Pro Ala Arg Phe Ser Gly
            450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
            485                 490                 495
Val Phe Gly Gly Gly Thr Lys Leu Thr Val Leu His His His His
            500                 505                 510
His
```

<210> SEQ ID NO 249
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Gln Val Gln Leu Gln Glu Ser Gly Gly Gly Leu Val Gln Ala Gly Gly
1               5                   10                  15

Ser Leu Arg Leu Ser Cys Ala Ala Ser Glu Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Met Ser Trp Ser Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365
```

```
Tyr Trp Ala Tyr Trp Gly Gln Gly Thr Leu Val Thr Val Ser Ser Gly
        370                 375                 380
Gly Gly Gly Ser Gly Gly Gly Ser Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
                420                 425                 430
Pro Asn Trp Val Gln Gln Lys Pro Gly Gln Ala Pro Arg Gly Leu Ile
                435                 440                 445
Gly Gly Thr Lys Phe Leu Val Pro Gly Thr Pro Ala Arg Phe Ser Gly
                450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His His
                500                 505                 510
His

<210> SEQ ID NO 250
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Gln Glu Ser Gly Gly Gly Leu Val Gln Ala Gly Gly
1               5                   10                  15
Ser Leu Arg Leu Ser Cys Ala Ala Ser Glu Arg Thr Phe Ser Ser Tyr
                20                  25                  30
Ala Met Gly Trp Phe Arg Gln Ala Pro Gly Lys Glu Arg Glu Phe Val
                35                  40                  45
Ala Ala Ile Ser Trp Ser Gly Gly Ser Thr Tyr Tyr Ala Asp Ser Val
                50                  55                  60
Lys Gly Arg Phe Thr Ile Ser Arg Asp Asn Ala Lys Asn Thr Val Tyr
65                  70                  75                  80
Leu Gln Met Asp Ser Leu Lys Pro Glu Asp Thr Ala Val Tyr Tyr Cys
                85                  90                  95
Ala Ala Gly Gly Ser Thr Arg Val Val Val Thr Thr Thr Pro Ile Val
                100                 105                 110
Lys Tyr Trp Gly Gln Gly Thr Gln Val Thr Val Ser Ser Gly Gly Gly
                115                 120                 125
Gly Ser Gly Gly Gly Ser Glu Val Gln Leu Val Glu Ser Gly Gly Gly
                130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
                180                 185                 190
Leu Tyr Ala Asp Ser Val Lys Gly Arg Phe Thr Ile Ser Arg Asp Asn
                195                 200                 205
```

```
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Leu Val Gln Pro
            260                 265                 270
Gly Gly Ser Leu Lys Leu Ser Cys Ala Ala Ser Gly Phe Thr Phe Asn
                275                 280                 285
Lys Tyr Ala Ile Asn Trp Val Arg Gln Ala Pro Gly Lys Gly Leu Glu
    290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
            355                 360                 365
Tyr Trp Ala Tyr Trp Gly Gln Gly Thr Leu Val Thr Val Ser Ser Gly
    370                 375                 380
Gly Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
    435                 440                 445
Gly Gly Thr Lys Phe Leu Val Pro Gly Thr Pro Ala Arg Phe Ser Gly
    450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His
                500                 505                 510
His
```

<210> SEQ ID NO 251
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

```
Gln Val Gln Leu Gln Glu Ser Gly Gly Gly Trp Val Gln Ala Gly Gly
1               5                   10                  15
Ser Leu Arg Leu Ser Cys Ala Ala Ser Gly Arg Thr Phe Ser Ser Tyr
            20                  25                  30
Ala Met Gly Trp Phe Arg Gln Ala Pro Gly Lys Glu Arg Glu Phe Val
        35                  40                  45
```

```
Ala Ala Ile Ser Trp Ser Gly Ser Ser Thr Tyr Tyr Ala Asp Ser Val
 50              55                  60

Lys Gly Arg Phe Thr Ile Ser Arg Asp Asn Ala Lys Asn Thr Val Tyr
 65                  70                  75                  80

Leu Leu Met Asp Ser Leu Lys Pro Glu Asp Thr Ala Val Tyr Tyr Cys
                 85                  90                  95

Ala Ala Gly Gly Ser Thr Arg Val Val Thr Thr Pro Val Val
                100             105             110

Lys Tyr Trp Gly Gln Gly Thr Gln Val Thr Val Ser Ser Gly Gly Gly
            115             120             125

Gly Ser Gly Gly Gly Ser Glu Val Gln Leu Val Glu Ser Gly Gly Gly
        130             135             140

Leu Val Gln Pro Gly Asn Ser Leu Arg Leu Ser Cys Ala Ala Ser Gly
145             150             155                 160

Phe Thr Phe Ser Lys Phe Gly Met Ser Trp Val Arg Gln Ala Pro Gly
                165             170             175

Lys Gly Leu Glu Trp Val Ser Ser Ile Ser Gly Ser Gly Arg Asp Thr
            180             185             190

Leu Tyr Ala Asp Ser Val Lys Gly Arg Phe Thr Ile Ser Arg Asp Asn
            195             200             205

Ala Lys Thr Thr Leu Tyr Leu Gln Met Asn Ser Leu Arg Pro Glu Asp
    210             215             220

Thr Ala Val Tyr Tyr Cys Thr Ile Gly Gly Ser Leu Ser Val Ser Ser
225             230             235                 240

Gln Gly Thr Leu Val Thr Val Ser Ser Gly Gly Gly Ser Gly Gly
                245             250             255

Gly Ser Glu Val Gln Leu Val Glu Ser Gly Gly Gly Leu Val Gln Pro
        260             265             270

Gly Gly Ser Leu Lys Leu Ser Cys Ala Ala Ser Gly Phe Thr Phe Asn
        275             280             285

Lys Tyr Ala Ile Asn Trp Val Arg Gln Ala Pro Gly Lys Gly Leu Glu
    290             295             300

Trp Val Ala Arg Ile Arg Ser Lys Tyr Asn Asn Tyr Ala Thr Tyr Tyr
305             310             315             320

Ala Asp Gln Val Lys Asp Arg Phe Thr Ile Ser Arg Asp Asp Ser Lys
                325             330             335

Asn Thr Ala Tyr Leu Gln Met Asn Asn Leu Lys Thr Glu Asp Thr Ala
            340             345             350

Val Tyr Tyr Cys Val Arg His Ala Asn Phe Gly Asn Ser Tyr Ile Ser
            355             360             365

Tyr Trp Ala Tyr Trp Gly Gln Gly Thr Leu Val Thr Val Ser Ser Gly
    370             375             380

Gly Gly Ser Gly Gly Gly Gly Ser Gly Gly Gly Ser Gln Thr
385             390             395             400

Val Val Thr Gln Glu Pro Ser Leu Thr Val Ser Pro Gly Gly Thr Val
                405             410             415

Thr Leu Thr Cys Ala Ser Ser Thr Gly Ala Val Thr Ser Gly Asn Tyr
                420             425             430

Pro Asn Trp Val Gln Gln Lys Pro Gly Gln Ala Pro Arg Gly Leu Ile
        435             440             445

Gly Gly Thr Lys Phe Leu Val Pro Gly Thr Pro Ala Arg Phe Ser Gly
450             455             460
```

```
Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
            485                 490                 495

Val Phe Gly Gly Gly Thr Lys Leu Thr Val Leu His His His His His
            500                 505                 510

His
```

<210> SEQ ID NO 252
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Leu
            20                  25                  30

Thr Val Ala Trp Phe Arg Gln Ala Pro Gly Lys Glu Arg Glu Phe Val
        35                  40                  45

Val Ala Ser Ile Pro Ser Gly Ser Asn Thr Gly Tyr Ala Glu Ser Val
50                  55                  60

Lys Gly Arg Phe Thr Ile Ser Arg Asp Ile Ala Lys Asn Thr Val Tyr
65                  70                  75                  80

Leu Gln Met Asn Ser Leu Lys Pro Glu Asp Thr Ala Met Tyr Phe Cys
                85                  90                  95

Ala Ala Arg Ile Tyr Phe Gly Ser Ser Arg Gly Tyr Asp Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300
```

```
Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
            325                 330                 335

Leu Gln Met Asn Asn Leu Lys Thr Glu Asp Thr Ala Val Tyr Tyr Cys
        340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
        370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
        450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505
```

<210> SEQ ID NO 253
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Thr Thr Tyr
            20                  25                  30

Thr Val Ala Trp Phe Arg Gln Ala Pro Gly Lys Glu Arg Glu Phe Leu
        35                  40                  45

Val Ala Ser Ile Pro Thr Gly Ser Asn Thr Ala Tyr Ala Glu Ser Val
    50                  55                  60

Lys Gly Arg Phe Thr Ile Ser Arg Gly Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Thr Tyr Phe Gly Ser Ser Arg Gly Tyr Asp Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160
```

Lys Phe Gly Met Ser Trp Val Arg Gln Ala Pro Gly Lys Gly Leu Glu
            165                 170                 175

Trp Val Ser Ser Ile Ser Gly Ser Gly Arg Asp Thr Leu Tyr Ala Asp
        180                 185                 190

Ser Val Lys Gly Arg Phe Thr Ile Ser Arg Asp Asn Ala Lys Thr Thr
    195                 200                 205

Leu Tyr Leu Gln Met Asn Ser Leu Arg Pro Glu Asp Thr Ala Val Tyr
210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505

<210> SEQ ID NO 254
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Gln Glu Ser Gly Gly Gly Leu Val Gln Ala Gly Asp

-continued

```
1               5                   10                  15
Ser Leu Arg Leu Ser Cys Ala Thr Ser Gly Arg Thr Phe Asn Leu Tyr
                20                  25                  30
Arg Val Gly Trp Phe Arg Gln Ala Pro Gly Lys Glu Arg Glu Phe Val
                35                  40                  45
Ala Arg Ile Thr Trp Ser Ala Asp Ile Thr Gln Tyr Ala Asp Ser Val
                50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Ile Tyr Tyr Cys
                85                  90                  95
Ala Thr Thr Leu Arg Lys Ser Ser Gly Ile Tyr His Val Asp Asp Tyr
                100                 105                 110
Asp Asp Trp Gly Gln Gly Thr Gln Val Thr Val Ser Ser Gly Gly Gly
                115                 120                 125
Gly Ser Gly Gly Gly Ser Glu Val Gln Leu Val Glu Ser Gly Gly Gly
                130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
                180                 185                 190
Leu Tyr Ala Asp Ser Val Lys Gly Arg Phe Thr Ile Ser Arg Asp Asn
                195                 200                 205
Ala Lys Thr Thr Leu Tyr Leu Gln Met Asn Ser Leu Arg Pro Glu Asp
                210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Gly Ser Gly Gly
                245                 250                 255
Gly Ser Glu Val Gln Leu Val Glu Ser Gly Gly Gly Leu Val Gln Pro
                260                 265                 270
Gly Gly Ser Leu Lys Leu Ser Cys Ala Ala Ser Gly Phe Thr Phe Asn
                275                 280                 285
Lys Tyr Ala Ile Asn Trp Val Arg Gln Ala Pro Gly Lys Gly Leu Glu
                290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
                340                 345                 350
Val Tyr Tyr Cys Val Arg His Ala Asn Phe Gly Asn Ser Tyr Ile Ser
                355                 360                 365
Tyr Trp Ala Tyr Trp Gly Gln Gly Thr Leu Val Thr Val Ser Ser Gly
                370                 375                 380
Gly Gly Gly Ser Gly Gly Gly Ser Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
                420                 425                 430
```

```
Pro Asn Trp Val Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
                500                 505                 510

His

<210> SEQ ID NO 255
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Gln Glu Ser Gly Gly Gly Leu Val Gln Ala Gly Gly
1               5                   10                  15

Ser Leu Arg Leu Ser Cys Ala Thr Ser Gly Arg Thr Phe Asn Leu Tyr
            20                  25                  30

Arg Val Gly Trp Phe Arg Gln Ala Pro Gly Lys Glu Arg Glu Phe Val
        35                  40                  45

Ala Arg Ile Thr Trp Ser Ala Asp Ile Thr Gln Tyr Thr Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Thr Thr Leu Arg Lys Ser Ser Gly Ile Tyr His Thr Asp Asp Tyr
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Gly Ser Gly Gly
                245                 250                 255

Gly Ser Glu Val Gln Leu Val Glu Ser Gly Gly Gly Leu Val Gln Pro
            260                 265                 270
```

Gly Gly Ser Leu Lys Leu Ser Cys Ala Ala Ser Gly Phe Thr Phe Asn
            275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
            500                 505                 510

His

<210> SEQ ID NO 256
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Tyr Lys Ile Gly Tyr Thr Asp Ser Thr
    50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Gly Thr Gln Trp Ser Trp Ser Leu Arg Asp Asn Thr Ser Arg
            100                 105                 110

```
Gly Gln Gly Thr Gln Val Thr Val Ser Ser Gly Gly Gly Ser Gly
            115                 120                 125
Gly Gly Ser Glu Val Gln Leu Val Glu Ser Gly Gly Leu Val Gln
130                 135                 140
Pro Gly Asn Ser Leu Arg Leu Ser Cys Ala Ala Ser Gly Phe Thr Phe
145                 150                 155                 160
Ser Lys Phe Gly Met Ser Trp Val Arg Gln Ala Pro Gly Lys Gly Leu
                    165                 170                 175
Glu Trp Val Ser Ser Ile Ser Gly Ser Gly Arg Asp Thr Leu Tyr Ala
                    180                 185                 190
Asp Ser Val Lys Gly Arg Phe Thr Ile Ser Arg Asp Asn Ala Lys Thr
                    195                 200                 205
Thr Leu Tyr Leu Gln Met Asn Ser Leu Arg Pro Glu Asp Thr Ala Val
210                 215                 220
Tyr Tyr Cys Thr Ile Gly Gly Ser Leu Ser Val Ser Ser Gln Gly Thr
225                 230                 235                 240
Leu Val Thr Val Ser Ser Gly Gly Gly Ser Gly Gly Gly Ser Glu
                    245                 250                 255
Val Gln Leu Val Glu Ser Gly Gly Gly Leu Val Gln Pro Gly Gly Ser
            260                 265                 270
Leu Lys Leu Ser Cys Ala Ala Ser Gly Phe Thr Phe Asn Lys Tyr Ala
            275                 280                 285
Ile Asn Trp Val Arg Gln Ala Pro Gly Lys Gly Leu Glu Trp Val Ala
            290                 295                 300
Arg Ile Arg Ser Lys Tyr Asn Asn Tyr Ala Thr Tyr Tyr Ala Asp Gln
305                 310                 315                 320
Val Lys Asp Arg Phe Thr Ile Ser Arg Asp Asp Ser Lys Asn Thr Ala
                    325                 330                 335
Tyr Leu Gln Met Asn Asn Leu Lys Thr Glu Asp Thr Ala Val Tyr Tyr
                    340                 345                 350
Cys Val Arg His Ala Asn Phe Gly Asn Ser Tyr Ile Ser Tyr Trp Ala
            355                 360                 365
Tyr Trp Gly Gln Gly Thr Leu Val Thr Val Ser Ser Gly Gly Gly Gly
            370                 375                 380
Ser Gly Gly Gly Gly Ser Gly Gly Gly Gly Ser Gln Thr Val Val Thr
385                 390                 395                 400
Gln Glu Pro Ser Leu Thr Val Ser Pro Gly Gly Thr Val Thr Leu Thr
                    405                 410                 415
Cys Ala Ser Ser Thr Gly Ala Val Thr Ser Gly Asn Tyr Pro Asn Trp
                    420                 425                 430
Val Gln Gln Lys Pro Gly Gln Ala Pro Arg Gly Leu Ile Gly Gly Thr
            435                 440                 445
Lys Phe Leu Val Pro Gly Thr Pro Ala Arg Phe Ser Gly Ser Leu Leu
450                 455                 460
Gly Gly Lys Ala Ala Leu Thr Leu Ser Gly Val Gln Pro Glu Asp Glu
465                 470                 475                 480
Ala Glu Tyr Tyr Cys Thr Leu Trp Tyr Ser Asn Arg Trp Val Phe Gly
                    485                 490                 495
Gly Gly Thr Lys Leu Thr Val Leu His His His His His
            500                 505                 510

<210> SEQ ID NO 257
<211> LENGTH: 510
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

```
Gln Val Gln Leu Gln Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Tyr Lys Ile Gly Tyr Thr Asp Ser Thr
    50                  55                  60

Lys Gly Arg Phe Thr Ile Ser Arg Asp Asn Ala Lys Asn Thr Leu Tyr
65                  70                  75                  80

Leu Gln Met Asn Ser Leu Asn Ala Glu Asp Thr Ala Val Tyr Tyr Cys
                85                  90                  95

Ala Lys Gly Thr Gln Trp Ser Trp Ala Leu Arg Asp Ser Thr Ser Arg
            100                 105                 110

Gly Gln Gly Thr Gln Val Thr Val Ser Ser Gly Gly Gly Gly Ser Gly
        115                 120                 125

Gly Gly Ser Glu Val Gln Leu Val Glu Ser Gly Gly Gly Leu Val Gln
    130                 135                 140

Pro Gly Asn Ser Leu Arg Leu Ser Cys Ala Ala Ser Gly Phe Thr Phe
145                 150                 155                 160

Ser Lys Phe Gly Met Ser Trp Val Arg Gln Ala Pro Gly Lys Gly Leu
                165                 170                 175

Glu Trp Val Ser Ser Ile Ser Gly Ser Gly Arg Asp Thr Leu Tyr Ala
            180                 185                 190

Asp Ser Val Lys Gly Arg Phe Thr Ile Ser Arg Asp Asn Ala Lys Thr
        195                 200                 205

Thr Leu Tyr Leu Gln Met Asn Ser Leu Arg Pro Glu Asp Thr Ala Val
    210                 215                 220

Tyr Tyr Cys Thr Ile Gly Gly Ser Leu Ser Val Ser Gln Gly Thr
225                 230                 235                 240

Leu Val Thr Val Ser Ser Gly Gly Gly Ser Gly Gly Gly Ser Glu
                245                 250                 255

Val Gln Leu Val Glu Ser Gly Gly Gly Leu Val Gln Pro Gly Gly Ser
            260                 265                 270

Leu Lys Leu Ser Cys Ala Ala Ser Gly Phe Thr Phe Asn Lys Tyr Ala
        275                 280                 285

Ile Asn Trp Val Arg Gln Ala Pro Gly Lys Gly Leu Glu Trp Val Ala
    290                 295                 300

Arg Ile Arg Ser Lys Tyr Asn Asn Tyr Ala Thr Tyr Tyr Ala Asp Gln
305                 310                 315                 320

Val Lys Asp Arg Phe Thr Ile Ser Arg Asp Asp Ser Lys Asn Thr Ala
                325                 330                 335

Tyr Leu Gln Met Asn Asn Leu Lys Thr Glu Asp Thr Ala Val Tyr Tyr
            340                 345                 350

Cys Val Arg His Ala Asn Phe Gly Asn Ser Tyr Ile Ser Tyr Trp Ala
        355                 360                 365

Tyr Trp Gly Gln Gly Thr Leu Val Thr Val Ser Ser Gly Gly Gly Gly
    370                 375                 380
```

```
Ser Gly Gly Gly Gly Ser Gly Gly Gly Ser Gln Thr Val Val Thr
385                 390                 395                 400

Gln Glu Pro Ser Leu Thr Val Ser Pro Gly Thr Val Thr Leu Thr
                405                 410                 415

Cys Ala Ser Ser Thr Gly Ala Val Thr Ser Gly Asn Tyr Pro Asn Trp
            420                 425                 430

Val Gln Gln Lys Pro Gly Gln Ala Pro Arg Gly Leu Ile Gly Gly Thr
                435                 440                 445

Lys Phe Leu Val Pro Gly Thr Pro Ala Arg Phe Ser Gly Ser Leu Leu
450                 455                 460

Gly Gly Lys Ala Ala Leu Thr Leu Ser Gly Val Gln Pro Glu Asp Glu
465                 470                 475                 480

Ala Glu Tyr Tyr Cys Thr Leu Trp Tyr Ser Asn Arg Trp Val Phe Gly
                485                 490                 495

Gly Gly Thr Lys Leu Thr Val Leu His His His His His His
                500                 505                 510
```

<210> SEQ ID NO 258
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 258

```
Gln Val Gln Leu Gln Glu Ser Gly Gly Leu Val Gln Ala Gly Gly
1               5                   10                  15

Ser Leu Thr Leu Ser Cys Thr Ala Ser Gly Ser Thr Phe Ser Ile Asn
                20                  25                  30

His Phe Ser Trp Tyr Arg Gln Ala Pro Gly Lys Gln Arg Glu Leu Val
                35                  40                  45

Ala Phe Ile Ser Ser Asp Gly Val Ser Ile Asp Val Glu Ser Val Lys
50                  55                  60

Gly Arg Phe Thr Ile Ser Gly Asp Asn Asp Lys Asn Thr Ala Tyr Leu
65              70                  75                  80

Gln Met Asn Gly Leu Lys Pro Glu Asp Thr Ala Val Tyr Tyr Cys Tyr
                85                  90                  95

Tyr Arg Gly Phe Trp Gly Gln Gly Thr Gln Val Thr Val Ser Ser Gly
                100                 105                 110

Gly Gly Gly Ser Gly Gly Gly Ser Glu Val Gln Leu Val Glu Ser Gly
            115                 120                 125

Gly Gly Leu Val Gln Pro Gly Asn Ser Leu Arg Leu Ser Cys Ala Ala
130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
                195                 200                 205

Glu Asp Thr Ala Val Tyr Tyr Cys Thr Ile Gly Gly Ser Leu Ser Val
                210                 215                 220

Ser Ser Gln Gly Thr Leu Val Thr Val Ser Ser Gly Gly Gly Gly Ser
```

```
225                 230                 235                 240
Gly Gly Gly Ser Glu Val Gln Leu Val Glu Ser Gly Gly Leu Val
                245                 250                 255
Gln Pro Gly Gly Ser Leu Lys Leu Ser Cys Ala Ala Ser Gly Phe Thr
                260                 265                 270
Phe Asn Lys Tyr Ala Ile Asn Trp Val Arg Gln Ala Pro Gly Lys Gly
                275                 280                 285
Leu Glu Trp Val Ala Arg Ile Arg Ser Lys Tyr Asn Asn Tyr Ala Thr
                290                 295                 300
Tyr Tyr Ala Asp Gln Val Lys Asp Arg Phe Thr Ile Ser Arg Asp Asp
305                                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Ala Asn Phe Gly Asn Ser Tyr
                340                 345                 350
Ile Ser Tyr Trp Ala Tyr Trp Gly Gln Gly Thr Leu Val Thr Val Ser
                355                 360                 365
Ser Gly Gly Gly Gly Ser Gly Gly Gly Gly Ser Gly Gly Gly Gly Ser
                370                 375                 380
Gln Thr Val Val Thr Gln Glu Pro Ser Leu Thr Val Ser Pro Gly Gly
385                                 390                 395                 400
Thr Val Thr Leu Thr Cys Ala Ser Ser Thr Gly Ala Val Thr Ser Gly
                405                 410                 415
Asn Tyr Pro Asn Trp Val Gln Gln Lys Pro Gly Gln Ala Pro Arg Gly
                420                 425                 430
Leu Ile Gly Gly Thr Lys Phe Leu Val Pro Gly Thr Pro Ala Arg Phe
                435                 440                 445
Ser Gly Ser Leu Leu Gly Gly Lys Ala Ala Leu Thr Leu Ser Gly Val
                450                 455                 460
Gln Pro Glu Asp Glu Ala Glu Tyr Tyr Cys Thr Leu Trp Tyr Ser Asn
465                                 470                 475                 480
Arg Trp Val Phe Gly Gly Gly Thr Lys Leu Thr Val Leu His His His
                485                 490                 495
His His His

<210> SEQ ID NO 259
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Gln Glu Ser Gly Gly Gly Leu Val Gln Pro Gly Gly
1               5                   10                  15
Ser Leu Thr Leu Ser Cys Thr Ala Ser Gly Ser Thr Phe Ser Ile Asn
                20                  25                  30
His Phe Ala Trp Tyr Arg Gln Ala Pro Gly Lys Gln Arg Glu Leu Val
                35                  40                  45
Ala Phe Ile Ser Ser Asp Gly Arg Ser Thr Asp Val Glu Ser Val Lys
                50                  55                  60
Gly Arg Phe Thr Ile Ser Gly Asp Asn Asp Lys Asn Thr Ala Tyr Leu
65                          70                  75                  80
Gln Met Asn Gly Leu Lys Pro Glu Asp Thr Ala Val Tyr Tyr Cys Tyr
```

```
                85                  90                  95
Tyr Arg Gly Ser Trp Gly Gln Gly Thr Gln Val Thr Val Ser Ser Gly
                100                 105                 110
Gly Gly Gly Ser Gly Gly Ser Glu Val Gln Leu Val Glu Ser Gly
                115                 120                 125
Gly Gly Leu Val Gln Pro Gly Asn Ser Leu Arg Leu Ser Cys Ala Ala
            130                 135                 140
Ser Gly Phe Thr Phe Ser Lys Phe Gly Met Ser Trp Val Arg Gln Ala
145                 150                 155                 160
Pro Gly Lys Gly Leu Glu Trp Val Ser Ser Ile Ser Gly Ser Gly Arg
                165                 170                 175
Asp Thr Leu Tyr Ala Asp Ser Val Lys Gly Arg Phe Thr Ile Ser Arg
                180                 185                 190
Asp Asn Ala Lys Thr Thr Leu Tyr Leu Gln Met Asn Ser Leu Arg Pro
            195                 200                 205
Glu Asp Thr Ala Val Tyr Tyr Cys Thr Ile Gly Gly Ser Leu Ser Val
            210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Gly Leu Val
                245                 250                 255
Gln Pro Gly Gly Ser Leu Lys Leu Ser Cys Ala Ala Ser Gly Phe Thr
            260                 265                 270
Phe Asn Lys Tyr Ala Ile Asn Trp Val Arg Gln Ala Pro Gly Lys Gly
            275                 280                 285
Leu Glu Trp Val Ala Arg Ile Arg Ser Lys Tyr Asn Asn Tyr Ala Thr
            290                 295                 300
Tyr Tyr Ala Asp Gln Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Ala Asn Phe Gly Asn Ser Tyr
                340                 345                 350
Ile Ser Tyr Trp Ala Tyr Trp Gly Gln Gly Thr Leu Val Thr Val Ser
            355                 360                 365
Ser Gly Gly Gly Gly Ser Gly Gly Gly Gly Ser Gly Gly Gly Gly Ser
            370                 375                 380
Gln Thr Val Val Thr Gln Glu Pro Ser Leu Thr Val Ser Pro Gly Gly
385                 390                 395                 400
Thr Val Thr Leu Thr Cys Ala Ser Ser Thr Gly Ala Val Thr Ser Gly
                405                 410                 415
Asn Tyr Pro Asn Trp Val Gln Gln Lys Pro Gly Gln Ala Pro Arg Gly
                420                 425                 430
Leu Ile Gly Gly Thr Lys Phe Leu Val Pro Gly Thr Pro Ala Arg Phe
            435                 440                 445
Ser Gly Ser Leu Leu Gly Gly Lys Ala Ala Leu Thr Leu Ser Gly Val
            450                 455                 460
Gln Pro Glu Asp Glu Ala Glu Tyr Tyr Cys Thr Leu Trp Tyr Ser Asn
465                 470                 475                 480
Arg Trp Val Phe Gly Gly Gly Thr Lys Leu Thr Val Leu His His His
                485                 490                 495
His His His
```

```
<210> SEQ ID NO 260
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Gln Glu Ser Gly Gly Gly Leu Val Gln Ala Gly Gly
1               5                   10                  15

Ser Leu Ser Leu Ser Cys Ala Ala Ser Glu Gly Thr Ile Ser His Ala
            20                  25                  30

Ala Met Gly Trp Phe Arg Gln Ala Pro Gly Lys Glu Arg Gln Phe Val
        35                  40                  45

Ala Tyr Asp Thr Trp Thr Gly Ser Thr Asn Tyr Ala Asp Ser Val
    50                  55                  60

Lys Asp Arg Phe Thr Ile Thr Gly Asp His Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Val Arg Gly Arg Tyr Ser Ala Ser Tyr Thr Tyr Thr Asn Pro Ala
            100                 105                 110

Ser Tyr Lys Tyr Trp Gly Gln Gly Thr Gln Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365
```

```
Ile Ser Tyr Trp Ala Tyr Trp Gly Gln Gly Thr Leu Val Thr Val Ser
    370                 375                 380
Ser Gly Gly Gly Gly Ser Gly Gly Gly Gly Ser Gly Gly Gly Gly Ser
385                 390                 395                 400
Gln Thr Val Val Thr Gln Glu Pro Ser Leu Thr Val Ser Pro Gly Gly
                405                 410                 415
Thr Val Thr Leu Thr Cys Ala Ser Ser Thr Gly Ala Val Thr Ser Gly
                420                 425                 430
Asn Tyr Pro Asn Trp Val Gln Gln Lys Pro Gly Gln Ala Pro Arg Gly
            435                 440                 445
Leu Ile Gly Gly Thr Lys Phe Leu Val Pro Gly Thr Pro Ala Arg Phe
    450                 455                 460
Ser Gly Ser Leu Leu Gly Gly Lys Ala Ala Leu Thr Leu Ser Gly Val
465                 470                 475                 480
Gln Pro Glu Asp Glu Ala Glu Tyr Tyr Cys Thr Leu Trp Tyr Ser Asn
                485                 490                 495
Arg Trp Val Phe Gly Gly Gly Thr Lys Leu Thr Val Leu His His His
            500                 505                 510

His His His
    515

<210> SEQ ID NO 261
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Gln Leu Gln Glu Ser Gly Gly Gly Leu Val Gln Ala Gly Gly
1               5                   10                  15
Ser Leu Arg Leu Ser Cys Ala Ala Ser Gly Gly Thr Phe Ser Ser Ser
            20                  25                  30
Ala Met Gly Trp Phe Arg Gln Ala Pro Gly Lys Glu Arg Glu Phe Val
        35                  40                  45
Ala Thr Ile Thr Gln Asn Asp Val Pro Thr Tyr Tyr Thr His Ser Val
    50                  55                  60
Lys Gly Arg Phe Thr Ile Ser Arg Asp Asn Ala Lys Asn Thr Met Tyr
65                  70                  75                  80
Leu Gln Met Asn Ser Leu Lys Pro Glu Asp Thr Ala Val Tyr Tyr Cys
                85                  90                  95
Ala Gln Arg Val Ala Gln Ala Ser Gly Trp Arg Thr Thr Ile Lys Asp
            100                 105                 110
Tyr Gly Tyr Trp Gly Gln Gly Thr Gln Val Thr Val Ser Ser Gly Gly
        115                 120                 125
Gly Gly Ser Gly Gly Gly Ser Glu Val Gln Leu Val Glu Ser Gly Gly
    130                 135                 140
Gly Leu Val Gln Pro Gly Asn Ser Leu Arg Leu Ser Cys Ala Ala Ser
145                 150                 155                 160
Gly Phe Thr Phe Ser Lys Phe Gly Met Ser Trp Val Arg Gln Ala Pro
                165                 170                 175
Gly Lys Gly Leu Glu Trp Val Ser Ser Ile Ser Gly Ser Gly Arg Asp
            180                 185                 190
Thr Leu Tyr Ala Asp Ser Val Lys Gly Arg Phe Thr Ile Ser Arg Asp
```

```
            195                 200                 205
Asn Ala Lys Thr Thr Leu Tyr Leu Gln Met Asn Ser Leu Arg Pro Glu
        210                 215                 220

Asp Thr Ala Val Tyr Tyr Cys Thr Ile Gly Gly Ser Leu Ser Val Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Lys Leu Ser Cys Ala Ala Ser Gly Phe Thr Phe
        275                 280                 285

Asn Lys Tyr Ala Ile Asn Trp Val Arg Gln Ala Pro Gly Lys Gly Leu
    290                 295                 300

Glu Trp Val Ala Arg Ile Arg Ser Lys Tyr Asn Asn Tyr Ala Thr Tyr
305                 310                 315                 320

Tyr Ala Asp Gln Val Lys Asp Arg Phe Thr Ile Ser Arg Asp Asp Ser
                325                 330                 335

Lys Asn Thr Ala Tyr Leu Gln Met Asn Asn Leu Lys Thr Glu Asp Thr
            340                 345                 350

Ala Val Tyr Tyr Cys Val Arg His Ala Asn Phe Gly Asn Ser Tyr Ile
        355                 360                 365

Ser Tyr Trp Ala Tyr Trp Gly Gln Gly Thr Leu Val Thr Val Ser Ser
    370                 375                 380

Gly Gly Gly Gly Ser Gly Gly Gly Ser Gly Gly Gly Ser Gln
385                 390                 395                 400

Thr Val Val Thr Gln Glu Pro Ser Leu Thr Val Ser Pro Gly Gly Thr
                405                 410                 415

Val Thr Leu Thr Cys Ala Ser Ser Thr Gly Ala Val Thr Ser Gly Asn
            420                 425                 430

Tyr Pro Asn Trp Val Gln Gln Lys Pro Gly Gln Ala Pro Arg Gly Leu
        435                 440                 445

Ile Gly Gly Thr Lys Phe Leu Val Pro Gly Thr Pro Ala Arg Phe Ser
    450                 455                 460

Gly Ser Leu Leu Gly Gly Lys Ala Ala Leu Thr Leu Ser Gly Val Gln
465                 470                 475                 480

Pro Glu Asp Glu Ala Glu Tyr Tyr Cys Thr Leu Trp Tyr Ser Asn Arg
                485                 490                 495

Trp Val Phe Gly Gly Gly Thr Lys Leu Thr Val Leu His His His His
            500                 505                 510

His His

<210> SEQ ID NO 262
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Gln Glu Ser Gly Gly Gly Leu Val Gln Ala Gly Gly
1               5                   10                  15

Ser Leu Arg Leu Ser Cys Ala Ala Ser Gly Leu Thr Ser Ser Thr Tyr
            20                  25                  30

Arg Met Ala Trp Phe Arg Gln Ala Pro Gly Lys Glu Arg Glu Phe Ala
```

```
                35                  40                  45
Ala Gly Ile Ser Tyr Ser Ala Asp Ser Gly Gly Ser Thr Asn Tyr Ala
 50                  55                  60

Asp Ser Val Lys Gly Arg Phe Thr Ile Ser Arg Asp Asn Ala Lys Asn
 65                  70                  75                  80

Thr Val Tyr Leu Gln Met Ser Ser Leu Lys Pro Glu Asp Thr Ala Val
                 85                  90                  95

Tyr Tyr Cys Ala Ala Gly Arg Tyr Ser Gly Thr Tyr Asn Ser Pro Tyr
            100                 105                 110

Ser Ser Ser Tyr Val Tyr Trp Gly Gln Gly Thr Gln Val Thr Val Ser
        115                 120                 125

Ser Gly Gly Gly Ser Gly Gly Gly Ser Glu Val Gln Leu Val Glu
    130                 135                 140

Ser Gly Gly Gly Leu Val Gln Pro Gly Asn Ser Leu Arg Leu Ser Cys
145                 150                 155                 160

Ala Ala Ser Gly Phe Thr Phe Ser Lys Phe Gly Met Ser Trp Val Arg
                165                 170                 175

Gln Ala Pro Gly Lys Gly Leu Glu Trp Val Ser Ser Ile Ser Gly Ser
            180                 185                 190

Gly Arg Asp Thr Leu Tyr Ala Asp Ser Val Lys Gly Arg Phe Thr Ile
        195                 200                 205

Ser Arg Asp Asn Ala Lys Thr Thr Leu Tyr Leu Gln Met Asn Ser Leu
    210                 215                 220

Arg Pro Glu Asp Thr Ala Val Tyr Tyr Cys Thr Ile Gly Gly Ser Leu
225                 230                 235                 240

Ser Val Ser Ser Gln Gly Thr Leu Val Thr Val Ser Ser Gly Gly Gly
                245                 250                 255

Gly Ser Gly Gly Gly Ser Glu Val Gln Leu Val Glu Ser Gly Gly Gly
            260                 265                 270

Leu Val Gln Pro Gly Gly Ser Leu Lys Leu Ser Cys Ala Ala Ser Gly
        275                 280                 285

Phe Thr Phe Asn Lys Tyr Ala Ile Asn Trp Val Arg Gln Ala Pro Gly
    290                 295                 300

Lys Gly Leu Glu Trp Val Ala Arg Ile Arg Ser Lys Tyr Asn Asn Tyr
305                 310                 315                 320

Ala Thr Tyr Tyr Ala Asp Gln Val Lys Asp Arg Phe Thr Ile Ser Arg
                325                 330                 335

Asp Asp Ser Lys Asn Thr Ala Tyr Leu Gln Met Asn Asn Leu Lys Thr
            340                 345                 350

Glu Asp Thr Ala Val Tyr Tyr Cys Val Arg His Ala Asn Phe Gly Asn
        355                 360                 365

Ser Tyr Ile Ser Tyr Trp Ala Tyr Trp Gly Gln Gly Thr Leu Val Thr
    370                 375                 380

Val Ser Ser Gly Gly Gly Gly Ser Gly Gly Gly Gly Ser Gly Gly Gly
385                 390                 395                 400

Gly Ser Gln Thr Val Val Thr Gln Glu Pro Ser Leu Thr Val Ser Pro
                405                 410                 415

Gly Gly Thr Val Thr Leu Thr Cys Ala Ser Ser Thr Gly Ala Val Thr
            420                 425                 430

Ser Gly Asn Tyr Pro Asn Trp Val Gln Gln Lys Pro Gly Gln Ala Pro
        435                 440                 445

Arg Gly Leu Ile Gly Gly Thr Lys Phe Leu Val Pro Gly Thr Pro Ala
    450                 455                 460
```

Arg Phe Ser Gly Ser Leu Leu Gly Gly Lys Ala Ala Leu Thr Leu Ser
465                 470                 475                 480

Gly Val Gln Pro Glu Asp Glu Ala Glu Tyr Tyr Cys Thr Leu Trp Tyr
                485                 490                 495

Ser Asn Arg Trp Val Phe Gly Gly Gly Thr Lys Leu Thr Val Leu His
            500                 505                 510

His His His His His
        515

<210> SEQ ID NO 263
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Val Gln Leu Gln Glu Ser Gly Gly Gly Leu Val Gln Thr Gly Gly
1               5                   10                  15

Ser Leu Arg Leu Ser Cys Ala Ala Ser Gly Ser Thr Phe Ser Arg Asn
            20                  25                  30

Thr Met Gly Trp Phe Arg Gln Ala Pro Gly Lys Glu Arg Val Phe Val
        35                  40                  45

Leu Gly Ile Ser Trp Ser Gly Ile Arg Ser Tyr Tyr Leu Asp Ser Ala
    50                  55                  60

Lys Ala Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gln Glu Gly Ser Pro Gly Pro Tyr Lys Tyr Trp Gly Gln
            100                 105                 110

Gly Thr Gln Val Thr Val Ser Ser Gly Gly Gly Ser Gly Gly Gly
        115                 120                 125

Ser Glu Val Gln Leu Val Glu Ser Gly Gly Gly Leu Val Gln Pro Gly
130                 135                 140

Asn Ser Leu Arg Leu Ser Cys Ala Ala Ser Gly Phe Thr Phe Ser Lys
145                 150                 155                 160

Phe Gly Met Ser Trp Val Arg Gln Ala Pro Gly Lys Gly Leu Glu Trp
                165                 170                 175

Val Ser Ser Ile Ser Gly Ser Gly Arg Asp Thr Leu Tyr Ala Asp Ser
            180                 185                 190

Val Lys Gly Arg Phe Thr Ile Ser Arg Asp Asn Ala Lys Thr Thr Leu
        195                 200                 205

Tyr Leu Gln Met Asn Ser Leu Arg Pro Glu Asp Thr Ala Val Tyr Tyr
    210                 215                 220

Cys Thr Ile Gly Gly Ser Leu Val Ser Ser Gln Gly Thr Leu Val
225                 230                 235                 240

Thr Val Ser Ser Gly Gly Gly Ser Gly Gly Gly Ser Glu Val Gln
                245                 250                 255

Leu Val Glu Ser Gly Gly Gly Leu Val Gln Pro Gly Gly Ser Leu Lys
            260                 265                 270

Leu Ser Cys Ala Ala Ser Gly Phe Thr Phe Asn Lys Tyr Ala Ile Asn
        275                 280                 285

Trp Val Arg Gln Ala Pro Gly Lys Gly Leu Glu Trp Val Ala Arg Ile

```
                290                 295                 300
Arg Ser Lys Tyr Asn Asn Tyr Ala Thr Tyr Tyr Ala Asp Gln Val Lys
305                 310                 315                 320

Asp Arg Phe Thr Ile Ser Arg Asp Ser Lys Asn Thr Ala Tyr Leu
                325                 330                 335

Gln Met Asn Asn Leu Lys Thr Glu Asp Thr Ala Val Tyr Tyr Cys Val
                340                 345                 350

Arg His Ala Asn Phe Gly Asn Ser Tyr Ile Ser Tyr Trp Ala Tyr Trp
                355                 360                 365

Gly Gln Gly Thr Leu Val Thr Val Ser Ser Gly Gly Gly Ser Gly
            370                 375                 380

Gly Gly Gly Ser Gly Gly Gly Ser Gln Thr Val Val Thr Gln Glu
385                 390                 395                 400

Pro Ser Leu Thr Val Ser Pro Gly Gly Thr Val Thr Leu Thr Cys Ala
                405                 410                 415

Ser Ser Thr Gly Ala Val Thr Ser Gly Asn Tyr Pro Asn Trp Val Gln
                420                 425                 430

Gln Lys Pro Gly Gln Ala Pro Arg Gly Leu Ile Gly Gly Thr Lys Phe
                435                 440                 445

Leu Val Pro Gly Thr Pro Ala Arg Phe Ser Gly Ser Leu Leu Gly Gly
                450                 455                 460

Lys Ala Ala Leu Thr Leu Ser Gly Val Gln Pro Glu Asp Glu Ala Glu
465                 470                 475                 480

Tyr Tyr Cys Thr Leu Trp Tyr Ser Asn Arg Trp Val Phe Gly Gly
                485                 490                 495

Thr Lys Leu Thr Val Leu His His His His His His
                500                 505

<210> SEQ ID NO 264
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Gln Glu Ser Gly Gly Gly Val Val Gln Val Gly Gly
1               5                   10                  15

Ser Leu Arg Leu Ser Cys Ala Ala Ser Gly Gly Thr Phe Gly Tyr Tyr
                20                  25                  30

Ala Val Gly Trp Phe Arg Gln Ala Pro Gly Lys Glu Arg Glu Phe Val
            35                  40                  45

Ala Ala Val Thr Trp Asn Gly Ala Tyr Leu Tyr Ser Asp Pro Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Ser Glu Asp Thr Ala Val Tyr Tyr Cys Gly
                85                  90                  95

Leu Asp Arg Trp Ser Ala Val Val Glu Ser Thr Pro Ser Thr Arg Gly
                100                 105                 110

Gln Gly Thr Gln Val Thr Val Ser Ser Gly Gly Gly Ser Gly Gly
            115                 120                 125

Gly Ser Glu Val Gln Leu Val Glu Ser Gly Gly Gly Leu Val Gln Pro
130                 135                 140
```

```
Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
            165                 170                 175

Trp Val Ser Ser Ile Ser Gly Ser Gly Arg Asp Thr Leu Tyr Ala Asp
        180                 185                 190

Ser Val Lys Gly Arg Phe Thr Ile Ser Arg Asp Asn Ala Lys Thr Thr
    195                 200                 205

Leu Tyr Leu Gln Met Asn Ser Leu Arg Pro Glu Asp Thr Ala Val Tyr
210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
            245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
            325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
            405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
            485                 490                 495

Gly Thr Lys Leu Thr Val Leu His His His His His
            500                 505
```

<210> SEQ ID NO 265
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

-continued

```
Gln Val Gln Leu Gln Glu Ser Gly Gly Gly Leu Val Gln Ala Gly
1               5                   10                  15

Ser Leu Arg Leu Ser Cys Ala Ala Ser Gly Gly Ala Phe Ser Ser Tyr
            20                  25                  30

Val Met Gly Trp Phe Arg Gln Ala Pro Gly Lys Glu Arg Glu Phe Val
        35                  40                  45

Ala Ala Val Ile Ser Trp Ser Gly Arg Ile Thr Asp Tyr Ala Asp Ser
    50                  55                  60

Val Lys Gly Arg Phe Ser Ile Ser Arg Asp Asn Ala Lys Ser Thr Val
65                  70                  75                  80

Tyr Leu Gln Met Asn Asn Leu Lys Pro Glu Asp Thr Ala Val Tyr Tyr
                85                  90                  95

Cys Ala Ala Lys Thr Gly Met Tyr Ile Asp Leu Arg Thr Ser Thr Phe
            100                 105                 110

Asp Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
            165                 170                 175

Lys Gly Leu Glu Trp Val Ser Ser Ile Ser Gly Ser Gly Arg Asp Thr
        180                 185                 190

Leu Tyr Ala Asp Ser Val Lys Gly Arg Phe Thr Ile Ser Arg Asp Asn
    195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
            245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
    275                 280                 285

Lys Tyr Ala Ile Asn Trp Val Arg Gln Ala Pro Gly Lys Gly Leu Glu
290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
            325                 330                 335

Asn Thr Ala Tyr Leu Gln Met Asn Asn Leu Lys Thr Glu Asp Thr Ala
        340                 345                 350

Val Tyr Tyr Cys Val Arg His Ala Asn Phe Gly Asn Ser Tyr Ile Ser
    355                 360                 365

Tyr Trp Ala Tyr Trp Gly Gln Gly Thr Leu Val Thr Val Ser Ser Gly
370                 375                 380

Gly Gly Ser Gly Gly Gly Gly Ser Gly Gly Gly Ser Gln Thr
385                 390                 395                 400

Val Val Thr Gln Glu Pro Ser Leu Thr Val Ser Pro Gly Gly Thr Val
            405                 410                 415
```

```
Thr Leu Thr Cys Ala Ser Ser Thr Gly Ala Val Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His His
            500                 505                 510

His

<210> SEQ ID NO 266
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Val Gln Leu Gln Glu Ser Gly Gly Gly Ser Val Gln Ala Gly Gly
1               5                   10                  15

Ser Leu Arg Leu Ser Cys Thr Ala Ser Gly Arg Thr Phe Thr Asp Tyr
            20                  25                  30

Thr Met Gly Trp Phe Arg Gln Ala Pro Gly Lys Glu Arg Glu Phe Met
        35                  40                  45

Leu Gly Ile Ser Ser Asn Gly Tyr Arg Arg Tyr Tyr Thr Gly Ser Met
    50                  55                  60

Lys Asp Arg Phe Thr Ile Ser Arg Asp Asn Val Lys Lys Thr Val Tyr
65                  70                  75                  80

Leu Gln Met Asn Asp Leu Lys Pro Glu Asp Thr Ala Val Tyr Tyr Cys
                85                  90                  95

Ala Ala Ser Glu Asp His Gly Ala Pro Arg Tyr Asp Tyr Trp Gly Gln
            100                 105                 110

Gly Thr Gln Val Thr Val Ser Ser Gly Gly Gly Gly Ser Gly Gly Gly
        115                 120                 125

Ser Glu Val Gln Leu Val Glu Ser Gly Gly Gly Leu Val Gln Pro Gly
130                 135                 140

Asn Ser Leu Arg Leu Ser Cys Ala Ala Ser Gly Phe Thr Phe Ser Lys
145                 150                 155                 160

Phe Gly Met Ser Trp Val Arg Gln Ala Pro Gly Lys Gly Leu Glu Trp
                165                 170                 175

Val Ser Ser Ile Ser Gly Ser Gly Arg Asp Thr Leu Tyr Ala Asp Ser
            180                 185                 190

Val Lys Gly Arg Phe Thr Ile Ser Arg Asp Asn Ala Lys Thr Thr Leu
        195                 200                 205

Tyr Leu Gln Met Asn Ser Leu Arg Pro Glu Asp Thr Ala Val Tyr Tyr
    210                 215                 220

Cys Thr Ile Gly Gly Ser Leu Ser Val Ser Ser Gln Gly Thr Leu Val
225                 230                 235                 240

Thr Val Ser Ser Gly Gly Gly Gly Ser Gly Gly Gly Ser Glu Val Gln
                245                 250                 255
```

Leu Val Glu Ser Gly Gly Gly Leu Val Gln Pro Gly Gly Ser Leu Lys
                260                 265                 270

Leu Ser Cys Ala Ala Ser Gly Phe Thr Phe Asn Lys Tyr Ala Ile Asn
            275                 280                 285

Trp Val Arg Gln Ala Pro Gly Lys Gly Leu Glu Trp Val Ala Arg Ile
290                 295                 300

Arg Ser Lys Tyr Asn Asn Tyr Ala Thr Tyr Tyr Ala Asp Gln Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
                340                 345                 350

Arg His Ala Asn Phe Gly Asn Ser Tyr Ile Ser Tyr Trp Ala Tyr Trp
            355                 360                 365

Gly Gln Gly Thr Leu Val Thr Val Ser Ser Gly Gly Gly Gly Ser Gly
                370                 375                 380

Gly Gly Gly Ser Gly Gly Gly Gly Ser Gln Thr Val Val Thr Gln Glu
385                 390                 395                 400

Pro Ser Leu Thr Val Ser Pro Gly Gly Thr Val Thr Leu Thr Cys Ala
                405                 410                 415

Ser Ser Thr Gly Ala Val Thr Ser Gly Asn Tyr Pro Asn Trp Val Gln
            420                 425                 430

Gln Lys Pro Gly Gln Ala Pro Arg Gly Leu Ile Gly Gly Thr Lys Phe
                435                 440                 445

Leu Val Pro Gly Thr Pro Ala Arg Phe Ser Gly Ser Leu Leu Gly Gly
450                 455                 460

Lys Ala Ala Leu Thr Leu Ser Gly Val Gln Pro Glu Asp Glu Ala Glu
465                 470                 475                 480

Tyr Tyr Cys Thr Leu Trp Tyr Ser Asn Arg Trp Val Phe Gly Gly Gly
                485                 490                 495

Thr Lys Leu Thr Val Leu His His His His His His
                500                 505

<210> SEQ ID NO 267
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
            35                  40                  45

Ala Ala Ile Ser Trp Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Pro Val Val
            100                 105                 110

```
Lys Tyr Trp Gly Gln Gly Thr Leu Val Thr Val Ser Ser Gly Gly
        115                 120                 125
Gly Ser Gly Gly Gly Ser Glu Val Gln Leu Val Glu Ser Gly Gly
        130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
                180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
        210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Gly Leu Val Gln Pro
        260                 265                 270
Gly Gly Ser Leu Lys Leu Ser Cys Ala Ala Ser Gly Phe Thr Phe Asn
        275                 280                 285
Lys Tyr Ala Ile Asn Trp Val Arg Gln Ala Pro Gly Lys Gly Leu Glu
        290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
                340                 345                 350
Val Tyr Tyr Cys Val Arg His Ala Asn Phe Gly Asn Ser Tyr Ile Ser
        355                 360                 365
Tyr Trp Ala Tyr Trp Gly Gln Gly Thr Leu Val Thr Val Ser Ser Gly
        370                 375                 380
Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
                420                 425                 430
Pro Asn Trp Val Gln Gln Lys Pro Gly Gln Ala Pro Arg Gly Leu Ile
                435                 440                 445
Gly Gly Thr Lys Phe Leu Val Pro Gly Thr Pro Ala Arg Phe Ser Gly
        450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His
        500                 505                 510

His
```

```
<210> SEQ ID NO 268
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

Ala Met Gly Trp Phe Arg Gln Ala Pro Gly Met Glu Arg Glu Phe Val
        35                  40                  45

Ala Ala Ile Ser Trp Ser Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365
```

```
Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
                420                 425                 430

Pro Asn Trp Val Gln Gln Lys Pro Gly Gln Ala Pro Arg Gly Leu Ile
                435                 440                 445

Gly Gly Thr Lys Phe Leu Val Pro Gly Thr Pro Ala Arg Phe Ser Gly
                450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
                500                 505                 510

His

<210> SEQ ID NO 269
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Val Gln Leu Val Glu Ser Gly Gly Gly Leu Val Gln Pro Gly Gly
1               5                   10                  15

Ser Leu Thr Leu Ser Cys Ala Ala Ser Gly Ser Thr Phe Ser Ile Asn
                20                  25                  30

His Phe Ser Trp Tyr Arg Gln Ala Pro Gly Lys Gln Arg Glu Leu Val
                35                  40                  45

Ala Phe Ile Ser Ser Asp Gly Val Ser Ile Asp Val Glu Ser Val Lys
                50                  55                  60

Gly Arg Phe Thr Ile Ser Gly Asp Asn Ser Lys Asn Thr Ala Tyr Leu
65                  70                  75                  80

Gln Met Asn Ser Leu Arg Ala Glu Asp Thr Ala Val Tyr Tyr Cys Tyr
                85                  90                  95

Tyr Arg Gly Phe Trp Gly Gln Gly Thr Leu Val Thr Val Ser Ser Gly
                100                 105                 110

Gly Gly Gly Ser Gly Gly Gly Ser Glu Val Gln Leu Val Glu Ser Gly
                115                 120                 125

Gly Gly Leu Val Gln Pro Gly Asn Ser Leu Arg Leu Ser Cys Ala Ala
                130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
                180                 185                 190

Asp Asn Ala Lys Thr Thr Leu Tyr Leu Gln Met Asn Ser Leu Arg Pro
                195                 200                 205
```

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
                340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
            450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His
                485                 490                 495

His His His

<210> SEQ ID NO 270
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Phe Ser Ser Tyr
            20                  25                  30

Ala Leu Gly Trp Phe Arg Gln Ala Pro Gly Lys Glu Arg Glu Phe Val
        35                  40                  45

Ala Ala Ile Ser Trp Ser Gly Gly Asn Thr Tyr Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Gly Gly Ser Thr Arg Val Val Val Thr Thr Pro Val Val
            100                 105                 110

Lys Tyr Trp Gly Gln Gly Thr Leu Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
                180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
        260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
        290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
            355                 360                 365

Tyr Trp Ala Tyr Trp Gly Gln Gly Thr Leu Val Thr Val Ser Ser Gly
        370                 375                 380

Gly Gly Ser Gly Gly Gly Gly Ser Gly Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
                420                 425                 430

Pro Asn Trp Val Gln Gln Lys Pro Gly Gln Ala Pro Arg Gly Leu Ile
                435                 440                 445

Gly Gly Thr Lys Phe Leu Val Pro Gly Thr Pro Ala Arg Phe Ser Gly
            450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
```

-continued

```
                485                 490                 495
Val Phe Gly Gly Gly Thr Lys Leu Thr Val Leu His His His His
                500                 505                 510
His
```

<210> SEQ ID NO 271
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

```
Glu Val Gln Leu Leu Glu Ser Gly Gly Gly Leu Val Gln Pro Gly Gly
1               5                   10                  15

Ser Leu Thr Leu Ser Cys Ala Ala Ser Glu Arg Thr Phe Ser Ser Tyr
                20                  25                  30

Thr Met Gly Trp Phe Arg Gln Ala Pro Gly Lys Glu Arg Glu Phe Val
            35                  40                  45

Ala Ala Met Ser Trp Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Gly Ser Thr Arg Val Val Val Thr Thr Thr Pro Val Val
            100                 105                 110

Lys Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
```

```
                    325                 330                 335
Asn Thr Ala Tyr Leu Gln Met Asn Asn Leu Lys Thr Glu Asp Thr Ala
                340                 345                 350
Val Tyr Tyr Cys Val Arg His Ala Asn Phe Gly Asn Ser Tyr Ile Ser
            355                 360                 365
Tyr Trp Ala Tyr Trp Gly Gln Gly Thr Leu Val Thr Val Ser Ser Gly
        370                 375                 380
Gly Gly Gly Ser Gly Gly Gly Ser Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
                420                 425                 430
Pro Asn Trp Val Gln Gln Lys Pro Gly Gln Ala Pro Arg Gly Leu Ile
            435                 440                 445
Gly Gly Thr Lys Phe Leu Val Pro Gly Thr Pro Ala Arg Phe Ser Gly
        450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His His
                500                 505                 510
His

<210> SEQ ID NO 272
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Glu Val Gln Leu Leu Glu Ser Gly Gly Gly Leu Val Gln Pro Gly Gly
1               5                   10                  15
Ser Leu Thr Leu Ser Cys Ala Ala Ser Gly Arg Thr Phe Ser Ser Tyr
            20                  25                  30
Ala Met Gly Trp Phe Arg Gln Ala Pro Gly Lys Glu Arg Glu Phe Val
        35                  40                  45
Ala Ala Ile Ser Trp Ser Gly Ser Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ala Gly Gly Ser Thr Arg Val Val Val Thr Thr Thr Pro Val Val
                100                 105                 110
Lys Tyr Trp Gly Gln Gly Thr Leu Val Thr Val Ser Ser Gly Gly Gly
            115                 120                 125
Gly Ser Gly Gly Gly Ser Glu Val Gln Leu Val Glu Ser Gly Gly Gly
        130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
```

165                 170                 175
Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
                405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
        435                 440                 445

Gly Gly Thr Lys Phe Leu Val Pro Gly Thr Pro Ala Arg Phe Ser Gly
    450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
                485                 490                 495

Val Phe Gly Gly Gly Thr Lys Leu Thr Val Leu His His His His
            500                 505                 510

His

<210> SEQ ID NO 273
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Val Gln Leu Gln Glu Ser Gly Gly Gly Leu Val Gln Ala Gly Gly

Ser Leu Arg Leu Ser Cys Ala Ala Ser
            20                  25

<210> SEQ ID NO 274
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Gln Val Gln Leu Gln Glu Ser Gly Gly Gly Leu Val Gln Ala Gly Gly
1               5                   10                  15

Ser Leu Arg Leu Ser Cys Glu Ala Ser
            20                  25

<210> SEQ ID NO 275
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 276
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gln Val Gln Leu Gln Glu Ser Gly Gly Gly Leu Val Gln Ala Gly Gly
1               5                   10                  15

Ser Leu Arg Leu Ser Cys Lys Ala Ser
            20                  25

<210> SEQ ID NO 277
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Val Gln Leu Gln Glu Ser Gly Gly Gly Leu Val Gln Ala Gly Asp
1               5                   10                  15

Ser Leu Arg Leu Ser Cys Ala Ala Ser
            20                  25

<210> SEQ ID NO 278
<211> LENGTH: 25
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 278

Gln Val Gln Leu Gln Glu Ser Gly Gly Gly Leu Val Gln Ala Gly Gly
1               5                   10                  15

Ser Leu Arg Leu Ser Cys Gln Ala Ser
            20                  25

<210> SEQ ID NO 279
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gln Val Gln Leu Gln Glu Ser Gly Gly Gly Leu Val Gln Pro Gly Gly
1               5                   10                  15

Ser Leu Thr Leu Ser Cys Ala Ala Ser
            20                  25

<210> SEQ ID NO 280
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gln Val Gln Leu Gln Glu Ser Gly Gly Gly Leu Val Gln Ala Gly Gly
1               5                   10                  15

Ser Leu Arg Leu Ser Cys Ser Ala Ser
            20                  25

<210> SEQ ID NO 281
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gln Val Gln Leu Gln Glu Ser Gly Gly Gly Leu Val Gln Pro Gly Asp
1               5                   10                  15

Pro Leu Arg Leu Ser Cys Ala Ala Ser
            20                  25

<210> SEQ ID NO 282
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Val Gln Leu Gln Glu Ser Gly Gly Gly Leu Val Gln Ala Gly Gly
1               5                   10                  15

Ser Leu Arg Leu Ser Cys Ala Val Ser
            20                  25
```

<210> SEQ ID NO 283
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gln Val Gln Leu Gln Glu Ser Gly Gly Gly Ser Val Gln Ala Gly Gly
1               5                   10                  15

Ser Leu Arg Leu Ser Cys Ala Phe Ser
            20                  25

<210> SEQ ID NO 284
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gln Val Gln Leu Gln Glu Ser Gly Gly Gly Leu Val Gln Ala Gly Gly
1               5                   10                  15

Ser Leu Gly Leu Ser Cys Ala Val Ser
            20                  25

<210> SEQ ID NO 285
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Val Gln Leu Gln Glu Ser Gly Gly Gly Leu Val Gln Ala Gly Asp
1               5                   10                  15

Ser Leu Arg Leu Ser Cys Ala Val Ser
            20                  25

<210> SEQ ID NO 286
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gln Val Gln Leu Gln Glu Ser Gly Gly Gly Leu Val Gln Ala Gly Gly
1               5                   10                  15

Ser Leu Arg Leu Ser Cys Arg Phe Ser
            20                  25

<210> SEQ ID NO 287
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

```
Gln Val Gln Leu Gln Glu Ser Gly Gly Gly Leu Val Gln Ala Gly Gly
1               5                   10                  15

Ser Leu Met Val Ser Cys Ala Ala Ser
            20                  25

<210> SEQ ID NO 288
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Val Gln Leu Gln Glu Ser Gly Gly Gly Leu Val Gln Val Gly Gly
1               5                   10                  15

Ser Leu Met Val Ser Cys Ala Ala Ser
            20                  25

<210> SEQ ID NO 289
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gln Val Gln Leu Gln Glu Ser Gly Gly Gly Leu Val Gln Leu Gly Asp
1               5                   10                  15

Ser Leu Met Val Ser Cys Ala Ala Ser
            20                  25

<210> SEQ ID NO 290
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Val Gln Leu Gln Glu Ser Gly Gly Gly Trp Val Gln Ala Gly Gly
1               5                   10                  15

Ser Leu Arg Leu Ser Cys Ala Ala Ser
            20                  25

<210> SEQ ID NO 291
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gln Val Gln Leu Gln Glu Ser Gly Gly Gly Leu Val Gln Ala Gly Asp
1               5                   10                  15

Ser Leu Arg Leu Ser Cys Ala Thr Ser
            20                  25

<210> SEQ ID NO 292
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 292

Gln Val Gln Leu Gln Glu Ser Gly Gly Gly Leu Val Gln Ala Gly Gly
1               5                   10                  15

Ser Leu Arg Leu Ser Cys Ala Thr Ser
            20                  25

<210> SEQ ID NO 293
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gln Val Gln Leu Gln Glu Ser Gly Gly Gly Leu Val Gln Pro Gly Gly
1               5                   10                  15

Ser Leu Arg Leu Ser Cys Lys Ala Ser
            20                  25

<210> SEQ ID NO 294
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gln Val Gln Leu Gln Glu Ser Gly Gly Gly Leu Val Gln Ala Gly Gly
1               5                   10                  15

Ser Leu Thr Leu Ser Cys Thr Ala Ser
            20                  25

<210> SEQ ID NO 295
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gln Val Gln Leu Gln Glu Ser Gly Gly Gly Leu Val Gln Pro Gly Gly
1               5                   10                  15

Ser Leu Thr Leu Ser Cys Thr Ala Ser
            20                  25

<210> SEQ ID NO 296
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gln Val Gln Leu Gln Glu Ser Gly Gly Gly Leu Val Gln Ala Gly Gly
1               5                   10                  15

Ser Leu Ser Leu Ser Cys Ala Ala Ser
            20                  25
```

<210> SEQ ID NO 297
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gln Val Gln Leu Gln Glu Ser Gly Gly Gly Leu Val Gln Thr Gly Gly
1               5                   10                  15

Ser Leu Arg Leu Ser Cys Ala Ala Ser
            20                  25

<210> SEQ ID NO 298
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gln Val Gln Leu Gln Glu Ser Gly Gly Gly Val Val Gln Val Gly Gly
1               5                   10                  15

Ser Leu Arg Leu Ser Cys Ala Ala Ser
            20                  25

<210> SEQ ID NO 299
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gln Val Gln Leu Gln Glu Ser Gly Gly Gly Ser Val Gln Ala Gly Gly
1               5                   10                  15

Ser Leu Arg Leu Ser Cys Thr Ala Ser
            20                  25

<210> SEQ ID NO 300
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Glu Val Gln Leu Leu Glu Ser Gly Gly Gly Leu Val Gln Pro Gly Gly
1               5                   10                  15

Ser Leu Thr Leu Ser Cys Ala Ala Ser
            20                  25

<210> SEQ ID NO 301
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Glu Val Gln Leu Val Glu Ser Gly Gly Gly Leu Val Gln Pro Gly Gly
1               5                   10                  15

Ser Leu Thr Leu Ser Cys Ala Ala Ser
            20                  25

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Trp Tyr Arg Gln Ala Pro Gly Lys Gln Arg Glu Trp Val Ala
1               5                   10

<210> SEQ ID NO 303
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Trp Tyr Arg Gln Ala Pro Gly Asn Glu Arg Glu Trp Val Ala
1               5                   10

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Trp Phe Arg Gln Ala Pro Gly Lys Gln Arg Glu Trp Val Ala
1               5                   10

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Trp Tyr Arg Gln Ala Pro Gly Arg Gln Arg Glu Trp Val Ala
1               5                   10

<210> SEQ ID NO 306
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Trp Phe Arg Gln Ala Pro Gly Lys Glu Arg Glu Phe Val Ala
1               5                   10

<210> SEQ ID NO 307

-continued

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Trp Phe Arg Gln Ala Pro Glu Lys Glu Arg Glu Phe Val Ala
1               5                   10

<210> SEQ ID NO 308
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Trp Phe Arg Gln Pro Pro Glu Lys Glu Arg Glu Phe Val Ala
1               5                   10

<210> SEQ ID NO 309
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Trp Phe Arg Gln Val Pro Gly Lys Glu Arg Glu Leu Ile Ala
1               5                   10

<210> SEQ ID NO 310
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Phe Arg Gln Val Pro Gly Lys Glu Arg Glu Phe Ile Ala
1               5                   10

<210> SEQ ID NO 311
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Trp Phe Arg Gln Val Pro Gly Arg Glu Arg Glu Phe Ile Ala
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312
```

-continued

Trp Phe Arg Gln Ala Pro Gly Met Glu Arg Glu Phe Val Ala
1               5                   10

<210> SEQ ID NO 313
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Trp Phe Arg Gln Ala Pro Gly Lys Glu Arg Glu Phe Val Val
1               5                   10

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Trp Phe Arg Gln Ala Pro Gly Lys Glu Arg Glu Phe Leu Val
1               5                   10

<210> SEQ ID NO 315
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Trp Val Arg Gln Ala Pro Gly Lys Gly Leu Glu Trp Val Ser
1               5                   10

<210> SEQ ID NO 316
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Trp Tyr Arg Gln Ala Pro Gly Lys Gln Arg Glu Leu Val Ala
1               5                   10

<210> SEQ ID NO 317
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Trp Phe Arg Gln Ala Pro Gly Lys Glu Arg Gln Phe Val Ala
1               5                   10

<210> SEQ ID NO 318
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 318

Trp Phe Arg Gln Ala Pro Gly Lys Glu Arg Glu Phe Ala
1               5                   10

<210> SEQ ID NO 319
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Trp Phe Arg Gln Ala Pro Gly Lys Glu Arg Val Phe Val Leu
1               5                   10

<210> SEQ ID NO 320
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Trp Phe Arg Gln Ala Pro Gly Lys Glu Arg Glu Phe Met Leu
1               5                   10

<210> SEQ ID NO 321
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Trp Phe Arg Gln Ala Pro Gly Lys Glu Arg Glu Phe Val Ala Ala
1               5                   10                  15

<210> SEQ ID NO 322
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Trp Phe Arg Gln Ala Pro Gly Met Glu Arg Glu Phe Val Ala Ala
1               5                   10                  15

<210> SEQ ID NO 323
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Arg Phe Ala Ile Ser Arg Asp Asn Ala Lys Asn Thr Val Tyr Leu Gln
1               5                   10                  15

Met Asn Asn Leu Lys Pro Glu Asp Thr Ala Val Tyr Tyr Cys Arg Val

```
<210> SEQ ID NO 324
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Arg Phe Ala Val Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Arg Val
            20                  25                  30

<210> SEQ ID NO 325
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Arg Val
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Arg Phe Thr Ile Ser Arg Asp Asn Ala Lys Asn Thr Ala Tyr Leu Gln
1               5                   10                  15

Met Asn Ser Leu Lys Pro Glu Asp Thr Ala Val Tyr Tyr Cys Arg Ile
            20                  25                  30

<210> SEQ ID NO 327
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Arg Leu
            20                  25                  30

<210> SEQ ID NO 328
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 328

Arg Phe Ala Ile Ser Arg Asp Asn Ala Lys Asn Thr Val Tyr Leu Gln
1               5                   10                  15

Met Asn Asn Leu Arg Pro Glu Asp Thr Ala Val Tyr Tyr Cys Arg Leu
                20                  25                  30

<210> SEQ ID NO 329
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Arg Ile
                20                  25                  30

<210> SEQ ID NO 330
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Arg Phe Ala Ile Ser Arg Glu Asn Ala Lys Asn Thr Val Tyr Leu Gln
1               5                   10                  15

Met Asn Ser Leu Lys Pro Glu Asp Thr Ala Val Tyr Tyr Cys Arg Val
                20                  25                  30

<210> SEQ ID NO 331
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Arg Phe Ala Ile Ser Arg Asp Asn Ala Lys Asn Met Val Tyr Leu Gln
1               5                   10                  15

Leu Asn Ser Leu Lys Pro Glu Asp Thr Ala Val Tyr Tyr Cys Arg Ile
                20                  25                  30

<210> SEQ ID NO 332
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Arg Phe Thr Ile His Arg Asp Asn Ala Lys Asn Thr Val Tyr Leu Gln
1               5                   10                  15

Met Asn Ser Leu Lys Pro Glu Asp Thr Ala Val Tyr Tyr Cys Ala
                20                  25                  30

<210> SEQ ID NO 333
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala
            20                  25                  30

<210> SEQ ID NO 334
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Arg Phe Thr Ile Ser Arg Asp Asn Ala Lys Asn Thr Val Tyr Leu Gln
1               5                   10                  15

Met Asp Ser Leu Lys Pro Glu Asp Thr Ala Ile Tyr Tyr Cys Ala
            20                  25                  30

<210> SEQ ID NO 335
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Arg Phe Thr Ile Ser Arg Asp Asn Ala Lys Asn Thr Val Phe Leu Gln
1               5                   10                  15

Met Asn Ser Leu Lys Pro Glu Asp Thr Ala Val Tyr Tyr Cys Ala
            20                  25                  30

<210> SEQ ID NO 336
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Arg Phe Thr Ile Ser Arg Asp Asn Ala Lys Asn Thr Val Ser Leu Val
1               5                   10                  15

Tyr Leu Gln Met Asn Ser Leu Lys Pro Asp Asp Thr Ala Val Tyr Tyr
            20                  25                  30

Cys Ala

<210> SEQ ID NO 337
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Arg Phe Thr Ile Ser Arg Asp Asn Ala Ala Asn Thr Val Tyr Leu Gln
```

```
                1               5                  10                 15
Met Asn Ser Leu Lys Pro Glu Asp Thr Ala Val Tyr Tyr Cys Ala
               20                  25                 30
```

<210> SEQ ID NO 338
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

```
Arg Phe Thr Ile Ser Arg Asp Asn Ala Lys Asn Thr Val Asn Leu Val
1               5                   10                  15
Tyr Leu Gln Met Asn Asp Leu Arg Pro Glu Asp Thr Ala Val Tyr Tyr
                20                  25                  30
Cys Ala
```

<210> SEQ ID NO 339
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

```
Arg Phe Thr Ile Ser Arg Asp Asn Ala Glu Asn Thr Val Tyr Leu Glu
1               5                   10                  15
Met Asn Ser Leu Lys Pro Glu Asp Thr Ala Val Tyr Ile Cys Ala
                20                  25                  30
```

<210> SEQ ID NO 340
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

```
Arg Phe Thr Ile Ser Arg Asp Asn Ala Lys Asn Thr Val Tyr Leu Gln
1               5                   10                  15
Met Asn Ser Leu Lys Pro Glu Asp Thr Ala Ile Tyr Tyr Cys Ala
                20                  25                  30
```

<210> SEQ ID NO 341
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

```
Arg Phe Thr Ile Ser Arg Asp Asn Ala Lys Asn Thr Val Tyr Leu Gln
1               5                   10                  15
Met Ser Ser Leu Lys Pro Gly Asp Thr Ala Val Tyr Tyr Cys Ala
                20                  25                  30
```

<210> SEQ ID NO 342
<211> LENGTH: 34
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 342

Arg Phe Thr Ile Ser Arg Asp Asn Ala Lys Asn Thr Glu Thr Leu Val
1               5                   10                  15

Tyr Leu Gln Met Asn Ser Leu Lys Pro Glu Asp Thr Ala Val Tyr Tyr
            20                  25                  30

Cys Ala

<210> SEQ ID NO 343
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Arg Phe Thr Ile Ser Arg Asp Asn Ala Lys Asn Thr Val Asn Leu Val
1               5                   10                  15

Tyr Leu Gln Met Asn Ser Leu Arg Pro Glu Asp Thr Ala Val Tyr Tyr
            20                  25                  30

Cys Ala

<210> SEQ ID NO 344
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Arg Phe Thr Ile Ser Arg Asp Asn Ala Lys Asn Thr Val Tyr Leu Gln
1               5                   10                  15

Met Asn Thr Leu Lys Pro Asp Asp Thr Ala Val Tyr Tyr Cys Ala Ala
            20                  25                  30

<210> SEQ ID NO 345
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Arg Phe Thr Ile Ser Arg Asp Asn Ala Lys Asn Thr Val Tyr Leu Gln
1               5                   10                  15

Met Asn Thr Leu Arg Pro Asp Asp Thr Ala Val Tyr Tyr Cys Ala Ala
            20                  25                  30

<210> SEQ ID NO 346
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Arg Phe Thr Ile Ser Arg Asp Asn Ala Lys Asn Thr Val Tyr Leu Gln
1               5                   10                  15

Met Asn Thr Leu Lys Pro Asp Asp Thr Gly Val Tyr Tyr Cys Ala Ala
            20                  25                  30

<210> SEQ ID NO 347
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Arg Phe Thr Ile Ser Arg Asp Asn Ala Lys Asn Thr Val Tyr Leu Gln
1               5                   10                  15

Met Asn Thr Leu Lys Ser Asp Asp Thr Ala Val Tyr Tyr Cys Ala Ala
            20                  25                  30

<210> SEQ ID NO 348
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Arg Phe Thr Ile Ser Arg Asp Asn Ala Lys Asn Thr Val Tyr Leu Gln
1               5                   10                  15

Met Asp Ser Leu Lys Pro Glu Asp Thr Ala Val Tyr Tyr Cys Ala
            20                  25                  30

<210> SEQ ID NO 349
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Arg Phe Thr Ile Ser Arg Asp Asp Ala Lys Asn Thr Val Tyr Leu Gln
1               5                   10                  15

Met Asp Ser Leu Lys Pro Glu Asp Thr Ala Val Tyr Tyr Cys Ala
            20                  25                  30

<210> SEQ ID NO 350
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Arg Phe Thr Ile Ser Arg Asp Asn Ala Lys Asn Thr Val Tyr Leu Leu
1               5                   10                  15

Met Asp Ser Leu Lys Pro Glu Asp Thr Ala Val Tyr Tyr Cys Ala
            20                  25                  30

<210> SEQ ID NO 351
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 351

Arg Phe Thr Ile Ser Arg Asp Ile Ala Lys Asn Thr Val Tyr Leu Gln
1               5                   10                  15

Met Asn Ser Leu Lys Pro Glu Asp Thr Ala Met Tyr Phe Cys Ala Ala
            20                  25                  30

<210> SEQ ID NO 352
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Arg Phe Thr Ile Ser Arg Gly Asn Ala Lys Asn Thr Val Tyr Leu Gln
1               5                   10                  15

Met Asn Ser Leu Lys Pro Glu Asp Thr Ala Met Tyr Tyr Cys Ala Ala
            20                  25                  30

<210> SEQ ID NO 353
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Ile Tyr Tyr Cys Ala Thr
            20                  25                  30

<210> SEQ ID NO 354
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Arg Phe Thr Ile Ser Arg Asp Asn Ala Lys Asn Thr Leu Tyr Leu Gln
1               5                   10                  15

Met Asn Ser Leu Thr Ala Glu Asp Thr Ala Val Tyr Tyr Cys Ala Lys
            20                  25                  30

<210> SEQ ID NO 355
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Arg Phe Thr Ile Ser Arg Asp Asn Ala Lys Asn Thr Leu Tyr Leu Gln
1               5                   10                  15

Met Asn Ser Leu Asn Ala Glu Asp Thr Ala Val Tyr Tyr Cys Ala Lys
            20                  25                  30
```

<210> SEQ ID NO 356
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Arg Phe Thr Ile Ser Gly Asp Asn Asp Lys Asn Thr Ala Tyr Leu Gln
1               5                   10                  15

Met Asn Gly Leu Lys Pro Glu Asp Thr Ala Val Tyr Tyr Cys Tyr Tyr
            20                  25                  30

<210> SEQ ID NO 357
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Arg Phe Thr Ile Thr Gly Asp His Ala Lys Asn Thr Val Tyr Leu Gln
1               5                   10                  15

Met Asn Ser Leu Lys Pro Glu Asp Thr Gly Val Tyr Tyr Cys Ala Val
            20                  25                  30

<210> SEQ ID NO 358
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Gln
            20                  25                  30

<210> SEQ ID NO 359
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Arg Phe Thr Ile Ser Arg Asp Asn Ala Lys Asn Thr Val Tyr Leu Gln
1               5                   10                  15

Met Ser Ser Leu Lys Pro Glu Asp Thr Ala Val Tyr Tyr Cys Ala Ala
            20                  25                  30

<210> SEQ ID NO 360
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Val Tyr Tyr Cys Ala
            20                  25                  30

<210> SEQ ID NO 361
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Arg Phe Thr Ile Ser Arg Asp Asn Ala Lys Asn Thr Val Tyr Leu Gln
1               5                   10                  15

Met Asn Ser Leu Lys Ser Glu Asp Thr Ala Val Tyr Tyr Cys Gly Leu
            20                  25                  30

<210> SEQ ID NO 362
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Arg Phe Ser Ile Ser Arg Asp Asn Ala Lys Ser Thr Val Tyr Leu Gln
1               5                   10                  15

Met Asn Asn Leu Lys Pro Glu Asp Thr Ala Val Tyr Tyr Cys Ala
            20                  25                  30

<210> SEQ ID NO 363
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Arg Phe Thr Ile Ser Arg Asp Asn Val Lys Lys Thr Val Tyr Leu Gln
1               5                   10                  15

Met Asn Asp Leu Lys Pro Glu Asp Thr Ala Val Tyr Tyr Cys Ala Ala
            20                  25                  30

<210> SEQ ID NO 364
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ala
            20                  25                  30

<210> SEQ ID NO 365
<211> LENGTH: 32
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 365

Arg Phe Thr Ile Ser Gly Asp Asn Ser Lys Asn Thr Ala Tyr Leu Gln
1               5                   10                  15
Met Asn Ser Leu Arg Ala Glu Asp Thr Ala Val Tyr Tyr Cys Tyr Tyr
            20                  25                  30

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Trp Gly Gln Gly Thr Gln Val Thr Val Ser Ser
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Trp Gly Arg Gly Thr Gln Val Thr Val Ser Ser
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Leu Gly Gln Gly Thr Gln Val Thr Val Ser Ser
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Trp Gly Gln Gly Thr Gln Val Thr Ala Ser Ser
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Arg Gly Gln Gly Thr Gln Val Thr Val Ser Ser
1               5                   10

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Trp Gly Gln Gly Thr Leu Val Thr Val Ser Ser
1               5                   10

<210> SEQ ID NO 372
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 373
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Ile Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
            85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                    165                 170                 175

Trp Val Gln Gln Lys Pro Gly Gln Ala Pro Arg Gly Leu Ile Gly
            180                 185                 190

Thr Lys Phe Leu Val Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
            210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
            245

<210> SEQ ID NO 374
<211> LENGTH: 6
<212> TYPE: PRT
<213> ORGANISM: Artificial Sequence
<220> FEATURE:
<223> OTHER INFORMATION: Description of Artificial Sequence: Synthetic
      6xhis tag

<400> SEQUENCE: 374

His His His His His His
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Gly Gly Gly Ser Gly Gly Gly Ser
1               5

<210> SEQ ID NO 376
<211> LENGTH: 5
<212> TYPE: PRT
<213> ORGANISM: Unknown
<220> FEATURE:
<223> OTHER INFORMATION: Description of Unknown:
      sortase recognition sequence

<400> SEQUENCE: 376

Leu Pro Glu Thr Gly
1               5

<210> SEQ ID NO 377
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-10 "Gly Ser"
      repeating units

<400> SEQUENCE: 377

Gly Ser Gly Ser Gly Ser Gly Ser Gly Ser Gly Ser Gly Ser Gly Ser
1               5                   10                  15

Gly Ser Gly Ser
            20

<210> SEQ ID NO 378
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-10 "Gly Gly Ser"
      repeating units

<400> SEQUENCE: 378

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 379
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 379

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40

<210> SEQ ID NO 380
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units
```

```
<400> SEQUENCE: 380

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 381
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Ser
      Gly Gly" repeating units

<400> SEQUENCE: 381

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Gly Ser Gly Gly Gly Gly Ser
        35                  40                  45

Gly Gly
    50

<210> SEQ ID NO 382
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units

<400> SEQUENCE: 382

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser
    50

<210> SEQ ID NO 383
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
```

Gly Gly" repeating units

<400> SEQUENCE: 383

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly
    50

<210> SEQ ID NO 384
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-10 "Gly Gly Gly"
      repeating units

<400> SEQUENCE: 384

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

<210> SEQ ID NO 385
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gly Gly Gly Gly Ser Gly Gly Gly Gly Ser Gly Gly Gly Gly Ser Gly
1               5                   10                  15

Gly Gly Gly Ser
            20

<210> SEQ ID NO 386
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Gly Gly Gly Gly Ser Gly Gly Gly Gly Ser Gly Gly Gly Gly Ser
1               5                   10                  15

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gly Gly Gly Gly Ser Gly Gly Gly Ser
1               5

<210> SEQ ID NO 388
<211> LENGTH: 993
<212> TYPE: PRT
<213> ORGANISM: Homo sapiens

<400> SEQUENCE: 388

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys

-continued

```
            355                 360                 365
Phe Ser Val Arg Phe Lys Ala Tyr Pro Gln Ile Arg Cys Thr Trp Thr
370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
                420                 425                 430
Leu Asn Ile Arg Arg Lys Pro Gln Val Leu Ala Glu Ala Ser Ala Ser
                435                 440                 445
Gln Ala Ser Cys Phe Ser Asp Gly Tyr Pro Leu Pro Ser Trp Thr Trp
        450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
                500                 505                 510
Lys Cys Cys Ala Tyr Asn Ser Leu Gly Thr Ser Cys Glu Thr Ile Leu
                515                 520                 525
Leu Asn Ser Pro Gly Pro Phe Pro Phe Ile Gln Asp Asn Ile Ser Phe
        530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
                580                 585                 590
Asp Phe Arg Glu Tyr Glu Tyr Asp Leu Lys Trp Glu Phe Pro Arg Glu
        595                 600                 605
Asn Leu Glu Phe Gly Lys Val Leu Gly Ser Gly Ala Phe Gly Lys Val
        610                 615                 620
Met Asn Ala Thr Ala Tyr Gly Ile Ser Lys Thr Gly Val Ser Ile Gln
625                 630                 635                 640
Val Ala Val Lys Met Leu Lys Glu Lys Ala Asp Ser Ser Glu Arg Glu
                645                 650                 655
Ala Leu Met Ser Glu Leu Lys Met Met Thr Gln Leu Gly Ser His Glu
                660                 665                 670
Asn Ile Val Asn Leu Leu Gly Ala Cys Thr Leu Ser Gly Pro Ile Tyr
                675                 680                 685
Leu Ile Phe Glu Tyr Cys Cys Tyr Gly Asp Leu Leu Asn Tyr Leu Arg
        690                 695                 700
Ser Lys Arg Glu Lys Phe His Arg Thr Trp Thr Glu Ile Phe Lys Glu
705                 710                 715                 720
His Asn Phe Ser Phe Tyr Pro Thr Phe Gln Ser His Pro Asn Ser Ser
                725                 730                 735
Met Pro Gly Ser Arg Glu Val Gln Ile His Pro Asp Ser Asp Gln Ile
                740                 745                 750
Ser Gly Leu His Gly Asn Ser Phe His Ser Glu Asp Glu Ile Glu Tyr
        755                 760                 765
Glu Asn Gln Lys Arg Leu Glu Glu Glu Asp Leu Asn Val Leu Thr
770                 775                 780
```

```
Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
            805                 810                 815

Val Leu Val Thr His Gly Lys Val Lys Ile Cys Asp Phe Gly Leu
        820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
            885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 389
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Glu Val Gln Leu Leu Glu Ser Gly Gly Gly Leu Val Gln Pro Gly Gly
1               5                   10                  15

Ser Leu Thr Leu Ser Cys Ala Ala Ser Gly Gly Thr Trp Ser Ser Tyr
            20                  25                  30

Ala Thr Gly Trp Phe Arg Gln Ala Pro Gly Lys Glu Arg Glu Leu Ile
        35                  40                  45

Ala Gly Ile Ser Arg Ser Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Tyr Phe Thr Ser Val Val Tyr Thr Ser Gly Asn
            100                 105                 110

Asp Tyr Asp Tyr Trp Gly Gln Gly Thr Leu Val Thr Val Ser Ser
        115                 120                 125

<210> SEQ ID NO 390
```

<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Glu Val Gln Leu Leu Glu Ser Gly Gly Gly Leu Val Gln Pro Gly Gly
1               5                   10                  15

Ser Leu Thr Leu Ser Cys Ala Ala Ser Gly Gly Thr Trp Ser Ser Tyr
            20                  25                  30

Ala Thr Gly Trp Phe Arg Gln Ala Pro Gly Lys Glu Arg Glu Leu Ile
        35                  40                  45

Ala Gly Ile Ser Arg Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Ala Arg Tyr Phe Thr Ser Ser Val Val Tyr Thr Ser Gly Asn
            100                 105                 110

Asp Tyr Asp Tyr Trp Gly Gln Gly Thr Leu Val Thr Val Ser Ser
        115                 120                 125

<210> SEQ ID NO 391
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Glu Val Gln Leu Leu Glu Ser Gly Gly Gly Leu Val Gln Pro Gly Gly
1               5                   10                  15

Ser Leu Thr Leu Ser Cys Ala Ala Ser Gly Gly Thr Trp Ser Ser Tyr
            20                  25                  30

Ala Thr Gly Trp Phe Arg Gln Ala Pro Gly Lys Glu Arg Glu Leu Ile
        35                  40                  45

Ala Gly Ile Ser Arg Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Tyr Phe Thr Ser Ser Val Val Tyr Thr Ser Gly Asn
            100                 105                 110

Asp Tyr Asp Tyr Trp Gly Gln Gly Thr Leu Val Thr Val Ser Ser Gly
        115                 120                 125

Gly Gly Gly Ser Gly Gly Gly Ser Glu Val Gln Leu Val Glu Ser Gly
    130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
            195                 200                 205

Asp Asn Ala Lys Thr Thr Leu Tyr Leu Gln Met Asn Ser Leu Arg Pro
        210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
        290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365

Ile Ser Tyr Trp Ala Tyr Trp Gly Gln Gly Thr Leu Val Thr Val Ser
        370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
        450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 392
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Glu Val Gln Leu Leu Glu Ser Gly Gly Gly Leu Val Gln Pro Gly Gly
1               5                   10                  15

Ser Leu Thr Leu Ser Cys Ala Ala Ser Gly Gly Thr Trp Ser Ser Tyr

```
            20                  25                  30
Ala Thr Gly Trp Phe Arg Gln Ala Pro Gly Lys Glu Arg Glu Leu Ile
        35                  40                  45
Ala Gly Ile Ser Arg Ser Gly Gly Arg Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Val Tyr Tyr Cys
                85                  90                  95
Ala Lys Ala Arg Tyr Phe Thr Ser Ser Val Val Tyr Thr Ser Gly Asn
            100                 105                 110
Asp Tyr Asp Tyr Trp Gly Gln Gly Thr Leu Val Thr Val Ser Ser Gly
        115                 120                 125
Gly Gly Gly Ser Gly Gly Gly Ser Glu Val Gln Leu Val Glu Ser Gly
    130                 135                 140
Gly Gly Leu Val Gln Pro Gly Asn Ser Leu Arg Leu Ser Cys Ala Ala
145                 150                 155                 160
Ser Gly Phe Thr Phe Ser Lys Phe Gly Met Ser Trp Val Arg Gln Ala
                165                 170                 175
Pro Gly Lys Gly Leu Glu Trp Val Ser Ser Ile Ser Gly Ser Gly Arg
            180                 185                 190
Asp Thr Leu Tyr Ala Asp Ser Val Lys Gly Arg Phe Thr Ile Ser Arg
        195                 200                 205
Asp Asn Ala Lys Thr Thr Leu Tyr Leu Gln Met Asn Ser Leu Arg Pro
    210                 215                 220
Glu Asp Thr Ala Val Tyr Tyr Cys Thr Ile Gly Gly Ser Leu Ser Val
225                 230                 235                 240
Ser Ser Gln Gly Thr Leu Val Thr Val Ser Ser Gly Gly Gly Gly Ser
                245                 250                 255
Gly Gly Gly Ser Glu Val Gln Leu Val Glu Ser Gly Gly Gly Leu Val
            260                 265                 270
Gln Pro Gly Gly Ser Leu Lys Leu Ser Cys Ala Ala Ser Gly Phe Thr
        275                 280                 285
Phe Asn Lys Tyr Ala Ile Asn Trp Val Arg Gln Ala Pro Gly Lys Gly
    290                 295                 300
Leu Glu Trp Val Ala Arg Ile Arg Ser Lys Tyr Asn Asn Tyr Ala Thr
305                 310                 315                 320
Tyr Tyr Ala Asp Gln Val Lys Asp Arg Phe Thr Ile Ser Arg Asp Asp
                325                 330                 335
Ser Lys Asn Thr Ala Tyr Leu Gln Met Asn Asn Leu Lys Thr Glu Asp
            340                 345                 350
Thr Ala Val Tyr Tyr Cys Val Arg His Ala Asn Phe Gly Asn Ser Tyr
        355                 360                 365
Ile Ser Tyr Trp Ala Tyr Trp Gly Gln Gly Thr Leu Val Thr Val Ser
    370                 375                 380
Ser Gly Gly Gly Gly Ser Gly Gly Gly Ser Gly Gly Gly Gly Ser
385                 390                 395                 400
Gln Thr Val Val Thr Gln Glu Pro Ser Leu Thr Val Ser Pro Gly Gly
                405                 410                 415
Thr Val Thr Leu Thr Cys Ala Ser Ser Thr Gly Ala Val Thr Ser Gly
            420                 425                 430
Asn Tyr Pro Asn Trp Val Gln Gln Lys Pro Gly Gln Ala Pro Arg Gly
        435                 440                 445
```

```
Leu Ile Gly Gly Thr Lys Phe Leu Val Pro Gly Thr Pro Ala Arg Phe
        450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 393
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Ile Ser Arg Ser Gly Gly Arg Thr Tyr Tyr Ala Asp Ser Val Lys
1               5                   10                  15

Gly

<210> SEQ ID NO 394
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Ile Ser Arg Ser Gly Gly Arg Thr Tyr Tyr Ala Asp Ser Val Lys
1               5                   10                  15

Gly

<210> SEQ ID NO 395
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Trp Phe Arg Gln Ala Pro Gly Lys Glu Arg Glu Leu Ile Ala
1               5                   10

<210> SEQ ID NO 396
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Arg Phe Thr Ile Ser Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 397
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Gly Phe Thr Phe Asn Lys Tyr Ala Ile Asn
1               5                   10

<210> SEQ ID NO 398
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Arg Ile Arg Ser Lys Tyr Asn Asn Tyr Ala Thr Tyr Tyr Ala Asp Gln
1               5                   10                  15

Val Lys

<210> SEQ ID NO 399
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

His Ala Asn Phe Gly Asn Ser Tyr Ile Ser Tyr Trp Ala Tyr
1               5                   10

<210> SEQ ID NO 400
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ala Ser Ser Thr Gly Ala Val Thr Ser Gly Asn Tyr Pro Asn
1               5                   10

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Gly Thr Lys Phe Leu Val Pro
1               5

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 402

Thr Leu Trp Tyr Ser Asn Arg Trp Val
1               5

<210> SEQ ID NO 403
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Phe Thr Phe Ser Lys Phe Gly Met Ser
1               5                   10

<210> SEQ ID NO 404
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ser Ile Ser Gly Ser Gly Arg Asp Thr Leu Tyr Ala Asp Ser Val Lys
1               5                   10                  15

<210> SEQ ID NO 405
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Gly Ser Leu Ser Val
1               5

<210> SEQ ID NO 406
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Trp Phe Arg Gln Val Pro Gly Lys Glu Arg Lys Leu Ile Ala
1               5                   10

<210> SEQ ID NO 407
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Trp Tyr Arg Gln Ala Pro Gly Lys Gln Arg Glu Leu Val Ala Phe
1               5                   10                  15